United States Patent
Weiner et al.

(10) Patent No.: US 9,028,798 B2
(45) Date of Patent: May 12, 2015

(54) MODULATION OF THE IMMUNE RESPONSE

(71) Applicant: The Brigham and Women's Hospital, Inc., Boston, MA (US)

(72) Inventors: Howard Weiner, Brookline, MA (US); Francisco J. Quintana, Jamaica Plain, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/745,416

(22) Filed: Jan. 18, 2013

(65) Prior Publication Data

US 2013/0336993 A1 Dec. 19, 2013

Related U.S. Application Data

(63) Continuation of application No. 12/743,680, filed as application No. PCT/US2008/083016 on Nov. 10, 2008, now abandoned.

(60) Provisional application No. 60/989,309, filed on Nov. 20, 2007, provisional application No. 61/070,410, filed on Mar. 21, 2008.

(51) Int. Cl.
| | |
|---|---|
| *A61K 51/10* | (2006.01) |
| *A61K 49/04* | (2006.01) |
| *A61K 31/427* | (2006.01) |
| *A61K 31/405* | (2006.01) |
| *C12N 5/0783* | (2010.01) |
| *G01N 33/50* | (2006.01) |
| *A61K 31/135* | (2006.01) |
| *A61K 31/357* | (2006.01) |
| *A61K 31/4045* | (2006.01) |
| *A61K 31/407* | (2006.01) |
| *A61K 35/12* | (2006.01) |

(52) U.S. Cl.
CPC .............. *A61K 31/427* (2013.01); *A61K 31/405* (2013.01); *A61K 2035/122* (2013.01); *C12N 5/0636* (2013.01); *C12N 2501/38* (2013.01); *C12N 2501/60* (2013.01); *G01N 33/5088* (2013.01); *A61K 31/135* (2013.01); *A61K 31/357* (2013.01); *A61K 31/4045* (2013.01); *A61K 31/407* (2013.01)

(58) Field of Classification Search
None
See application file for complete search history.

(56) References Cited

U.S. PATENT DOCUMENTS

| | | | |
|---|---|---|---|
| 5,145,684 | A | 9/1992 | Liversidge et al. |
| 5,262,176 | A | 11/1993 | Palmacci et al. |
| 5,492,814 | A | 2/1996 | Weissleder |
| 6,270,806 | B1 | 8/2001 | Liversidge et al. |
| 7,060,121 | B2 | 6/2006 | Lin et al. |
| 7,232,474 | B2 | 6/2007 | Bouvrette et al. |
| 7,291,598 | B2 | 11/2007 | Sung et al. |
| 7,348,030 | B1 | 3/2008 | Sung et al. |
| 7,569,352 | B2 | 8/2009 | Von Stein et al. |
| 2005/0129671 | A1 | 6/2005 | Cooper et al. |
| 2006/0222595 | A1* | 10/2006 | Mukherjee et al. .......... 424/9.34 |
| 2006/0257405 | A1 | 11/2006 | Golz et al. |
| 2007/0043092 | A1 | 2/2007 | Deluca et al. |
| 2007/0154487 | A1 | 7/2007 | Littman et al. |
| 2007/0253901 | A1 | 11/2007 | Deng et al. |
| 2007/0253962 | A1 | 11/2007 | Hirsch et al. |
| 2008/0166706 | A1 | 7/2008 | Zhang et al. |

FOREIGN PATENT DOCUMENTS

| | | |
|---|---|---|
| WO | WO00/61191 | 10/2000 |
| WO | WO2007/000193 | 1/2007 |
| WO | WO2009/067349 | 5/2009 |

OTHER PUBLICATIONS

Loaiza-Pérez et al. Aryl hydrocarbon receptor mediates sensitivity of MCF-7 breast cancer cells to antitumor agent 2-(4-amino-3-methylphenyl) benzothiazole. 2002 Mol. Pharmacol. 61: 13-19.*
Fujii-Kuriyama et al. Molecular mechanisms of AhR functions in the regulation of cytochrome P450 genes. 2005 Biochem. Biophys. Res. Commun. 338: 311-317.*
Allan, S., "T cells. Tuning T cells through the aryl hydrocarbon receptor," Nature Reviews Immunology, 8(5):326 (2008).
Amir-Kroll et al., "Proteins and their derived peptides as carriers in a conjugate vaccine for *Streptococcus pneumoniae*: self-heat shock protein 60 and tetanus toxoid," J. Immunol., 170:6165-6171 (2003).
Anand et al., "Bioavailability curcumin: Problems and promises," Molecular Pharmaceutics, American Chemical Society, 4(6):807-818 (2007).
Baccarelli et al., "Immunologic effects of dioxin: new results from Seveso and comparison with other studies," Environ. Health Perspect. 110, 1169 (2002).
Baker et al., "Insights into the mechanisms of action of the MAO inhibitors phenelzine and tranylcypromine: a review," J. Psychiatry Neurosci., 17:206-214 (1992).
Bettelli et al., "Foxp3 interacts with nuclear factor of activated T cells and NF-kappa B to repress cytokine gene expression and effector functions of T helper cells," Proc. Natl. Acad. Sci. USA, 102:5138-5143 (2005).
Bettelli et al., "Reciprocal developmental pathways for the generation of pathogenic effector TH17 and regulatory T cells," Nature 441, 235-8 (2006).
Bettelli et al., "T(H)-17 cells in the circle of immunity and autoimmunity," Nat. Immunol., 8.345-350 (2007).
Boehm and Bleul, "The evolutionary history of lymphoid organs," Immunol., 8.131-135 (2007).
Boehm, "Quality control in self/nonself discrimination," Cell, 125:845-858 (2006).
Brenchley and Douek, "HIV infection and the gastrointestinal immune system," Muc. Immunol., 1(1):23-30 (2008).
Brenchley et al., "Differential Th17 CD4 T-cell depletion in pathogenic and nonpathogenic lentiviral infections," Blood, 112:2826-2835 (2008).

(Continued)

*Primary Examiner* — Michael G Hartley
*Assistant Examiner* — Jennifer Lamberski
(74) *Attorney, Agent, or Firm* — Fish & Richardson P.C.

(57) ABSTRACT

Methods for identifying compounds that modulate the generation of regulatory T cells (Treg) in vivo and in vitro, i.e., compounds that act on the transcription factors that increase or decrease expression of Foxp3.

9 Claims, 77 Drawing Sheets

(56) References Cited

OTHER PUBLICATIONS

Brusko et al., "Functional defects and the influence of age on the frequency of CD4+ CD25+ T-cells in type 1 diabetes," Diabetes, 54, 1407-14 (2005).

Cecchinato et al., "Altered balance between Th17 and Th1 cells at mucosal sites predicts AIDS progression in simian immunodeficiency virus-infected macaques," Muc. Immunol , 1(4):279-288 (2008).

Chae et al., "The mutant leucine-zipper domain impairs both dimerization and suppressive function of Foxp3 in T cells," Proc. Natl. Acad. Sci. USA, 103, 9631-6 (2006).

Chang et al., "Ligand-Independent Regulation of Transforming Growth Factor Expression and Cell Cycle Progression by the Aryl Hydrocarbon Receptor," Molecular and Cellular Biology, 27(17): 6127-6139; Abstract (2005).

Chen et al., "Conversion of peripheral CD4+CD25− naive T cells to CD4+CD25+ regulatory T cells by TGF-beta induction of transcription factor Foxp3," J. Exp. Med., 198:1875-1886 (2003).

Clay et al., "Tumor necrosis factor signaling mediates resistance to mycobacteria by inhibiting bacterial growth and macrophage death," Immunity, 29:283-294 (2008).

Cooper and Alder, "The evolution of adaptive immune systems," Cell, 124:815-822 (2006).

Danilova et al., "B cells develop in the zebrafish pancreas," Proc. Nat. Acad. Sci. USA, 99,:13711-6 (2002).

Davis et al., "Davis et al., "Real-time visualization of mycobacterium-macrophage interactions leading to initiation of granuloma formation in zebrafish embryos," Immunity 17:693-702 (2002)," Immunity 17:693-702 (2002).

Denison et al., "Activation of the aryl hydrocarbon receptor by structurally diverse exogenous and endogenous chemicasls," Annu. Rev. Pharmacol. Toxicol. 43:309-334 (2003).

Dinauer et al., "Selective targeting of antibody-conjugated nanoparticles to leukemic cells and primary T-lymphocytes," Biomaterials, 26: 5898-5906; Abstract (2005).

Douek et al., "Emerging concepts in the immunopathogenesis of AIDS," Annu. Rev. Med., 60:471-484 (2009).

Ehrenstein et al., "Compromised function of regulatory T cells in rheumatoid arthritis and reversal by anti-TNFalpha therapy," J. Exp. Med., 200:277-85 (2004).

European Search Report issued in 08851241 on Oct. 18, 2011.

European Search Report issued in EP 09721374 on May 2, 2011.

Flores et al., "The zebrafish retinoid-related orphan receptor (ror) gene family," Gene Expr. Patterns, 7:535-543 (2007).

Fritsche et al., "Lightening up the UV response by identification of the arylhydrocarbon receptor as a cytoplasmatic target for ultraviolet B radiation," Proc. Natl. Acad. Sci. USA, 104:8851-8856 (2007).

Funatake et al., "Cutting Edge: Activation of the Aryl Hydrocarbon Receptor by 2,3,7,8-Tetrachlorodibenzo-p-dioxin Generates a Population of CD4+CD25+ Cells with Characteristics of Regulatory T Cells," Journal of Immunology, 175:4184-4188 (2005).

Gunimaladevi et al., "Identification, cloning and characterization of interleukin-17 and its family from zebrafish," Fish Shellfish Immunol., 21:393-403 (2006).

Gurench et al., "Receptor rigidity and ligand mobility in trypsin-ligand complexes," Proteins 58(2) 407-417 (2005).

Halbreich et al., "Biomedical applications of maghemite ferrofluid," Biochimie, 80 (5-6):379-390 (1998).

Hauben et al., "Activation of the aryl hydrocarbon receptor promotes allograft-specific tolerance through direct and dendritic cell-mediated effects on regulatory T cells," Blood, 112(4):1214-1222 (2008).

Hayashi et al., "Expression of Ah receptor (TCDD receptor) during human monocytic differentiation," Carcinogenesis. 16:1403 (1995).

Heath-Pagliuso et al., "Activation of the Ah receptor by tryptophan and tryptophan metabolites," Biochemistry. 37:11508 (1998).

Henry et al., "A potential endogenous ligand for the aryl hydrocarbon receptor has potent agonist activity in vitro and in vivo," Arch Biochem Biophys. 450:67-77 (2006).

Hogemann et al., "Improvement of MRI probes to allow efficient detection of gene expression," Bioconjug. Chem., 11(6):941-6 (2000).

Huber, J., "Method Development in In Vitro Immune Response," for the degree of Baccalaureate of Science in Bioscience Research, Toxicology Option, presented on Jun. 12, 2007.

International Preliminary Report on Patentability dated Sep. 30, 2010 from International Application No. PCT/US2009/037696, 7 pages.

International Search Report and Written Opinion dated Apr. 22, 2009 from PCT/US2008/083016.

International Search Report and Written Opinion dated Jul. 16, 2009 from International Application No. PCT/US2009/037696, 8 pages.

Ivanov et al., "Transcriptional regulation of Th17 cell differentiation," Seminars in Immunology, 19(6):409-417 (2008).

Josephson et al., "High-efficiency intracellular magnetic labeling with novel superparamagnetic-Tat peptide conjugates," Bioconjug. Chem.,10(2):186-91 (1999).

Kim et al., "Regulatory T cells prevent catastrophic autoimmunity throughout the lifespan of mice," Nat. Immunol., 8.191-7 (2007).

Komura et al., "Aryl hydrocarbon receptor/dioxin receptor in human monocytes and macrophages," Mol. Cell Biochem., 226:107 (2001).

Korn et al., "IL-21 initiates an alternative pathway to induce proinflammatory T(H)17 cells," Nature, 448:484-487 (2007).

Langenau et al., "In vivo tracking of T cell development, ablation, and engraftment in transgenic zebrafish," Proc. Natl. Acad. Sci. USA, 101:7369-74 (2004).

Langenau et al., "The zebrafish: a new model of T-cell and thymic development," Nat. Rev. Immunol., 5:307-17 (2005).

Laupeze et al., "Polycyclic aromatic hydrocarbons affect functional differentiation and maturation of human monocyte-derived dendritic cells," J. Immunol., 168:2652 (2002).

Lieschke et al., "Animal models of human disease: zebrafish swim into view," Nat. Rev. Genet., 8:353-67 (2007).

Lindley et al., "Defective suppressor function in CD4(+)CD25(+) T-cells from patients with type 1 diabetes," Diabetes, 54:92-9 (2005).

Loser et al., "Epidermal RANKL controls regulatory T-cell numbers via activation of dendritic cells," Nat. Med., 12:1372-1379 (2006).

Mantel et al., "Molecular Mechanisms Underlying FOXP3 Induction in Human T Cells," Journal of Immunology, 176:3593-3602 (2006).

Milner et al., Nature, 452:773-777 (2008).

Mori et al., "Chemoprevention of 2-amino- 1 -methyl-6-phenylimidazo [4,5-b]pyridine-induced mammary carcinogenesis in rats," Cancer Letters, 143(2):195-198 (1999).

Mudd et al., "Regulatory T cells and systemic lupus erythematosus," Scand. J. Immunol. 64(3):211-218 (2006).

Nagy et al., "Development of a green fluorescent protein-based cell bioassay for the rapid and inexpensive detection and characterization of ah receptor agonists," Toxicol. Sci., 65:200-210 (2002).

Nagy et al., Biochem. 41:861-68 (2002).

O'Quinn and Palmer, "Emergence of the Th17 pathway and its role in host defense," Adv. Immunol., 99:115-163 (2008).

Okey et al., "Detection and characterization of a low affinity form of cytosolic Ah receptor in livers of mice nonresponsive to induction of cytochrome P1-450 by 3-methylcholanthrene," Mol. Pharmacol., 35:823-30 (1989).

Ovcharenko et al., "Mulan: multiple-sequence local alignment and visualization for studying function and evolution," Genome Res., 15:184-94 (2005).

Paciotti et al., "Colloidal gold: a novel nanoparticle vector for tumor directed drug delivery," Drug Deliv., 11:169 (2004).

Pancer and Cooper, "The evolution of adaptive immunity," Annu. Rev. Immunol., 24:497-518 (2006).

Pocar et al., "Molecular interactions of the aryl hydrocarbon receptor and its biological and toxicological relevance for reproduction," Reproduction, 129(99): 379-389 (2005).

Qian et al., "In vivo tumor targeting and spectroscopic detection with surface-enhanced Raman nanoparticle tags," Nat. Biotechnol., 26(1):83-90 (2008).

Quintana et al., "Control of Treg and TH17 cell differentiation by the aryl hydrocarbon receptor," Nature 453:65-71 (2008).

(56) References Cited

OTHER PUBLICATIONS

Quintana et al., "Functional immunomics: microarray analysis of IgG autoantibody repertoires predicts the future response of mice to induced diabetes," Proc. Natl. Acad. Sci. USA, 101 Suppl 2:14615-21 (2004).
Robertson, "The interferon system of teleost fish," Fish Shellfish Immunol., 20:172-191 (2006).
Robinson et al., "Protein microarrays guide tolerizing DNA vaccine treatment of autoimmune encephalomyelitis," Nat. Biotechnol., 21:1033-1039 (2003).
Roncarolo and Gregori, "Is FOXP3 a bona fide marker for human regulatory T cells?," Eur. J. Immunol., 38:925 (2008).
Roncarolo et al., "Interleukin-10-secreting type 1 regulatory T cells in rodents and humans," Immunol. Rev. 212:28 (2006).
Sakaguchi et al., "Immunologic self-tolerance maintained by activated T cells expressing IL-2 receptor alpha-chains (CD25). Breakdown of a single mechanism of self-tolerance causes various autoimmune diseases," J. Immunol., 155:1151-64 (1995).
Sakaguchi et al., "Naturally arising CD4+ regulatory t cells for immunologic self-tolerance and negative control of immune responses," Ann. Rev. Immunol, 22:531-562 (2004).
Sakaguchi et al., "Study on cellular events in postthymectomy autoimmune oophoritis in mice. I. Requirement of Lyt-1 effector cells for oocytes damage after adoptive transfer," J. Exp. Med., 156:1565-76 (1982).
Sanvicens and Marco, "Multifunctional nanoparticles—properties and prospects for their use in human medicine," Trends Biotech., 26(8): 425-433 (2008).
Shen et al., "Magnetically labeled secretin retains receptor affinity to pancreas acinar cells," Bioconjug. Chem., 7(3):311-6 (1996).
Siegrist and Aspinall, "B-cell responses to vaccination at the extremes of age," Nat. Rev. Immunol., 9:185-194 (2009).
Song et al., "A ligand for the aryl hydrocarbon receptor isolated from lung," Proc. Natl. Acad. Sci. USA, 99:14694 (2002).
Stroud et al., "Structure of the forkhead domain of FOXP2 bound to DNA," Structure, 14:159-66 (2006).
Takizawa et al., "Molecular cloning and expression analysis of T-bet in ginbuna crucian carp (*Carassius auratus* langsdorfii)," Mol. Immunol., 45:127-136 (2008).
Tan et al., "Immunolipoplexes: an efficient, nonviral alternative for transfection of human dendritic cells with potential for clinical vaccination," Mol. Ther., 11:790-800 (2005).
Traver et al., "Transplantation and in vivo imaging of multilineage engraftment in zebrafish bloodless mutants," Nat. Immunol., 4:1238-46 (2003).
Veldhoen et al., "TGFb in the Context of an Inflammatory Cytokine Milieu Supports De Novo Differentiation of IL-17-Producing T Cells," Immunity, 24: 179-189; Abstract; p. 186, Cell Purification. (Feb. 2006).
Veldhoen et al., "The aryl hydrocarbon receptor links TH17-cell-mediated autoimmunity to environmental toxins," Nature, 453(7191):1476-4687 (2008).
Viglietta et al., "Loss of functional suppression by CD4+CD25+ regulatory T cells in patients with multiple sclerosis," J. Exp. Med., 199:971-9 (2004).
Vojdani et al., "Regulatory T Cells, a Potent Immunoregulatory Target for CAM Researchers: Modulating Tumor Immunity, Autoimmunity and Alloreactive Immunity (III)," eCAM 3(3):309-316 (2006).
Vorderstrasse and Kerkvliet, "2,3,7,8-Tetrachlorodibenzo-p-dioxin affects the Number and function of murine splenic dendritic cells and their expression of accessory molecules," Toxicol. Appl. Pharmacol., 171:117 (2001).
Weber et al., Tissue Distributiion and Toxicokinetics of 2, 3, 7, 8-Tetrachlorodibenzo- p-dioxin in Rats after Intravenous Injection, Fundamental and Applied Toxicology, Society of Toxicology, 21(4):523-534 (1993).
Wei et al., "Rapid and transient induction of CYP1A1 gene expression in human cells by the tryptophan photoproduct 6-formylindolo[3,2-b]carbazole," Chem Biol Interact, 110(1-2):39-55 (1998).
Wu et al., "FOXP3 controls regulatory T cell function through cooperation with NFAT," Cell, 126:375-87 (2006).
Wu et al., "Preparation, physicochemical characterization, and antioxidant effects of quercetin nanoparticles," International Journal of Pharmaceutics, 346(1-2):160-168 (2007).
Yang et al., "IL-21 and TGF-beta are required for differentiation of human T(H)17 cells," Nature, 454(7202):350-352 (2008).
Ziegler, "FOXP3: of mice and men," Annu. Rev. Immunol, 24:209-26 (2006).

* cited by examiner

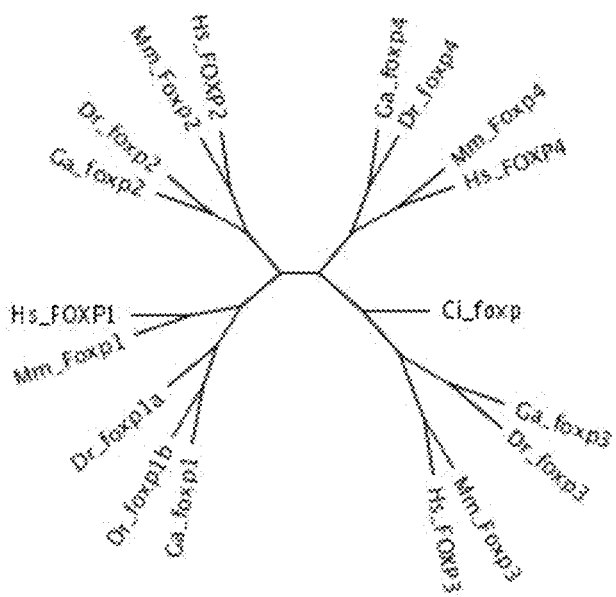
FIG. 1G
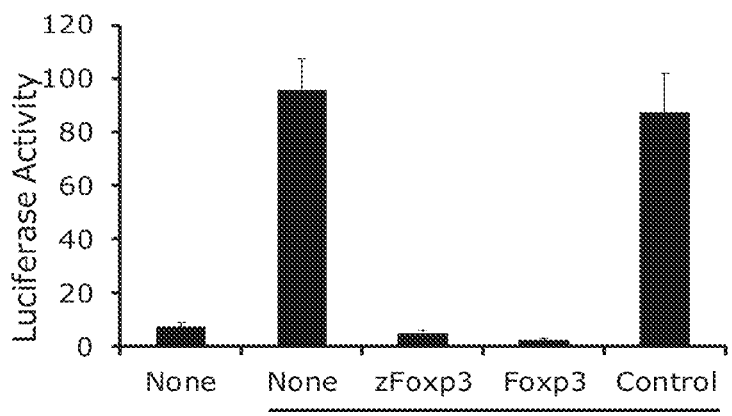
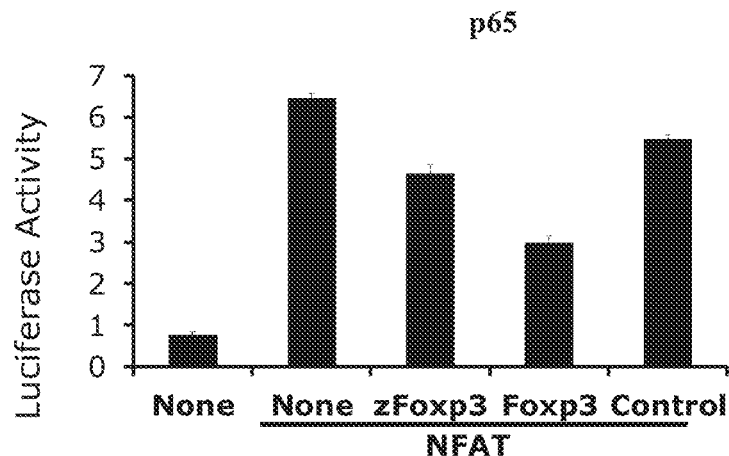
FIG. 2A

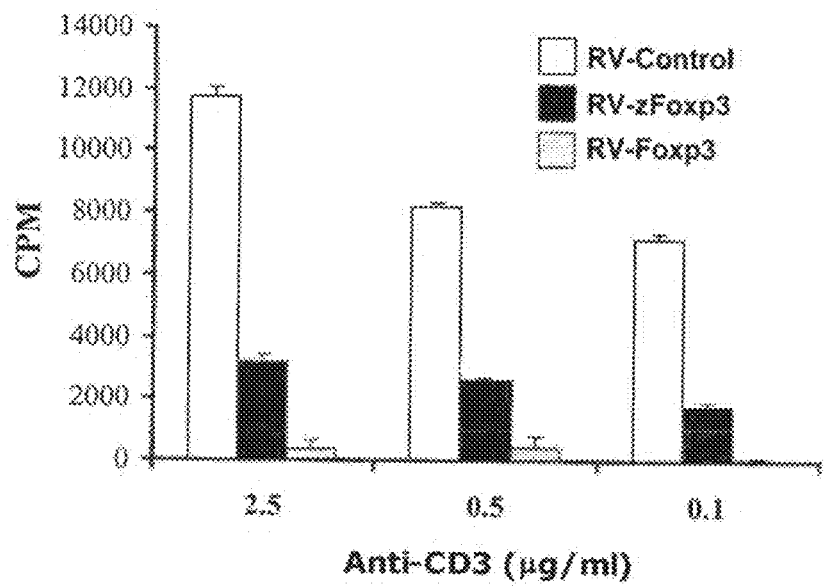
Figure 2D-i
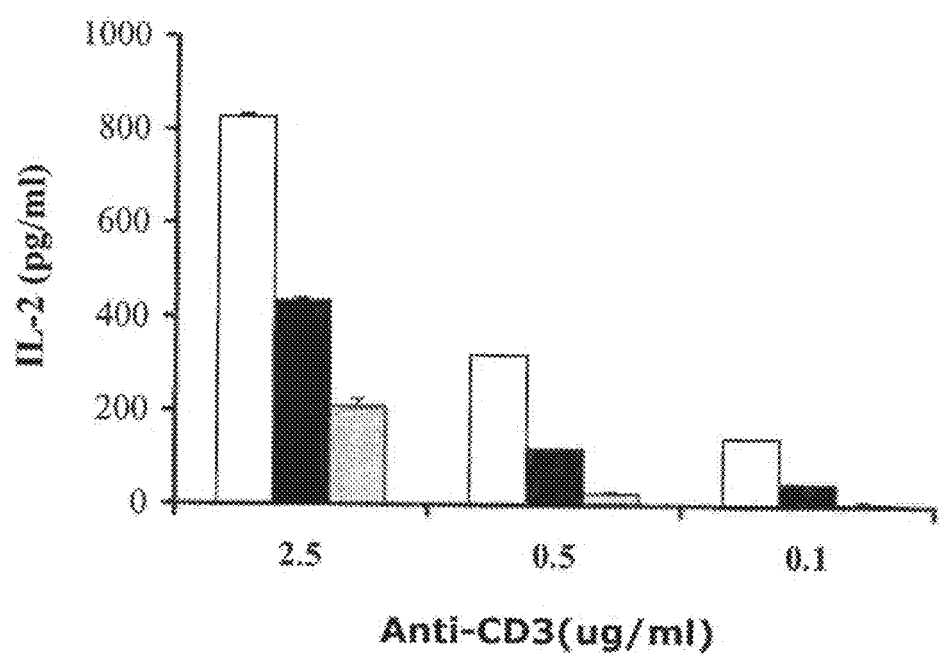
Figure 2D-ii

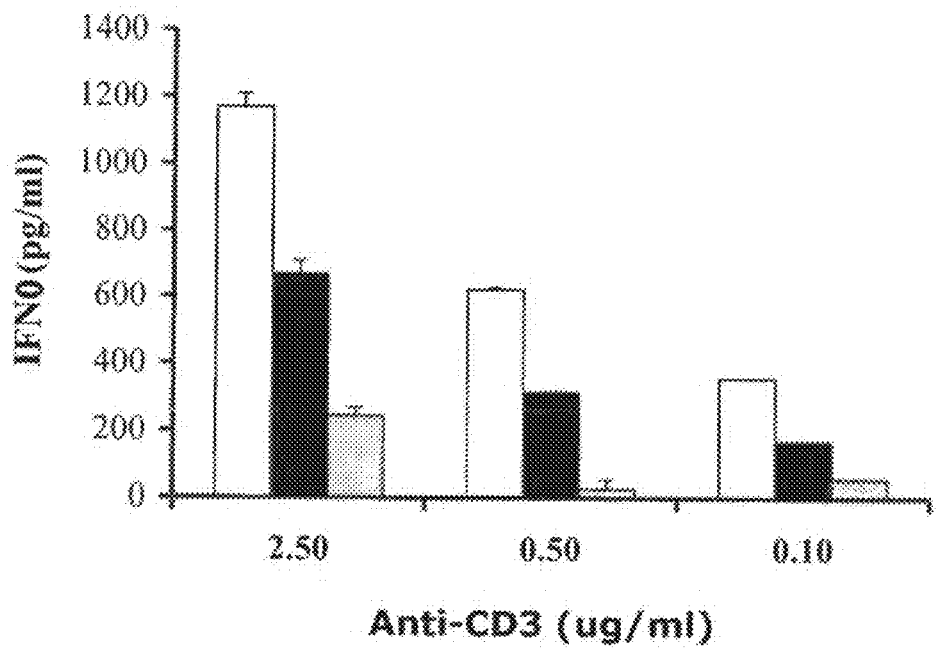
Figure 2D-iii
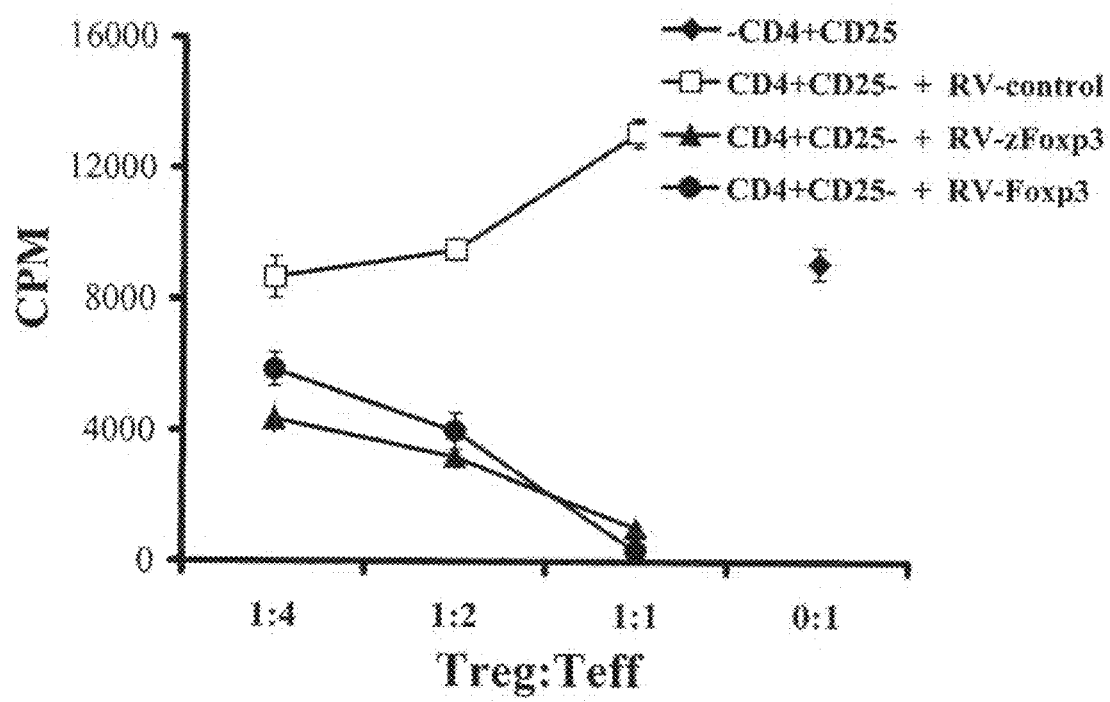
Figure 2E-i

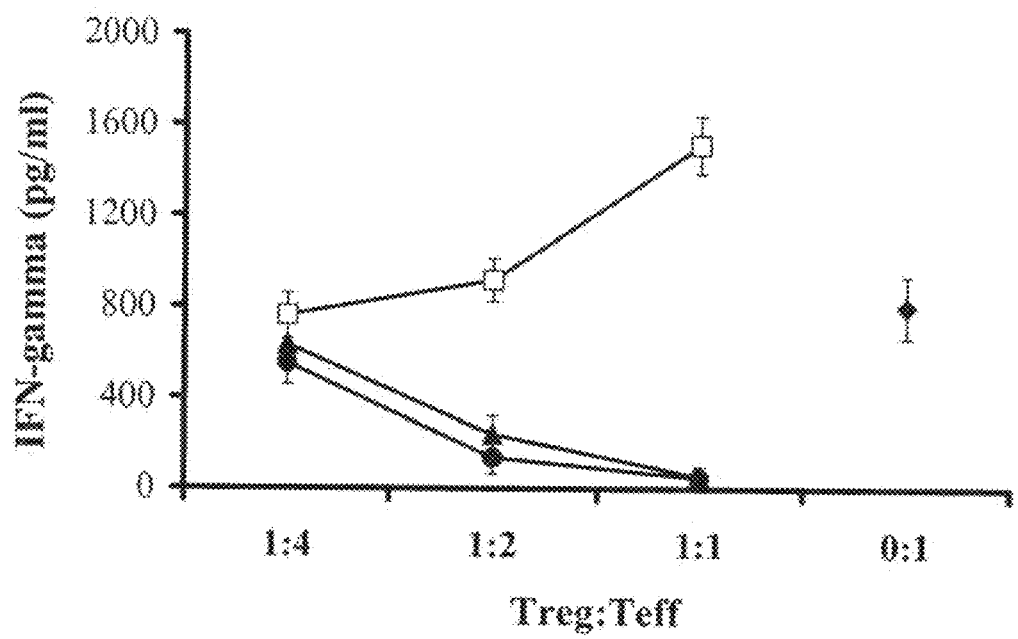
Figure 2E-ii
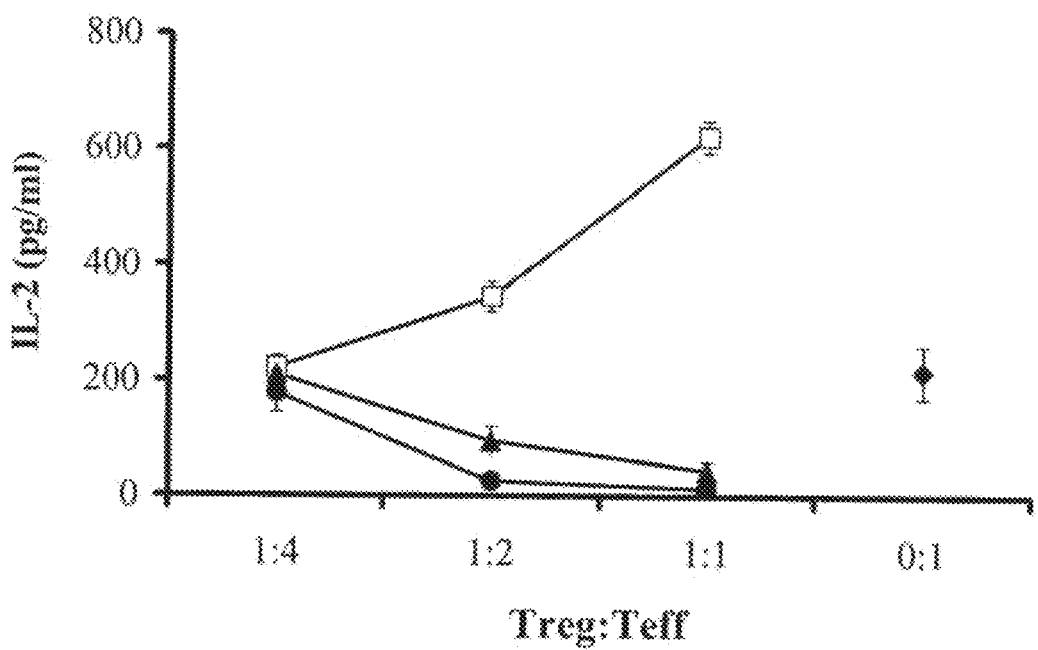
Figure 2E-iii

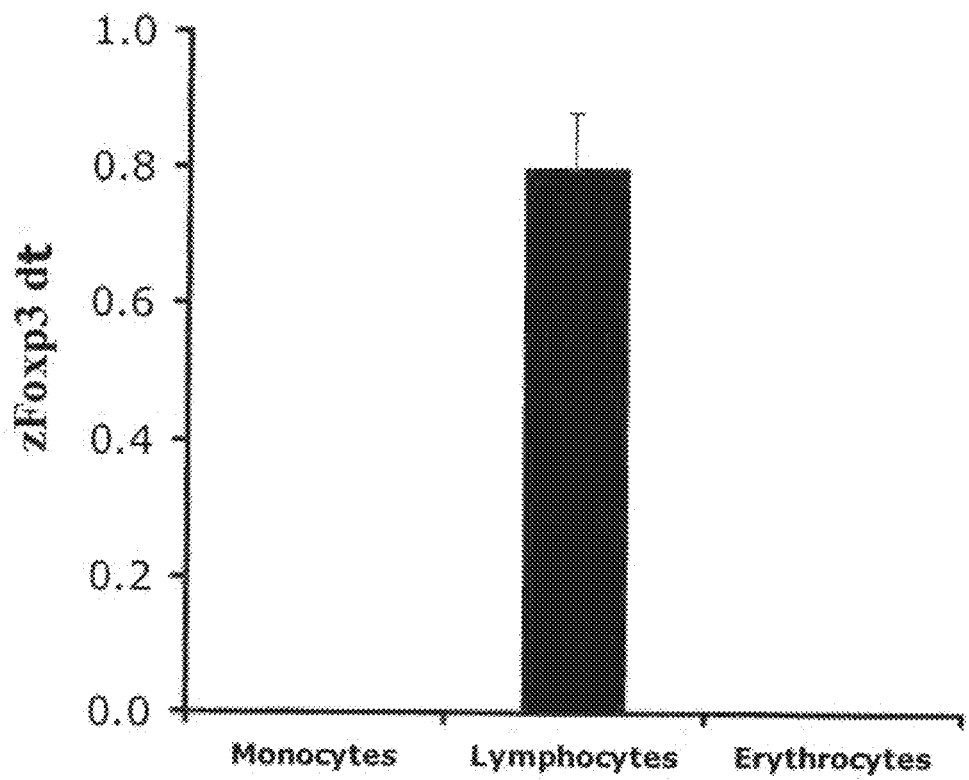
Figure 3A
```
Danio rerio    AAGTGCTTTGTGCGTGTTGAAGGAAGGA
Homo sapiens   AAGTGCTTTGTGCGGGTGGAGAGCGAGA
Mus musculus   AAGTGCTTTGTGCGAGTGGAGAGCGAGA
               *************  **  **  *   **
```
Figure 3B
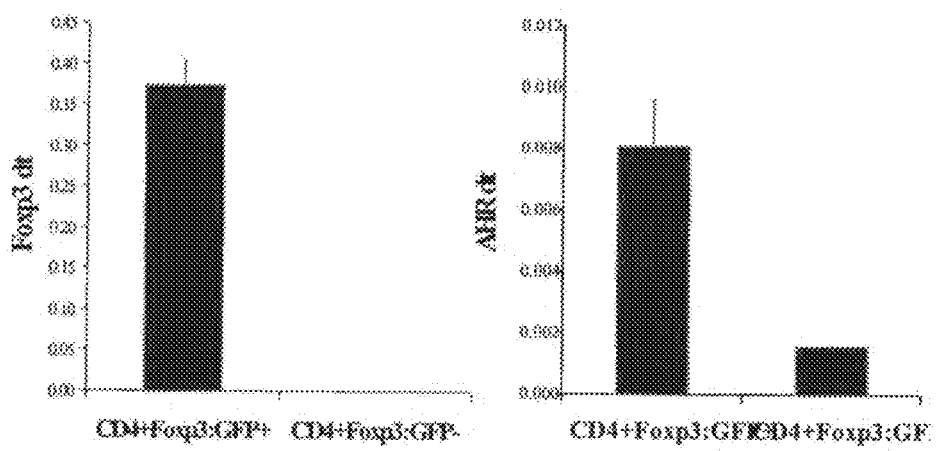
Figure 3C

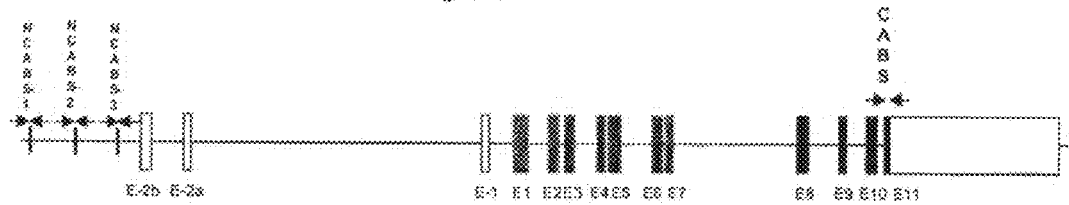
Figure 3I
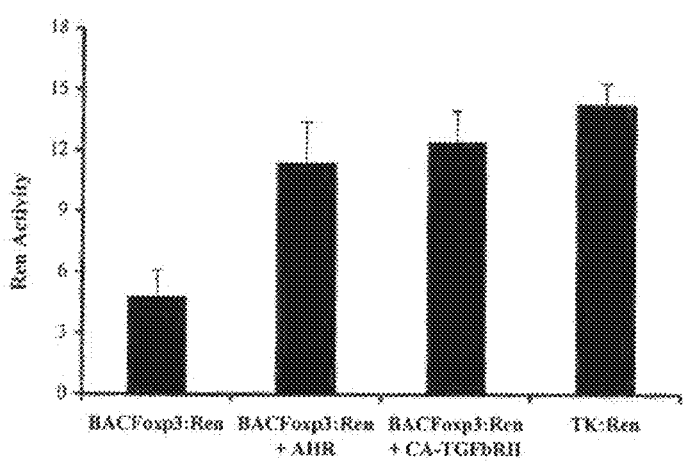
Figure 3J
Figure 3K
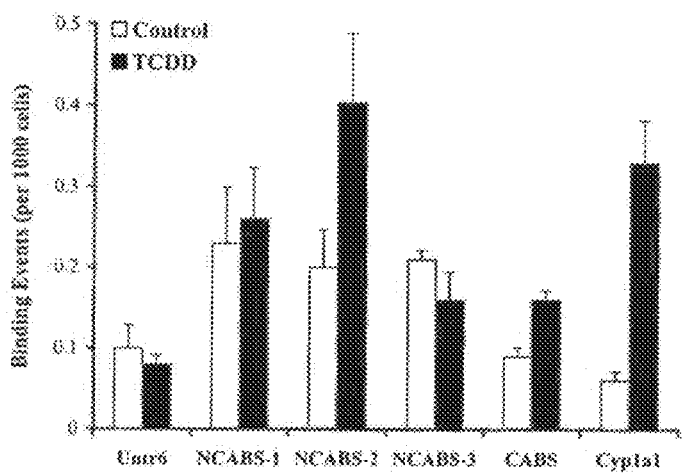
Figure 3L

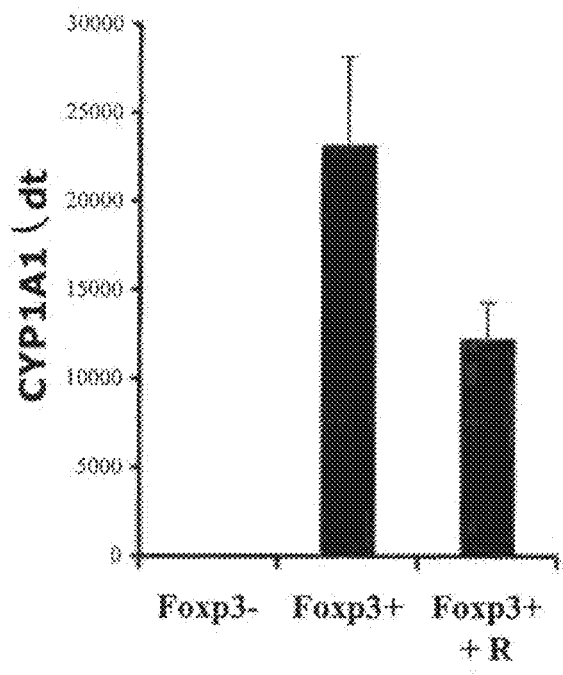
Figure 3N(ii)
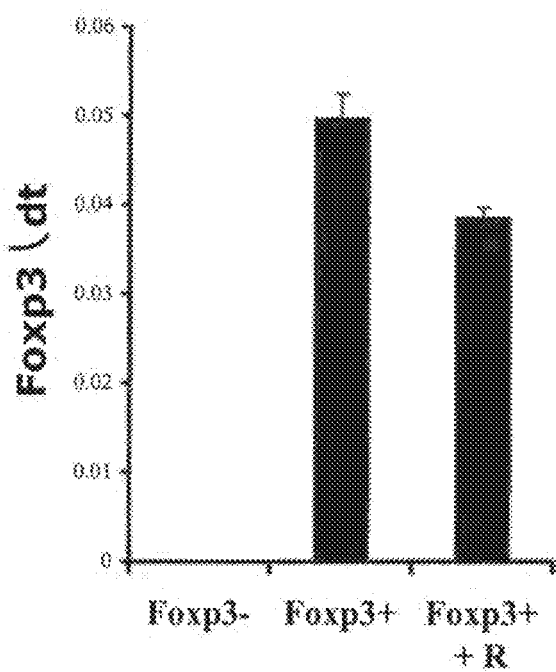
Figure 3N(iii)

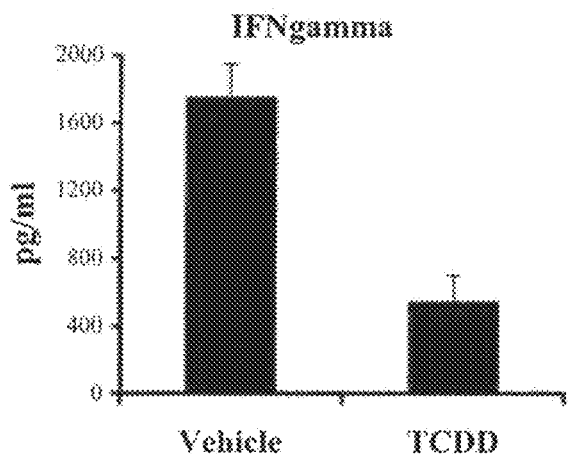
Figure 4E(i)
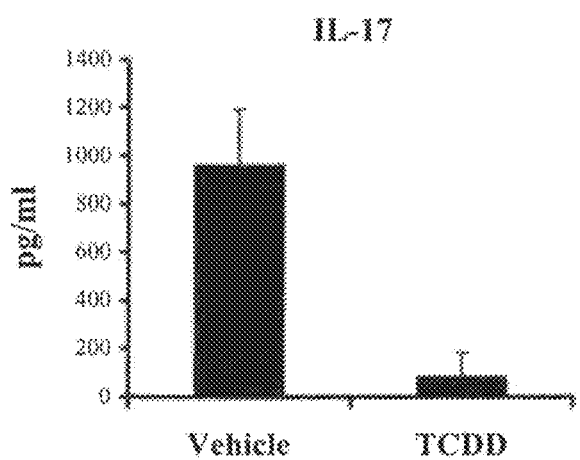
Figure 4E(ii)
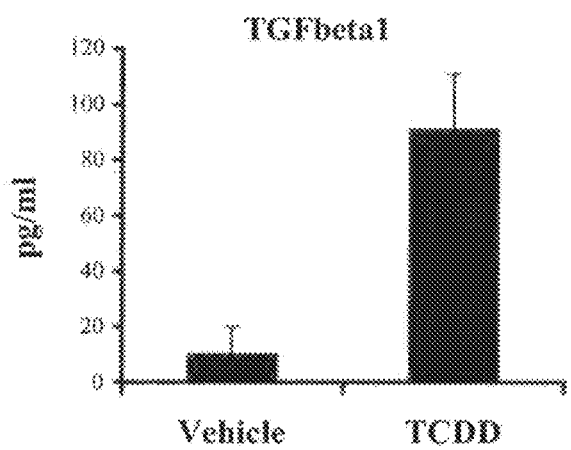
Figure 4E(iii)

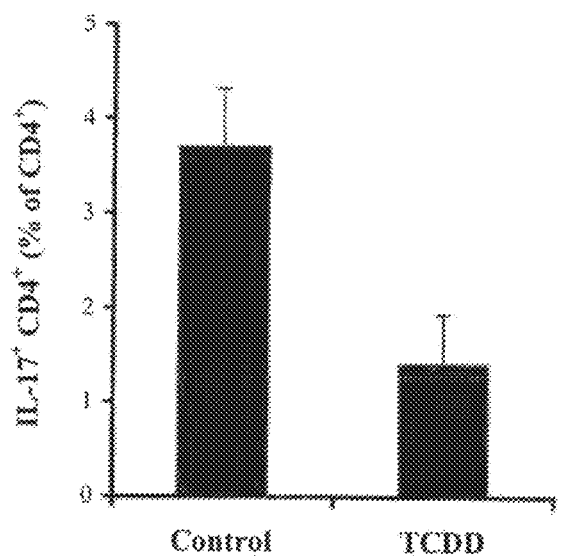
Figure 4F(i)
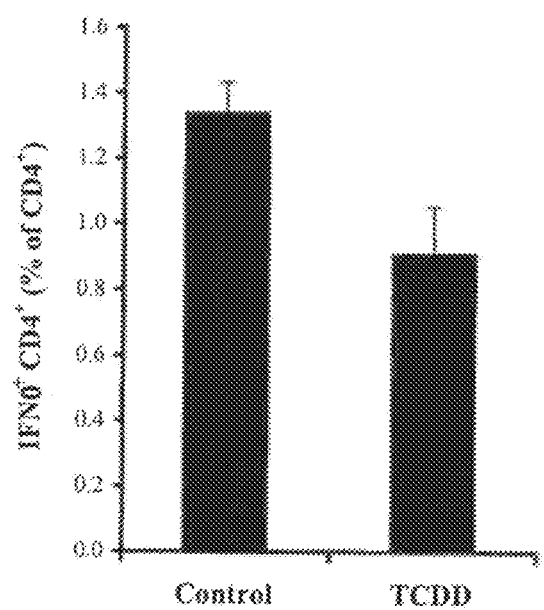
Figure 4F(ii)

| | | |
|---|---|---|
| V$EGR1_01 | 137 (+) | cAGCGCGGGCGg |
| V$EGR2_01 | 137 (+) | cAGCGCGGGCGg |
| V$EGR3_01 | 137 (+) | caGCGCGGGCGg |
| V$NGFIC_01 | 137 (+) | cAGCGCGGGCGG |
| V$NGFIC_01 | 282 (-) | CCACCGCCGCCa |
| V$NGFIC_01 | 412 (-) | CCACCGCCGCCt |
| V$EGR_Q6 | 459 (+) | GGGGGCGcggg |
| V$EGR_Q6 | 555 (+) | GCGGGGCagg |
| V$EGR1_01 | 623 (+) | gAGCGTAGGCGg |
| V$EGR2_01 | 623 (+) | gAGCGTAGGCGg |
| V$EGR3_01 | 623 (+) | gaGCGTAGGCGg |
| V$NGFIC_01 | 623 (+) | gAGCGTAGGCGG |
| V$EGR3_01 | 669 (-) | aCAGCCACGCGg |
| V$DELTAEF1_01 | 689 (-) | tacAGGTGatt |
| V$EGR1_01 | 731 (-) | aCGCCCGCGCGt |
| V$EGR2_01 | 731 (-) | aCGCCCGCGCGt |
| V$EGR3_01 | 731 (-) | aCGCCCGCGCgt |
| V$NGFIC_01 | 731 (-) | ACGCCCGCCGCGt |
| V$EGR1_01 | 737 (+) | gCGCGTGGGCGg |
| V$EGR2_01 | 737 (+) | gCGCGTGGGCGg |
| V$EGR3_01 | 737 (+) | gcGCGTGGGCGg |
| V$NGFIC_01 | 737 (+) | gCGCGTGGGCGG |
| V$EGR_Q6 | 741 (+) | GTGGGCGggat |
| V$EGR_Q6 | 901 (+) | ATGGGGCaaac |
| V$EGR1_01 | 954 (+) | tTGCGTAGGCGg |
| V$EGR2_01 | 954 (+) | tTGCGTAGGCGg |
| V$EGR3_01 | 954 (+) | ttGCGTAGGCGg |
| V$NGFIC_01 | 954 (+) | tTGCGTAGGCGG |
| V$EGR_Q6 | 1181 (+) | GCGGGCGgggg |
| V$EGR_Q6 | 1185 (+) | GCGGGGGgggg |
| V$DELTAEF1_01 | 1221 (-) | tgaAGGTGgga |
| V$EGR_Q6 | 1226 (+) | GTGGGAGcgag |
| V$EGR2_01 | 1435 (+) | gTGCATAGGCTg |
| V$EGR3_01 | 1435 (+) | gtGCATAGGCTg |
| V$EGR_Q6 | 1648 (-) | gctgGCCCCAC |
| V$EGR_Q6 | 1961 (-) | ccccCCCCCAC |
| V$NGFIC_01 | 2945 (-) | CCAACCACACAa |
| V$DELTAEF1_01 | 2989 (+) | actCACCTcag |
| V$EGR2_01 | 3001 (-) | aCACCCACACTg |
| V$EGR3_01 | 3001 (-) | aCACCCACACtg |
| V$EGR1_01 | 3282 (-) | aCACTCCCGCAc |
| V$NGFIC_01 | 3262 (-) | ACACTCCCGCAc |
| V$EGR_Q6 | 3287 (-) | cccgCACCCAC |
| V$EGR_Q6 | 3630 (-) | ttccCTCCCAC |
| V$EGR1_01 | 3633 (-) | cCTCCCACACAc |
| V$EGR2_01 | 3633 (-) | cCTCCCACACAc |
| V$EGR3_01 | 3633 (-) | cCTCCCACACac |
| V$NGFIC_01 | 3633 (-) | CCTCCCACACAc |
| V$NGFIC_01 | 3719 (-) | CCTCCCTCTCAa |
| V$EGR1_01 | 4026 (+) | tTGTTGGGGCGg |
| V$EGR_Q6 | 4028 (+) | GTTGGGGcggg |
| V$EGR_Q6 | 4034 (+) | GCGGGGGgagg |
| V$DELTAEF1_01 | 5115 (-) | cccAGGTGggt |
| V$EGR_Q6 | 5234 (+) | GTGGGGGgagt |
| V$EGR_Q6 | 5800 (-) | ccccCCCCCAC |
| V$EGR2_01 | 5826 (-) | aCACACACTCAt |
| V$NGFIC_01 | 5826 (-) | ACACACACTCAt |
| V$DELTAEF1_01 | 5981 (-) | ccaAGGTGagc |
| V$EGR_Q6 | 6003 (-) | ctctCCCCCAC |
| V$EGR2_01 | 6053 (+) | gAGGGTGGGTGt |
| V$EGR3_01 | 6053 (+) | gaGGGTGGGTGt |
| V$NGFIC_01 | 6053 (+) | gAGGGTGGGTGT |
| V$NKX22_01 | 7123 (+) | tTAAGGGGTT |
| V$DELTAEF1_01 | 7200 (-) | tttAGGTGigt |
| V$EGR1_01 | 7593 (+) | tTACGTGGGTGc |
| V$EGR2_01 | 7593 (+) | tTACGTGGGTGc |
| V$NGFIC_01 | 7593 (+) | tTACGTGGGTGC |
| V$NKX22_01 | 8000 (+) | tTAAGTCTTT |
| V$EGR_Q6 | 9128 (-) | gcagCCCCCAC |
| V$EGR_Q6 | 9134 (-) | cccaCCCCCAG |
| V$DELTAEF1_01 | 9957 (-) | tttAGGTGgtt |
| V$NKX22_01 | 9958 (+) | tTAGGTGGTT |
| V$NKX22_01 | 10675 (+) | aCAAGTATTT |
| V$EGR1_01 | 11611 (-) | cCTGCCACGCCa |
| V$NGFIC_01 | 11811 (-) | CCTGCCACGCCa |
| V$DELTAEF1_01 | 12817 (-) | tgcAGGTGagg |
| V$EGR1_01 | 12899 (+) | tGGCGGGGGGGg |
| V$NGFIC_01 | 12899 (+) | tGGCGGGGGGGG |
| V$EGR_Q6 | 12901 (+) | GCGGGGGgggg |
| V$EGR_Q6 | 12910 (+) | GGGGGGGgggc |
| V$EGR3_01 | 14102 (-) | cTTCCCACGCtc |
| V$DELTAEF1_01 | 14130 (-) | gacAGGTGagt |
| V$EGR2_01 | 14166 (-) | cTGCCCACACCt |
| V$EGR1_01 | 14182 (-) | cCACCCCTGCAc |
| V$NGFIC_01 | 14182 (-) | CCACCCCTGCAc |
| V$EGR1_01 | 14834 (+) | tTGCGTGGCCAg |
| V$EGR2_01 | 14834 (+) | tTGCGTGGCCAg |
| V$EGR3_01 | 14834 (+) | ttGCGTGGCCAg |
| V$NGFIC_01 | 14834 (+) | tTGCGTGGCCAG |
| V$EGR1_01 | 14850 (+) | tTGCATGGGCTg |
| V$EGR2_01 | 14850 (+) | tTGCATGGGCTg |
| V$EGR3_01 | 14850 (+) | ttGCATGGGCTg |
| V$NGFIC_01 | 14850 (+) | tTGCATGGGCTG |
| V$EGR_Q6 | 15004 (+) | GTGGGGGgggg |
| V$DELTAEF1_01 | 15550 (+) | tccCACCTaat |
| V$EGR1_01 | 15582 (-) | aCGCCTACTCTg |
| V$EGR2_01 | 15582 (-) | aCGCCTACTCTg |
| V$EGR3_01 | 15582 (-) | aCGCCTACTCtg |
| V$EGR_Q6 | 16246 (+) | GTGGTGGcggc |
| V$EGR_Q6 | 16249 (+) | GTGGCGGcggc |
| V$EGR1_01 | 16911 (-) | cCACCTACATAa |
| V$EGR3_01 | 16911 (-) | cCACCTACATAa |
| V$NGFIC_01 | 16927 (-) | CCAACCAAGCAa |
| V$EGR_Q6 | 17842 (-) | ctcaCCCCCAC |
| V$DELTAEF1_01 | 17870 (+) | ctgCACCTgag |
| V$EGR_Q6 | 18038 (-) | tccgTCCCCAC |
| V$DELTAEF1_01 | 18468 (+) | tttCACCTatg |
| V$EGR_Q6 | 18847 (-) | gctgCTCCCTC |
| V$DELTAEF1_01 | 18867 (+) | ttcCACCTgac |
| V$DELTAEF1_01 | 19037 (-) | ggaAGGTGagt |
| V$NKX22_01 | 19188 (+) | aCAAGTGCTT |
| V$EGR1_01 | 19270 (-) | aCGCCCAACAa |
| V$EGR1_01 | 19318 (+) | aAAGGTGGGCGg |
| V$EGR3_01 | 19318 (+) | aaAGGTGGGCGg |
| V$EGR_Q6 | 19322 (+) | GTGGGCGgggg |
| V$EGR1_01 | 19324 (+) | gGGCGGGGGAGg |
| V$EGR3_01 | 19324 (+) | ggGCGGGGGAGg |
| V$NGFIC_01 | 19324 (+) | gGGCGGGGGAGG |
| V$EGR_Q6 | 19361 (-) | GTGGGGGcaag |
| V$NGFIC_01 | 19844 (-) | CCACACAGGCAt |
| V$EGR1_01 | 20054 (+) | aTGCCTAAGCGt |
| V$EGR2_01 | 20054 (+) | aTGCCTAAGCGt |
| V$EGR3_01 | 20054 (+) | atGCCTAAGCGt |
| V$EGR_Q6 | 20553 (-) | cttcCCTCCAC |
| V$DELTAEF1_01 | 20583 (+) | ctcCACCTaaa |
| V$EGR_Q6 | 21182 (-) | cccgCCTCCAC |
| V$EGR1_01 | 21436 (+) | aTGTGTTGGAGt |
| V$DELTAEF1_01 | 21663 (-) | cctAGGTGgga |

Figure 10

>ref|NT_039700.6|MmX_39746_36:741773-763973 Mus musculus chromosome X
genomic contig, strain C57BL/6J
GCACGCGCACCAACCCGCGCACCA▓▓▓▓▓▓▓▓CCCCAGGCACCCACACCCCGGAACCCCCGGGAAC    F-1
CGCTCCAGGAGCGGCAGCAGCGCCTCCAACTCCAC▓▓▓▓▓▓▓▓CCAACCGCTCCAGACGGCCCAGC    F-2
GCGGGCGGCAACGAAAATGTGGGCACCAGGTAAAACCCCCGCCAGCGGCAACGGCGCACGGCGGAGAGG
GATGGGAAAGCCTCCTCTTCCTCCTCCCCTTCATCCCCATCCTCGCCATCGTCTTCCTCATCAGCCCC
GCCACCGCTGCCATCTTGCCCGGCGTCGCCGGCCGGCCCATCTTTGCCCGGCTCGGCCCCCCACGGCCGGTAG
CGGCGTAGCTGCGGCCAGAGCAGCCCCAGGGCCCTCGTCAGCGAACAGCACCCTCGGCGGCCACCGCCG
CCTGAGCCGAGCGCGGGGCTCTCCCGCAGCCGGCGACGGGGCGCGGGATGCCGCAGCGGTGGCTGCAC
AGGGCCGTGCGCGCCATATCGCCGCGCGGCGGCGGCACCGACGGCACCGGCGGTGGGACCGCCGGCG
GCAGGGCCTGAAAAGGCGGCAGCCAATGAGAAAGCCAGAACAGGGCGGTGGCGCTCCAGTGGAGCGTAG    F-3
GCGGTGAGCTAGAGACAGGTACGCCCAACAGCCAATGGAC▓▓▓▓▓▓▓▓AGTGACGTACAGGTGATTG    F-4
ACAAGCAGGAGAAGCTAGCAACCAATGAGGACGCC▓▓▓▓▓▓▓▓GCGATGGAAGCCGGGATGATAACG
GAATCAATGGAGAGGCCTGACTAGGGTTAATGCGGCCTCGAAGATGTAGCAGCAGGAGTATGACAATTAG
TGGGAAAGTCTGAGCACGAAGGGCATGGTAGGCGGCGGGAAGATGAAATGGCTACAAGCAATGGGGCAA    F-5
CGGGGAGCGGAACCCAGAGGTCCAAAAACTGGGAGA▓▓▓▓▓▓▓▓GGTGAGACGTAAGACAG    F-6
ATAAAATGAACAGCCAATGGAGA▓▓▓▓▓▓▓▓TGATGTAGAGACAGAATGACGATAATAGTTGCAAT
GAGCCAATGCAGGGAGTCTAGTGACGCACACTATGGCTTCAAGAGGTGGTAACAAGGTAGATCTAGCCAA
TACAGAGACTGAACAGCAGACGGGAAGGCTGTGTGTGATCACATGGAGGCGGCCGCTGTAGCGGCGCGG
GGGGCGGGAGCACTAAGGCATGTGAGCAGTGAAGGTGGGAGCGACAAAGAAATGGGGATCCAGGGTGAA
GGCTGTTATATCTCAAGGCACAGTGCCAGTATGGGATTAACCAAAGCTGAAACTAGACAAATGTAGCCAG
AAGGAAACTTTGGAGGCAAGATGGGAACTCATACCCACGGATGGTAGTGTAGGGTGCTGTGAAGGAAAGCA
TGAGTAGCCAATAAATAGGCTGAGTTGGAAGAAGGTGCATAGGGCTGAGCCTGAGCTATTGACTGATTGAG
CGCAGAATCGAATTCATTCAACCAGTAAGATCGGACCTCTGGGGAATGGCTTTACCTTTCCCTAATCTT
CCATGACTCCCTATGGCTCCACGAATACCCAGAGCTCCTAAAACCCAGACTGCACCGGATTGTGAGACC
AAAGCAAAACAGTTCTATCAGTTACTGGCTGTGTCCTGCTGGCCCCACACCACCACACACACCTCCCAGC
CTTATTGTGACCAATGCAACTAGCCATGAACGTTCTTAACTGTTCCTTAAAGTCCCCAGTTGAGCATTGA
TGTTCTTCAGGACTTGGCACTATTGCATGAATCAATCGCAAAATAGGAAATAGAACCTTTTTCGGAAGAAT
TAGCCTTTTTCCAACTCACACTTAGCACACATTGACTGATATGTCATCACAAGCTTATCAGCTAATGT
ACATTCAAATCAGAGTCCTCGCCCTTCCTGCTCATTTTGACACTTTTGCACCCCACAGTGGCTTTCTTCTCC
CCCCCGCCCCACTTTCCCATCTCCTCTGCTTAGAGTGCTGTCCCATCTGTTTCTTTCATCTAGTGAATTC
TTCCATTCTCCCTCTGATGGCACCTCCTATGGGAATGACCTGGACTTTGCCATCGTGTTCATTCACA
TATCCCCCACTCCCATTTACTAACTTAGTAAGACTTAGTGTTTGCCATATGCCAGGTTCAGGGAGTGCTT
TTATCTAACCCTCATAAGACCCCTAACAGGAAGGCCCCCACAGTCTCTCTGCTCCTCCTGTCTGTCTCCA
GGGTCATGAAAGGAATATGTCCAGCTACAAGTAGCAGAAGAATAATGGCATAATGAAGGTAGAACTTTTT
TTTCTCATCTGAAAGTTCAAGGCAGCAAGTGCTCTCAGGACTCCATCCTATCTGCCCATTTGGGTATCA    F-7
ACTGTC▓▓▓▓▓▓▓▓GTCTCATTCTTCAGCAAATCCTGCAGGTTATCTACCCAACGCATTT
TCCAAGCAGGATATGGTGATGTATGCCTGTAATCCCAGCACTCAAGGGGCTGAGGCAGGAGAATCACGGA
ATTCCAAGCCTAGGCTACAAGTGTGACCTTGTCTAAAAATAAAAAGGGTTAAGTGTAGCTCAGCGGTAA
AAACCACTTCCTAGAAAGTGCATGGGCCCATCTCTAGCATCATTTTTTTTAAATCCCAAATCCACCTTT
TCACTACCACTCCATCAACAGGACCAGCCACCAGTCCATATTCAGCCATCTAAGACATCCTCTTAAGTCCTAA
CAGCAATGTCTCTCCTCTCGCTCCCAACACCCTCTGGCTTCCTCTACAGTAAGAGGAAGAGCCAACCTTCA
CCATGTCGTAAGCGCACAAGCCAGCTAGCCCGTCTGACCTTCCTCCTGTTCTCTCCCTTCCAGTCATGT
CACTCCAACCACACAAGACTCCTTGCTGACCCTGTACATATCCAGCACACTCACCTCAGGACACCCACAC
TGACCCTTCTCTCCTGGATCTGCAGATCTCCCCATCACTCTCTTCTTCATCTATGCCTGCTCTTTGTCAA
AGATCCCTTTCCCTGGGAATGCTCCCCTGACCTGTTAAATCCTGCCCCATTCACCATCAACTCCTAGCC

Figure 11A

```
CTCCCAGTTGCTCCCCAGGAACCTACATGAGCCAATATAGTAATGGTGGAGAGCAAATACCACCCTCT
GACAAGCAAAACCCTAGCCACCATGCTGCAAAGACCCTAGCTTTACACTTCAGTAACCTTAACACTCCCG
CACCCACAGCCCCATTCAAATAGCCTCCTGGAAACCTGTGTCACTTACCCCTCATTTACTTATCCTGCCA
CCTCTCTGACCAAGTTTTCGCAGAATGGCAGGAAGATGGTGACGAGGATATAAAGGAAGATGCAGACCAA
ACCATGGACCCTGAGAAAATGAGTACCTATTCCAAAAAGAGACAGGTGACAGGGCAGGGACTAGAACTG
TCTCAGAGACATAGAAGATACAGGCACTAGTTGGGCCCAAGTGTACAGGGAGCAGGGACCATTAACTTTG
GGGCATAGCTACAGTCAGCTGCCCATTACCTGTTAGGTATGCTCTTCACCCCTCCCCTATTCCTCCCAC
ACACAACCACAACTGTTAAGCTCCTAAGATCCATGCAGACCTCCAAAGTAAGAGGACCTCATCCCACCTC
TGCCCCTCCC░░░░░░░░░░░░░░░CTCCCCCGCTTCCAGGCACCACACAGGCCATGTTTGGTCTT  F-8
AGATGTGTCCCACCAACTTAGAAGCCCCAACCAGTGAAAGTTTTGCTTTGAACTAATGATAGGAGGGTT
GAGGGTTTTTTTTTTTAATTGTTGTTGTTGTTGGCTGGTATTTTGGGTCTTTTTTTTTCTATTCACT
TTGTTTTCCCCTCTTGTCTTTATAAAGCCAAGCCATCAGTTCCAGTCTTGTTATTTCCAAAAAGGTGAGT
TAAGATGAGGAAAGTCAGTCTCTTTTTTGTTGTTGTTGTTGGGCCGGGGGAGGTGCTCAGAAGATAGCC
GAAAGGGACAAAAGTGCAAATGAGGGAAAGAGCAAAGGAGTGTGGGAATTGTTTACTAGGTTAGCATCA
TGTGAATAAAAACGTATTTCTACTTTCTCTTCCTCAGGCCTGAAGCCAGTCTTGCAAAGAGGTGGTGGTG
GCCATGCAGTTGGATACCTGGAACTCTTAGCTCTCTGGAGGATGCCAGGGCACCAAAGGCTGGAAGCCTT
AGCCGTGCCTTGTCAGCAAAACTCTGTGGAGGCTGGTCTGTAGTAAACAGTGGTTACAGGGAGCCGGTC
TGTGCCAAATCGG░░░░░░░░░░░TGCCAGATCGTTGAATACAAACCTTAAAACCTCACAAACATCAAGTT  F-9
CCAGAGGAGTCTCCAAGTCCTAGAACTTCTATGCACACTTGTTGGCTTCAGGAAAACTGGTCACTTCAGAGC
CCAATGCTAAGGACCCCTATTTCCCAAAATTGTGATCTTAAGCAAGCTGCACCTCCATTTGCCCATCGG
TCTAAAAACAATACAGCCATGATGAGATGGACCTCAGAGGGTGAGAAGTGTTTGGCTCTGTCTGGAATGT
AGAAAATTCTAGGTAAATGTTGGCTACCAAAATTATGACAGCTGTTTAGAATCCTAAACCTTTGCAAACG
GGAGTGTTTCTTTCCTTTGTTTGTGGTTTGGTTTTTGTTTTTGTGTGTTTTGTGTGTTTTTGTTTTTTT
CTTTTTCTTTTACACGGAATCTGGCTATATAGCCCTAAGCAACCTAAAACTCTTGATTCTTCTGCCTCA
GTTTCTGGGGTGCTGGGATTACTGGTATGTGATACTGGATGAAACTGGAACTTTTCAGAGTAGACTGTTA
CAAAGTTTAGAATCATCAGGCTATGCTATATTGTTCCTGACAGGACTAGGACCCTGGGCCGCTATGTGT
ATGGTTTTTTGTTTGTTTGTTTAACAACCCAGAGCCT░░░░░░░░░░RACAAGCACTCTGGCACTGA  F-10
GCTGCAATGGCCAGCCTTTCTTCCCCTTGCCCTTCTTGGTGATGCTGGCTGCATTAACAGCCACTGGGC
TGTTCCCAGGTGGGTGGCTGCTGCGGTCAGGGCACTCAGCACAAACATGATGTGGGGCTGACTCAGAGACT
CGCAGCAGCTTCTGGGAGCCAGCCATTCTGAGACTCTCTGATTCTGTGAATTTGTGGGCGGAGTACAGCC
CACTTTTTTCTCCAGGAATTGCTTTCCATGCCTCTTGCCTTCTGTGGAAAGAAAGCTACAGGAGTGGCC
AGCTCTGCCAAGCCTTGGCAACATGATGGTGGTGATCATATGCATGCTTGCTAAGGAAATACTGAGGTTT
GGAGCAGAAGGAAAGCCTCTGGAGACAGAGCCACTACCCCACCTCTCCCTGGCTGCTTCCCATTCACATGG
CAGGCTTCAGGATCCTTCTGTTCAACCCAGCCGATCCTCCAACGTCTCACAAACACAATGCTGTCTCT
ACCTGCCTGGGATGCCTTTGTGATTTGACTTATTTTCCCTCAGTTTTTTTTTCTGACTCTACACACTT
TTGTTTAAGAAATTGTGGTTTCTCATGAGCCCTGTTTATCTCATTGATACCTTTTACCTCTGTGGTGAGGG
GAAGAAATCATATTTTCAGATGACTTGTAAAGGGCAAAGAAAAAACCCAAAATTTCAAAATTTCCGTTTA
AGTCTCATAAGAAAAGAATAAACAAAGTAAGAGAGCAAAGAAAAAAACTACAAGAACCCCCCCCCCAC
CCTGCAATTATCAGCACACACACTCATCAAAAAAATTGGATTATTAGAAGAGCGAGGTCTGCGGCTTC
CAGGCCGTGGTTTTTCTTCTCGGTATAAAAGCAAAGTTGTTTTTGATAATGTGGCAGTTTCCCACAAGCC
AGGCTGATCCCCCTCTAGCAGTCCACTTCACCAAGGGTGAGCGAGTGTCCCTGCTCTCCCCCACCAGACAC
AGCTCTGCTGGCAAAGTGGCAGAGAGGTATTGAGGGTGGGTGTCAGGAGCCCACCAGTACAGCTGGAAA
CACCCAGCCACTCCAGGTAAGGCACTTTGGAAACTAATACCATTCATCCTAAATGCCAGATACGTGAGCA
GTTGGTCCTTAGACAGGGGCAAAAGAAGTACTTTGATTGTTTGATGCACAGATAAACAGGATTTTTTTT
TAACATATGTCTATCAACTGCTGGTCTCCAGGAATGCCGGAGCTTAGGCAACTCAAGATGCTGTCCAGC
TATAACTAGAAACTAGAAGTGCATCTCTTGTTTCTTTTCCCCCTGCTGTCTTCCATTTCTTCTCCTGTCT
CCCCCTGCTTCTTTGCCTGTCTCTGCCTTCCATCAGTGCCCAGTCTCTGTCTCTTTCCCAGGCTCTGACT
```

```
CAGAAAGACCCCAGCCTTCCTCCATCACATACTCTTCCCAGTCTAGAACGGCAAACTGGGCTCAGAGATG
GACAGGAAGGCCCCTTTGTCCCAAGAGGGCAAAGCCTGACCCCAGATCAGGACAGTAGAGGGTTTTCCAA
TCCTCTGTCATAATGGAGCTCAGGAGGGACGGAGGCTGACATTCCAGAGCCAGCAAGAGGCCTTATGGAG
TTTTAAGCTTCCTGGCTTTAGGTGGTTCCCATTTCTTTGGGCTCTGGGACATCAATACACACAGTAAGAA
GGTGGATCCATGCACCCTACAGAGTCTGTGTTCTTGAGATTCTAAAATCCGTTGGCTTTGAGAAATGATA
TCGTACAGTTCTGAGTTTCTGTTACTACAGCATTTGAAGACTCAAGGCGGTCTCAATATCCATGAGGCCT
GCTAATACTCACCAAGCATCCAACCTTGGGCCCCTCTGGCATCCAAGAAAGACAGAATCGATAGAACTT
GGGTTTTGCATGGTAGCCAGATGGACGTCACCTACCACATCCGCTAGCACCCACATCACCCTACCTGGGC
CTATCCGGCTACAGGATAGACTAGCCACTTCTCGGAACGAAACCTGTGGGGTAGATTATCTGCCCCCTTC
TCTTCCTCCTTGTTGCCGATGAAGCCCAATGCATCCGGCCGCCATGACGTCAATGGCAGAAAAATCTGGC
CAAGTTCAGGTTGTGACAACAGGGCCCAGATGTAGACCCCGATAGCAAAACATATTCTATGTCCCAGAAA
CAACCTCCATACAGCTTCTAAGAAACAGTCAAACAGGAACGCCCAACAGACAGTGCAGGAAGCTGGCTG
GCCAGCCCAGCCCTCCAGGTCCCTAGTACCACTAGACAGACCATATCCAATTCAGGTCCTCTTTCTGAGA
ATGTACTGATGCATCACACAGTCACACCAGTTCCACAAGTATTTAAGGAGGAGATTTCTTATAAGTTCTG
ACCAAACATAAGAGCACTTCAAAAGTGACCATGGTCCAGCCATATGGGTTAAGCCAATATAGTGGAAAA
TTCTACTCACCAAACCTGATCCGCA▓▓▓▓▓▓▓▓▓▓▓▓▓TACTGTAATGAAGTATCACAAACTGGGGGACTTA    F-13
CATAGCATAGAATTATCATGTTAGCGTTCTGGAGGCTATAAGACCAAGATGAAGACGTCAGCAGGGTTGA
TTCCTCCTGTAAGTCCTGGCCTCCTTCTCATCTCTGATGCTTTCCTTTGCTGTTCTTTCTTGGAGGAGCA
TCACCTCATGGCTGCCTGCCTGCAGTCTTTCAGCTCATCGCATCACGGTTCTAGGAAGCCAGTCTCAGCT
TCCACAGACCCAGACTCCTCTTTTCATGCTAATGTTTTAGCCCGTGACACACTAGTCTTAATACCTAGGT
TCTCATATAAATCTCTCAACTCTGATAAGCCCCAGACATGATAGCAAAGAAGATGCAATTGCCTTCCAAA
ACCCTTCCGTGCTTCCCCAGGCTGTTCTCAGAAGCTACATGCCCAACACATGTAGTATATAGTAGAACG
GAGAATGACATATTCACATGCACAACACAAACACAGCAGGGAAAATGTACATATATATACTTCCTAGAGAA
AAATGAGGCAGTATAGCCTGAAATGGTGGTTTATAATCCCAGTACTCAGAATGCAGAAACAAGGAGTTC
AAGGACAGCCTGGGTATATAAGGAGTTCCAGACTACAAGAAACCCTATCTAAAAAGAAAGGAGGTCCCA
GGCCATGAGAAGACTATAGAATTCTCAACCTGGCTATCCTCTTAATTAAAATCAGGGTAGAATTCTATAG
TCAGTTCAAGATCTGGTTCCCTCTCTGACTGGAAGTATAGGATCCTGAAAAACGAAAGCCACACTTTTAA
GGGACTGTAAGGTAGTGAGGCTCAGCACAGGGACCTGGGTCACCATGTAGAGCCTTTGAAGAGGAAATCAG
AAGACTGCAGTATGGCTAAGGGAAGAAGTGGACTTCCAAGCTTGGCACAGATTGCAGCTAGTTTGAGGAG
CGCCCAGGGACCCTCAATCAAGCAACCCTATCCCTCTTTTTTTCCTGGCACC▓▓▓▓▓▓▓▓▓▓▓▓▓▓▓▓▓▓▓    F-14
ACAGAAGAAAGCTTAGAGAAGACAGACCCATGCTGTGGCCCTGAGTCTGCAGTACTGAATTCAGCTGCA
AGTCTTCCCTGCCTCTACTGCTTACCTTTGCATTTAGCCACATCTGACTATCACTGTATACTCTGCTCCT
CCATCCTCTACCCTCCATCTCCAGTAATGCTCCTGTTGTAGCTGCTTCTGCCAAAAACCTAGACATCATC    F-15
TTGACCCTTTCTCTCATCTCCTCCATCCAAGCTCCCGCAACTTCTCCTGACTCTCCCT▓▓▓▓▓▓▓▓▓▓▓▓
▓▓▓▓▓▓▓▓▓ACAGTCACATCTCAGCAGCTCCTCTGCCGTTATCCAGGTTGGTAGCAGCAACACCACTCGCCT
CACTATTGCAGTACACTTCCCACTAGCACAGTTCCCTGGAGCCTTCCTGCTCACAGCATCCAACTGAATC
TTGTGAGGCTATGCCCAAGTCATTGGAATAAAAGATGAGAAGAGAGTCCAAGACAAGCCCCAGTAGAAT
CAGCAAAGACTATGTGGCCTGCACAGAGTGCAGGGGGTACTGGAGGGTCCCACAAACCAACTCCCCATCA
CCCCACATTCACGACAGAGTGGTATGGTGTATGTAAGCAAGTGAGGTGCTGGACATGTGCATGTGTAGAA
TATATCCATCAATCTGTGTTCCTGCTGTCAGGGTAGCATATATGTATGTAAGACAGACCGAGGTGTAGT    F-16
TATGAGGCTATCTTGCACCA▓▓▓▓▓▓▓▓▓▓▓▓▓▓CTCCATTCCACTGTTATCCCTGCCAGCCTGCCT
CTGACAAGAACCCAATGCCCACCCTAGGCCAGCCAAGCCTATGGCTCCTTCCTTGGCCCTGGCCCATC
CCCAGGAGTGTTTCCAAGCTGGAAGACTGCACCCAAGGGCTCAGAACTTCTAGGGACAGGGGCTCTGGG
GGACCCTTGCAAGGTGGGGACCTGCGAAGTGGGGCCCACACCTCTTCTTCCTTGAACCCCCTGCCACCAT
CCCAGCTGCAGGTGAGCCCGGGGCCCAGAATGGGGTAAGCAGGGTGGGGTACTTGGGCCTATAGGTGTC
GACTTTACTGTGGCATGTGGCCGGGGGGGGCGGGGGCTGGGGCACAGGAAGTGTTTATGGC▓▓▓▓▓▓▓▓▓    F-17
▓▓▓▓▓▓▓▓▓▓▓▓TATGCAGATATTGCAGGGCCAAGAAAATCCCCACTCTCCGGCTTCAGAGATTCAAG
GCTTTCCCCACCCCTCCCAATCCTCATCCCGATAGGAGACTTATGATTCCATGGACATAGCCATGTATC
```

Figure 11D

```
CTCATCCCACTGTGACGAGATGGCTGGGGCCCAAGAAGGTAACAGTGTTGGGGCCAGCTCTACCCCTTGA
AACTGTTGGACCTTGATACATTCACTCTCCACGAGCCTGAGATTCCACTGATGTGAACTGGATAGTTCCA
TTGTTGCTACCGTGTGAGACTTTAGTAAAGAGCTAATGAATGAGACACAGAACTATTAAGATGAGGCTCA
TGGTATCTCATGGCATCTCCCTTCTCTCTTCAGCTGCCTACAGTGCCCCTAGTCATGGTGGCACCGTCTG
GGGCCCGACTAGGTC▓▓▓▓▓▓▓▓▓▓▓▓▓CCCTTCTCCAGGACAGACCACACTTCATGCATCAGGT   [F-18]
ATGGAATGGAGCAGGCTGGTAGCAGGGAACAAAGAGGGACAGCTGTGGAGCAGAGGCCCAAGCCCCGCTG
AGCCATGGTCCATGTGTTCCCCAGCTCTCCACTGTGGATGCCCATGCCCAGACCCCTGTGCTCCAAGTGC
GTCCACTGGACAACCCAGCCATGATCAGCCTCCCACCACCTTCTGCTGCCACTGGGGTCT▓▓▓▓▓▓▓▓   [F-19]
▓▓▓▓▓▓▓▓▓▓▓CTGGTACACCTTCACAGTATCTCCAAGTTCTCTAATCTTTGAGCATGTC
CAATGTAAACTTTTCTGAATTATAGCCCTATGGAGGTATAGAAGGGTCTTAAC▓▓▓▓▓▓▓▓▓▓▓▓▓▓▓▓   [F-20]
▓CTCCAAAAAAAAAAAATATCAGACTTAGAACCTTGAAGACATAGAATGCAAAAAAAACCACAAATCGCTA
TTATCAGTCAAAATGCCATCACTTACGAATGGGCATCTTTAGGCTGTATGTCAGAAGCCCTTGACTGTG
GGAACAGCAGAGTACTATGAGGAGTCTTCAAGGCTCAGGAAGGGGACGGGGCTTCTGGAACAAGCTG
TACAGTCTAACCTGCAGCTCCAGAAGTACCCTGTCTCTACCCACAGGGATCAATGTGGCCAGTCTGGAAT
GGGTGTCCAGGGAGCCAGCTCTACTCTCCACCT▓▓▓▓▓▓▓▓▓▓▓GGTACACCCAGGAAAGACAGGTGAGT [F-21]
TGGCAGGGCTGGCAAGAAACGGCCCCTGCCCAGACCTCAGCCCAGCCTGCACCCTATTCCTCTGCTGACA
TCCATATTCTCCCATCCCCAGCAACCTTTTGGCTGCACCCCAAGGATCCTACCCACTGCTGGCAAATGG
AGTCTGCAAGTGGCCTGGTTGTGAGAAGGTCTTGGAGGCAGCCAGAAGAGTTTCTCAAGTGAGTAGCCTGA
CCCTACCCAGAGAGTTCTGCTGTCTAGGCTTCACGTCTCAACTCACCATCCTCTCAATGGATGATAATAA
GAATCATAAAGATTCAGACTCCATCCCTCCCTGCTCTGTGATCTTGGGCAAGTTATGGGTCTCTAGGCC
CAGTTTACCTGGCATGTATGAAGAGACATAATAATAAGGTATGTGCTCATAGTTACCTTCCTG▓▓▓▓▓▓   [F-22]
▓▓▓▓AGGATCTAAGGCCACAGAGAATTAAGGGTCAATCAAGCTCACACAGGACCTAAGTGATGAATCTT
GAATATGAACACAGGCAGCCAGGTTCCAGAGCCCACACGCCTAACTGCTTTGTCCCGCTTCC▓▓▓▓▓▓▓   [F-23]
▓▓▓ACATTCCTGATCCTCCAATTTCTGTTCCTCTAGATGACTATAGAGCTCTTGCCTCTCTGCTCTCT
ATCTGCTGTCCCTCCCCTTCTGTATCTTGCTAGTCACCCTAACTTTTGGCAAT▓▓▓▓▓▓▓▓▓▓▓▓▓▓▓▓   [F-24]
▓▓AGGCCTTTGCATGGGCTGTGCCTGACACCTGAAATGCCATACCCCTGCATACCCTGCCCTGTCTAACGTC
ATCCCAGCATTTTGGCAGACTCAAAGGGTAAATAAGGTCAGGCCTGGCAGCCCAGAGTTGCTGAAGCAC
ATGTC▓▓▓▓▓▓▓▓▓▓▓▓▓▓▓▓GTGGCGGGGGAGCACTGAGCATAGAGAAATCTCCCAAACGGTCTAG   [F-25]
GCCGTCCCTAACTGATACACTAAGCCAAGAGGCCCTGACCCACCATGGTCAGCTACATGGAATCTTCTCCT
TACTCAGGCACTGCCAAGCAGATCATCTCCTGGATGAGAAAGGCAAGGCCTAGTGCCTCCTCCAGAGAGA
AGTGGTGCAGTCTCTGGAGCAGCAGGTAATGCCTGCAGGGTGTGGCTGCGGGTGTGGCTGCGGGAAAGA
AGGATGGGAGGGAGGACCCTGTGAGGGAAGGCATGGGCAAAAGTGTGCCTGAGAACGACCAGGTGGAAGC
CCCACTTTGGTGTACATCCCCACAGCTGGAGCTGAAAAGGAGAAGCTGGAGCTATGCAGGCCCACCTG  [F-26]
GCTGGGAAGATGGCGCTGGCCAAC▓▓▓▓▓▓▓▓▓▓▓▓▓▓▓ACCCCAAGTCCAGAGGCAGCAGACTTCA   [F-27]
ACTGCTGAGGGCAAGACAGGAGCCCATAAGGACCAAATGTCTTCTTC▓▓▓▓▓▓▓▓▓▓▓▓▓CTGT
ACAGACCATTCCCACCTAATTAATATGCCAGATCCAAAGACACGCCTACTCTGCTTACAAACCTTCTGAC
CTCCAAAACATTATGATTCTGCCTTTTCAGGGCACATACAGAAGGCAGTGAACTCACAGGGCCACTGCAA
AAAAGGAAAATGGAGGGCCTTATGTTCAAATTTCAAGATAAGCTCAGAACATGGAACAGTGTGTGACCAC
ACATTTCACATACCCAGTCTCAGGCTGATATGAGTCTTATACTATAACAGAGGTAGCTACCACCATCATC
CTAATGCACAAATGAGGACAACTTAGGTCAGGAAGATTTAGTTGATGCTCCCACGGTTCACAGTTGGTGCT
AGGGGATTCCAATTCTGCCCCT▓▓▓▓▓▓▓▓▓ATCTATGGCTTCATCGCATGCTCATGCCTG           [F-28]
TACTCTAAGATGCTGCTTTACAGAGCTCCACCAGAGCCTGCAATTGACTATAGGGTGGTGCCCTTCTCAA
AAGCATTGACCTTACTGGACACAGTGGCATGCACTTGTAGTCCTGGCTACTGGAGAGGCTGAAGGAGGAG
CACTTGAACCCTCAAGTTCAAAACCAGCCTGGTCAACACAGAGACACCCTGACTCTTCTAAAAACACAAAG
AAACACGGTTGGGGACAAACTTGAGAGGGAAAAGTGATTGCCATACAAGGATAAGGACCTGAGTTTTGCT
```

```
AGATGACAGACACCATCCTAATATTTACTCAACCCAAACCCTAAAACATGAAGAGCCTGCCTTGGTACAT
TGGTGAACTTTCAAAGTTAGTCATGC░░░░░░░░░░░░░░░░░░TCCTACTGACTCACACCCCAAAGCAC   F-30
TCACCCACAACATCTGGAACCACGCGGCACTATCACACATAGGTGTATATACAGACCCTTACACAGCAACA
GCACTGGAACCTTCACAATTACATCCCCCCAAACCACACAGGCATAACTGATCATACGGCAGCCTCAAGCA
ATGCCCAAAATACAAGTCAGACACAGCTTGTCT░░░░░░░░░░░GTGCACGTACACACATGCAGCCCCT   F-31
CTACTCTAT░░░░░░░░░░░░░░░░ACACACGACTCTCCAAGATGTACCCCACGTCTCACTTGCCAC    F-32
TGACCCCAGTTCCCTACCCACAAGCCCCAATCCATGCCTAAGCGTGGCCCACAGAAGAACTTCTCTTTTA
TTTGGGATCCAAGGCCCCTGGCCCCCAGTGCCCATCCAATAAACTGTGGTCAGCTGGACAATCACCCTGA
TCAGATATGCGAACATATAAGCAGACAGCTGGGTTTAAGATCCCAGCAGGAGAAAGCGGATACCAAATGA
AAGAGAGTGCTAGAACAGGTGCCTCAGCACTGTCTCCAGCACCCCAAATTCCTGCCTGTGGTTAGGAGAC
ATCCATCAGGGCTCTAGGCCTCTCGGACCCGGCCCAAGAGGCCAGCATTCTCCTGGCGAAGGGCTCGGTA
GTCCTCACAGATCTTCTCCAGGTTGCTCAAAGTCTTCTTGCCCATCTCTGTCTCAATCTAAGAAAACAGG
ATGCACACTTCTTCAGCCCCTGCAGGCTGCCCCTCTACTGAACTCCTCCCTGCTCCTCCTATTCCCGTAA
CAGCAGCCTGTTCCTTCCCATCACTGGGCTTCTGGGTATGTCCTTCCCTCCACTCCACCTAAAGCAGCAA
CTTCTGCCATGGGCTCTGGGAGGCATTAGGAGCCCGCAAGCTAAAAGCCAGGGCTCAGAGTAGGCTACTGG
CTAGCTTCAGGTCCCAGGCACAGTGGGCACGAAGGCAAAGCCTCTAGCTGTTAGTTGTCTGGTTTCAAAG
ACTCTCAGCGCAAAACAAGGAACTATCCCCTGGCCTGTCTCCATTCCCCTTACCAGTCCCAGGTCTCACC
TGCTCCTCAAGATCTCGAACTTCCCTCATGATAGTGCCTGTGTCCTCAATGGTCTGGATGAGCTGACTGC
AATTCTGGAGACAGCAAGAATACAAGGCTTGCACCTATGCTGGCCCTCTCCAGCCAACCCACCAGGCACA
TGGCTCCCCTCACCTCATGCAGGGCAGCTAGGCTACTTGTAGGCTTTCCGAACAGCATCATCCTTCTTAGC
ATCCTGATAAGACAAAGGGGATCTCCGAGATATCAGCAAGCCATTCCCCCTTTTCCACTACTCTATGCCC
CTATAAGACCACCCTTTACTAGTACTTTGCCTTCATCCTCCACAGAGCAAAGCTAGGCCCCAAGCAACAG
TGCACCTAAAGGACTCACAGAGGCGCAGGCAACAACTCAGTCCCGCCTCCACCCTCCCGGAGGCCAGCCT
GCTCCATACCTTGAACACAAGCTCATCAGTCACTGCAAATGTCCGGTCGAGCTTCCAGAGAGAGAGTTG
ATTTCCTTCTGCAGTTCCTTTGTGTCCGACAAGATCTGGTAGAAACCAGGGTAACTATCAGTGCACATCT
TGGGCAACGTAGCTGATCAGTGATAACACTCACGTGCCTATACTTACATCCAGTCAGGGCCCATGTCCCT
GTGTTGGGGTGACTATTATGTGTTGGACTGTGCCTGAACAGCTCTGCCTAGTAGTGAGCATAAAGTCCCT
GTGTGATCACCCTATGCTTGTCTGCCTACATGAGCCATCAATCAGAGCCACAGTGACATCATACCTTAG
TGATCTCTTCCTTCTGCTTCCGGATGTTGCCCACAATCTCCAGGATGCGCTGGTATAGGCCAGCCGGGA
CACATCTTTTGGCAGAGTCTCCAGCTCTGACACCTAGGTGGGAACATGC░░░░░░░░░░CCAAGCCCTA   F-33
TACCACAACCACCCTTACAACCCAGGGCCCTAAAGTAGGCCTTACCAGCTGCTTATAGACCTCCTCCTTC
CGGCGAGCCTCCTCTGCAGCTGCTCGAACAC
```

Figure 11Q

>ref|NW_644989.1|DrUn_WGA1980_1:565000-583000 Danio rerio chromosome
Un genomic contig
AGACCTCGGTATAAGCCCGACGTCTTCCTCTGTTTCTTCTTCATCTTCATCGTTACTATTGTCTTCAGAA
CGTTCAACTCTAACCGTCTTGAAAAGACCCTGTTGTGAGGCGATAGATAGGAAATTGTTGTTATTTCCCT
GCCCCATTGCGTCTGTTTCTGCTGTCAGATTGCGCTGCTTTACATAGTGCCACCGGAGACCCGAGAG
GGTCCGTCACCGTCCTCGCCTCGACCGATCTAGGCCTGAATCATTGACATAAACGAGAACCGCGTTCGG
AGCTCATACTGCACACACGCGAATAAATGTCTAAATTTAGTAGGAAGAACGTCCATGCTTTTCCAGAGGT
CAGTAGGAAGACGGGTTCTGCTGGATTATCCCTCCCACCGAGCTCCTGTTGGTCGCTCCAAACCGCACAC
GCCCCCCTCAGCTATTTAAAGTTTAAAGACAACTTGGGTTTATTGTGAGAATAAACATTCCTCATCATA
ATAATTGCAAAGAAAAAAAAAAAAAACCTTTATCACCCTAATGATACTTCAATATCAATAGTTATTAC
TATCTCCTCAGTAACTAATTATTGTTAGGCCTATTTTCTTTTTTTAAATCATGTGTTATATATTAATGTT
ATGATCTTTCTATTAGGTCTAAAACAAATAAGAAATATTAAAATAATATTATGACAACAGGAACAATTAA
TCTTTATTGTTGTCTGTGTTGTTAATTAAAATGATGTCAGTGCAGGATAATTTACGTGCTTAACATGTGT
TTTTAACTAATATTATTGTCCATTAAAATTCTTATTTCATTATTTGTTTATATAAACAGAACACATTTAC
AAACATATAAGTCATATAATAATAATAATAATAATAATTATTATTATTATTATTAATTTGAATTACTTTA
TATTACAATAGTGTATATTTATATTATAATAAATATGTTTACACATTATAAACAGCAAATTGTTTTT
AAACAGTGTTATGCAAAGGTTTGGCAACCCCTTGCAGAATCTGTAAAAACATGAAAATATTCAACAAAAT
AAGAGAGATGAAACAATGTTATTTTTTATTTAGCACTGTCCTGAGTAAAGCATTTACAGAAAATATGTT
TACGTATATTCTACAAGGCAGAAGAAAATAGCTGAAATCATTCAAATAATCCCCTGCTACAGTGTGTCAA
CCTTTGGTTTTAATACTATCAGTTTTTTAATGTTTATTCATGAGTGCCTTGTTTGTTCTAAACAGTTA
AACTGCTTTCATTCTTCAGAAAATCCTCCTTGTCCGCACATTCTTCAGTCTTCCAGCATATTTTGCATA
TTCAAACCCTTTCCAGCAGCGACTGTGTAATTTTGAATCCATTTTTAATACTGAGGACAATCGAGGGA
CACTATTACACTATTAAAAAGGTTCAAATTTTCACTGATGCTCAATGGAAACATGATGTATTAAGGGATG
CATTATGATCGCTTATATTTTGTCATAATTATTTACATTTTTACAGAAGACAACAAATATTAGTTTCTTT
CTTTCTTTGGTGTGTCACATTAAACCACAGAGTGCTGCAATTTCAAATTAAAGTTATAAATTATTCAAAATA
TCAACACATGTAAAGATTAAGTTCAGAATTTACAACAAATTGAGTCTCTTTGAGACATTGAAAATACTTA
CTAGATGCTCATAGGAAAAAAAACAAATACAGGCAAATTTATACAATTACAGTGCATTTTTGCTAAATCA
GATTGTGCTCTCAGGCATTATTAGAATTATTCAAATAAGTTTCCAGCCTTTTTGTCACTATTTTTAAATG
TATTTTATAAAAACTTTACTTTTTAGATAATTATATTAGTTTTTTCAAAGTCAAAGTCTTAGCCAAACAG
CTATAGCATTTCAATGAAGATTTCCACACCATTTACTCGCACTCAAGTGGTTTAAAAATTACAATTATTT
GTTTGTCTGTTGAACACAAAATAATTAATTTTGAAGAATGTTGAAAAGAAAACAACCATTGACTTCCATA
ATAGGTACAAAAATACCATAAAATGTTTTTGTCCTAACATTCTTCAAAATATCTTCGTTTGTGTTCAACA
GAAACTCAGAAAGAACAGAAAGAAACTCAAAACAGGTTTGGAATAAGTGGAAGATGAATAAATGATGATG
ACAAAATGGGTGAACTATCCCTTTAAGGCCTTTTAGGGAAGCAGGCACCTATAACGTTCCAATAGCTTTA
AAAATCTTTATGAAATTTAAGACCAACAATTTTTCCAAACAAGATTTTCACAGACAAATGGTGCCCCTTA
AAATACATTTCTTATTGCGTAATTCAATCGGTGATTTTTGAGATGCAACTGCTTTTATTAGGTCAGCTAA
CAAGATCAAATGGTGAGAAAGAAAGCGCTCGATTACAGACCGATGGTGTTTAAAGTTATTGATTGCTAAG
CTTTTTTTAACACTTAGACTGAGCAATCAATCTTGCTTAATATACTGAAATCAATATATGCTACAAGTGC
TGCATCAAGGATTCGACTTGCTGCATATAGTGAGAAACCAGGAATGCATTCATAACCATTTATGTCTAAC
CTTTGGTCCTTAAACACAAAAAAGCTGTCTGCCACTTTGAATTATCCCTCACAGTTTATAAAATAGACCTT
AATGATGTGGAATAGACCGTTTCAATGTGGTAATGTCAATGGTCATGAACATTTCCTGCTTGTTGGTCAAA
CAACTTCACAACCGTAAAAAGAGGCAAATTTAATCACATCTCAGTGTTAGTTAATACATCAGTTATTGTAT
TGTTATTGTTGACATCCCTCAAAATGGTCTATATATACAAAAGATATAAATTGCTATAACCTATAACTTAT
TATATGGTGCTACATTAACAATATGACAAAAAAAACATTAATTAAAAAATGACAACACAGTTTGCTTTA
ATGTTAATCTTACTTGTGTTTTTGTATCTACTACATCTCTGTCTAAATCATTAGCGCAGGAACATACTC
AAGATGACATGAGCTGCTGTAAAACTTACACACTCTTCACATTGAATGTTGACTTGACTGACAGCTGCAG
TCAGATTGTATTTAACACGTCTTTTTCCTCTCTCTGTTAGGTTTGCTGAAAATCAAAAGATTGAAA
AAAGGAGACTATGATGGAGATTGCAGTTGGTAAAGCTTTTTTTATTTCTGTCAGGTATTGTATTAGAGAT

Figure 13A

```
TAATCTTGATTAACCATAATAAAGAATACTCATATTTATCAGGAAATACCAGCTATTGTTGTTTTTTATG
CCTATATTTAAACCAGGAGTAAAAAAAGTATACGAAATACCCTTTATGAAATACAATGTGATGTAATATA
AGTCACATATAGACAATTAATAAGGAAAATGTTCAAACTAAGTAGTTTTGTTTTAATATTTGTCTATTCA
TGGCTTATATAATTTTATAGGATGTTCAAACTGACTAACATAAATACTGTTGTATATGAAGTATAATGCA
GTTCAATCTATGTGAGGAAATATCAAGATTACATTTTAGCTTACAAAGAGTAAATGTTTCATTTGAAATA
ATTAAAAACTAATTTGGTGTTAATTTTCCTTTATTTTTACTTTTCAAAGTCCTTTAATAATTCATATGGG
TTTGAATTATGAATATAAGAATATAATATATATAAATATTTATTTTATTTATTTATTTTTGTACTTGAT
CTTCCCATTGCTAAGACATATGCTTAAACAATCTATTAGCTTTTCATCTTCATAAATAGTTCTGAATGTT
CGTTTTTATATGCATGTATTAAGCTGGTTAAAAAAAAAATGTTTGCAAGTCTGCATTACGGTACATGCGC
TTTGGAGTGTCATTATTGTTGAACAATTTGTTCAAAAACACTCAAATAACCTTTTCAACCACAGGATGAG
GATGTTTTTTTCCTGCGTTATTCTAATCGACACACATGCGATCGACATGTACATATGTTCAGTCTCCCCC
CCAGAACCCGAATACAACGTCACACACACACTGCAAACGGACTTTCCGAACACGTAATAGGTTATTTCT
CTCGAAATCTCATTTTCCGGTCTTCCGGAATGGACTTTACCAGGTTTGATGTGAAATAGCCATCATGTGC
CTTAAACTAACATAAATAATGTTCAGTGTTATTTAATTATTAATAATTTTGTAATTTAATCTCAGCTATT
AAATCAGAATGGAAGATGCGGTCCATAAAAATTACTTTTTTAGTAATAAGTAGTATGTTTTAAAATATAT
GAAACACATATAAGAAAATATATATTGCAAACAAAACATGCAGAGTCTTTTTGTAATAGTTAAGATGGTT
TTGGGATTGAACACCTCAACATCCAAGCGATAGTTTGTAAAAATTGTTTAGATTGTAAACCACTTTTAAG
CAATACAAAAAACAATAGTAAAACCAAATATTGATAAAAAATGTAAGTGTAAACCCCATCAGAAATCACT
CAGGAAAATAAAATCGTATTCTGCTGCAATAAGAAGCTTCTAAAATAGGAAACAGAAATAACAAAATGCC
ACATAATTTTTAAAGAAGATGTAAAGAGAGTTAAAACTACACACTTGTGTATCTGAAAACACACACACAC
ACACCAACACCCAGTAGGGAAACTGTGTCTATTTTCCACTGAATGTCACGCTAAACATTATAAAAGGGGT
GACCTGAACATTTTCCAGATCACTCTAATTGCTCACTCATCGCATGCATCCGACACTTGCACAACAGGTA
AGTTCTTTTTGTTTTTGTATTTGACTTACTTGCCTTTAAACCTTTATTGCCTTTATTGCATAAAATAAAAA
AGCCATTTAATCACTGAAATTTCATAATTTAAAAGCTTAATATACAATATATTATAATATAGAGACTTTT
GCTATTTCTTTCCTAAAATTGTTGCCCTTTGTAGATAATTGACAGCAGTGTTTGGAAATGAAAGAGTTAA
TTTGTTAAATCTGTTGTTAGATTATGATTACGATTGACTCACAGCATTGCATCATCAAATGTGCACAATA
TTTGGTCAGTTTTTGACACAACATCCTGCTTTGACTTTTTTCATATTCAAAGTAATTTATTAATCATTTA
TTTATCAATGGATGATTTGAAGCAAGATTAAACAATTCAAACAGTGCTAAAACAGATTTTAAAAGTCAAT
ATTTTGACTTCTTAAAATATTCTCATATATTTTTTTCTTTATATTGCCATTCATTATACACAAAATCGCA
TTGGAAATTTAGATTAATGTACAACACTAAAGCTACTGTAAAAAATAGTTATAAACTTGATGTTTCTATT
TATCTCAACATCTCAAGCTGACTAAAATATTAAGTTAAACTTTGTAAAACCTTAACAAATTAACAAATCT
ATTTTAATAAAACTTTTTTTGTCATATCACTTTTTAGCCTATTTTTTTTCTTTTCGTGACAGAAAAACA
CTTAACAAGCTTAGCATAAAAAGACTAGCAACCAAACTGTTTTTTCCTAAAGTGCAGATGCAAAATGAGG
TCTGTGCACAGAGTCAGACTCAGGGTTTGGTCTTTCTTTCCTGCTCAGATGCACCACAAACCCGTTGCT
GAGGAAAGAAAAGCTAAAGAACATATAGAGTGACAGTCTCAAGGAAAAGGGCGACAGACAAAGAAAGGTG
TGGGAGGTAAAACATCCTTTCTTCTACAGAGATCCTGTAGTTATCATAGCAATTCCATCATGTGTTAGCT
AAGCTACTACCTATGAAATCAATGTTCCATACTATAGGAGCATCACCACACAGACCGATGTAAAGGGTAA
GTTACAAAACTAAAAATACACTTCTAGCGTATCTGAGGAGAAAATGAGTAGGTGCGACATTTTCGAGAAA
AAAAAACCTAAACAAACAACAAGGTCGACGCCTCAAGTTCTTTACCAAGAAATCAAGTTGCTAATATAAG
TAATGTCTCTCTGAATGTTGTTTTAAAAAACTCTATTGCAATTTATTCTTGTGAAAACAAACATCTATAT
CAAGAACATTTTTGTTGGCTTGAGTAAGTTTTTCAGTTGTTCTAAAGTTTTCTTTATTAATTTTTATAAC
AGTTCTTGATCTTGCACTACAATTCATTTAAGAGATTCTTAAAAATATCGGTGCCACATGGGTCTTCAAA
ATAACTAGAGGACAAACAGTACTAAGAGGAAATCGTAACGATTTTGCTTTGCATCAGGCTGTAATGACTT
GCTTGGTTTTAACCCCTTATTTTATGAGTTTGATAGCATTAGTTAGGTATAATTGTGAAATAAACAGTATC
TCTAAGGGTTCGATCACCTAAATTTTATGTTCAACATCTTAAATATGTGTTTTAACGTGTAAAATTTGTTT
TCATTATTGGCATTGATGCTTCTATACAGAACTTTTAAAATCAAAGACATTTTCCAATTCTTTAGAGCAG
ACAAATGCTCTGTAAAATAAACTGTGTTTTTTAAAACCAACAAACTGTTATACTTGTAAAGCTGTTCAAT
```

Figure 12B

```
TTTTGGGGGGAAACCTAAAATGGTTTTTCTACAGGATCATTGCACAGAATTCAATTTCAGAACCTTTGTT
TTTAAGTGTATGACACCTTGATATTACTCTTCATACGATAGGCTGGTAACTATAAATATATTCCCGTTAT
TGTTGATAACTTGATTGGCAGATATTGTACATATTCTATACAGTTTTTATAAAGGACAGTGATGGGCACT
AAACTGACAGTCATCAACAAAAGGAACAAACTTCATTGAGTTTTGTTGGATAAATGTATTAACGCTGCAA
TTTTGTGTTCATTTTTAGCAGTCGATCTGTGTTTGCTGGATCACAGAATGTCGAACTGATGCATTGTAAT
TTGATGTTTATTAATTGGTCAGCATCTCACAGTGCAGTGGGAGTTTGTTCACCCAAAAATTAAAATTTAC
TCACCGTTAACTTACCCACAATTGTTCCAAATCTTTGTTAGTTTCTTTAATCTGTTCAACATAAAAGATA
TCTTTAAGAATGCTGGAAACCGGTTGCCATTGACATTCATAGCAGGAAACAAAAATGCAATTCAAATATC
TCCCAGTTTCGAACAGAACCTCTATTGTGTTAACAGAAGAAAGAAACTCAAAGAGGGTTGGAACAAGTG
GAAGGTGACAGAATTTTCATATTGGGTGAACTATGCTTTTAAGTAAATAAAAAAATGATGAATAGCTAT
TTTTGTATTCTAATGAAACACAATTACTGTATGAAGAGACAAGTTCTTACCTTGGTTGTTTCGCATACTG
TATGCCATAGTGCCTAAACGTCTTACTAAACGTCCCCCATTTATTTGTTTTATTTTCTTCAATTTGCACA
TGTTCAGCAACTGCCGCAGACAATGCAATGGTGTTAATGCAATAGTTAATTTAGAACTCCCTAAATTAA
ACAATAAATAAATCAAACCTAAAATCAGTAATTATCAACAGTAATAAATCAAGATGGCGAAACTGGGTCT
GCCCAAATATTCAAAACTGTCGTTTTACTCTCAAATTTACAGTACAGTACAGTACATACCCTAAATATCC
TGGTCTTTGATTTTTATCATATCACTTGTTCAGAGAAATGTAAGCGTAAATGAGTGGGTATGACCAGAGA
AATGGAAAAAAGTGAGTCAAAATGTAATTTGTATGTTCGTGGAGAGCATTGAGGACAGAATGCACTTT
GTGTTCTATATTTGTAATTGTTTTTTAATCATTAATTACAGGTTTCAGGTTTAATTCCACATCTCTGTTG
ATTGATAGCATTAGCATTCATACCGACACTCTGAGGTCAGGTGACTCACAGCTCAGCTCTAATAATTATC
GTTGTGACTATAAATTCCACCGAAGAACATGAAAGTTAAAACTGACTTCACTGAATAGAAGAGTTTCTAA
AGTATCGCAATTTCAAAATGAAACTTGAAACTGTCAGTCCAGACTGTTGTCATATCTTGATGGATTTAAT
TTTGGTGAATGGAACTGAGAGAAGACTGTATTCAGACTGAGAGATGAATAATGAGTTTCATTGGGTTCAA
TAATCCCGGTCTTATCAATATCAACTCTCTGAGGAAAAATGATTGGTGCGGCATTCACTAAATACAATGAC
AACAACACTGAGAACTACTGAAATGTAAAGAACCAAAAATGACATCCCCTTGCATGTACAATATAAAGAA
TGATAGATTCTACACAATTGATTTGTGTTGGGACAACATGAAGGAATTAAGTAGATTGACCATAAAACAA
TTAAGTTTTCTACTCAAAAAAGTAAAAAAATTGTGTTGTTTCAGCTCAATTTAAAGTTTAAATTGGTTT
GAACAATCAGCAAATATAATTTTTTTTTGTGTACGCTGTACAAAAATGCTGGGTTCCATGCAGTTACTTC
ATGTTGCACCAACACAAATCGATTTTTTTGATTTAAAGTTAAAATTTCGAAGTTAAATCGAAGTTAACTT
TTAACATTTTTACAAATTTAAGTGAATTAAACAAAGCAATTAAGTTGTCCCCCCCAAAAAAACACAAAAG
AATTCGGCTCAGTTTTAATAAGCAGTTTGACAAACAGCAAATGTCAGTTTTTTTGAGTGTGTGTATTAGT
TTAAATTCAGAGGGATTCCACTGCTTTTAGAAACGTGATGCATAAAATAGTTAATTTGTAGCATACAAAA
TGCATTTCTAGCATTATTTGAAAACAATAAAAATAAAATGTTTTTACTATTCAGCATCTATTAAGTCTCC
TTCTGATCACATCTAGTTGCTTGCTTGGAAAACCCCCCAGGTGAAAAAATGACATTTATCCTACATTTG
ATGTGGTTAATGTGAAATGTCAAAGAGAATAAGCAACACACGACTTCTTGAGCAGTTTCAGAAAACCGCA
ATGAAATGGTGCTCTAAAATCCAAAAACTTTTTTTTTAAAATTATTTCTCAGAAGTTATATGCAACATCC
TTGCCGTAAGTCCATCCTGGGTTTTATAATCAATTGTGGGTAATTTCTCAATTTGTGTAATTAACTAT
CAAAGTGAAGCAAATCACAACTTTTTAAAATTTTTATATTAATAATGAGAACAGATTGCAAAGGGTTCAT
TTAATAGTTCAGTAAAAATACAAATTAAGATATAATAAAAGGCGAGTAAGCATGCATACATTTCTGTGA
AATGTGAAGGTTTGTGAAATTTAGTGGTACTAAAATTATTAATTTTGTACTACAATCGTCAAATTACTTA
AATGTGCTGTTGCAATCTGTATAATTGCCTTTTATTTCTATTTATAACCTATTTATTATAACGCTCACA
AATCTAACTGGATTTCAAACATACAAAAATTATGTAATTCAACTATTTGCATAAAAAATTGCACATATTT
TAAATGTCCAGTGCATTTATAAAGTATTAAAATACATATCATGCATTTAACTTAGAAAAATGTTTGTTTC
ACAGTATGTGCAAATGATGTTTTTGCAAAAATATGTGGGGCCCACCTCCGCTTTCCTGACCTCTTGGTCC
TTGCTCAATGTGAAATGTGGTTTGTGTTCAGAAAGCACCTGCAAATGTGAAACAAGAAAAGGAAAAACAA
CCCTTCATTTCATTTATTAATGCATAATTATGCTATTTTTGGAAACAAAGCAAAAGCTGAAGCTATCTAAG
CAGGAAATACCTTGTGTTAGTATTTGGAGGTTGATTCATTTCACTCCTAATTTAGTAGTATGGTTATTAA
```

Figure 12C

```
AAGTCATTTGTGTCTTCCTGCTTATTTCTATATAGGTATGCTTCTTAATGCTACTGGAACACACAGAGGG
GATGATAACAGGAGTAGTCACCAACATCTGTACCAAGATGAAGACTGTGCCACCTTTTCCATCATACAGA
TGAAGTCCAGAATAAGCAATTCTCTTCTGACCTCACCAAAACCAATGGCTACCAAGGTAATGAAGCAGAA
GCTGTCATTTCTTTGTATTACTACATGAACAATCTTATTCAACAGAATAAATAATTGTTCTCTGGTTCTC
GCCTGACTTCAAATCCATGATCCAACTAAAATATGGATGCTGGAAATCCTTGAAAATGTTTTAATTTTAA
TATAGTGTTTGACAAAGTGCTTAGGTTTTGGATAAAGTGCTTGAAACCAAAGTACATTTAAGGCAAGTCA
TTTCACTTGGCGGCCATCTTTAAAATACACATACTCGGGCCAACTTCAAATTATCCAAAACTGCTTGACA
AGCTTGCGGTTAAATTCATATTATTTTCATATTAAGAATCAACAATAAAATTAAACAACAACTATCTCT
TTAGTTTTCATTCGTTTATTCTTTATTCATTTCTTCTCGGCTTAGTCCCTTTGTTATTCCAGGGTCGC
CACACTGGAATGAACCGCCAACTTATCTAGCACGTTTTTAAGCAGCGGATGCCCTTCCAGCCGCAACCCC
TTTCTGGGAAACTTCCACACACACATTCACACTCATACACTATGACCAATTTTAGCCTACCCAGTTCCCC
TGCACTACATGTCTTTGGACTGTGGGGAAAACCGGAGCACCCGGAGGAAACCCACGTGAAAGCAGGGCAA
ACTCCACACAGAAACACCAGCTGATCCAGCTGAGGCTCGAACCAACGACCTTCTTGCTGTGAGGCAACAG
CACTACCTATTGCGCCACTGCGTCACCTCTCTTTAGTTTTATTTCTAAATAGTTGAATCACACAAAATCT
GCTGAAATTATGTCTGGTTCAAGCCCCTCCACTAGAGACTCATCAGTACTGTATATAGTGATCACTGATT
GGCTCCTGTACTAGAAGGCGGGGCTTCATTCGCATTATTGACCGTTATAATTTTTCCCATTCAAAACTAT
ACGAGTGAGACATTTTGTGCATTATATTGACCTTATTCTTTACGTTTGAGCGGGTACAGCCATTTGAATT
TTCTTTGTTTGAGACATCCATTCTCATTCACTTGCATTGATATATAGACATTTTAAATGGCTTGTTATGC
TGTTTCATGTTGCAAACTGAGATTTTCACATTATAATATTTTACTTTTTAGGTATAGGCATGAACACACT
TGCTTGTAGAGCAAGCAGTTTGACCATTTTCCGCCGTTTATTATTCCTAGTCATTTCTCCCATAAGCAAC
TGAATCGGAAGTTCTAAAACAATCGGAAAAATTAGTGCACTTCCGCATTGCAGAATAAGGTCAATAGTCT
TTGTTGAGAGTGCTTGAGAATGTAATTTTGTTGCTTTCATAATAATTGATCTTAATAAATAGGAAATAAT
AATGAACTATTTAAATAAAATTAAATACATATTTTTCCTTCTGCATAAACAATTTAAACAGAATGCATGG
ATATTATCACTTTATGGGTGAACAATGCCTGACTCTAAAATGAATGTAAATTTAAGAAGAAAGATTTCCT
CCATAGTCCAAAGACATATGGTATAGGTAAATTGGATAAACTAAATTGGCCGTAGTGCATGAGTCTGTGT
GTGAATGAGAAATGTGTGGGTGTTACCCAGCACTGGGGGTTCACAAGTTTTTTTTTGTTGATCTATCTAA
TAAACTTTTACAGATATAACAAAGTAATTTTACAGAGAAATTTAAACAAATATTATTTCCACCCCTAGCC
TCTAAACAAGTTGAAAGAGAGAAAAGAAGAAAAAAATAATGATAATTTTAGAAAGTAAACAAACAATTAT
AAAAAAATAATAAATAATAAATAAATAAATAAATTACGAAATAAAAAACAAATTAATTGAAAATAACATC
TGTACAGAATACACACATACCTTGATAACCCAATTATTACAAAAATTAATCCTCAGGTATTTATATAACGT
ACCTAATTATGTTTGCATTGCAATCGAAAGGCCTTAAGACTTAGATTTACAGTTTGTAGAGATACTTACA
TGCTCAGAAAAGAAAATTCTAAATGTTTCAGAAAAGCTCTAGTATTGCCATTTATTGTAAACCTGATTT
TTTTTTTTCAAATGGTGAAGTTCATTGCATCCAGTTGTCAAAACTCAGGGGAAATCTTTGATAATAACAGA
ATACACCGTCTTGCTAACAGTGTCAAAAATGCAAGGGCGTTTGCAGTACAGCTCGATAACCCTACCATAT
TCAGAGAAAGTCCAAAAAGTGCAAAAAGAGGACACGGTTCGATGTGTATCTTTGTCACAGAAGGGAAACA
CTTGAAAATTGATAGCCAAAAAGAAATGATTGATGGACAAAGCCAAAACATATGTATATGCATGCAAAAC
ATAGGTGCTTGATTAAAGTGATCAAATATAGAGTCCATGTGTTGAGTTATTTTTGCCAACCTCACTTTTG
TCCAGTATAATCGAACTCGAACTAATTGTAATTGGATGAGGCAATGTCGTGCACAGATAGAGGAGGTATG
AGCACGGGACAAAATCTGGTCCCACGTCTTGTCCTCGAATGTAAGATTAAAGTCTGACTCCAACTGTTAT
TTAATAAAGGAAAGAGAGGTAGTAGAAAAAGAGGAGATCAGCCTGTATAAAATAGACGTTGTACCTTTGT
TATGTAAGGGTACTTAAAAAATGTGGTCAAGTTCAGATTTTTGGTGGAAGGTTCGCAAAATCTGGATATGA
GTTTTAACAAAATTTCTGCGTTGCAAGTATCTAAAGAAATGAGTGCTAGGAAGAGACAATTTTGTATTAA
ATGTGAAAAGCTGAGAAAAATATTATCGACATAAAAATCACTGACAGTGGATATTCTTGCCCTCTGCCAA
ATATTAAATGCTTTATCATTAAATGATGTGGCCAGTGCTGTTTTCTTACTGGAAGGGCATCCACTACGTA
AAACATATGCCCGAGAAATTGACAGTTCATTTTGCTGTGGCAACCCACAGCAGCGATCATGGACTAAGCC
GAAAGAAAATTAATGAATGAATGAAAGATGACACATTTAAGAGAGTTCATTAAAGTAGTTTAATGTTGGC
CTGGGGCTAACATGCCATTTAAAAATGTCCTTACTATACTATGCTATGCTATGCTAAGTGCTATAGTGC
```

Figure 12D

```
TCAAGATTGTATTTTTTGGGGATTTCAAAGATATCTGTTGCCTTGGAGAGTGACCTCAGAGGCCTCGGCT
CATCTCGCAATCAGAATTTCACTCTACAAAAGCAGGTACAGTCCAGTTGTAATAGGTTTCACTTTTAAAT
CAACACTAAAGGATCACAAAGAATTGAAAATAAATTAAAAACTCTAAGATGTCGCATAATTTGATCTAAA
ACATGATCCTTGATTTGTTTCTGCTTCCTTTACCTAGAGTGCCAGTGGAAGTACAACCAAATACTTTAAA
CAACACAGACCATCAGTGCTACGTAAAGGCAACCAGCCTTTTCCACAAGGTACTGCTTCTGTAGACTATA
AAATATAGAAAACTATTTACTTTCAACAGCCACTTTATTAGGTACACTTTGTAGTACTGGGATAAACTCC
CTACTGTACTTGCACCATTTTACGCTTTATAATATATGGTTTCATATTTTTACACCAATTTCTGCTTTCA
TCATGTCACATAAGAAATAAAACTCATCAAACCAGGCAACCGTTTATTATTCTTCTGTTGGTGAGCTAT
TGTTTATTATAGCTCAGTTTCCTGTTTTTTTTCTTCTTTGCTGTCAAGAGTGGCACTGTTGTGCTCTT
CTGCTGCTGTAGCACATCTGCTTCACGGTTTGATGCGTTGTTTTGCTTCTCAAACCAGTCTGATCATTCC
TCTCACGTCTGTCATCAACAAAGCTTTCAAAAAAAAGCCACTTACTTAATATTTCTTTTTTTCTGACAA
ATTTCTGTAATATGATTGTGGATAAAAATCTAGAATCTAGAAATTTCAGAAAAACCCATCACATTCAAAC
AAACATGCCACATTCAAAGTCATTAAAATCCCCCTTTCCCCTGTTCTAATGAACTTCAGCAAATCCTCTT
GATCATGTCTGCATGCCTAAATGTATTGAGTTGCTATAAAAGACAATTGAACAGGTGTACCTAATAAAGT
GACCAGTTAGTGCATCTCTGAAAGTGAATTTTTCATAATGCTCTGCAGCATGCAGTGCTCATGATTGGGT
TGTGGACACCGTGTCTAAGACAGAACCTGACAGTGAACCATCAGATGCCATCCCTCTTTACACTGGCCAG
TCTGAAAGCAGAATCGGTGCTTATGCGTCAAGCCCTCAGCCTGGCAGCCCGGAGTATACTGGGAAGTGAG
TATGTAGTTTGAGAAAACAAACACAAATTAGGATATTCAGTGCTGGAATGAAAATGTGGACATCCACTTT
GTAACATTATTGTGTCTATATTCATTTCACTTTTACAAATAAGATATAATGCAATATGTTTTGAGCTAAA
TTAAGCATTTATTATTATTATCCGCAGGCATCCATATAGTCTTTCAGGTGACTATCTGTGTGTTAAAGGA
CAATGCAGATGGCCAGGGTGCTCAAAGAGCGAAGATGTATTCACAGAATATGGACATTTCTTAAGGTGAG
ACACAAAGTTAACTAAAACAATCTAAATAAATACAGCAATATCCTATAGCAGTGTGTCTGTTTCATAATC
TAGGCACCTTTCTACTGACCATGCTCCTGGAGACAGAAGCATAGGCCAGCTGAGGATGCAGAAAGACAGA
GTACAGCACATGGAGAATCAGGTATCTTTACCTCTTATGTCACAGGGACTAAATAAATAGGGGTCAGGAG
GTTACAATATTAATAATTGTATTATAAATGGATGCTTGTTTATGATCCTGCATTATATTTCCTTTATGAA
CACTACTGATAGTTGACTGCAGAAAGACAAAAACTGCAGGCTATGCAGCTACACTTGCTTGATGTGAAAT
CTACCTCTGAGGTAAGTTTTTTTAATAAAATTTTATAAGAAAAATACACTCACTGGCAACTGTATTAGGT
ACACATAACTAGTATCGGGTTGGACCCCCTTTGCCTTCAGAACTGCCTTAATCCTTTGTGGCATAGATT
CAACACGGCACTGGAAATATTTCTCAGAGATTTTCATATTGACATAAGAGTATCATGCAGTTGCTGCAGA
TTTGTCAGTTACACATCCACGATGCAAATATCTCATTCCAGCTACTCTACTGGATTGAGATCTGGTGAAT
GTGGAGGCCATTTGAGTACAGTGAACTCATTGTCATGTTCAAGAAACCAGTCTGAGATGATTCGCGCCTT
ATGACATGGCGCATTATCCTGCTGGAAGTAGCCATCAGAAGATGGGTACACTGTGGTCATAAAGAGATAG
ACATGGTCAGCAACAATACTCAAGTAGGCTGTAGCCTTTTACACAATGCCCAATTGGTACTTATGGACCCA
AAATGTGCCAAGAAAATATCCCCCACACCATTACACCACCACCTGCCTGAACTGTTGATACAAGGCAGGA
GGGATCCATGCTCTTATGTTGGTGATGCCAAATGACCCTACCATCTGAATGTTACAGCAGAAATCGAGAC
TCATCCGACCAGGCAACGTTTTTCCAATTTTCTATTGTCCAATTTTTGGTGAGAACTGGTTTGAACTGCA
GCAGATTGTCTTGACCATGTCTACATGCTTAAATGCATTGAGTTGCTGCCATGTGATTGGCTGATTAGAA
ATTTGCGTTAACGAGCAGTTGGACTGGTGTACCTAATAAAGTGGCCAGTGAGTGTATACTGTAAATATAA
AAGTTATTGGACAACGTTGGTTTGTTCTGGAGAAAAAAAATCTTAGGCAGTTATTAATACTGACCTTTAA
AATTGTTTAAAAAATGTAAAGACTGATTTTATTACAGCCAAAATAAAAGAAATAAGACTTTCCTCAAGA
AAAGAATATTATAGGTAATACTGTGAAAATTTCAAAATCACTTGGTAAGAATATGTGTATGGAATAAGGT
AAAATATGTCTATGGTAAAAAATTATAATATCTGTGTATGGAAGCAAGGAAAAATGGTAGCATTTTAGGA
ATGTATGTAATGAACATTGCAGTCTCCTATCAGCTAACTGTCATGTATGCTTATAAAAGGGATATTCATC
TTGCTTTTTAACTCCTTAATTAATTAGTTTTCACACCACTGTATTCTTGAGACTAAAGTTTTGACCTGAA
ATTACATCACACCAGACATCAATGATCCTCAGCTAACCTACAAGACTAAAACAGGGAGAGTTATAAAAAC
CAAGTCAAAACCTTGTGTGAGTGACCGATACTTTAATGCCGGTAATCAAATTATGCCATCATGACTGTGG
GATCTGTTTAGGTTCTGGTTGTCATTGTGGTTAGTATTAGCTACATTTAGGGCCAGATGAAGGCCAGG
```

Figure 12B

```
TGATATTTGATGCCAAAAATTATATATTGATGTGATTTTCTCCTTCTGATCTTAGGGTGGCAACATTGTG
GAAAAGCCGGCACRTCTGTCAGGACTTCTGCAACCTGCATCATCAAATGATCACTATGACTGTGAGAGAG
CAGCAACTGAAGCGCTAACACAAGGATACTGGCAGATCTCTACCTCACAAGTTATACCAGGTCATTAAAA
TTATACTATAAAACACCAATTTAGAAATCTAGCTTGTAAATTTAACTCAATAACATCAGTCATGCAAATC
TCTACACACAACACAGTATGTGTTATTGTTTTCTATTTCTGCCCATAGGGATTATCCCCAGCTTTGAG
TATTATAAGTTCACAAACATGAGGCCACCTTTCACCTACGCCTCCATGATACGATGGGTAAGTATTGCTG
AATTAACATCCTGCATGTTACCTTTTGATTTCCTGTCAGTCACATCAACAATGTATGTTATGTCAGGCA
ATCCTGAAGTCCCCAGAAAAGCAGCTTACACTGAAAGAAATTTATCAGTGGTTTACCAGCATGTTCTTCT
ACTTCCGTCACAACACTGCTACATGGAAGGTATGAGATGTAATGTTTGTATTGTACACTTTTATTTGTCA
TTCCATGACTCATTGGCCACAAACAAGCCAATCCCGAAACCCACAGCCTCTGTTGTATATACACCTGAAA
ACTTTCAGAAGTTGCACTTGCATGTCAATGAATGAATGACTTGATGACCCGACTGTGAAATTACTGTGTT
GTGGATGACTAATATGTAACTTCAGTGTATAGGTAATTCTTCTTCTCTCTGTCTGTGTGTAGAATGCGGT
TCGACATAACCCTCAGCCTTCATAAGTGCTTTGTGCGTGTTGAAGGAAGGAAAGGTTCAGTTTGGACTGTG
GATGAAGAGGAATTTCTTAGAAGAAAAGGTCAAAAGTTACACAGGTAAACTCATTTACTCATTATATGGA
TGACTGCAACTGCATTGTTGTTGTATAGTTAGTTGTATATGTACAAGATGTTAAAAAAAGCTGATTTAG
GCCTACTGTAAATTAAAAACATCTGCTTAAATGGATCTGATTAAGCTGCTTTTATCGTTGGAGGCGTTTG
GTGAGGTTCTGATTATATAATTATATAAATGAGCAAATCAAATTACACCCCTTTTCACTTCAGGGATCAT
GATATGGACTGGATGGCACCATTTCAGCTGTTTCCTTTGACTCCACAAGGTGAATCTTACCAGATGTGAG
GCCCCAAAATGGCCTCTGACTTACATTAATACAACTAATGTTATTAGCTACATTAAAAACACGATCGATG
TAAACGACACCATTTACATAAATGTGCAGTCTAAATATACATAAATGCTGGCAGTCTATGTGAGAAATCA
GTTGTTGTTTAGTTTGAATGTTTTGTGTCACAAATATTGTAAGAATGTATATTATTTACCAAAGTAAAAG
TTTGTAATTGTTATAATCTTTCATAGATTTAAATAAAATTAATTTAATCAAAAATGATAATGCTTAATGA
TATCGTTAAGTGTGTAAATACATTCAATAAGATAAATGAATGTTGATGATATGTCCTTAAACATTTTATT
TTACATCGTATTTTTACTAATTGTCCAAATAAAGCAATCCAATCAAGCACTGTCGGGCTGTTTTTCAGTG
CATTATACACA
```

Figure 12F

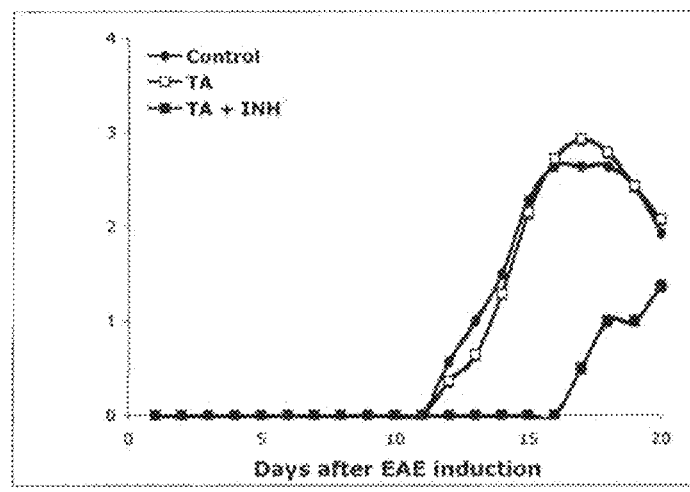

Figure 13

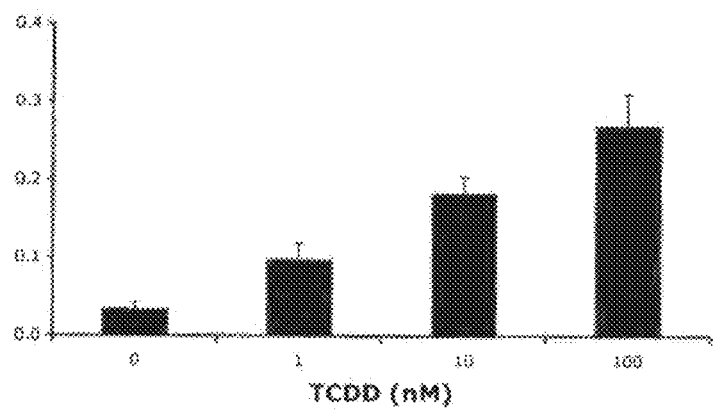
Figure 14
Figure 15A
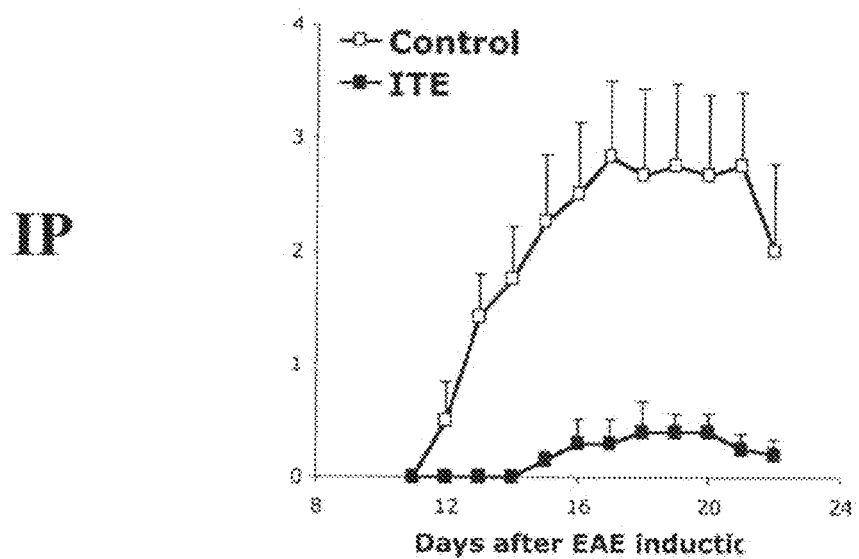
IP
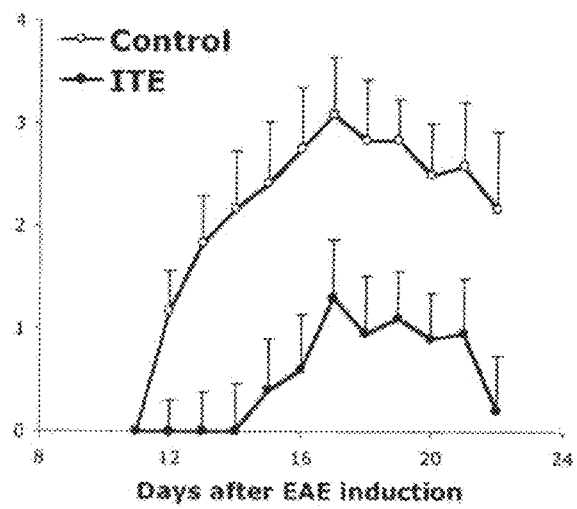
Oral
Figure 15B

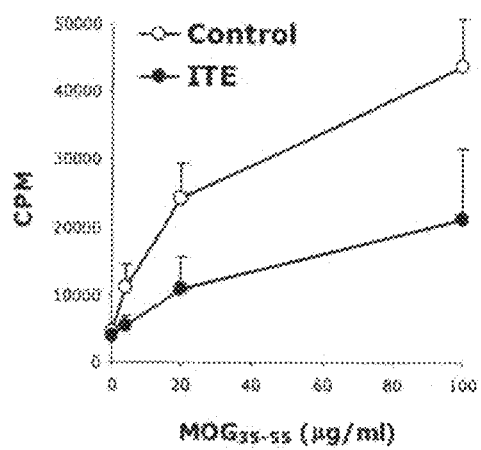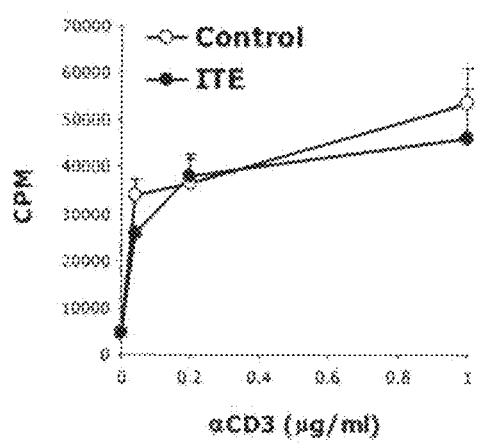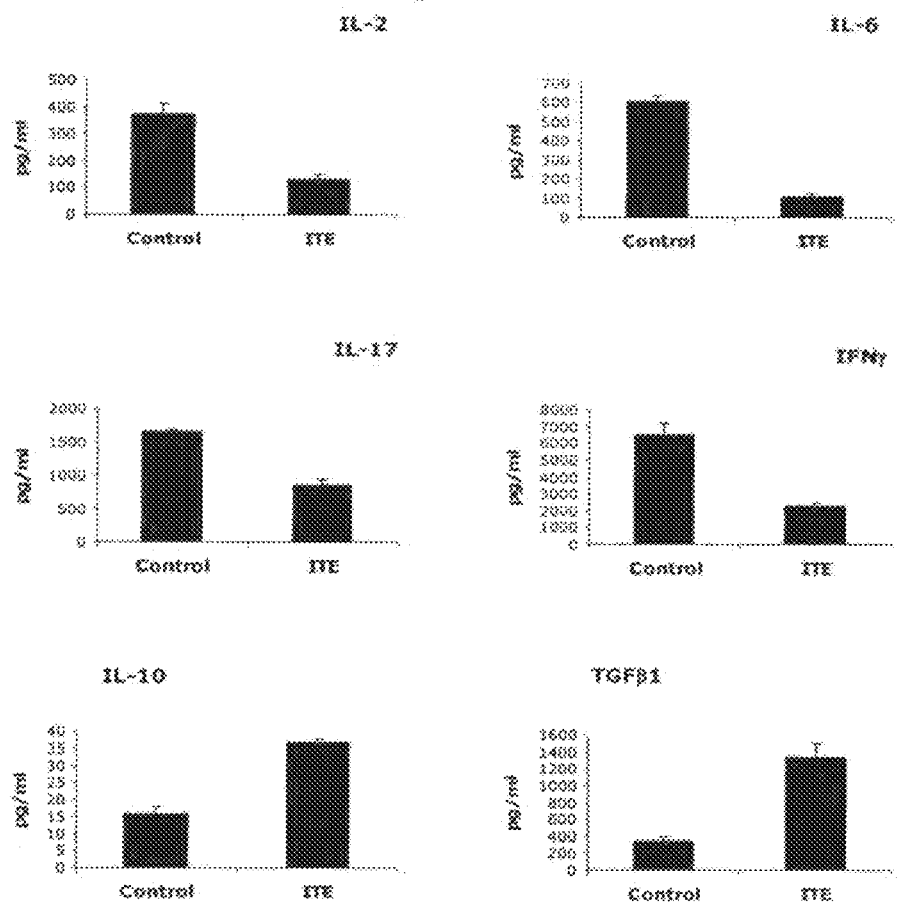

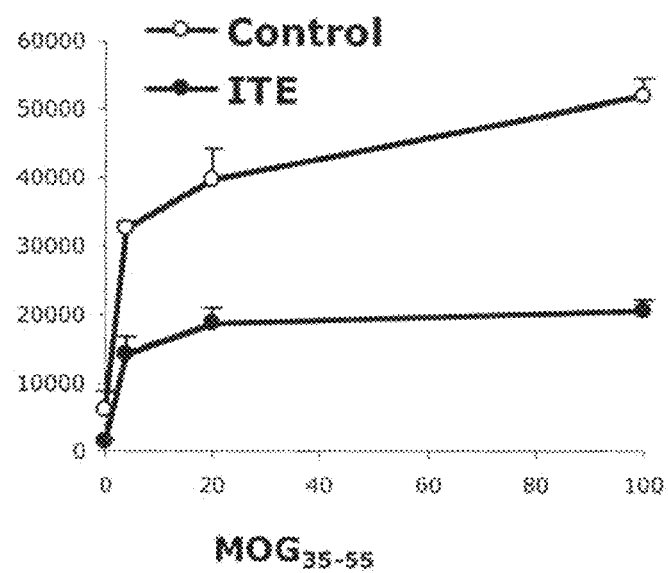
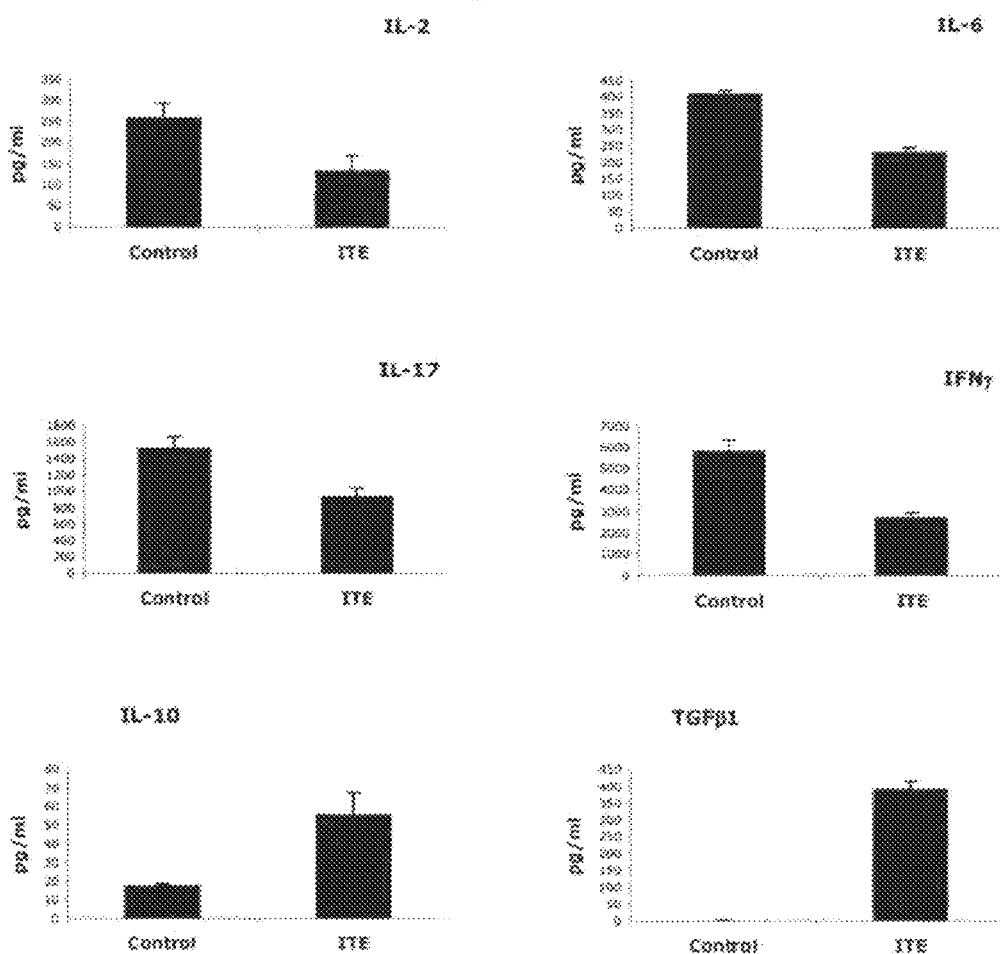

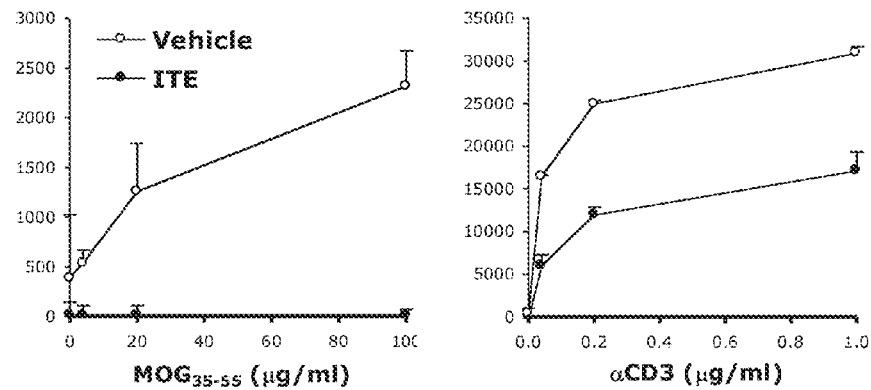
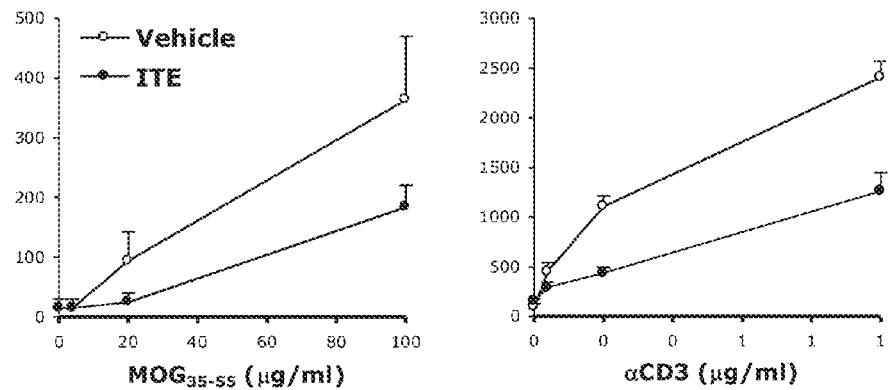
FIG. 24B

Control
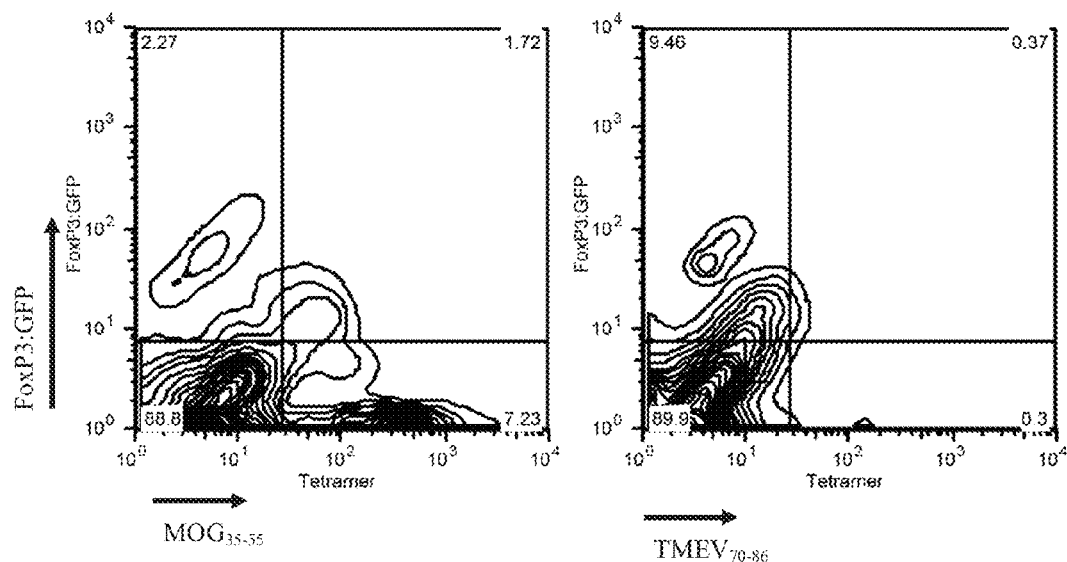
ITE
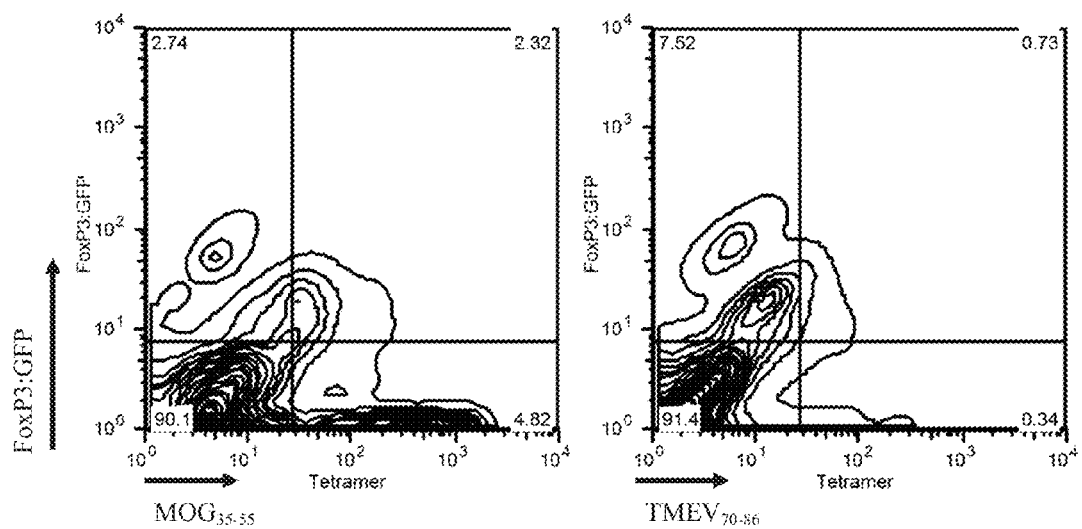
FIG. 25A

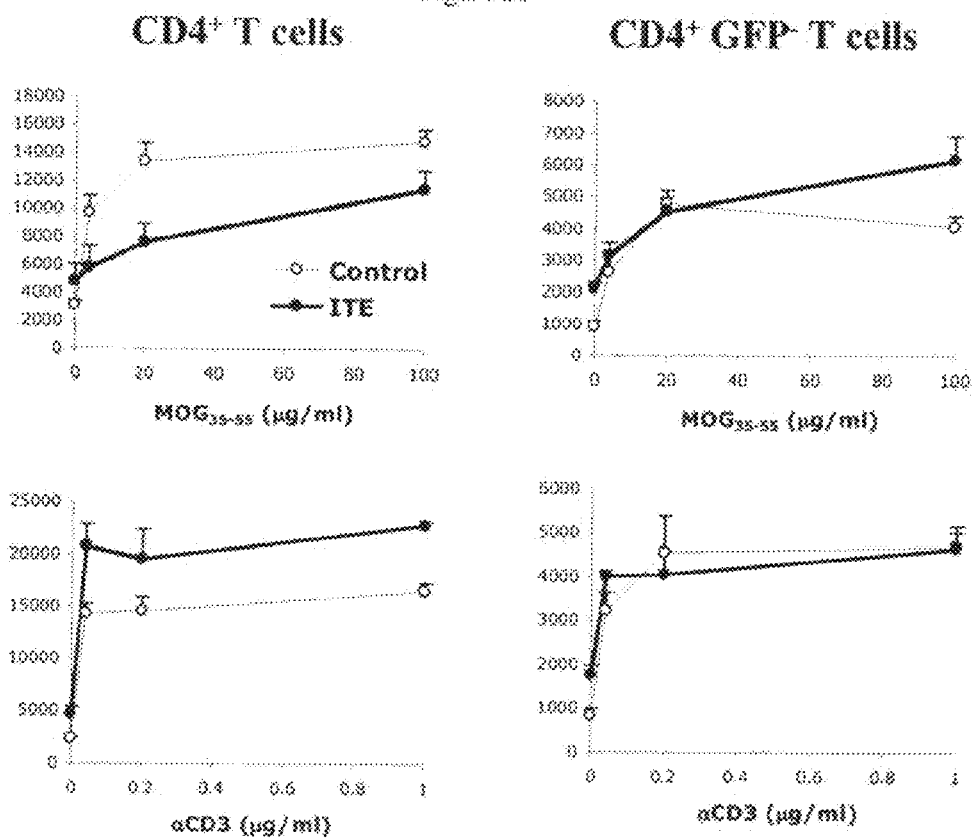
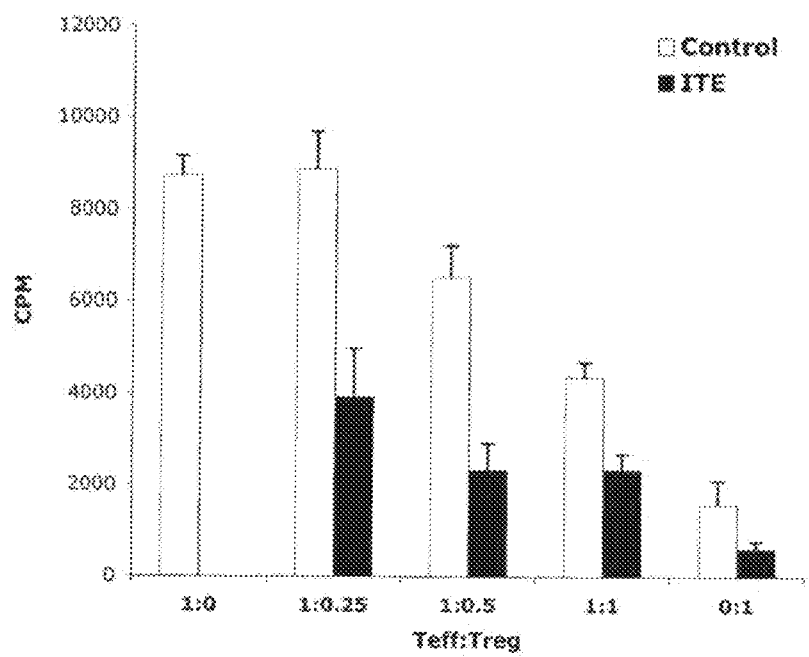

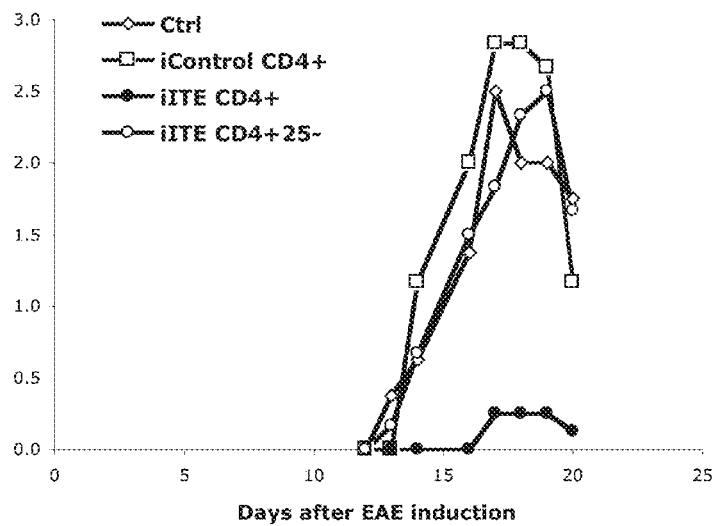
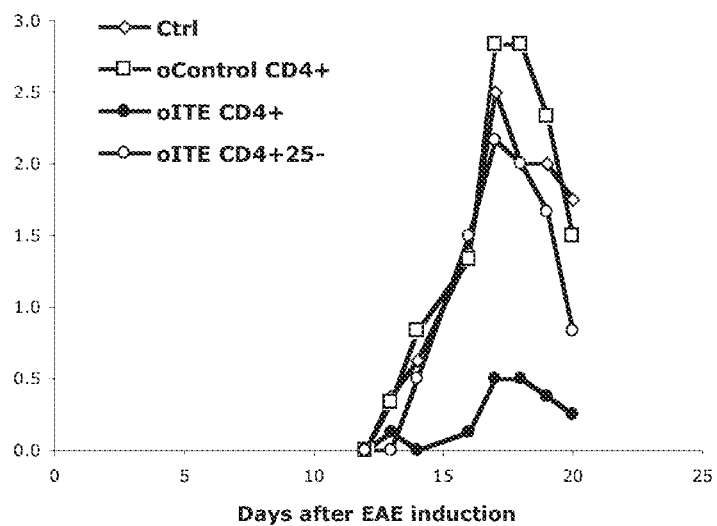
FIG. 28

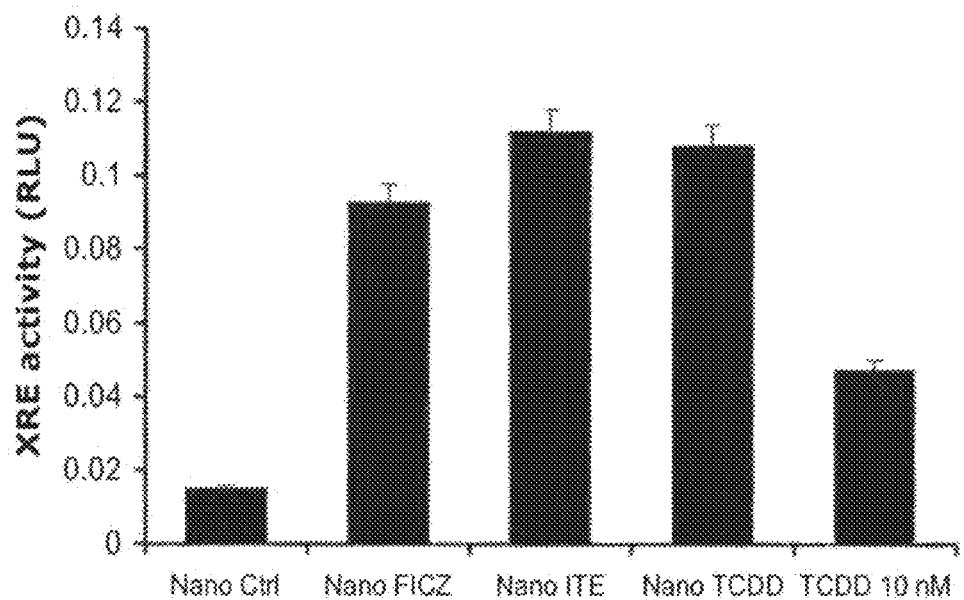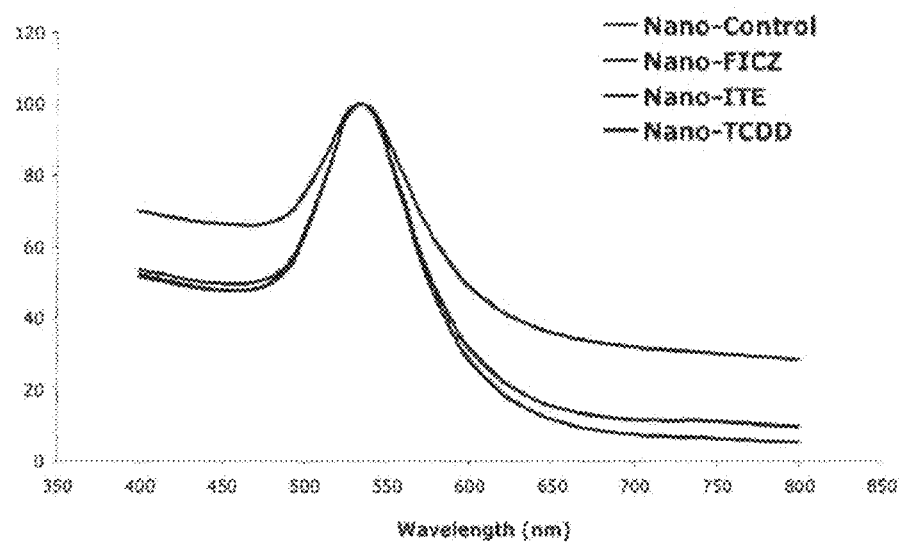
Figure 32

Figure 35B
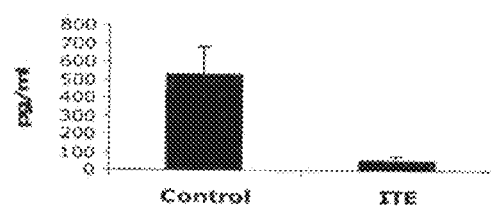
IL-6
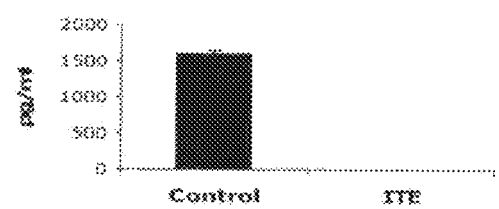
IL-17
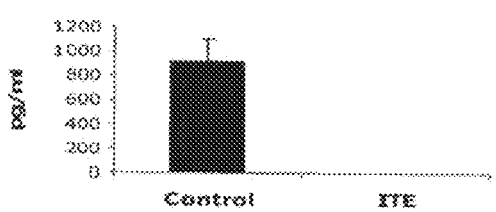
IL-22
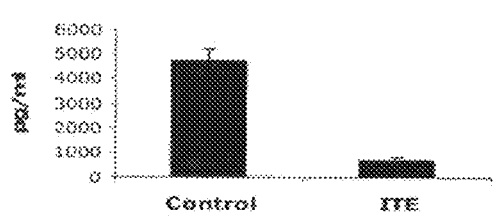
IFNγ
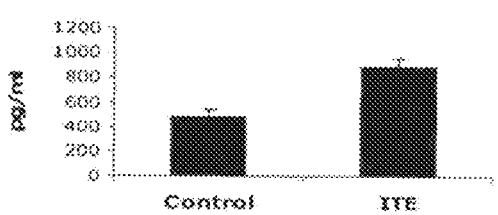
TGFβ1
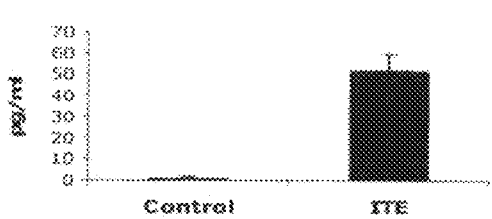
IL-10

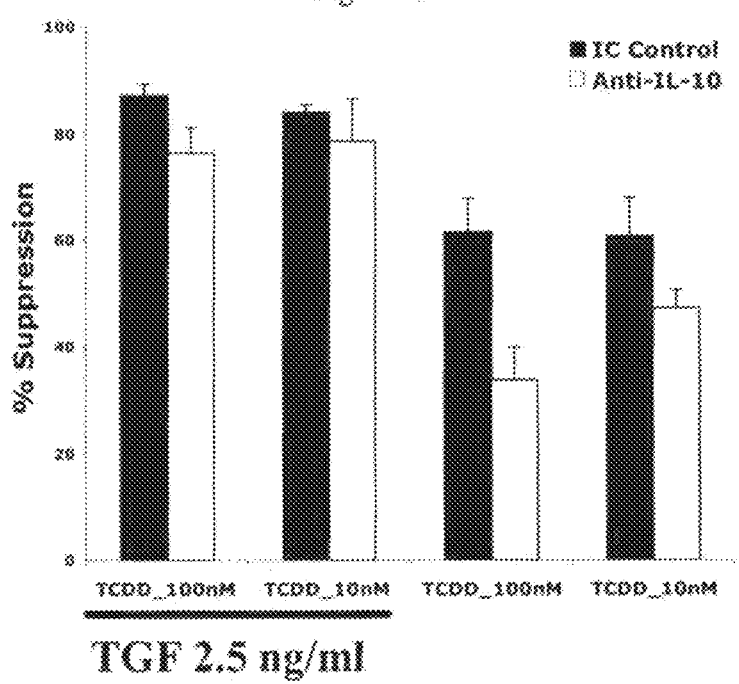

ature, and ƒICZ.In some embodiments, the composition also includes an

MODULATION OF THE IMMUNE RESPONSE

CLAIM OF PRIORITY

This application is a continuation of U.S. patent application Ser. No. 12/743,680, filed on Aug. 26, 2010, which is the national stage of International Application Number PCT/US2008/083016, filed on Nov. 10, 2008, and claims the benefit of U.S. Provisional Patent Application Serial Nos. 60/989,309, filed on Nov. 20, 2007, and 61/070,410, filed on Mar. 21, 2008, the entire contents of which are hereby incorporated by reference.

FEDERALLY SPONSORED RESEARCH OR DEVELOPMENT

This invention was made with Government support under Grant Nos. AI435801, AI043458, and NS38037 awarded by the National Institutes of Health. The Government has certain rights in the invention.

TECHNICAL FIELD

This invention relates to methods and compositions for increasing the number and/or activity of regulatory T cells (Tregs) in vivo and in vitro.

BACKGROUND

Regulatory T cells (Treg) control the autoreactive components of the immune system. Consequently, Treg dysfunction is linked to severe autoimmunity, and compounds that increase Treg numbers or activity are expected to be useful in the treatment of autoimmune disorders such as multiple sclerosis.

Treg cells are a specialized subset of T cells involved in the control of pathogenic autoimmunity (Sakaguchi et al., Ann. Rev Immunol., 22:531-562, 2004. The importance of Treg for immunoregulation is highlighted by the immune disorders that result from Treg depletion with antibodies (Sakaguchi et al., J. Immunol. 155, 1151-64 (1995)), as a result of the thymectomy of 3 day old newborns (Sakaguchi et al., J Exp Med. 156, 1565-76 (1982)); or treatment with diphtheria toxin in transgenic mice with a Treg-restricted expression of the diphtheria toxin receptor (Kim et al., Nat Immunol. 8, 191-7 (2007)). In addition, Treg deficiencies have been described in several autoimmune diseases such as multiple sclerosis (Viglietta et al., J. Exp. Med. 199, 971-9 (2004)), rheumatoid arthritis (Ehrenstein et al., J Exp Med. 200, 277-85 (2004)), diabetes (Brusko et al., Diabetes. 54, 1407-14 (2005); Lindley et al., Diabetes. 54, 92-9 (2005)), and lupus (Mudd et al., Scand. J. Immunol. 64(3):211-218 (2006)).

SUMMARY

The present invention is based, at least in part, on the discovery that transcription factors capable of modulating (e.g., increasing or decreasing) the expression and/or activity of the Foxp3 gene provide useful targets for therapeutic immunomodulation. Accordingly, the present invention provides, inter alia, compositions and methods for the prevention or treatment of diseases caused by an abnormal (e.g., autoimmune) or absent (e.g., including insufficient) immune response.

In one aspect, the present invention features compositions including a ligand that bids specifically to an aryl hydrocarbon receptor (AHR) transcription factor, lined to a biocompatible nanoparticle. The ligand can be, e.g., a small molecule that competes for binding to the AHR competitively with 2,3,7,8 tetrachlorodibenzo-p-dioxin (TCDD) and activates AHR-dependent signaling. In some embodiments, the ligand is 2,3,7,8 tetrachlorodibenzo-p-dioxin (TCDD), tryptamine (TA), 2-(1'H-indole-3'-carbonyl)-thiazole-4-carboxylic acid methyl ester (ITE), or 6-formylindolo[3,2-b]carbazole (FICZ).

In some embodiments, the composition also includes an inhibitor of degradation of the ligand, e.g., a monoamine oxidase inhibitor such as tranylcypromine. The inhibitor can be present on (i.e., linked to) the same nanoparticles, linked to different nanoparticles (of the same or different types) or free in solution. In some embodiments, the methods and compositions described herein include the use of a ligand that binds specifically to an aryl hydrocarbon receptor (AHR) transcription factor, and an inhibitor of degradation thereof, e.g., tryptamine and tranylcypromine, wherein neither is linked to a nanoparticle.

In some embodiments, the composition also includes an antibody that selectively binds to an antigen present on a T cell, a B cell, a dendritic cell, or a macrophage. The antibody can be present on (i.e., linked to) the same nanoparticles, linked to different nanoparticles (of the same or different types) or free in solution.

In a further aspect, the invention features methods for increasing the number or activity of CD4/CD25/Foxp3-expressing T regulatory (Treg) cells in a population of T cells. The methods include contacting the population of cells with a sufficient amount of a composition comprising one or more AHR ligands selected from the group consisting of 2,3,7,8 tetrachlorodibenzo-p-dioxin (TCDD), tryptamine (TA), and 2)-(1'H-indole-3'-carbonyl)-thiazole-4-carboxylic acid methyl ester (ITE), wherein the ligand is linked to a biocompatible nanoparticle, and optionally evaluating the presence and/or number of CD4/CD25/Foxp3-expressing cells in the population. The method results in an increase in the number and/or activity of regulatory T cells (Treg).

In some embodiments, the initial population of T cells includes one or both of naïve T cells or CD4$^+$ CD62 ligand$^+$ T cells. The population of T cells can be isolated, i.e., in vitro, or in a living mammalian subject, e.g., a subject who has an autoimmune disorder, e.g., multiple sclerosis. In embodiments where the T cells are in a living subject, the methods can include administering the one or more ligands orally, mucosally, or intravenously.

In some embodiments, Treg cells generated or activated using a method described herein are administered to a subject suffering from an autoimmune disorder, in an amount sufficient to improve or ameliorate a symptom of the disorder.

Also provided herein are methods for identifying candidate compounds that increase generation or activity of regulatory T cells (Treg). The methods include providing a cell expressing a reporter construct comprising a binding sequence for the Aryl Hyrocarbon Receptor (AHR) in a mammalian Foxp3 promoter sequence, wherein said binding sequence is operably linked to a reporter gene, for example a reporter gene selected from the group consisting of luciferase, green fluorescent protein, and variants thereof; contacting the cell with a test compound; and evaluating an effect of the test compound on expression of the reporter gene. A test compound that increases or decreases expression of the reporter gene is a candidate compound that modulates generation of Treg.

The methods can optionally include measuring expression of the reporter construct in the presence of a known AHR ligand selected from the group consisting of TCDD, tryptamine, and (ITE), or a compound that binds to the AHR competitively therewith; determining whether the candidate compound competes for binding to the AHR with the known compound; and selecting the candidate compound if it binds the AHR competitively with the known compound.

In one aspect, the present invention provides methods of identifying candidate compounds that modulate the generation of regulator T cells (Treg). These methods include providing a cell expressing a reporter construct containing a binding sequence for a transcription factor operably linked to a reporter gene. Suitable binding sequences for inclusion in the reporter construct include NKX22, AHR, EGR1, EGR2, EGR3, NGFIC, and Delta EFI. The cell is then contacted with a test compound, and the effect of the test compound on expression of the reporter gene is evaluated. A test compound that increases or decreases expression of the reporter gene is a candidate compound that modulates generation of Treg.

In another aspect, the present invention provides methods of identifying candidate compounds that modulate generation of regulator T cells (Treg). These methods include providing a living zebrafish, e.g., a zebrafish embryo, e.g., 30 minutes after the egg is laid; contacting the zebrafish with a test compound, e.g., by putting the test compound in water in which the zebrafish is living or microinjecting the compound into an embryo; and evaluating an effect of the test compound on Foxp3 expression in the zebrafish, wherein a test compound that increases or decreases expression of Fox-3 in the zebrafish is a candidate compound that modulates generation of Treg.

In a further aspect, the present invention provides compositions comprising transcription factor ligands capable of promoting increased expression, activity, or both of a Foxp3 gene.

In yet another aspect, the present invention provides methods for increasing the numbers of Treg in a population of T cells. These methods include contacting the cell with one or more transcription factor ligands, e.g., selected from the group consisting of 2,3,7,8 tetrachlorodibenzo-p-dioxin (TCDD), tryptamine (TA), and 2-(1'H-indole-3'-carbonyl)-thiazole-4-carboxylic acid methyl ester (ITE), wherein the method results in an increase in the number and/or activity of regulatory T cells (Treg). In some embodiments, the methods include determining levels of Foxp3 expression in the cells.

In an additional aspect, the resent invention provides methods for increasing the numbers of Treg in a patient. These methods include administering one or more transcription factor ligands to a patient selected for treatment, e.g., 2,3,7,8 tetrachlorodibenzo-p-dioxin (TCDD), tryptamine (TA), and/or 2-(1'-indole-3'-carbonyl)-thiazole-4-carboxylic acid methyl ester (ITE), wherein the method results in an increase in the number and/or activity of regulatory T cells (Treg).

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient of the symptoms, that can be attributed to or associated with treatment by the compositions and methods of the present invention.

The terms "effective amount" and "effective to treat," as used herein, refer to am amount or a concentration of one or more of the compositions described herein utilized for a period of time (including acute or chronic administration and periodic or continuous administration) that is effective within the context of its administration for causing an intended effect or physiological outcome.

The terms "patient" is used throughout the specification to describe an animal, human or non-human, rodent or non-rodent, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical patients include humans, farm animals, and domestic pets such as cats and dogs.

The term gene, as used herein refers to an isolated or purified gene. The terms "isolated" or "purified," when applied to a nucleic acid molecule or gene, includes nucleic acid molecules that are separated from other materials, including other nucleic acids, which are present in the natural source of the nucleic acid molecule. An "isolated" nucleic acid molecule, such as an mRNA or cDNA molecule, can be substantially free of other cellular material, or culture medium when produced by recombinant techniques, or substantially free of chemical precursors or other chemicals when chemically synthesized.

An "isolated" or "purified" polypeptide, peptide, or protein is substantially free of cellular material or other contaminating proteins from the cell or tissue source from which the protein is derived, or substantially free from chemical precursors or other chemicals when chemically synthesized. "Substantially free" means that the preparation of a selected protein has less than about 30%, (e.g., less than 20%, 10%, or 5%) by dry weight, or non-selected protein or of chemical precursors. Such a non-selected protein is also referred to herein as "contamination protein". When the isolated therapeutic proteins, peptides, or polypeptides are predominantly produced, it can be substantially free of culture medium, i.e., culture medium represents less than about 20%, (e.g., less than about 10% or 5%) of the volume of the protein preparation. The invention includes isolated or purified preparations of at least 0.01, 0.1, 1.0, and 10 milligrams in dry weight.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1G is a raidal gene tree showing the Foxp1, Foxp2, Foxp3 and Foxp4 proteins in mammals and fish, where the Ciona intestinalis Foxp sequence is the outgroup. The branch lengths are proportional to the distance between the sequences. Mm, Mus musculus; Hs, Homo sapiens; Dr, Danio rerio; Ga, Gasterosteus aculeatus (stickleback); Ci, Ciona intestinalis.

FIG. 2A is a pair of bar graphs of 293T cells co-transfected with reporter constructs coding for luciferase under the control of a NF-kB or NFAT responsive promoters, and p65 NF-kB (top graph) or NFAT (Bottom graph) in the presence of vectors coding for zFoxp3, Foxp3 or control (empty vector). Luciferase activity was normalized to the renilla activity of a co-transfected control (mean+s.d. of triplicates).

FIGS. 2D(i)-(iii) and 2E(i)-(iii) are bar graphs of MACS-purified $CD4^+ CD25^+$ T-cells transduced with a bicistronic retrovirus coding for GFP and zFoxp3, Foxp3 or an empty control retrovirus. The $GFP^+$ population was analyzed for its proliferation, IL-2 and IFNg secretion upon activation with plate bound antibodies to CD3 (mean cpm or pg/ml+s.d. in triplicate wells) and (e) its suppressive activity on the proliferation and IL-2 and IFNg secretion of mouse $CD4^+ CD25^+$ T-cells activated with plate-bound antibodies to CD3 (mean cpm or pg/ml+s.d. in triplicate wells).

FIG. 3A is a bar graph of expression of zFoxP3 determined by real time PCR in zebrafish monocytes, lymphocytes and erythrocytes sorted by FACS (mean+s.d. of triplicates).

FIG. 3B is a list of conserved AHR biding site (CABS) on zebrafish, human and mouse Foxp3 sequence indicated and highlighted in yellow.

FIG. 3C is a pair of bar graphs of FoxP3 (left) and AHR (right) expression in FACS sorted $CD4^+Foxp3:GFP^+$ and $CD4^+Foxp3:GFP^-$ T cells as measured by real time PCR (mean+s.d. of triplicates normalized to GAPDH expression).

FIG. 3I Sequences corresponding to non-evolutionary conserved AHR-binding sites (NCABS)-1, -2 and -3.

FIG. 3J is a schematic representation of the foxp3 gene. Arrows indicate location of PCR primers used in ChIP assays, exons are depicted in red, with their number indicated below them.

FIG. 3K is a bar graph of activation of the transcription of Renilla luciferase-tagged foxp3 (BACFoxp3:Ren) by expression in EL-4 cells of mouse AHR or a constitutively activated TGFβ receptor II Renilla activity was normalized to the luciferase activity of a co-transfected control (mean+s.d. of triplicates).

FIG. 3L is a bar graph of ChIP analysis of the interaction of AHR with NCABS and CABS in foxp3 and cypIa1 in CD4+ T cells treated with TCDD. (c) AHR, CYPIA1 and Foxp3 expression measured by real time PCR on CD4+Foxp3:GFP− T cells (GFP−), CD4+Foxp3:GFP+ Treg (GFP+) and CD4+ Foxp3:GFP+ Treg treated with resveratrol for 5 h (GFP+ +R) (mean+s.d. of triplicates normalized to GAPDH expression).

FIGS. 4E(i)-(iii) are bar graphs of cytokine secretion (expressed as pg/ml) triggered by $MOG_{35-55}$ in lymph node cells taken from TCDD or control treated animals 10 days after immunization with $MOG_{35-55}$/CFA.

FIGS. 4F(i)-(iii) are bar graphs of cytokine secretion (expressed as pg/ml) triggered by $MOG_{35-55}$ in lymph node cells taken from TCDD or control treated animals 10 days after immunization with $MOG_{35-55}$/CFA.

FIGS. 4F(i)-(ii) are bar graphs showing the decreased frequency of $CD4^+IL17^+$ and $CD4^+IFNg^+$ T cells associated to the inhibition of EAE by AHR activation with TCDD. Draining lymph node cells were isolated from TCDD or control treated mice 10 days after immunization with $MOG_{35-55}$/CFA, activated with $MOG_{35-55}$, and stained for intracellular Foxp3, IL-17 or IFNg. Data represent the mean percentage of cytokine$^+$ cells within the effector $CD4^+Foxp3^-$ T cell population+s.d., five mice were included per group. *P<0.04, unpaired t-test.

FIGS. 8A-E show an increase in FOXP3 (8A) and NKX2.2 (8B), and a decrease in EGR1 (8C), EGR2 (8D), and EGR3 (8E) in transfected cells. FIGS. 9A-D show an increase in NKX2.2, and a decrease in EGR1, EGR2, and EGR3 expression in Foxp3 transfected cells at days 3 and 6.

FIG. 10 is a list of the binding sites of NKX22, EGR1, EGR2, EGR3, NGFIC and Delta EF1 is the mouse Foxp3 gene, relative to the numbering of the gene as shown in GenBank Acc. No. NT_039700.6.

FIGS. 11A-G are a list of all the AHR binding sites on the mouse Foxp3 gene, GenBank Acc. No. NT_039700.6.

FIGS. 12A-F is the genomic sequence of the zebrafish Foxp3, NW_644989.1.

FIG. 13 is a bar graph showing the effect of the monoamine oxidase inhibitor Tranylcypromine on the suppression of EAE by TA. C57BL/6 mice (4-7/group) were treated with TA or TA and Tranylcypromine (INH), EAE was induced and the mice were monitored for the development of EAE.

FIG. 14 is a bar graph of the expression of a *renilla*-tagged mouse foxp3 locus on zebrafish embryos in the presence of increasing amounts of TCDD.

FIGS. 15A-B are bar graphs of IP- and oral-ITE suppression of EAE. EAE was induced in B6 mice (n=10), the mice were treated daily with ITE (200 µg/mouse) or vehicle administered orally or intraperitoneally, and the mice were scored for EAE development on daily basis.

FIGS. 22A and B are line graphs showing the ZIP-ITE suppresses the recall response to MOG. EAE was induced in B6 mice (n=3), the mice were treated with ITE or vehicle, and the recall response to MOG$_{35-55}$ (22A) or αCD3 (22B) on splenocytes was analyzed at day 17 after EAE induction.

FIG. 22 is a set of six bar graphs of cytokine expression in the same cells as in 22A and B.

FIGS. 23A and B are a line graph (23A) and a set of six bar graphs (23B) showing that IP-ITE interferes with the generation of T$_H$1 and T$_H$17 cells. EAE was induced in B6 mice (n=3), the mice were treated with ITE or vehicle, and the induction of T$_H$1 and T$_H$17 cells was followed at day 17 after EAE induction by FACS and by ELISA.

FIG. 26 is a set of four line graphs showing that IP-ITE suppresses the CD4+ T cell response to MOG$_{35-55}$. FoxP3$^{gfp}$ mice (n=3) were immunized with MOG$_{35-55}$ and treated with ITE or vehicle, and the recall response of sorted T cell populations was analyzed at day 10 after immunization.

FIG. 28 is a pair of line graphs showing that CD4$^+$ T cells can transfer the protection against EAE induced by IP and oral-ITE. T cells were sorted out from EAE B6 mice treated with vehicle or ITE on day 20 after disease induction, 3 million cells were transferred to naïve B6 mice (n=5) and EAE wad induced in the recipients 2 days after the cell transfer.

FIG. 32 is a pair of graphs showing the functionality of gold nanoparticles containing AHR-ligands. Nanoparticles were evaluated for their ability to activate the luciferase activity of an AHR reporter cell line.

FIG. 35B shows the cytokine response in the same cells.

FIG. 42 is a bar graph showing the suppressive activity of human CD4$^+$ CD25$^{High}$ T cells induced with TCDD is dependent on IL-10. CD4$^+$ CD62L$^+$ CD45RO$^-$ T cells were isolated by FACS and differentiated in vitro for 5 days with antibodies to CD3 and CD28 in the presence of TCDD or TFGβ1 2.5 ng/ml or both, and after re-purification by FACS, CD4$^+$ CD25$^{High}$ T cells were assayed for their suppressive activity on on-treated effector T cells activated with antibodies to CD28 and CD3 in the presence of blocking antibodies to IL-10.

DETAILED DESCRIPTION

Figure 1A:
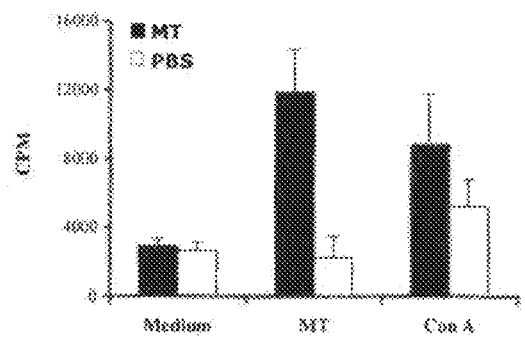
FIG. 1A is a bar graph of proliferative response to MT or ConA of splenocytes from six-month old zebrafish, 14 days after immunization with MT or PBS in IFA. Results are presented as the mean cpm+s.d. of triplicates.

Because of the importance of the central role Tregs play in immunomodulation, characterization of the pathways and identification of compounds capable of modulating these pathways, e.g., to promote the generation (e.g., differentiation of cells to or toward) Treg cells or that promote increased activity of Tregs is important for the treatment of, e.g., autoimmunity, infections and cancer.

The present invention provides, inter alia, compositions and methods useful for therapeutic immunomodulation.

Accordingly, the present invention is based, at least in part, on the discovery that modulation of the AhR by compounds described herein can be used to modulate (e.g., increase or decrease the number and/or activity of) immunomodulatory cells in vitro and in vivo.

In some embodiments, the present invention is based on the identification of the ligand-activated transcription factor aryl hydrocarbon receptor (AHR) as a Foxp3 dependent regulator of Treg differentiation (e.g., generation) and/or activity in vitro and in vivo. Also described herein are ligands of a transcription factor (e.g., AHR) that cause increased Treg expression and/or activity. More specifically, the data presented herein demonstrates the use of AHR-specific ligands, e.g., the high affinity AHR ligand 2,3,7,8-tetrachlorodibenzo-p-dioxin (TCDD), tryptamine (TA), and/or 2-(1'H-indole-3'-carbonyl)-thiazole-4-carboxylic acid methyl ester (ITE), to promote an increase in the number and/or activity of Treg immunomodulatory cells, which will be useful to suppress the immune response in the treatment of diseases or disorders caused by an abnormal (e.g., an excessive, elevated, or inappropriate) immune response, e.g., an autoimmune disease or disorder. Surprisingly, effective doses of TCDD can be administered intravenously or orally.

Other potentially useful AHR transcription factor ligands are described in Denison and Nagy, Ann. Rev. Pharmacol. Toxicol., 43:309-34, 2003, and references cited herein, all of which are incorporated herein in their entirety. Other such molecules include planar, hydrophobic HAHs (such as the polyhalogenated dibenzopdioxins, dibenzofurans, and biphenyls) and PAHs (such as 3-methylcholanthrene, benzo(a)pyrene, benzanthracenes, and benzoflavones), and related compounds. (Denison and Nagy, 2003, supra). Nagy et al., Toxicol. Sci. 65:200-10 (2002), described a high-throughput screen useful for identifying and confirming other ligands. See also Nagy et al., Biochem. 41:861-68 (2022). In some embodiments, those ligands useful in the present invention are those that bind competitively with TCDD, TA, and/or ITE.

In some embodiments, the present invention provides methods useful for identifying transcription factors (e.g., ligand-activated transcription factors) and/or ligands (e.g., ligands capable of promoting an increased association between a ligand-activated transcription factor and Foxp3) capable of modulating (e.g., increasing or decreasing) Foxp3 expression or activity.

Therapeutic Sequences

As sated above, the present invention includes the identification of specific transcription factor binding sites in the Foxp3 gene. These binding sites include, i.e., NKX22, AHR, EGR1, EGR2, EGR3, NGFIC, and Delta EF1. As described herein, manipulating activity and/or levels of those TFs can alter expression of Foxp3, and thus modulate (e.g., promote) generation and/or increased activity of Treg in vivo and in vitro. Compounds that modulate the activity and/or levels of those TFs to increase generation and/or activity of Treg are useful, e.g., in the treatment of disorders in which it is desirable to decrease an aberrant immune response, e.g., autoimmune diseases.

Sequences useful in the methods described herein include, but are not limited to, e.g., NKX22, AHR, EGR1, EGR2, EGR3, NGFIC and Delta EF1 sequences, and TF binding sequences therefore, all of which are known in the rt. In some embodiments the methods include the use of nucleic acids or polypeptides that are at least 80% identical to a human NKX22, AHR, EGR1, EGR2, EGR3, NGFIC, or Delta EF1 sequence, e.g., at least 80%, 85%, 90%, or 95% identical to a human sequence as described herein.

To determine the percent identity of two sequences, the sequences are aligned for optimal comparison purposes (e.g., gaps can be introduce din one or both of a first and a second amino acid or nucleic acid sequence for optimal alignment and non-homologous sequences can be disregarded for comparison purposes). The length of a reference sequence aligned for comparison purposes is at least 60%. e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In the present methods, the percent identity between two amino acid sequences is determined using the Needleman and Wunsch ((1970) J. Mol. Biol. 48:444-453) algorithm which has been incorporated into the GAP program in the GCG software package (available on the world wide web at gcg.com), using a Blossum 62 scoring matrix with a gap penalty of 12, a gap extend penalty of 4, and a frameshift gap penalty of 5.

Active fragments of TFs useful in the methods described herein are those fragments that bind to the same DNA sequence (e.g., promoter sequence) that the full-length TF binds to, and has at least 30% of the transcription initiating activity of the full-length TF, e.g., at least 40%, 50%, 60%, 70%, 80%, 90% or more of the activity of the full-length protein, on the same promoters and the same genes as the full-length protein.

Foxp3

At least in some species, Treg differentiation and function is driven by the transcription factor Foxp3 (Fontenot et al., Nat. Immunol., 4:330-336, 2003; Hori et al., Science, 299: 1057-61, 2003). Foxp3 may also be important for human Treg; mutations in Foxp3 have been linked to various immunological conditions (e.g., autoimmune conditions), for example, autoimmune syndrome immune dysregulation, polyendocrinopathy, and enteropathy X-linked (IPEX) (Chatila et al., J. Clin. Invest., 106:R75-81 (2000); Gavin et al., Proc. Natl. Acad. Sci. U.S.A., 103: 6659-64 (2006)). In humans, Foxp3-negative Tregs have also been described, see, e.g., Roncarolo and Gregori, Eur J Immunol. 38, 925 (2008).

Exemplary human Foxp3 mRNA sequences are known in the art and include Genbank Acc. No. NM_014009.2; the amino acid sequence of the protein is Genbank Acc. No. NP_054728.2. The sequence of the human Foxp3 gene can be found at NC_000023.9; the mouse gene is at NT_039700.6. The Foxp3 promoter has been identified and sequenced, see, e.g., Mantel et al., J. Immunol. 176 (6): 3593 (2006). All of the binding sites for AHR in the mouse Foxp3 gene are highlighted, e.g., in FIGS. 11A-G; the binding sites for the other TFs are identified in FIGS. 10A-B.

Transcription Factors that Increase Transcription of Foxp3

As described herein, NKX22, AHR, and Delta EF1 increase transcription of Foxp3. Therefore, compounds that increase levels and/or activity of these TFs would increase the generation and/or activity of Treg. Conversely, compounds that decrease levels and/or activity of these TFs would be expected to decrease generation of Tregs, thereby increasing the immune response.

AHR

Exemplary human AhR mRNA sequences are known in the art and include Genbank Acc. No. NM_001621.3; the amino acid sequence of the protein is Genbank Acc. No. NP_0014612.1. Active fragments of AhR are DNA binding fragments with transcription activity, and contain at least one PAS region, e.g., amino acids 122-224 or 282-381 of NP_001612.1. Consensus recognition sequences that bind AhR include the sequence TNGCGTG.

DeltaEF1

Exemplary human Delta EF1 mRNA sequences are known in the art and include Genbank Acc. No. NM_030751.3; the amino acid sequence of the protein is Genbank Acc. No. NP_110378.2. Consensus recognition sequences that bind DeltaEF1 include the sequences CACCT and CACCTG (Sekido et al., Genes Cells 2:7771-783 (1997).

NKX2.2

Exemplary human NKX2.2 mRNA sequences are known in the art and include Genbank Acc. No. NM_00250902; the amino acid sequence of the protein is Genbank Acc. No. NP_002500.1 Consensus recognition sequences that bind NKX2.2 include the sequences ACTTGAT and T(T/C)AAGT (A/G)(C/G)TT (Watada et al., Proc. Natl. Acad. Sci. U.S.A. 97(17):9443-9448 (2000))

Transcription Factors that Decrease Transcription of Foxp3

As described herein, EGR1, EGR2, EGR3, and NGFIC (EGR4) decrease transcription of Foxp3. Therefore, compounds that increase levels and/or activity of these TFs would decrease generation of Treg, thereby increasing the immune response. Conversely, compounds that decrease levels and/or activity of these TFs would be expected to increase generation of Tregs, reducing the immune response.

EGR1

The sequence of human egr1 protein is available in the GenBank database at Accession No. NP_001955.1; the mRNA is at Accession No. NM_001964.2. Additional information regarding egr1 can be found on the internet at ncbi.nlm.nih.gov, in the UniGene database at UniGene Hs.326035, and in the Entrez Gene database at GeneID: 1958. Consensus recognition sequences that bind EGR1 include the sequence 5'GCG(G/T)GGGCG3' (Nakagama et al., Mol. Cell. Biol., 15 (3):1489-1498 (1995).

Active fragments of egr1 include those portions of the protein that bind DNA, e.g., one or more of the two C2H2 type DNA-binding zinc fingers (see, e.g., Sukhatme et al., 1988, supra), e.g., amino acids 338-362 and/or 368-390 of GenBank Acc. No. NP_001655.1. Exemplary active fragments are described in Huang et al., Cancer Res. 1995; 55(21): 50545062, and in Jain et al., J. Biol. Chem. 1996; 271(23): 13530-6.

Inhibitors of egr-1 are described in WO2007/118157.

EGR2

The sequence of human egr2 protein is available in the GenBank database at Accession No. NP_000390.2; the mRNA is at Accession No. NM_000399.2.

Consensus recognition sequences that bind EGR2 include the sequences GCGGGGGCG and T-G-C-G-T/g-G/A-G-G-C/a/t-G-G/T (lowercase letters indicate bases selected less frequently) (Swirnoff and Milbrandt, Mol. Cell. Biol. 15:2275-2287 (1995)).

EGR3

The sequence of human egr3 protein is available in the GenBank database at Accession No. NP_004421.2; the mRNA is at Accession No. NM_004430.2. The gen Consensus recognition sequences that bind EGR3 include the sequences GCGGGGGCG and T-G-C-G-T/g-G/A-G-G-C/a/t-G-G/T (lowercase letters indicate bases selected less frequently) (Swirnoff and Milbrandt, Mol. Cell. Biol. 15:2275-2287 (1995)).

NGFIC (EGR4)

Exemplary human NGFIC mRNA sequences are known in the art and include Genbank Acc. No. NM_001965.2; the amino acid sequence of the protein is Genbank Acc. No. NP_001956.2. See Crosby et al., Mol. Cell Biol. 11(8):3835-41 (1991).

Consensus recognition sequences that bind NGFIC include the sequences GCGGGGGCG and T-G-C-G-T/g-G/A-G-G-C/a/t-G-G/T (lowercase letters indicate bases selected less frequently) (Swirnoff and Milbrandt, Mol. Cell. Biol. 15:2275-2287 (1995)).

Methods of Identifying Compounds that Modulate Expression, Levels or Activity of One or More of NKX22, AHR, EGR1, EGR2, EGR3, NGFIC and Delta EF1

A number of methods are known in the art for evaluating whether a compound alters expression, levels or activity of one or more of NKX22, AHR, EGR1, EGR2, EGR3, NGFIC, and/or Delta EF1.

Methods of assessing expression are well known in the art and include, but are not limited to, Northern analysis, ribonuclease protection assay, reverse transcription-polymerase chain reaction (RT-PCR), real time PCR, and RNA in situ hybridization (see, e.g., Sambrook et al., *Molecular Cloning: A Laboratory Manual*, 3$^{rd}$ Ed., Cold Spring Harbor Laboratory Press (200)). Levels of peptides can be monitored by, e.g., Western analysis, immunoassay, or in situ hybridization. Activity, e.g., altered promoter binding and/or transcription activity, can be determined by e.g., electrophoretic mobility shift assay, DNA footprinting, reporter gene assay, or a serine, threonine, or tyrosine phosphorylation assay. In some embodiments, the effect of a test compound on expression, level or activity is observed as a change in glucose tolerance or insulin secretion of the cell, cell extract, co-culture, explant, or subject. In some embodiments, the effect of a test compound on expression, level, or activity of one or more of NKX22, AHR, EGR1, EGR2, EGR3, NGFIC, and/or Delta EF1, is evaluated in transgenic cell or non-human animal, or explant, tissue, or cell derived therefrom, having altered glucose tolerance or insulin secretion, and can be compared to a control, e.g., wild-type animal, or explant or cell derived therefrom.

The effect of a test compound on expression, level, or activity can be evaluated in a cell, e.g., a cultured mammalian cell, a pancreatic beta cell, cell lysate, or subject, e.g., a non-human experimental mammal such as a rodent, e.g., a rat, mouse, or rabbit, or a cell, tissue, or organ explant, e.g., pancreas or pancreatic cells.

In some embodiments, the ability of a test compound to modulate level, expression or activity of one or more of NKX22, AHR, EGR1, EGR2, EGR3, NGFIC and/or Delta EF1 is evaluated in a knockout animal, or other animal having decreased expression, level, or activity of one or more of NKX22, AHR, EGR1, EGR2, EGR3, NGFIC and/or Delta EF1 conditional knockout transgenic animal.

In some embodiments, the ability of a test compound to modulate, e.g., increase or decrease, e.g., permanently or temporarily, expression from one or more of NKX22, AHR, EGR1, EGR2, EGR3, NGFIC, and/or Delta EF1 promoter can be evaluated by e.g., a routine reporter (e.g., LacZ or GFP) transcription assay. For example, a cell or transgenic animal whose genome includes a reporter gene operably linked to an NKX22, AHR, EGR1, EGR2, EGR3, NGFIC, and/or Delta EF1 promoter can be contacted with a test compound; the ability of the test compound to increase or decrease the activity of the reporter gene or gene product is indicative of the ability of the compound to modulate expression of the TF. In another example, a cell or transgenic animal whose genome includes a reporter gene operably linked to a promoter comprising a recognition sequence for one of those TFs, e.g., all or a portion of the Foxp3 promoter comprising recognition sequences for one of those TFs, can be contacted with a test compound; the ability of the test compound to increase or decrease the activity of the reporter gene or gene product is indicative of the ability of the compound to modulate activity of the TF.

The test compound can be administered to a cell, cell extract, explant, or subject (e.g., an experimental animal) expressing a transgene comprising an NKX22, AHR, EGR1, EGR2, EGR3, NGFIC, and/or Delta EF1 promoter or recognition sequence fused to a reporter such as GFP or LacZ (see, e.g., Nehls et al., Science, 272:886-889 (1996), and Lee et al., Dev. Biol., 208:362-374 (1999), describing placing the beta-galactosidase reporter gene under control of the whn promoter). Enhancement or inhibition of transcription of a transgene, e.g., a reporter such as LacZ or GFP, as a result of an effect of the test compound on the promoter or factors regulating transcription from the promoter, can be used to assay an effect of the test compound on transcription of one or more of the TFs identified herein. Reporter transcript levels, and this promoter activity, can also be monitored by other known methods, e.g., Northern analysis, ribonuclease protection assay, reverse transcription-polymerase chain reaction (RT-PCR) or RNA in situ hybridization (see, e.g., Cuncliffe et al., Mamm. Genome, 13:245-252 (2002); Sambrook et al., *Molecular Cloning: A Laboratory Manual*, 3$^{rd}$ Ed., Cold Spring Harbor Laboratory Press (2001). Test compounds can also be evaluated using a cell-free system, e.g., an environment including a promoter-reporter transgene (e.g., an ARNT promoter-LacZ transgene), transcription factors binding the promoter, a crude cell lysate or nuclear extract, and one or more test compounds (e.g., a test compound as described herein), wherein an effect of the compound on promoter activity is detected as a color change.

In one embodiment, the screening methods described herein include the use of a chromatin immunoprecipitation (ChIP) assay, in which cells, e.g., pancreatic beta cells, expressing one or more of the TFs identified herein, are exposed to a test compound. The cells are optionally subjected to crosslinking, e.g., using UV or formaldehyde, to form DNA-protein complexes, and the DNA is fragmented. The DNA-protein complexes are immunoprecipitated, e.g., using an antibody directed to one or more of the TFs identified herein. The protein is removed (e.g., by enzymatic digestion) and analyzed, e.g., using a microarray. In this way, changes in binding of the transcription factor to its target genes can be evaluated, thus providing a measure of activity of the TFs identified herein.

Test Compounds

Test compounds for use in the methods described herein are not limited and can include crude or partially or substantially purified extracts of organic sources, e.g., botanical (e.g., herbal) and algal extracts, inorganic elements or compounds, as well as partially or substantially purified or synthetic compounds, e.g., small molecules, polypeptides, antibodies, and polynucleotides, and libraries thereof.

A test compound that has been screened by a method described herein and determined to increase expression, levels, or activity of one or more of the TFs described herein can be considered a candidate compound for the treatment of a disorder treatable with immune therapy (i.e., by increasing or decreasing control of the immune response by increasing or decreasing levels of Treg), e.g., cancer, or an autoimmune disorder. A candidate compound that has been screened, e.g., in an in vivo model of a disorder treatable with immune therapy, e.g., cancer, or an autoimmune disorder, and determined to have a desirable effect on the disorder, e.g., on one or more symptoms of the disorder, can be considered a candidate therapeutic agent. Candidate therapeutic agents, once screened and verified in a clinical setting, are therapeutic agents. Candidate therapeutic agents and therapeutic agents can be optionally optimized and/or derivatized, and formulated with physiologically acceptable excipients to form pharmaceutical compositions.

Methods of Treatment

As described above, the present invention is based, at least in part, on the identification of useful targets for therapeutic immunomodulation. Accordingly, the present invention provides compositions and methods for treating a patient (e.g., a human) with an immunological condition. Immunological conditions that will benefit from treatment using the present invention include those diseases or disorders caused by an autoimmune response or an absent or insufficient immune response.

Autoimmunity

Autoimmunity is presently the most common cause of disease in the world and is the third most prevent disease in the U.S. Autoimmune conditions that may benefit from treatment using the compositions and methods described herein include, but are not limited to, for example, Addison's Disease, alopecia, ankylosing spondylitis, autiphospholipid syndrome, autoimmune hemolytic anemia, autoimmune hepatitis, autoimmune oophoritis, Bechet's disease, bullous permphigoid, celica disease, chronic fatigue immune dysfunction syndrome (CFIDS), chronic inflammatory demyelinating polyneuropathy, Churg-Strauss syndrome, cicatricial pemphigoid, cold agglutinin disease, CREST Syndrome, Crohn's disease, diabetes (e.g., type I), dysautonomia, endometriosis, eosinophilia-myalgia syndrome, essential mixed cryoglubulinemia, fibromyalgia, syndrome/fibromyositis, Graves' disease, Guillain Barré syndrome, Hashimoto's thyroiditis, idiopathic pulmonary fibrosis, idiopathic thrombocytopenia purpura (ITP), inflammatory bowel disease (IBD), lichen planus, lupus, Ménière's disease, mixed connective tissue disease (MCTD), multiple sclerosis, myasthenia gravis, pemphigus, pernicious anemia, polyarteritis nodosa, polychondritis, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, spondyloarthropathy, stiff-man syndrome, Takayasu arteritis, temporal arteritis/giant cell arteritis, thyroid disease, ulcerative colitis, uveitis, vaculitis, vitiligo, and Wegener's granulomatosis.

As described herein, a patient with one or more autoimmune conditions can be treated by increasing the number of Treg cells and/or the activity of Treg cells in the patient using, e.g., a therapeutically effective amount of one or more transcription factors (e.g., a ligand-activated transcription factor such as AHR) and/or one or more transcription factor ligands (e.g., TCDD, tryptamine (TA), and/or 2-(1'H-indole-3'-carbonyl)-thiazole-4-carboxylic acid methyl ester (ITE)) that are capable of promoting an increase in the expression and/or activity of Foxp3, and thereby promoting an increase in the number or activity of Treg cells in vitro and/or in vivo.

In some embodiments, the methods include administering (e.g., to a population of T cells or to a subject) a composition comprising a nucleic acid encoding a transcription factory as described herein, e.g., e.g., NKX22, AHR, EGR1, EGR2, EGR3, NGFIC, and/or Delta EF1. The nucleic acid can be in an expression vector, e.g., a modified viral vector such as is known in the art, e.g., a lentivirus, retrovirus, or adenovirus. Methods for using these vectors in cell or gene therapy protocols are known in the art. For cell therapy methods, it is desirable to start with a population of T cells taken from the subject to be treated.

In some embodiments, the methods include administering a composition comprising a ligand that activates a transcription factor described herein, e.g., the AHR receptor. In some embodiments, the ligand is co-administered with one or more inhibitors of its degradation, e.g., tryptamine together with a monoamine oxidase inhibitor, e.g., tranylcypromine. The inhibitor can be administered in the same or in a separate composition. Thus the invention also includes compositions comprising tryptamine and an inhibitor of its degradation, e.g., a MAOI, e.g., tranylcypromine.

In some embodiments, a patient in need of treatment can be administered a pharmaceutically effective dose of one or more ligands capable of promoting an increase in the expression and/or activity of Foxp3 and thereby promoting an increase in the number or activity of Treg cells in Vitro and/or in vivo (e.g., TCDD, tryptamine (TA), and/or 2-(1'H-indole-3'-carbonyl-thiazole-4-carboxylic acid methyl ester (ITE)).

Alternatively or in addition, a population of cells capable of differentiation into Treg cells (e.g., naïve T cells and/or CD4$^+$ CD62 ligand$^+$ T cells) can be contacted with a transcription factor ligand capable of promoting increase in Foxp3 expression and/or activity (e.g., TCDD, tryptamine (TA), and/or 2-(1'H-indole-3'-carbonyl)-thiazole-4-carboxylic acid methyl ester (ITE)) in vitro, thereby effectively promoting an increase in the number of Treg cells in the population. Alternatively or in addition, a population of cells containing Treg cells (e.g., isolated Treg cells (e.g., 100%) or a population of cells containing at least 20, 30, 40, 50, 60, 70, 80, 90, 95, or 99% Treg cells) can be contacted with a transcription factor ligand capable of promoting an increase in Foxp3 expression and/or activity (e.g., TCDD, tryptamine (TA), and/or 2-indole-3'-carbonyl-thiazole-4-carboxylic acid methyl ester (ITE)), thereby effectively promoting an increase in the activity of the Treg cells in the population. Alternatively or in addition, the cells can be contacted with an expression vector, e.g., a viral vector such as a lentivirus, retrovirus, or adenovirus, comprising a nucleic acid encoding a transcription factor described herein, e.g., NKX22, AHR, EGR1, EGR2, EGR3, NGFIC, and Delta EF1. In some embodiments, the cells are also activated, e.g., by contacting them with an effective amount of a T cell activating agent, e.g., a composition of one or both of anti-CD3 antibodies and anti-CD28 antibodies. One or more cells from these populations can then be administered to the patient alone or in combination with one or more ligands capable of promoting an increase in the expression and/or activity of Foxp3 and thereby promoting an increase in the number or activity of Treg cells in vitro and/or in vivo (e.g., TCDD, tryptamine (TA), and/or 2-(1'H-indole-3'-carbonyl-thiazole-4-carboxylic acid methyl ester (ITE).

Patient Selection

The compositions and methods described herein are of particular use for treating a patient (e.g., a human) that would benefit from therapeutic immunomodulation (e.g., a patient in need of a suppressed immune response). The methods include selecting a patient in need of treatment and administering to the patient one or more of the compositions described herein. A subject in need of treatment can be identified, e.g., by their medical practitioner.

In some embodiments, the methods include determining presence and/or levels of autoantibodies to an autoantigen specific for the disease, e.g., the presence and/or levels of autoantibodies to an autoantigen listed in Table 1 or 2. The results can be used to determine a subject's likelihood or risk of developing the disease; subjects can be selected for treatment using a method described herein based on the presence and/or levels of autoantibodies.

Validation of Treatment/Monitoring Treatment Efficacy

During and/or following treatment, a patient can be assessed at one or more time points, for example, using methods known in the art for assessing severity of the specific autoimmune disease or its symptoms, to determine the effectiveness of the treatment. In some embodiments, levels of autoantibodies to an autoantigen specific for the disease can also be monitored, e.g., levels of autoantibodies to an autoantigen listed in Table 1 or 2; a decrease (e.g., a significant decrease) in levels of autoantibodies would indicate a positive response, i.e., indicating that the treatment is successful; see, e.g., Quintana et al., Proc. Natl. Acad. Sci. U.S.A., 101(suppl. 2):1465-14621 (2004). Treatment can then be continued without modification, modified to improve the progress or outcome (e.g., increase dosage levels, frequency of administration, the amount of the pharmaceutical composition, and/or change the mode of administration), or stopped.

Administration

A therapeutically effective amount of one or more of the compositions described herein can be administered by standard methods, for example, by one or more routes of administration, e.g., by one or more of the routes of administration currently approved by the United States Food and Drug Administration (FDA; see, for example world wide web address fda.gov/cder/dsm/DRG/drg00301.htm), e.g., orally, topically, mucosally, intravenously or intramuscularly.

In some embodiments, one or more of the ligands described herein can be administered orally with surprising effectiveness.

Pharmaceutical Formulations

A therapeutically effective amount of one or more of the compositions (e.g., including, but not limited to, one or more of the small molecule ligands, for example TCDD, tryptamine (TA), and/or 2-(1'H-indole-3'-carbonyl-thiazole-4-carboxylic acid methyl ester(ITE)) described herein can be incorporated into pharmaceutical compositions suitable for administration to a subject, e.g., a human. Such compositions typically include the composition and a pharmaceutically acceptable carrier. As used herein the language "pharmaceutically acceptable carrier" is intended to include any and all solvents, dispersion media, coating, antibacterial and antifungal agents, isotonic and absorption delaying agents, and the like, compatible with pharmaceutical administration. The use of such media and agents for pharmaceutically active substances are know. Except insofar as any conventional media or agent is incompatible with the active compound, such media can be used in the compositions of the invention. Supplementary active compounds can also be incorporated into the compositions, e.g., an inhibitor of degradation of the ligand.

In some embodiments, the composition can also include an autoantigen, e.g., an autoantigen listed in Table 1 or 2, or another autoantigen known in the art to be associated with an autoimmune disease.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BSAF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms to be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible biding agents, and/or adjuvant materials can be included as part of the composition. The tablets, pills, capsules, troches and the like can contain any of the following ingredients, or compounds of a similar nature: a binder such as microcrystalline cellulose, gun tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery system. Biodegradable, biocompatible polymers can be used, such as ethylene vinyl acetate, polyanhydrides, polyglycolic acid, collage, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Nucleic acid molecules can be inserted into vectors and used as gene therapy vectors. Gene therapy vectors can be delivered to a subject by, for example, intravenous injection, local administration (see U.S. Pat. No. 5,328,470) or by sterotactic injection (see e.g., Chen et al., PNAS 91:3054-3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be include in a container, pack, or dispenser together with instructions for administration. In one aspect, the pharmaceutical compositions can be included as a part of a kit.

Generally the dosage used to administer a pharmaceutical compositions facilitates an intended purpose for prophylaxis and/or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if require, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

AHR Ligand-Nanoparticles

As demonstrated herein, compositions comprising nanoparticles linked to AHR ligands are surprisingly effective in delivering the ligand, both orally and by injection, and in inducing the Treg response in living animals. Thus, the invention further includes compositions comprising AHR ligands linked to biocompatible nanoparticles, optionally with antibodies that target the nanoparticles to selected cells or tissues.

AHR Transcription Factor Ligands

AHR-specific ligands, e.g., the high affinity AHR ligand 2,3,7,8-tetrachloro-dibenzo-p-dioxin (TCDD), tryptamine (TA), and/or 2-(1'H-indole-3'-carbonyl-thiazole-4-carboxylic acid methyl ester (ITE), promote an increase in the number and/or activity of Treg immunomodulatory cells, which will be useful to suppress the immune response in the treatment of diseases or disorders cause by an abnormal (e.g., an excessive, elevated, or inappropriate) immune response, e.g., an autoimmune disease or disorder.

Other potentially useful AHR transcription factor ligands are described in Denison and Nagy, Ann. Rev. Pharmacol. Toxicol., 43:309-34, 2003, and references cited herein, all of which are incorporated herein in their entirety. Other such molecules include planar, hydrophobic HAHs (such as the polyhalogenated dibenzopdioxins, dibenzofurans, and biphenyls) and PAHs (such as 3-methylcholanthrene, benzo(a)pyrene, benzanthracenes, and bensoflavones), and related compounds. (Denison and Nagy, 2003, supra). Nagy et al., Toxicol, Sci. 65:200-10 (2002), described a high-throughput screen useful for identifying and confirming other ligands. See also Nagy et al., Biochem. 41:861-68 (2002). In some embodiments, those ligands useful in the nanoparticle compositions are those that bind competitively with TCDD, TA, and/or ITE.

Biocompatible Nanoparticles

The nanoparticles useful in the methods and compositions described herein are made of materials that are (i) biocompatible, i.e., do not cause a significant adverse reaction in a living animal when use din pharmaceutically relevant amounts; (ii) feature functional groups to which the binding moiety can be covalently attached, (iii) exhibit low non-specific binding of interactive moieties to the nanoparticle, and (iv) are stable in solution, i.e., the nanoparticles do not precipitate. The nanoparticles can be monodisperse (a single crystal of a material, e.g., a metal, per nanoparticle) or polydisperse (a plurality of crystals, e.g., 2, 3, or 4, per nanoparticle).

A number of biocompatible nanoparticles are known in the art, e.g., organic or inorganic nanoparticles. Liposomes, dendrimers, carbon nanomaterials and polymeric micelles are examples of organic nanoparticles. Quantum dots can also be used. Inorganic nanoparticles include metallic nanoparticle, e.g., Au, Ni, Pt and $TiO_2$ nanoparticles. Magnetic nanoparticles can also be used, e.g., spherical nanocrystals of 10-20 nm with a $Fe^{2+}$ and/or $FE^{3+}$ core surrounded by dextran or PEG molecules. in some embodiments, colloidal gold nanoparticles are used, e.g., as described in Qian et al., Nat. Biotechnol. 26(1):83-90 (2008); U.S. Pat. Nos. 7,060,121; 7,232, 474; and U.S. P.G. Pub. No. 2008/0166706. Suitable nanoparticles, and methods for constructing and using multifunctional nanoparticles, are discussed in e.g., Sanvicens and Marco, Trends Biotech., 26(8): 425-433 (2008).

In all embodiments, the nanoparticles are attached (linked) to the AHR ligands described herein via a functional groups. In some embodiments, the nanoparticles are associated with a polymer that includes the functional groups, and also serves to keep the metal oxides dispersed from each other. The polymer can be a synthetic polymer such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxymethyl dextran, and/or reduced carboxymethyl dextran. The metal oxide can be a collection of one or more crystals that contact each other, or that tare individually entrapped or surrounded by the polymer.

In other embodiments, the nanoparticles are associated with non-polymeric functional group compositions. Methods are known to synthesize stabilized, functionalized nanoparticles without associated polymers, which are also within the scope of this invention. Such methods are described, for example, in Halbreich, et al., Biochimie, 80 (5-6):379-90, 1998.

In some embodiments, the nanoparticles have an overall size of less than about 1-100 nm, e.g., about 25-75 nm, e.g., about 40-60 nm, or about 50-60 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 60 nm.

Synthesis of Nanoparticles

There are varieties of ways that the nanoparticles can be prepared, but in all methods, the result must be a nanoparticle with functional groups that can be used to link the nanoparticle to be binding moiety.

For example, AHR ligands can be linked to the metal oxide through covalent attachment to a functionalized polymer or to non-polymeric surface-functionalized metal oxides. In the latter method, the nanoparticles can be synthesized according to a version of the method of Albrecht et al., Biochimie, 80 (5-6): 379-90, 1998. Dimercapto-succinic acid is coupled to the nanoparticle and provides a carboxyl functional group. By functionalized is meant the presence of amino or carboxyl or other reactive groups that can be used to attach desired moieties to the nanoparticles, e.g., the AHR ligands described herein or antibodies.

In another embodiment, the AHR ligands are attached to the nanoparticles via a functionalized polymer associated with the nanoparticle. In some embodiments, the polymer is hydrophilic. In a specific embodiment, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles. Methods for synthesizing functionalized, coated nanoparticles are discussed in further detail below.

Carboxy functionalized nanoparticles can be made, for example, according to the method of Gorman (see WO 00/61191). Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be treated with periodate to form aldehyde groups. The aldehyde-containing nanoparticles can then be reacted with diamine (e.g., ethylene diamine or hexanediamine), which will form a Schiff base, followed by reduction with sodium borohydride or sodium cyanoborohydride.

Dextran-coated nanoparticles can also be made and crosslinked, e.g., with epichlorohydrin. The addition of ammonia will react with epoxy groups to generate amine groups, see Hogemann et al., Bioconjug. Chem. 2000. 11(6):941-6, and Josephson et al., Bioconjug. Chem., 1999, 10(2):186-91.

Carboxy-functionalized nanoparticles can be converted to amino-functionalized magnetic particles by the use of watersoluble carbodiimides and diamines such as ethylene diamine or hexane diamine.

Avidin or streptavidin can be attached to nanoparticles for use with a biotinylated binding moiety, such as an oligonucleotide or polypeptide. See e.g., Shen et al., Bioconjug. Chem., 1996, 7(3):311-6. Similarly, biotin can be attached to a nanoparticle for use with an avidin-labeled binding moiety.

In all of these methods, low molecular weight compounds can be separated from the nanoparticles by ultra-filtration, dialysis, magnetic separation, or other means. The unreacted AHR ligands can be separated from the ligand-nanoparticle conjugates, e.g., by size exclusion chromatography.

In some embodiments, colloidal gold nanoparticles are made using methods known in the art, e.g., as described in Qian et al., Nat. Biotechnol. 26(1):83-90 (2008): U.S. Pat Nos. 7,060,597; 7,232,474; and U.S. P.G. Pub. 2008/0166706.

In some embodiments, the nanoparticles are pegylated, e.g., as described in U.S. Pat. Nos. 7,291,684; 5,145,684; 6,270,806; 7,348,030, and others.

Antibodies

In some embodiments, the nanoparticles also include antibodies to selectively target a cell. The term "antibody," as used herein, refers to full-length, tow-chain immunoglobulin molecules and antigen-binding portions and fragments thereof, including synthetic variants. A typical full-length antibody includes two heavy (H) chain variable regions (abbreviated herein as VH), and two light (L) chain variable regions (abbreviated herein as VL). The term "antigen-binding fragment" of an antibody, as used herein, refers to one or more fragments of a full-length antibody that retain the ability to specifically bind to a target. Examples of antigen-binding fragments include, but are not limited to: (i) a Fab fragment, a monovalent fragment consisting of the VL, VH, CL and CH1 domains, (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1998); and Huston et al. Proc. Natl. Acad. Sci. USA 85:5879-5883 (1988)). Such single chain antibodies are also encompassed within the term "antigen-binding fragment."

Production of antibodies and antibody fragments is well documented in the field. See, e.g., Harlow and Lane 1998. *Antibodies, A Laboratory Manual*. Cold Spring Harbor, New York: Cold Spring Harbor Laboratory. For example, Jones et al., Nature 321: 522-525 (1986), which discloses replacing the CDRs of a human antibody with those from a mouse antibody. Marx, Science 229:455-456 (1985), discusses chimeric antibodies having mouse variable regions and human constant regions. Rodwell, Nature 342-99-100 (1989), discusses lower molecular weight recognition elements derived from antibody CDR information. Clackson, Br. J. Rheumatol. 3052: 36-39 (1991), discusses genetically engineered monoclonal antibodies, including Fv fragment derivatives, single chain antibodies, fusion proteins chimeric antibodies and humanized rodent antibodies. Reichman et al., Nature 332: 323-327 (1988) discloses a human antibody on which rat hypervariable regions have been grafted. Verhoeyen, et al., Science 239: 1534-1536 (1988), teaches grafting of a mouse antigen binding site onto a human antibody.

In the methods described herein, it would be desirable to target the compounds to T cells, B cells, dendritic cells, and/or macrophages, therefore antibodies selective for one or more of those cell types can be used. For example, for T cells, anti-CXCR4, anti-CD28, anti-CD8, anti-TTLA4, or anti-CD3 antibodies can be used; for B cells, antibodies to CD20, CD19, or to B-cell receptors can be used; for dendritic cell targeting, exemplary antibodies to CD11c, DEC205, MHC class I or class II, CD80, or CD86 can be used; for macrophages, exemplary antibodies to CD11b, MHC class I or class II, CD80, or CD86 can be used. Other suitable antibodies are known in the art.

Kits

The present invention also includes kits. In some embodiments the kit comprise one or more doses of a composition described herein. The composition, shape, and type of dosage form for the induction regiment and maintenance regimen may vary depending on a patients requirements. For example, dosage form may be a parenteral dosage form, an oral dosage form, a delayed or controlled release dosage form, a topical, and a mucosal dosage form, including any combination thereof.

In a particular embodiment, a kit can contain one or more of the following in a package or container: (1) one or more doses of a composition described herein; (2) one or more pharmaceutically acceptable adjuvants or excipients (e.g., a pharmaceutically acceptable salt, solvate, hydrate, stereoisomer, and clathrate); (3) one or more vehicles for administration of the dose; (5) instructions for administration. Embodiments in which two or more, including all, of the components (1)-(5), are found in the same container can also be used.

When a kit is supplied, the different components of the compositions include can be packaged in separate containers and admixed immediately before use. Such packaging of the components separately can permit long term storage without loosing the active components' functions. When more than one bioactive agent is included in a particular kit, the bioactive agents may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally reserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents. Exemplary containers may include, without limitation, test tubes, vials, flasks, bottles, syringes, and the like.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on a internet web site or may be distributed to the user as an electronic mail.

EXAMPLES

The invention is further described in the following examples, which do not limit the scope of the invention described in the claims.

Example 1

Cloning and Characterization of Zebrafish Foxp3

The zebrafish is an experimental model of vertebrate development; as described herein, it can also be used as an immunogenic model. This example describes the cloning and characterize of the zebrafish (*Danio rerio*) functional homologue of mammalian Foxp3 (herein termed zFoxp3).

Identification of zFoxp3

Figure 1B:
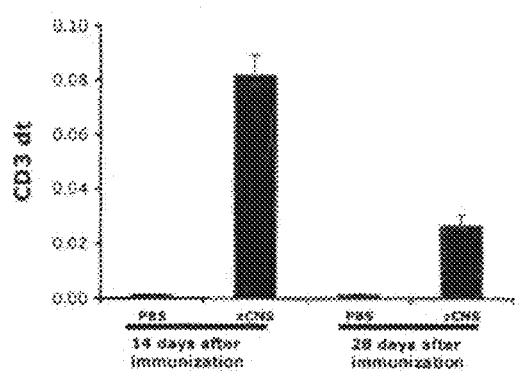
FIG. 1B-1D are bar graphs of expression of CD3 (1B), IL-17 (1C) and IFNg (1D) in six month old zebrafish 14 or 28 days after immunization with zebrafish brain homogenate (zCNS) or PBS in CFA, as measured by real time PCR (mean+s.d. of triplicates).
Figure 1C:
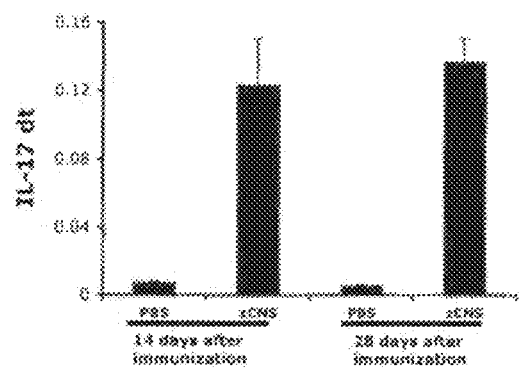
Figure 1D:
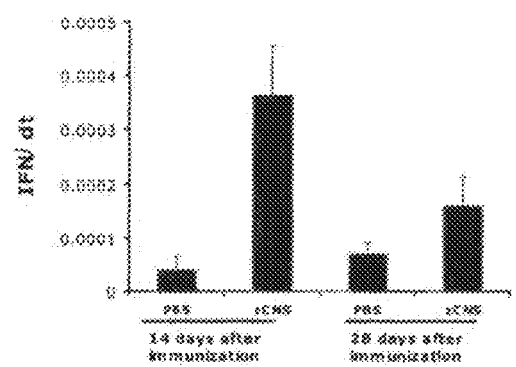
Figure 1F:
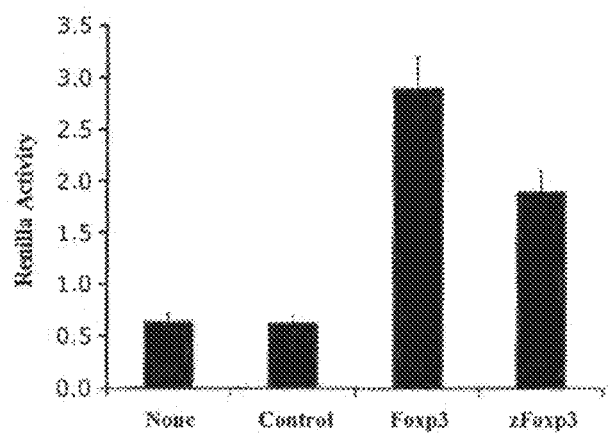
FIG. 1F is a bar graph of zFoxp3 expression in 293T cells cotransfected with constructs coding for His-labeled zFoxp3 and Renilla-labeled Foxp3. The results are normalized for the total amount of luciferase before precipitation (mean+s.d. of triplicates).
Figure 1E:
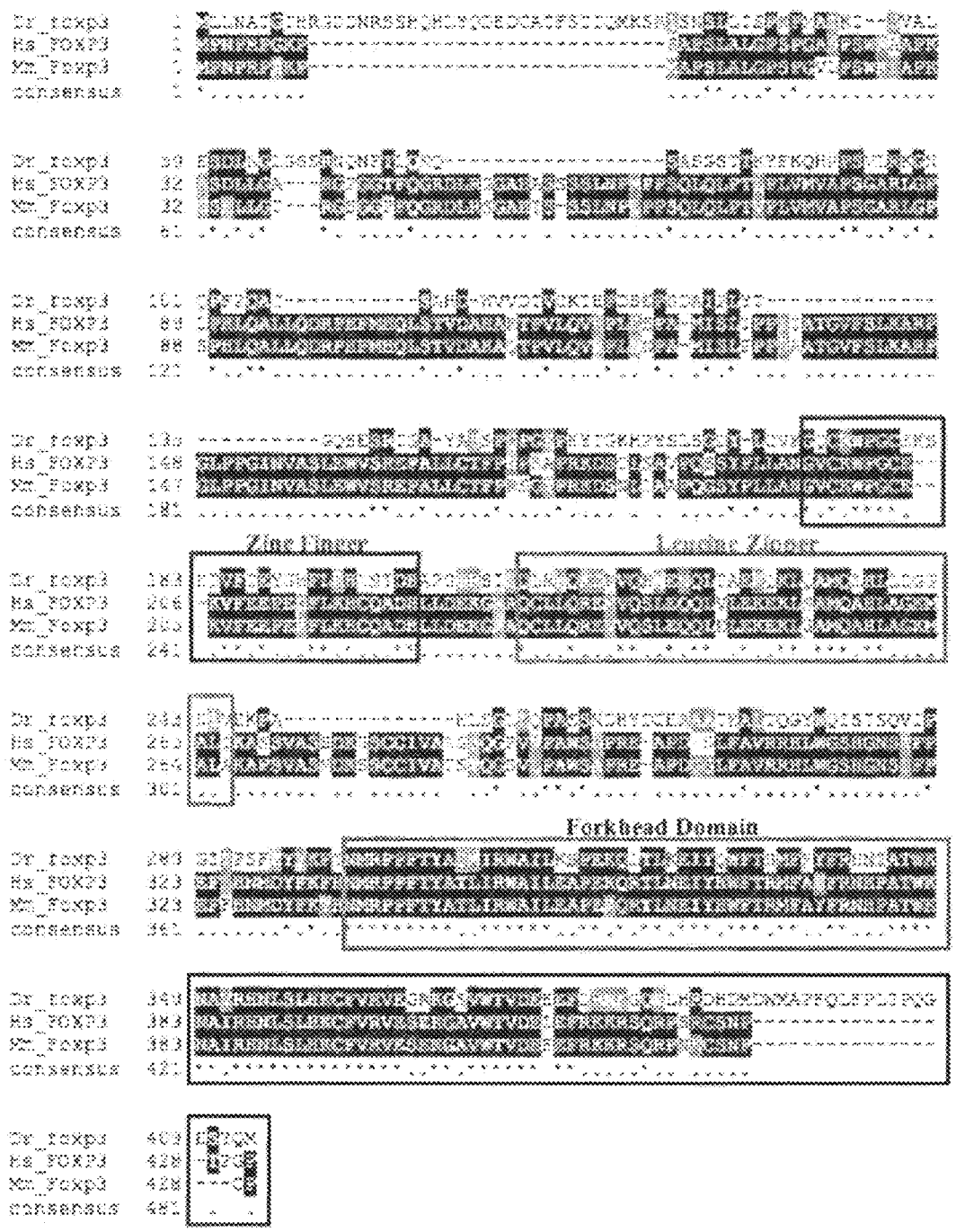
FIG. 1E is a sequence comparison of putative FoxP3 genes of zebrafish, human and mouse. The stars indicate identity, dashes were introduced for optimal alignment. The zinc finger, leucine zipper and forkhead domains are highlighted with a blue, green or red box, respectively.

To investigate whether Foxp3-dependent immunoregulatory mechanisms operate in the zebrafish, we searched the zebrafish genome for a Foxp3 homologue, which we termed zFoxp3 (FIG. 1E). A phylogenetic analysis placed zFoxp3 in a sub-tree together with mammalian and other fish orthologous predictions, suggesting that zFoxp3 is the zebrafish ortholog for mammalian Foxp3 (FIG. 1F). In mammals Foxp3 is located in a well-conserved synteny block. Indeed, we found several orthologous genes between mammalian chromosome X and zebrafish chromosome 8 in the region where zFoxp3 is located (suv39h1, cacna1s, tspy12, wasp), strengthening the likelihood of zFoxp3 being the fish ortholog of Foxp3.

The accession numbers for the amino acid sequences use din the gene tree analysis are as follows: *Danio rerio* Foxp1a Q08BX8 BC124513; Foxp1b Q2LE08 NM_001039637; Foxp2 Q4JNX5 NM_001030082; Foxp3 annotated (EST CK028390); Foxp4 annotated. *Homo sapiens*: Foxp1 Q9H334 NM_001012505, Foxp2 O15409 NM_148899, Foxp3 Q9BZS1 NM_014009, Foxp4 Q8IVH2 NM_138457; *Mus musculus:* Foxp1 P58462 NM_053202, Foxp2 P58463 NM_053242, Foxp3 Q99JB6 NM_054039, Foxp4 Q9DBY0 NM_028757; *Ciona intestinalis* Foxp Q4H3H6. The amino acid sequence of the apparent stickleback orthologues of Foxp1, Foxp2, Foxp3 and Foxp4 were obtained from Ensembl.

Cloning zFoxp3 zFoxp3 was cloned from cDNA prepared from zebrafish kidney by using a TOPO® PCR cloning kit (Invitrogen, CA, USA) according to the manufacturer's instructions.

Characterization of Foxp3

The amino acids (aa) predicted to mediate the interaction of the forkhead domain with DNA (Stroud et al., Structure. 14, 159-66 (2006) or the transcription factor NFAT (Wu et al., Cell 126, 375-87 (2006)) in mammalian Foxp3 are conserved in zFoxp3, as well as aa found to be mutated in humans with impaired Foxp3 activity (Ziegler, Annu Rev Immunol. 24, 209-26 (2006)) (FIG. 1E). The zinc finger/leucine zipper domain is important for the homodimerization of Foxp3 and its transcriptional regulatory activities (Chae et al., Proc Natl Acad Sci USA 103, 9631-6 (2006)). To study the ability of zFoxp3 to dimerize, we designed a pull-down assay using His-tagged zFoxp3 and a *renilla luciferase*-tagged Foxp3 (Foxp3-Ren). 293 cells were transfected as described (Bettelli et al., Proc Natl Acad Sci USA 102, 5138-43 (2005)) and the cells were analyzed after 24 or 48 hours with the dual luciferase assay kit (New England Biolabs, Ipswich, Mass.) (cells were lysed, and zFoxp3 was pulled-down with Ni-Agarose and the *renilla luciferase* activity in the pellet was quantified). Tk-*Renilla* was used for standardization. Alternatively, the transfected cells were lysed and immuno-precipitation was carried out as described (Bettelli et al., Proc Natl Acad Sci USA 102, 5138-43 (2005)); hemagglutinin (HA) labeled NFAT and NF-kB were detected with anti-HA and anti-P65 antibodies obtained from Santa Cruz Biotechnology (Santa Cruz, Calif. USA).

As shown in FIG. 1G, zFoxp3 pulled-down Foxp3-Ren indicating that zFoxp3 can homodimerize. Hence, zFoxp3 has structural features common to mammalian Foxp3.

Figure 2B:
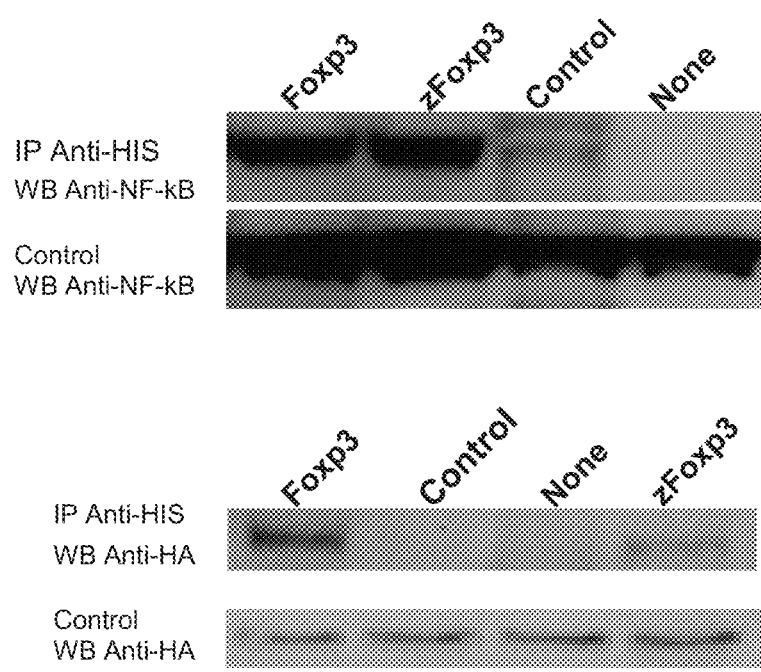
FIG. 2B is a pair of Western blots of 293T cells co-transfected with His-tagged zFoxp3, Foxp3 and NF-kB (top graph) or HA-flagged NFAT (bottom graph) and immunoprecipitated with antibodies to His antibodies. The precipitates were resolved by PAGE-SDS and detected by western blot with antibodies to NF-kB or HA antibodies.

Foxp3 can physically interact with NK-kB and NFAT to down-regulate their transcriptional activities (Wu et al., (2006), supra; Bettelli et al., (2005), supra). As shown in FIG. 2a, Foxp3 interfered with the activation of NFAT and NF-κB responsive promoters. This effect was stronger for NF-κB. Co-immunoprecipitation experiments showed that zFoxp3 interacts both with NF-κkB and NFAT. In agreement with the reduced inhibitory effect of Foxp3 on NFAT-driven reporters (see FIG. 2a), the zFoxp3-NFAT interaction was weaker (see FIG. 2b). These results suggest that zFoxp3 can directly interact with NFAT and NF-κB to interfere with their transcriptional activities.

MSCV GFP-RV retroviral DNA plasmids were transfected into the Phoenix packaging cell line and 72 hours later the retrovirus-containing supernatants were collected. MACS-purified CD4+ T cells were activated 24 hours later with plate-bound antibodies to CD3 and CD28, and infected by centrifugation (45 minutes at 2000 rpm) with retrovirus-containing supernatant supplemented with 8 μg/ml Polybrene (Sigma-Aldrich) and recombinant human IL-2 (25 units/ml). Cells were cultured in serum-free X-VIVO 20™ media (Bio Whittaker, Walkersville, Md., USA) for 72 hours. During the last 16 hours, cells were pulsed with 1 μCi of [$^3$H] thymidine (PerkinElmer, Waltham, Mass., USA) followed by harvesting on glass fiber filters and analysis of incorporated [$^3$H]thymidine in a beta-counter (1450 Microbeta, Trilux, PerkinElmer). Alternatively, culture supernatants were collected 48 after activation and the cytokine concentration was determined by ELISA using antibodies for IFN-γ, IL-17, IL-4, IL-10 from BD Biosciences and antibodies to TGF-β from R&D Systems. For suppression assays, MACS purified $CD4^+$ $CD25^-$ T cells from naïve C57BL/6 mice ($1-5\times10^4$ cells/well) were stimulate with antibodies to CD3 and C57BL/6 irradiated spleen cells ($0.3-1.5\times10^4$ cells/well) for 3 days in the presence of different ratios of $CD4^+GFP^+$ retrovirus-transduced T cells.

Figure 2C:
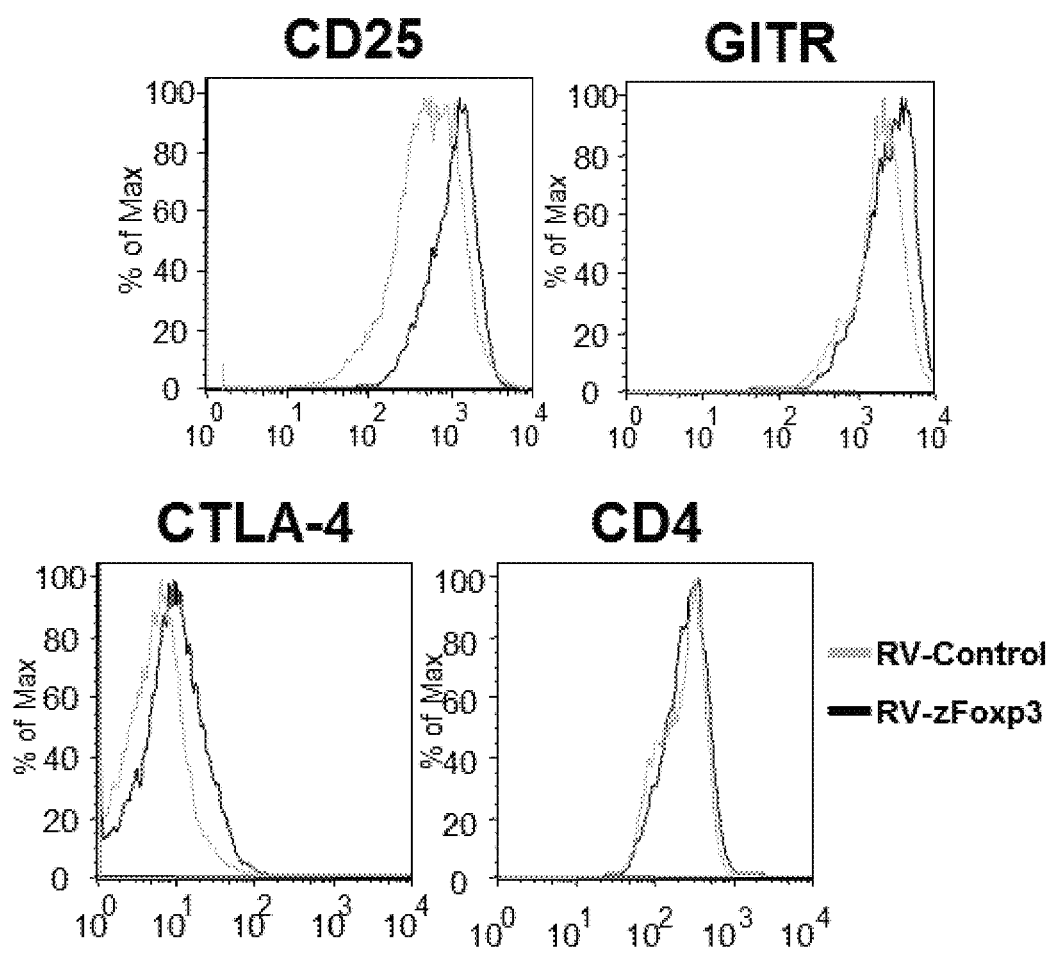
FIG. 2C is a set of four graphs of MACS-purified $CD4^+ CD25^+$ T-cells that were transduced with a bicistronic retrovirus coding for GFP and zFoxp3 or an empty control retrovirus, and the $GFP^+$ population was analyzed for the surface expression of (from left to right) CD25, GITR, CD152 and CD4.

Retroviral transduction of zFoxp3 into mouse T cells led to the up-regulation of surface molecules associated with Treg function such as CD25, CTLA-4 and GITR (see FIG. 2c). Moreover, ectopic expression of zFoxp3 in mouse T cells led to a significant decrease in their proliferation and cytokine secretion upon activation with antibodies to CD3 (see FIG. 2d). Moreover, zFoxp3 transduced T cells could inhibit the activation of other T cells, both in terms of T cell proliferation and of cytokine secretion, in a dose dependent manner (see FIG. 2e). In summary, expression of zFoxp3 in mouse T cells induced a Treg-like phenotype. These data suggest that zFoxp3 is a functional homologue of mammalian Foxp3, and that Foxp3 is capable of promoting a Treg like phenotype.

Western blot studies of zebrafish tissues identified a Foxp3 cross-reactive protein in thymus, kidney and spleen compatible with the predicted size of zFoxp3. The expression of zFoxp3 was then analyzed by real-time PCR on FACS-sorted lymphocytes, myelomonocytes and erythrocytes (Traver et al., Nat Immunol 4, 1238-46 (2003)). RNA was extracted from cells using RNAeasy columns (Qiagen, Valencia, Calif., USA), complementary DNA was prepared as recommended (Bio-Rad Laboratories, Hercules, Calif., USA) and used as template for real time PCR. The expression of Foxp3 was quantified with specific primers and probes (Applied Biosystems, Foster City, Calif., USA) on the GeneAmp 5500 Sequence Detection System (Applied Biosystems). Expression was normalized to the expression of the housekeeping gene, GAPDH.

Figure 3D:
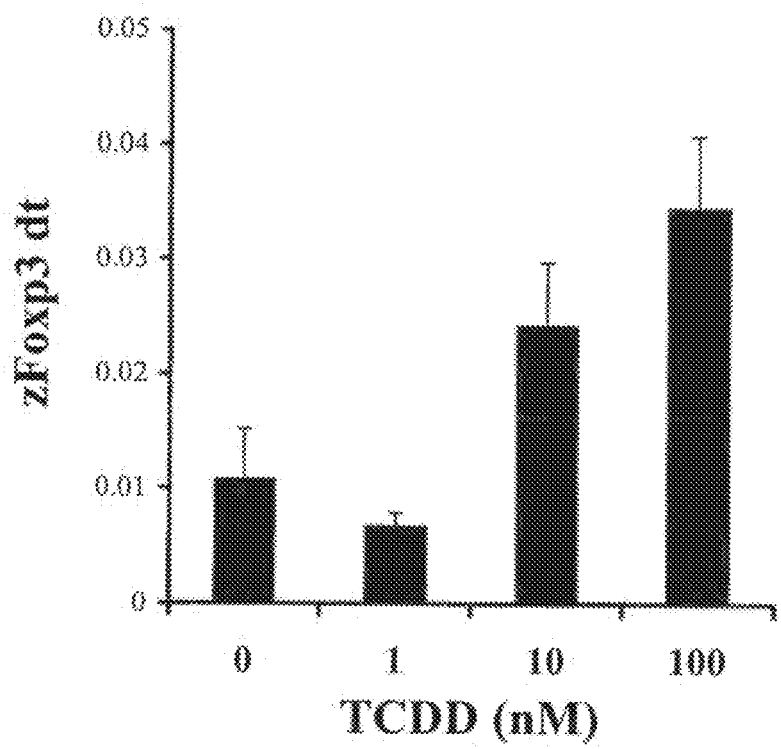
FIG. 3D is a bar graph of zFoxp3 expression 72 hours after TCDD was added to the water of three-day post-fertilization zebrafish embryos, as determined by real time PCR (mean+s.d. of triplicates normalized to GAPDH expression).

As shown in FIG. 3a, zFoxp3 expression was restricted to the lymphocyte fraction. This observation is consistent with the expression pattern of mammalian Foxp3 and supports the conservation of the regulatory mechanisms of gene expression that control tissue specificity.

Example 2

Identification of Transcription Factor Binding Sites in Foxp3

The elements regulating gene expression in genomic DNA are under selective pressure, and therefore are more conserved than the surrounding nonfunctional sequences. Phylogenetic footprinting is a method based on the analysis of sequence conservation between orthologous genes from different species to identify regions of DNA involved in the regulation of gene expression. Once identified, these conserved regions can be analyzed with TFBS detection algorithms to generate a list of putative TFBS.

We performed a phylogenetic footprinting analysis aimed at identifying regulatory regions within the zebrafish, mouse and human Foxp3 gene (Ovcharenko et al., Genome Res 15, 184-94 (2005)). The inclusion of distance species like the zebrafish is highly informative because it facilitates the identification of conserved regulatory sequences amidst DNA regions that were not subjected to any selective pressure (Ovcharenko et al., Genome Res 15, 184-94 (2005)).

Figure 7A:
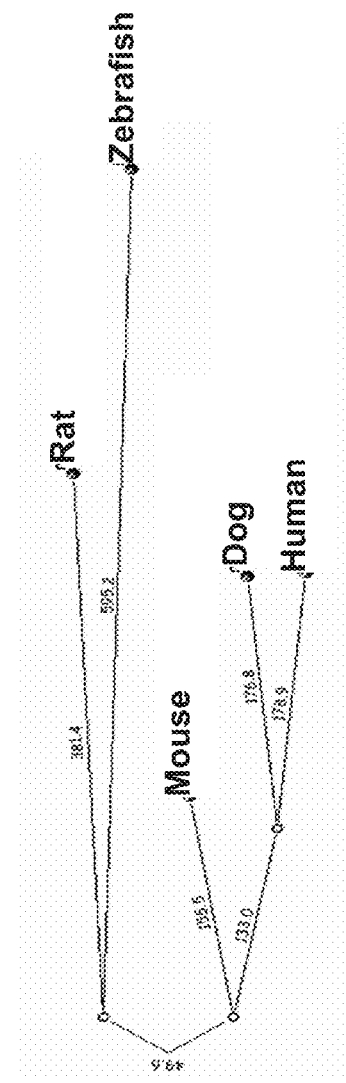
FIGS. 7A-B show the results of phylogenetic footprinting for the identification of putative TFBS. The genomic sequences of human, mouse, rat, dog and zebrafish Foxp3 were analyzed by phylogenetic footprinting. 7A presents a phylogenetic tree; Tree distances are in # of substitutions per 1 kb. 7B is a graph illustrating the dynamic visualization of the location of putative TFBS conserved between human (SEQ ID NO: 1) and zebrafish (SEQ ID NO: 2).
Figure 7B:
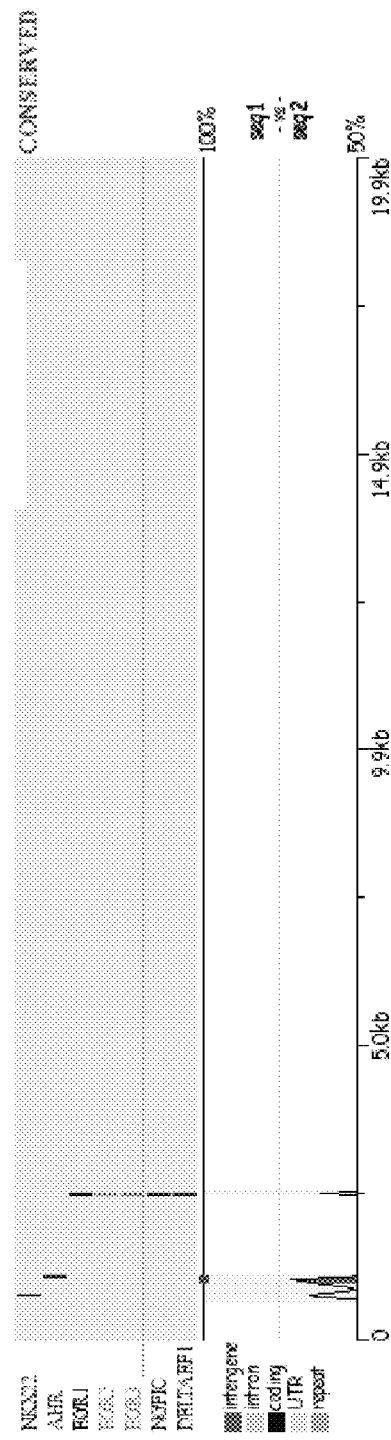

The Mulan server (mulan.dcode.org) was used to perform a phylogenetic footprinting analysis of Foxp3. Mulan brings together different algorithms in a web-based user-friendly interface: programs for the rapid identification of local sequence conservation connected to the multiTF/TRANSFAC database for the detection of evolutionarily conserved TFBS in multiple alignments. FIGS. 7A-B show the results obtained using the sequences of Foxp3 in rat, mouse, dog, human and zebrafish. Putative TFBS were found for 6 transcription factors, all of them known to be expressed and functional in T cells: NKX22, AHR, EGR1, EGR2, EGR3, NGFIC, and Delta EF1. These TF identified by phylogenetic footprinting are other potential regulators of Foxp3 expression and Treg development.

Example 3

Adaptive Cellular Immunity and Foxp3-Dependent Immunoregulation in Zebrafish

The adaptive cellular immune response of 6 month old zebrafish immunized intraperitoneally (ip) with heat killed M. tuberculosis (MT) or PBS in incomplete Freud's adjuvant (IFA) was studied.

As shown in FIG. 1A, spleen cells prepared 14 days after immunization with MT or PBS proliferated in response to stimulation with Concanavalin A (ConA), but only cells taken from MT-immunized fish proliferated upon activation with MT.

Another group of six month old zebrafish were anesthetized with 0.02% tricaine (Sigma-Aldrich) and immunized i.p. with 10 μl/fish of zebrafish brain homogenate (zCNS) emulsified in complete Freud's adjuvant (CFA). As shown in FIGS. 1b-d, this resulted in the accumulation of CD3, IFNg and IL-17 expressing cells in the brain.

These results demonstrated that zebrafish can mount adaptive antigen-specific cell-mediated immune and autoimmune responses.

C. elegans and D. melanogaster have been extremely useful for the identification of the genes governing innate immunity (Lemaitre et al., Nat Rev Immunol 4, 521-7 (2004)). These experimental models, however, lack an adaptive immune system and therefore cannot be used to study vertebrate-specific immune processes. The zebrafish harbors both innate and adaptive immune systems with functional macrophages (Davis et al., Immunity 17, 693-702 (2022)), B cells (Danilova et al., Proc Natl Acad Sci USA 99, 13711-6 (2002)) and T cells (Danilova et al., Dev Comp Immunol 28, 744-67 (2004); Langenau et al., Proc Natl Acad Sci USA 101, 7369-74 (2004)). Taking together the presence of basic components of the adaptive immune system (Langenau et al., Nat Rev Immunol. 5, 307-17 (2005)) with the experimental advantages offered by the zebrafish for the realization of large scale genetic and chemical screens (Lieschke et al., Nat Rev Genet. 8, 353-657 (2007)), the zebrafish can serve as an experimental model for the study of pathways controlling adaptive immune processes such as Treg development.

Example 4

AHR Controls Foxp3 Expression and Treg Generation

Using the methods described above, a conserved binding site for the aryl hydrocarbon receptor (AHR) was identified in the genomic sequence of Foxp3 (see FIGS. 3b and 3j), which was termed the conserved AHR binding site (CABS). A similarly located regulatory sequence controls the expression of the AHR-regulated cytochrome P4501A2 (CYPIA2). In addition, three non-evolutionary conserved AHR-binding sites (NCABS) were identified in the zFoxp3 promoter (termed NCABS-1, -2, and -3) (see FIGS. 3i and 3j).

First, Foxp3 expression was measured in mouse Treg isolated from Foxp3$^{gpf}$ knock in mice. Foxp3$^{gpf}$ knock in mice have a GFP reporter inserted in the Foxp3 gene, producing GFP in Foxp3$^+$ Treg, which facilitates the identification and FACS sorting of GFP:Foxp3$^+$ Treg (Bettelli et al., Nature 441, 235-8 (2006)).

CD4+ T cells were purified from Foxp3gfp knock in mice using anti-CD4 beads (Miltenyi, Auburn, Calif., USA), and sorted (FACSAria™ cell sorter, BD Biosciences) into naive CD4$^+$ Foxp3:GFP$^-$ or CD4$^+$Foxp3:GFP$^+$ T cells. CD4$^+$ Foxp3:GFP$^-$ T cells were stimulated with plate bound 1 μg/ml of anti-CD3 (145-2C11, eBioscience) and 2 μg/ml of anti-CD28 (37.51, eBioscience) for 5 days. supplemented with recombinant IL-2 (50 U/ml) at day 2 and 4, and analyzed by FACS at day 5 for their differentiation into CD4$^+$ Foxp3: GFP$^+$ Treg. TGFβ1 (2.5 ng/ml) was used as a positive control.

Higher levels of AHR expression were detected on FACS-sorted CD4$^+$ GFP:Foxp3$^+$ Treg than in CD4$^+$ GFP:Foxp3$^+$ T cells (see FIG. 3c), highlighting a possible link between AHR and Foxp3 expression. The relationship between AHR and Foxp3 was then further analyzed using RT-PCR.

Briefly, CD4+ T cells were purified from Foxp3gfp knock in mice as described above. RNA was then extracted using RNAeasy columns (Qiagen, Valencia, Calif., USA). Complementary DNA was prepared as recommended (Bio-Rad Laboratories, Hercules, Calif., USA) and used as template for real time PCR. The expression of Foxp3 was quantified with specific primers and probes (Applied Biosystems, Foster City, Calif., USA) on the GeneAmp 5500 Sequence Detection System (Applied Biosystems). Expression was normalized to the expression of the housekeeping genes, GAPDH or actin.

Figure 3E:
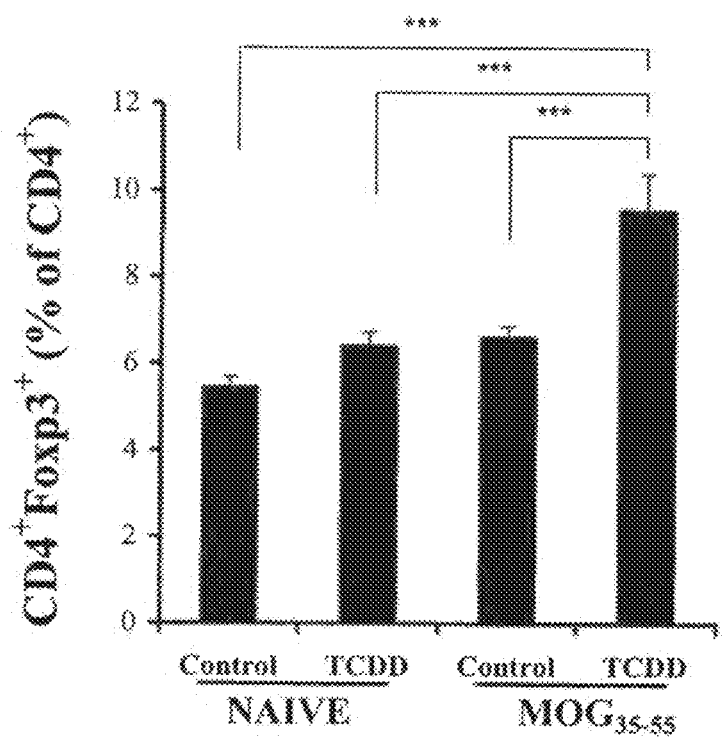
FIG. 3E is a bar graph of frequency of $CD4^+FoxP3^+$ T cells in the $CD4^+$ T-cell population as determined in the draining lymph nodes by FACS from naïve C57BL/6J mice 11 days after after administration of 1 mg/mouse TCDD or corn oil as control, and 10 days after the mice were immunized (or not) with 100 mg/mouse $MOG_{35-55}$/CFA (mean+s.d. of three mice).
Figure 3F:
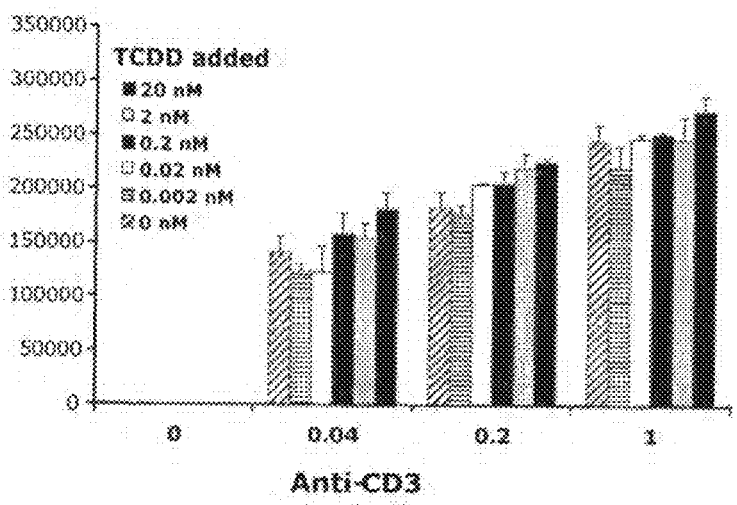
FIG. 3F is a bar graph of proliferation of purified $CD4^+$ T cells stimulated with plate bound antibodies to CD3 in the presence of different concentrations of TCDD for 72 hours. Cell proliferation is indicated as cpm+s.d. in triplicate wells (***$P<0.0001$, one-way ANOVA, n=3).
Figure 3G:
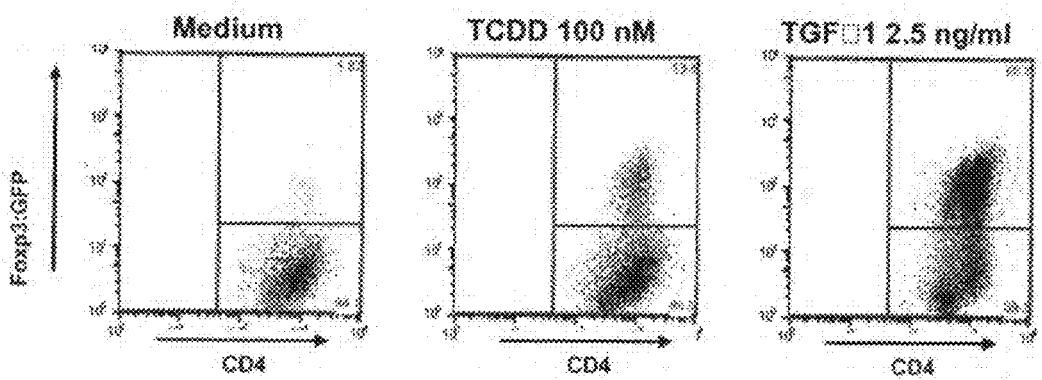
FIG. 3G is a set of three FACS plots of $CD4^+Foxp3$:GFP T cells in the $CD4^+$ T-cell population from Fox $p3^{gfp}$ knock in mice stimulated with plate bound antibodies to CD3 and CD28 for 5 days in the presence of normal media (control, left panel) TCDD (middle panel) or TGFb1 (right panel).
Figure 3H:
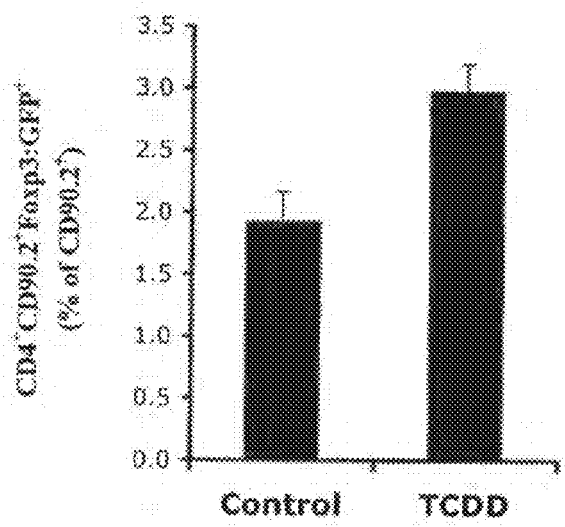
FIG. 3H is a bar graph of Foxp3:GFP CD4+ T-cells positive for the donor-specific marker CD90.2, isolated and analyzed by FACS from host mice that received FACS-purified $CD4^+$ Foxp3:$GFP^-$ 2D2 T cells from CD 90.2 $Foxp3^{gfp}$ knock in donor mice treated with 1 mg/mouse of TCDD or corn oil as control and then immunized with 100 mg/mouse $MOG_{35-55}$/CFA. The results are presented as the mean+s.d., five mice were included per group. *$P<0.02$, unpaired t-test.
Figure 3M:
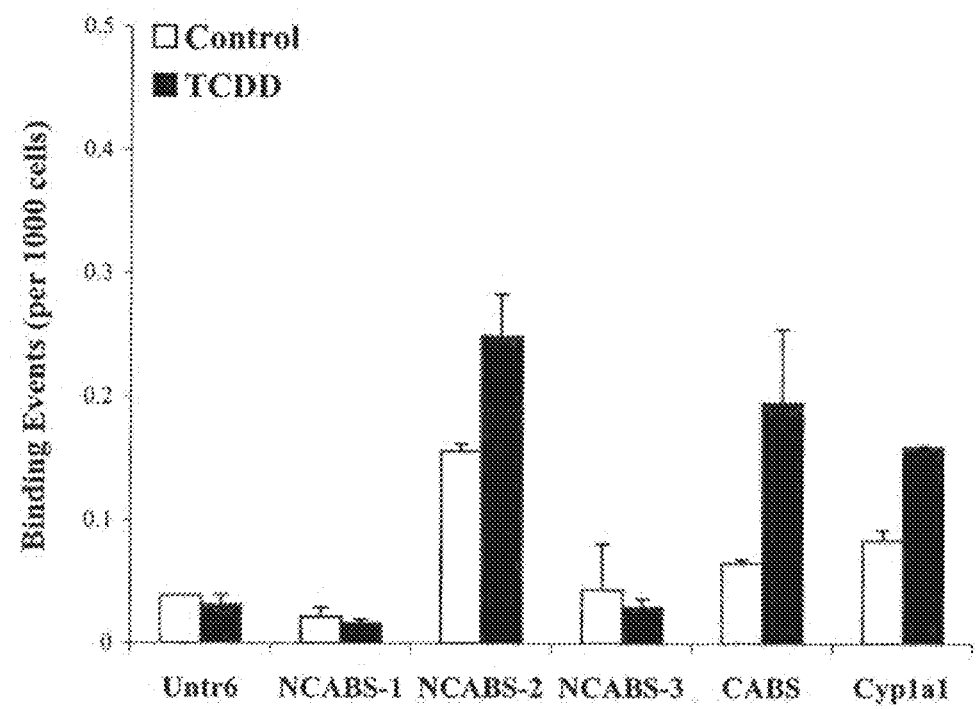
FIG. 3M is a bar graph of ChIP analysis of the interaction of AHR to the CABS and NCABS in foxp3 and cypIa1 in thymic $CD4^+$ cells from $TCDD^-$ or control-treated mice.
Figure 3N:
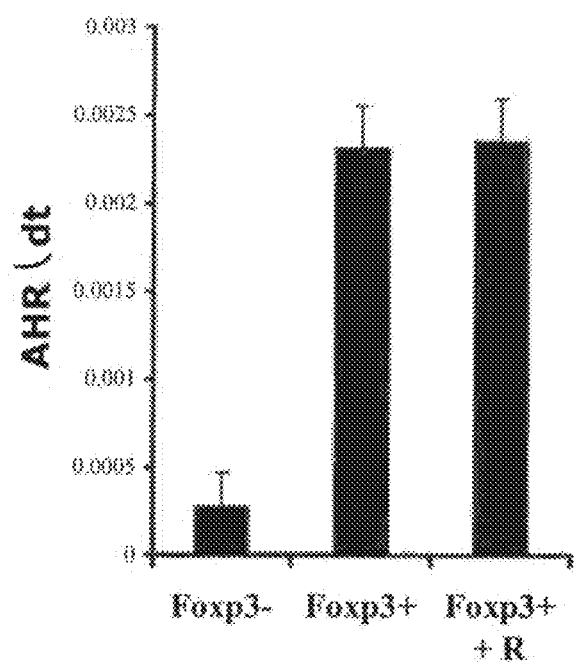
FIG. 3N(i)-(iii) are bar graphs of AHR (N(i)), CYPIA1 (N(ii) and Foxp3 (N(iii)) expression measured by real time PCR on CD4+Foxp3:GFP−T cells (GFP−), $CD4^+Foxp3$:$GFP^+$ Treg ($GFP^+$) and $CD4^+Foxp3$:$GFP^+$ Treg treated with resveratrol for 5 h ($GFP^+$+R) (mean+s.d. of triplicates normalized to GAPDH expression).
Figure 3O:
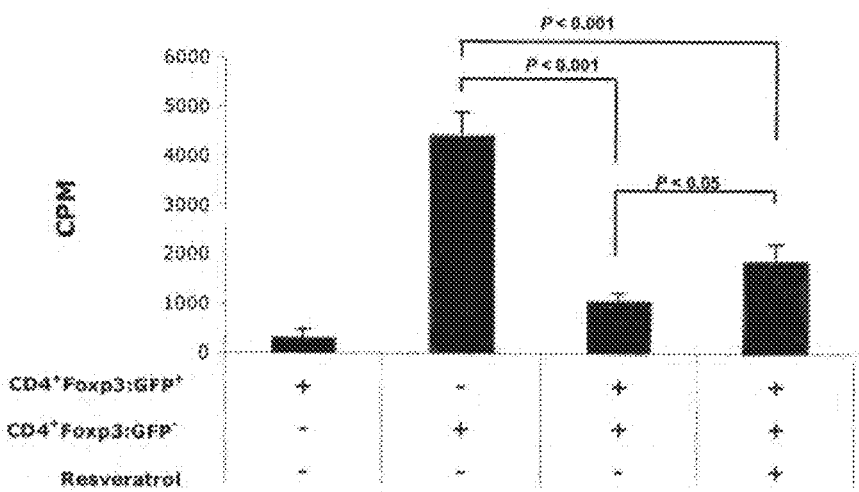
FIG. 3O is a bar graph of the effect of AHR-inactivation with resveratrol on the suppressive activity of $CD4^+Foxp3$:$GFP^+$ Treg that were FACS-sorted from naive Foxp3gfp mice, assayed using $CD4^+$ Fox p3:$GFP^-$ cells activated with antibodies to CD3 as effector T cells in the presence of resveratrol. Cell proliferation is indicated as cpm+s.d. in triplicate wells.

Data generated using RT-PCR corroborated the observed association between AHR and Foxp3. In addition, CYPIA1 expression, a AHR responsive gene, was also observed in CD4$^+$ GFP:Foxp3$^+$ Treg cells. Furthermore, as shown in FIG. 3n, treatment of the cells with the AHR antagonist resveratrol resulted in a significant decrease in both Foxp3 and CYPIA1 expression levels (P<0.0023 and P<0.0235, respectively). Decreases in the suppressive activity was also noted in resveratrol treated cells (FIG. 3o). Together, these results strongly suggest that the detected AHR is functional.

To investigate whether AHR directly controls Foxp3 expression, we used a bacterial artificial chromosome that contained the entire foxp3 locus tagged with a Renilla luciferase reporter after the ATG start codon. More specifically, we used the RP23-267C15 BAC clone, which contains 200 kb of mouse genomic DNA, including the entire locus of the Foxp3 gene. A Renilla cDNA cassette was the cloned immediately after the ATG start codon of Foxp3 gene by homologous recombination using the Red recombineering system contained in the DY 380 bacteria strain. The final construct was designated BACFoxp3:Ren.

As shown in FIG. 3k, cotransfection of BACFoxp3:Ren with a construct coding for mouse AHR resulted in a significant up-regulation of Renilla activity (P<0.01), similar to that achieved with a constitutively activated TGFβ receptor II. This observation demonstrates that AHR is capable of directly controlling Foxp3 expression.

Chromatin immunoprecipitation (ChIP) was then applied to analyze the interaction of AHR with the CABS and NCABS shown in FIGS. 3b and 3i, respectively.

Briefly, cells were treated for 90$^+$ with TCDD, fixed with 1% formaldehyde for 15 minutes and quenched with 0.125 M glycine. Chromatin was isolated and sheared to an average length of 300-500 bp by sonication. Genomic DNA (input) was prepared by treating aliquots of chromatin with RNase, proteinase K and heat for de-crosslinking, followed by ethanol precipitation. AHR-bound DNA sequences were immuno-precipitated with an AHR-specific antibody (Biomol SA-210). Crosslinks were reversed by incubation overnight at 65° C., and ChIP DNA was purified by phenol-chloroform extraction and ethanol precipitation. Quantitative PCR reactions were then performed using the following primer pairs:

```
Cyp1a1 -845 F:
                                          (SEQ ID NO:)
aggctcttctcacgcaactc
and Cyp1a1 -845 R:
                                          (SEQ ID NO:)
ctggggctacaaagggtgat;

Foxp3 (NCAB-1) -2269 F:
                                          (SEQ ID NO:)
agctgcccattacctgttag
and Foxp3 (NCAB-1) -2269 R:
                                          (SEQ ID NO:)
ggaggtctgcatggatcttag;

Foxp3 (NCAB-2) -1596 F:
                                          (SEQ ID NO:)
gccttgtcaggaaaaactctg
and Foxp3 (NCAB-2) -1596 R:
                                          (SEQ ID NO)
gtcctcgatttggcacagac;
```

-continued

Foxp3 (NCAB-3) -800 F:
cttgcccttcttggtgatg
and
(SEQ ID NO)

Foxp3 (NCAB-3) -800 R:
ttgtgctgagtgccctgac;
(SEQ ID NO)

Foxp3 (CAB) +13343 F:
gctttgtgcgagtggagag
and
(SEQ ID NO)

Foxp3 (CAB) +13343 R:
agggattggagcacttgttg.
(SEQ ID NO)

The Untr6 region in chromosome 6 located at chr6:
120,258,582-120,258,797 was amplified as a
control using Untr6 F:
tcaggcatgaaccaccatac
and
(SEQ ID NO)

Untr6 R:
aacatccacacgtccagtga.
(SEQ ID NO)

Experimental Ct values were converted to copy numbers detected by comparison with a DNA standard curve run on the same PCR plates. Copy number values were then normalized for primer efficiency by dividing by the values obtained using Input DNA and the same primer pairs. Error bars represent standard deviations calculated from the triplicate determinations.

ChIP analysis of the interaction of AHR with CABS and NCABS in Foxp3 and CYP1A1 was then performed in control and 2,3,7,8-tetrachlorodibenzo-p-dioxin (TCDD; a high affinity AHR ligand) treated CD4$^+$ T cells and T cells isolated form mice.

As shown in FIG. 3l, treatment of CD4+ T cells with TCDD increased AHR binding to the CABS and NCABS-2 (p<0.05). This up-regulation was comparable to that detected in the promoter of the AHR-regulated gene cytochrome P4501A1 (CYPIA1) gene. No significant increase in AHR binding was seen in NCABS-1, NCABS-3, or the control sequence UTR6. As shown in FIG. 3m, similar results were obtained when CD4 T cells were purified from TCDD treated mice. These data suggest that AHR controls Foxp3 expression.

TCDD was also used to characterize the functional relationship between AHR and Foxp3. Treatment of 3-day post-fertilization zebrafish embryos with TCDD led to a dose-dependent increase in zFoxp3 expression, expression suggesting that the conserved AHR binding site in the zFoxp3 sequence is functional (see FIG. 3D).

Figure 3P:
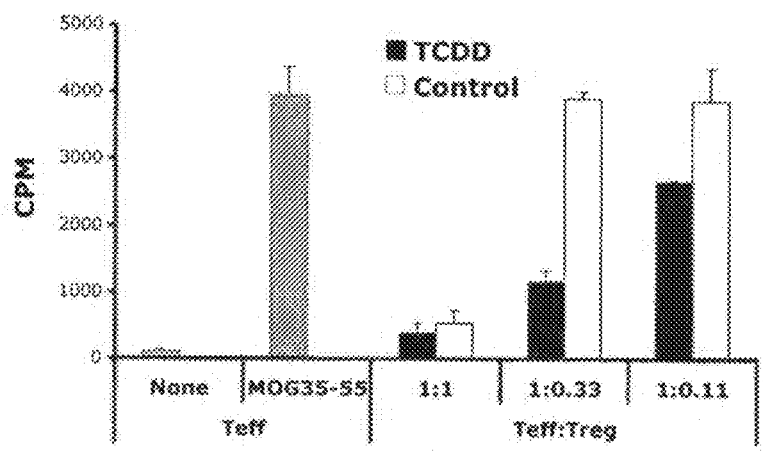
FIG. 3P is a bar graph of $MOG_{35-55}$-specific suppressive activity of Treg purified from TCDD or control-treated mice, assayed using $CD4^+$ Foxp3:$GFP^-$ 2D2 T cells. Cell proliferation is indicated as cpm+s.d. in triplicate wells.
Figure 3Q:
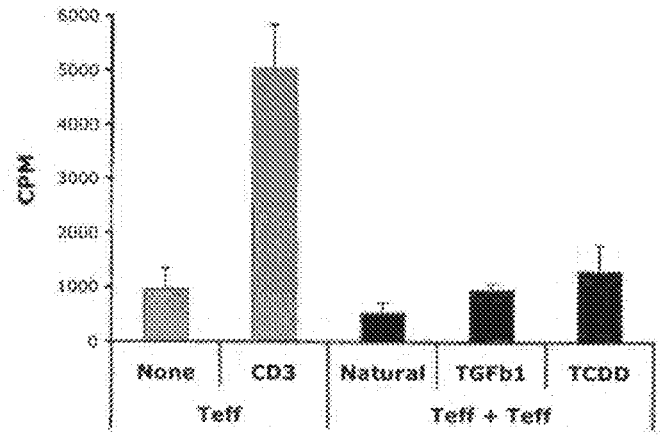
FIG. 3Q is a bar graph of suppressive activity of natural Treg, or Treg induced with TGFβ1 (TGFb1) or TCDD (TCDD). Cell proliferation is indicated as cpm+s.d. in triplicate wells.

We then studied the effect of AHR activation on mouse Treg numbers. Naïve C57BL/6 mice were treated with TCDD (1 mg/mouse, ip) and immunized 24 hours later with MOG$_{35-55}$ in CFA. Draining lymph nodes were prepared 10 days later and CD4$^+$Foxp3$^+$ Treg were quantified by FACS. Administration of TCDD led to a small increase in the number of CD4$^+$Foxp3$^+$ Treg (see FIG. 3E). Moreover, a single administration of TCDD followed by immunization with MOG$_{35-55}$ led to a significant increase in the number of the CD4$^+$Foxp3$^+$ T cells (see FIG. 3E). Furthermore, the CD4$^+$ Foxp3:GFP$^+$ T cells expanded in vivo by TCDD administration and MOG$_{35-55}$ immunization were functional and showed increased MOG$_{35-55}$-specific suppressive activity (see FIG. 3P).

To rule out any direct cytotoxic or pro-apoptotic effect of TCDD on effector T cells, purified mouse CD4$^+$CD25$^+$ T cells were activated in vitro with antibodies to CD3 in the presence of TCDD. Incubation with TCDD did not increase T cell apoptosis as measured by annexin-FITC staining and did not decrease the proliferative response (see FIG. 3F). Taken together, these data suggest that AHR controls Foxp3 expression and Treg expansion both in zebrafish and in mice.

To establish if TCDD (triggered the conversion of CD4$^+$ Foxp3$^-$ T cells into new Foxp3$^+$ Treg cells. FACS sorted CD4$^+$ Foxp3:GFP$^-$ T cells were activated in vitro with antibodies to CD3 and CD28 in the presence of TCDD, and the generation of CD4$^+$ Foxp3:GFP$^+$ Treg was followed by FACS. TGFb1 was used as a positive control. As shown in FIG. 3G, TCDD triggered the conversion of approximately 13% of the cells in culture into CD4$^+$Foxp3:GFP$^+$ Treg. Additionally, as shown in FIG. 3, CD4$^+$ Foxp3:GFP$^+$ Treg induced by TCDD showed a suppressive activity similar to that of Treg induced in vitro with TGFβ1 or CD4$^+$ Foxp3:GFP$^+$ Treg sorted from naïve Foxp3gpf mice.

Thus, AHR activation by the high affinity AHR ligand TCDD can trigger the conversion of CD4$^+$ Foxp3$^-$ T cells into functional CD4$^+$GFP$^+$ Treg.

Figure 3R:
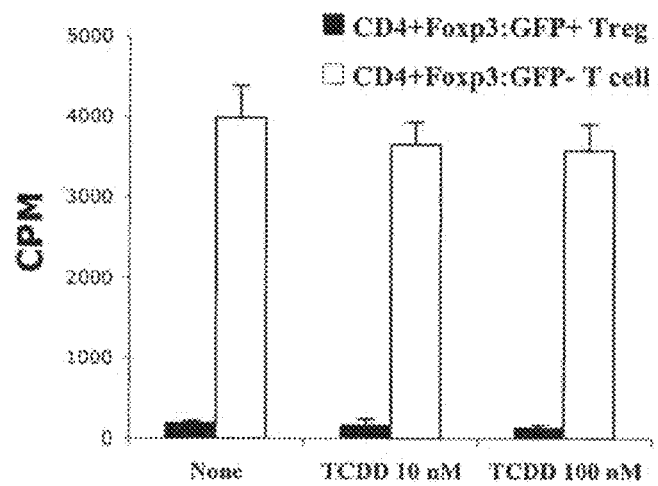
FIG. 3R is a bar graph showing the effect of AHR activation with TCDD on the proliferation of $CD4^+$ Foxp3:$GFP^+$ Treg and $CD4^+$ Foxp3:$GFP^-$ T cells that were FACS-sorted from naive Foxp3gfp mice. Cell proliferation is indicated as cpm+s.d. in triplicate wells.
Figure 3S:
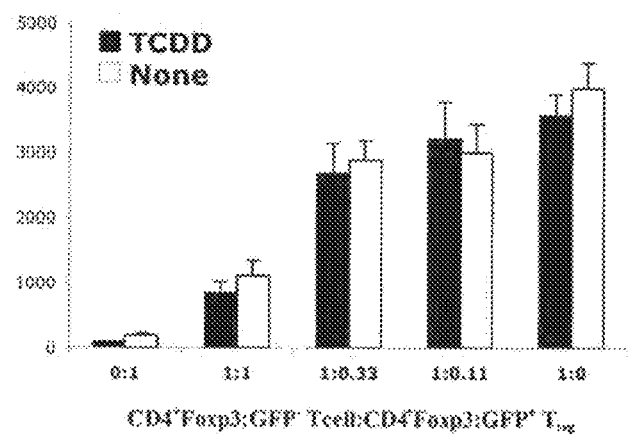
FIG. 3S is a bar graph of the effect of AHR-activation with TCDD on the suppressive activity of $CD4^+$ Foxp3:$GFP^+$ Treg that were FACS-sorted from naive Foxp3gfp mice, assayed using $CD4^+$ Foxp3:$GFP^-$ cells activated with antibodies to CD3 as effector T cells in the presence of resveratrol. Cell proliferations indicated as cpm+s.d. in triplicate wells.

As shown in FIGS. 3r and 3s, treatment with the AHR antagonist resveratrol (50 μM) interfered with the induction of Treg by TGFβ1 and TCDD, but had a stronger effect on the Treg conversion triggered by TCDD (P=0.0053, FIG. 1h). CD4$^+$Foxp3:GFP$^+$ Treg purified from naïve mice did not proliferate and did not show increased suppressive activity upon stimulation with antibodies to CD3 and CD28 and TCDD. These observations suggest that AHR is more important for the differentiation of new Treg than for the activity of established Treg.

To investigate if new Treg could also be generated in vivo following TCDD administration, we transferred CD4$^+$ Foxp3:GFP$^-$ 2D2 T cells from CD90.2 donors into wild type CD90.1 recipients. CD4$^+$Foxp3:GFP$^-$ 2D2 T cells express a MOG$_{35-55}$-specific T cell receptor. The recipients were administered 1 μg/mouse TCDD and were immunized 2 days later with MOG$_{35-55}$. CD4$^+$Foxp3:GFP$^+$ CD90.2 T cells (donor cells that underwent conversion into Treg upon treatment with TCDD) were then quantified by FACS. As shown in FIG. 3h, TCDD promoted a significant (P<0.02, unpaired t-test, n=5) conversion of CD4$^+$Foxp3:GFP$^-$ CD90.2 donor T cells into Treg cells.

Thus, the increase the frequency of Treg that follows activation of AHR with TCDD is due, at least in part, to the conversion of CD4$^+$Foxp3:GFP$^-$ T cells into CD4$^+$Foxp3:GFP$^+$ Treg.

Example 5

AHR Activation by TCDD Suppresses EAE

To analyze the functionality of the Treg cells induced by AHR activation, we studied the effect of TCDD on EAE development.

C57BL/6 mice were given a single intraperitoneal (ip) does of TCCD, and one day later EAE was induced by immunization with MOG$_{35-55}$ in CFA. TCDD was also administered orally (1 μg/mouse) to determined whether an effective dose of this ligand can be delivered via oral administration and whether this dose is capable of reducing EAE development. EAE was induced by injecting the mice subcutaneously with 100 ml of the MOG$_{35-55}$ peptide (MEVGWYRSPFSRVVH-LYRNGK (SEQ ID NO: )) in complete Freund adjuvant oil. In addition, the mice received 150 ng of pertussis toxin (Sigma-Aldrich) ip on days 0 and 2. Clinical signs of EAE were assessed according to the following score: 0, no signs of disease; 1, loss of tone in the tail; 2, hind limb paresis; 3, hind limb paralysis; 4, tetraplegia; 5, moribund.

Figure 4A:
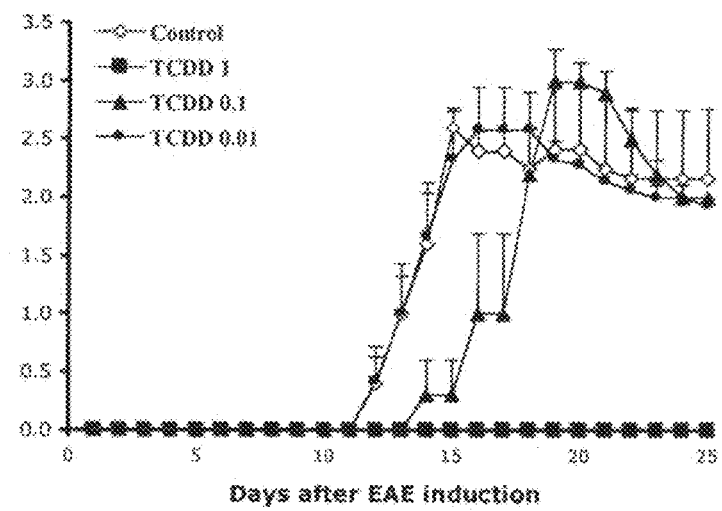
FIG. 4A is a line graph showing the effect on EAE of TCDD, or oil as control, administered ip to C57BL/6 mice. EAE was induced 24 hours later by immunization with $MOG_{35-55}$/CFA. The course of EAE in these mice is shown as the mean EAE score+s.e.m. (P<0.0001, two-way ANOVA, n=6).

As shown in FIG. 4a and Table 3, ip administered TCDD had a dose-dependent effect on the clinical signs of EAE. 1 µg/mouse markedly inhibited the clinical signs of EAE (P<0.001; n=6).

TABLE 3

TCDD Treatment Suppresses EAE

| Treatment (µg per mouse) | Incidence (positive/total) | Mean day of onset (Mean ± standard deviation (SD)) | Mean maximum score (mean ± SD) |
|---|---|---|---|
| Control | 42/49 (87%) | 13.6 ± 2.8 | 2.4 ± 1.4 |
| TCDD 1 µg | 4/40 (10%) | 21.8 ± 1.5* | 0.2 ± 0.6* |
| TCDD 0.1 µg | 5/5 (100%) | 17.0 ± 1.2 | 3.1 ± 0.5 |
| TCDD 0.01 µg | 7/7 | 14.1 ± 2.9 | 2.7 ± 0.6 |

Mice treated with corn oil (control) or TCDD (ip) were immunized with MOG$_{35-55}$ peptide in CFA and monitored for EAE development. Statistical analysis was performed by comparing groups using one-way analysis of variance.
*P < 0.0001.

Figure 4B:
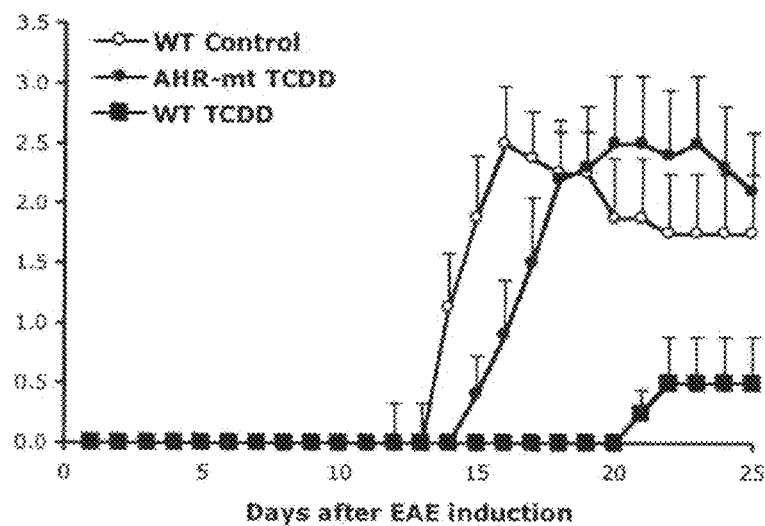
FIG. 4B is a line graph showing the effect on EAE of TCDD, or oil as control, administered ip to C57BL/6 wild type or AHR-mt mice. EAE was induced 24 hours later by immunization with $MOG_{35-55}$/CFA. The course of EAE in these mice is shown as the mean EAE score+s.e.m. (P<0.0001, two-way ANOVA, n=10).
Figure 4C:
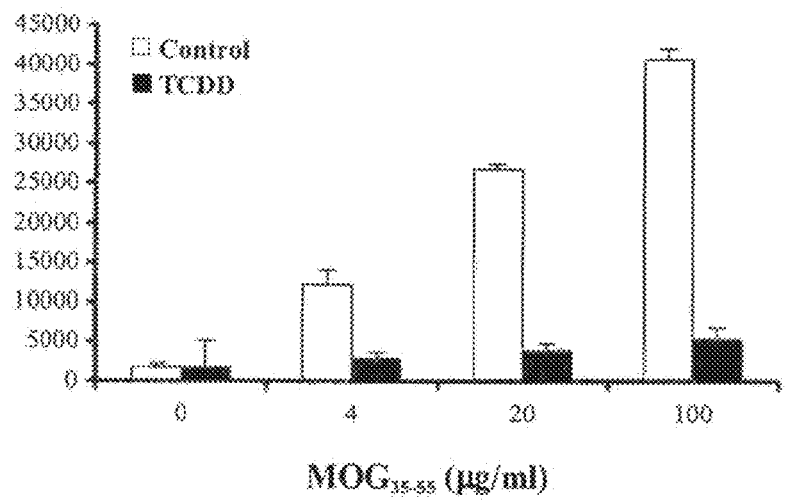
FIGS. 4C-D are bar graphs of the proliferative response to $MOG_{35-55}$ (4C) or antibodies to CD3 (4D) of lymph node cells taken from TCDD or control treated animals 10 days after immunization with $MOG_{35-55}$/CFA. Cell proliferation is indicated as cpm+s.d. in triplicate wells.
Figure 4D:
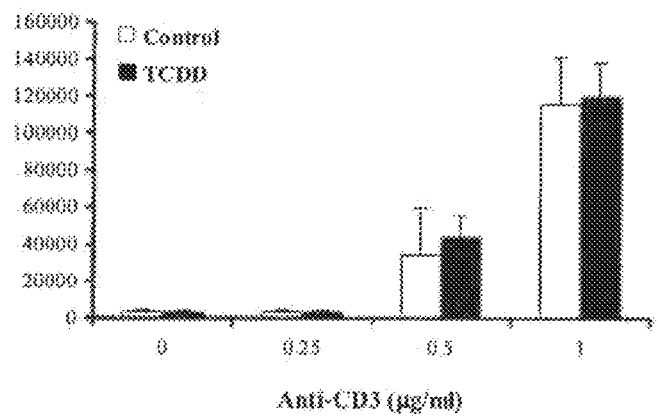
Figure 4G:
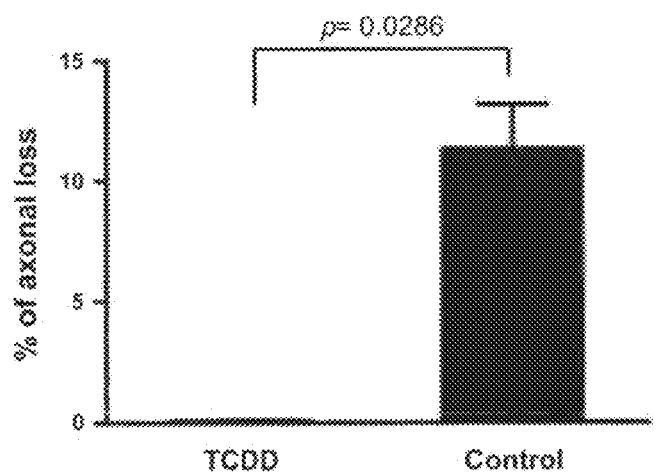
FIGS. 4G-I are bar graphs showing that AHR activation by TCDD inhibits CNS inflammation, demyelination and axonal loss. Briefly, quantification of the cellular infiltrate, demyelination and axonal loss on the spinal cord of TCDD-treated and control mice. Spinal cords were taken on day 19 after EAE induction and stained with hematoxylin & eosin, luxol fast blue or silver stain to quantify the cellular infiltrate (g), demyelination (h) and axonal (i), respectively. The effect of TCDD-treatment was analyzed using Student's t-test.
Figure 4H:
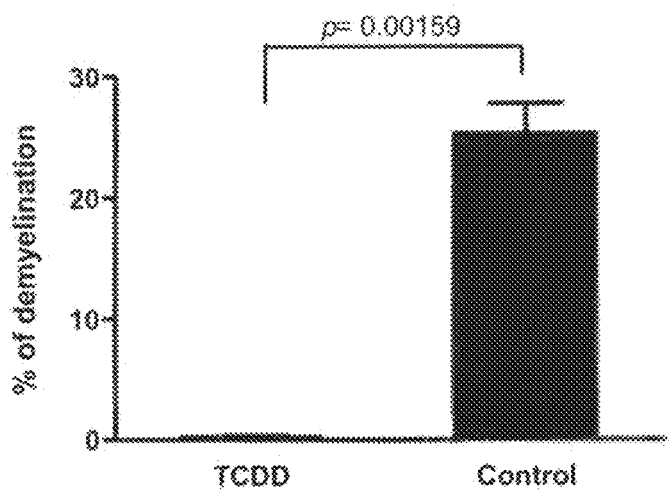
Figure 4I:
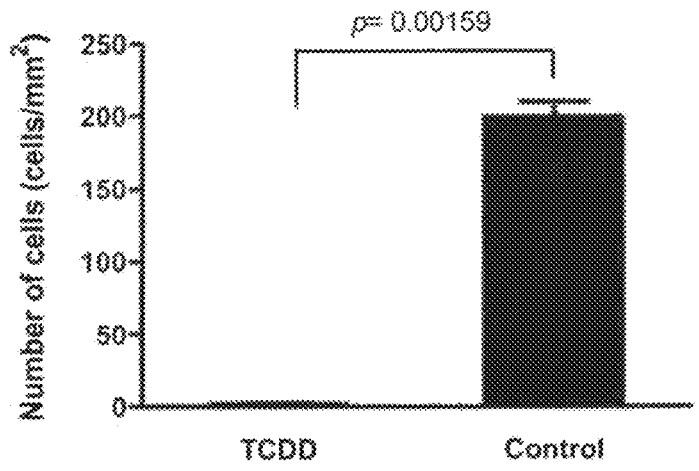

As shown in FIGS. 4G-4I, IP administered TCDD also reduced the histopathological signs of EAE.

In addition, orally administered of 1 µg/mouse of TCDD, one day before EAE induction, also prevented EAE development (P<0.001, two-way ANOVA, n=10), This observation suggests that an effective dose of TCDD can be administered orally.

To confirm that the effects on EAE were mediated by the activation of AHR, we used C57BL/6 mice carrying the d allele of the ahr gene (AHR-d mice). This allele codes for a mutant AHR with a 10 fold reduction in its affinity for TCDD and other ligands (Okey et al., Mol Pharmacol. 35, 823-30 (1989)) due to mutations in its ligand binding sites. The administration of TCDD (1 µg/mouse) to AHR-d mice did not increase the levels of CD4$^+$ Foxp3$^+$ Treg in AHR-mt mice, and did not inhibit the progression of EAE, as shown in FIG. 4B and Table 4.

TABLE 4

TCDD Treatment of AHR-d Mice

| Treatment | Incidence (positive/total) | Mean day of onset (Mean ± SD) | Mean maximum score (mean ± SD) |
|---|---|---|---|
| WT control | 12/14 (86%) | 13.9 ± 1.9 | 2.4 ± 1.4 |
| AHR-d + TCDD | 9/11 (82%) | 17.3 ± 3.0† | 2.2 ± 1.4 |
| WT + TCDD | 1/10 (10%)# | 21 | 0.2 ± 0.6* |

C57BL/6 (WT) and AHR-d mice treated with corn oil (control) or TCDD (1 µg/mouse) were immunized with MOG$_{35-55}$ peptide in CFA and monitored for EAE development. Statistical analysis was performed by comparing groups using one-way analysis of variance.
*P < 0.001 vs WT control group and P < 0.01 vs AHR-d TCDD group;
†P = 0.0046 vs WT control group;
P = 0.0005 vs WT control group, P = 0.0019 vs AHR-d TCDD group.

Taken together, these results show that TCDD-dependent AHR activation can inhibit or suppress the development and/or progression of EAE. The data presented in Example 3 indicate that this effect is due to the TCDD-dependent AHR activation that promotes the induction of functional Treg.

Antigen microarrays were then used to study the antibody response to myelin in mice that did not develop EAE as consequence of AHR activation by TCDD. The antigens listed in Table 1 were spotted onto Epoxy slides (TeleChem, Sunnyvale, Calif. USA) as described (Quintana et al., Proc Natl Acad Sci USA 101 Suppl 2, 114615-21 (2004)). Antigens were spotted in replicates of 6, the microarrays were blocked for 1 h at 37° C. with 1% bovine serum albumin, and incubated for 2 hours at 37° C. with a 1:100 dilution of the test serum in blocking buffer. The arrays were then washed and incubated for 45 min at 37° C. with goat anti-mouse IgG Cy3-conjugated detection antibodies (Jackson ImmunoResearch Labs, West Grove, Pa., USA). The arrays were scanned with a ScanArray 4000X scanner (GSI Luminomics, Billerica, Mass., USA). Antigen reactivity was defined by the mean intensity of binding to the replicates of that antigen on the microarray. Raw data were normalized and analyzed using the GeneSpring software (Silicon Genetics, Redwood City, Calif., USA) with the non-parametric Wilcoxon-Mann-Whitney test, using the Benjamini and Hochberg method with a false discovery rate (FDR) of 0.05 to determine significance. The samples were clustered using a pairwise average linkage algorithm based on Spearman's rank correlation as a distance measure.

The microarrays consisted of a collection of 362 CNS-related autoantigens including tissue lysates, recombinant proteins, peptide libraries spanning the whole sequence of myelin proteins and lipids found in the central and peripheral nervous system, a complete list of the antigens used is provided in Table 1.

TABLE 1

362 CNS-Related Autoantigens

| | |
|---|---|
| Heat Shock Proteins (HSP) | 27 kDa Heat Shock Protein |
| | 32 kDa Heat Shock Protein |
| | 40 kDa Heat Shock Protein |
| | 47 kDa Heat Shock Protein |
| | 60 kDa Heat Shock Protein |
| | 60 kDa Heat Shock Protein peptide: aa 106-125; aa 1-20; aa 121-140; aa 136-155; aa 151-170; aa 16-35; aa 166-185; aa 181-199; aa 195-214; aa 210-229; aa 225-244; aa 240-259; aa 255-275; aa 271-290; aa 286-305; aa 301-320; aa 31-50; aa 316-335; aa 331-350; aa 346-365; aa 361-380; aa 376-395; aa 391-410; aa 406-425; aa 421-440; aa 436-455; aa 451-470; aa 466-485; aa 46-65; aa 481-500; aa 496-515; aa 511-530; aa 526-545; aa 541-560; aa 556-573; aa 61-80; aa 76-95; or aa 91-110 |
| | 65 kDa Heat Shock Protein *M. tuberculosis* |
| | 70 kDa Heat Shock Protein |
| | 70 kDa Heat Shock Protein peptide aa 106-125; aa 1-20; aa 121-140; aa 136-155; aa 151-170; aa 16-35; aa 166-185; aa 181-199; aa 195-214; aa 210-229; aa 225-244; aa 240-259; aa 255-275; aa 271-290; aa 286-305; aa 301-320; aa 31-50; aa 316-335; aa 331-350; aa 346-365; aa 361-380; aa 376-395; aa 391-410; aa 406-425; aa 421-440; aa 436-455; aa 451-470; aa 466-485; aa 46-65; aa 481-500; aa 496-515; aa 511-530; aa 526-545; aa 541-560; aa 556-575; aa 571-590; aa 586-605; aa 601-620; aa 616-635; aa 61-80; aa 631-640; aa 76-95; or aa 91-110 |
| | 71 kDa Heat Shock Protein *M. tuberculosis* |
| | 90 kDa Heat Shock Protein |
| | GroEL |
| CNS | 2',3'-cyclic nucleotide 3'-phosphodiesterase peptide aa 106-125; aa 1-20; aa 121-140; aa 136-155; aa 151-170; aa 16-35; aa 166-185; aa 181-200; aa 196-215; aa 211-230; aa 226-245; aa 241-260; aa 256-275; aa 271-290; aa 286-305; aa 301-320; aa 31-50; aa 316-335; aa 331-350; aa 346-365; aa 361-380; aa 376-395; aa 391-410; aa 406-421; aa 46-65; aa 61-80; aa 76-95; or aa 91-110 |
| | Acetyl Cholinesterase |
| | ADAM-10 |
| | alpha-Cristallin |
| | beta-Cristallin |
| | bovine Myelin Basic Protein |
| | Brain Extract I |
| | Brain Extract II |
| | Brain Extract III |
| | Glial Filament Acidic Protein Research Diagnostic |

TABLE 1-continued

362 CNS-Related Autoantigens

|  |  |
|---|---|
|  | guinea pig Myelin Basic Protein |
|  | human Myelin Basic Protein |
|  | Myelin-Associated Oligodendrocytic Basic Protein peptide aa 106-125; aa 1-20; aa 121-140; aa 136-155; aa 151-170; aa 16-35; aa 166-185; aa 181-200; aa 31-50; aa 46-65; aa 61-80; aa 76-95; aa 91-110; aa 106-125; aa 1-20; aa 121-140; aa 136-155; or aa 151-170 |
|  | Myelin/oligodendrocyte glycoprotein peptide aa 16-35; aa 166-185; aa 181-200; aa 196-215; aa 211-230; aa 226-247; aa 31-50; aa 35-55; aa 46-65; aa 61-80; aa 76-95; or aa 91-110 |
|  | murine Myelin Basic Protein |
|  | Myelin Associated Glycoprotein |
|  | Myelin Basic Protein peptide aa 104-123; aa 11-30; aa 113-132; aa 1-20; aa 121-138; aa 124-142; aa 138-147; aa 141-161; aa 143-168; aa 155-178; aa 26-35; aa 31-50; aa 41-60; aa 51-70; aa 61-80; aa 71-92; aa 84-94; aa 89-101; aa 173-186; or aa 93-112 |
|  | Myelin Protein 2 peptide aa 106-125; aa 1-20; aa 121-132; aa 16-35; aa 31-50; aa 46-65; aa 61-80; aa 76-95; or aa 91-110 |
|  | Neurofilament 160 kd |
|  | Neurofilament 200 kd |
|  | Neurofilament 68 kd |
|  | Neuronal Enolase |
|  | Nicastrin |
|  | NMDA receptor |
|  | NOGO |
|  | Olygodendrocyte-Specific Protein peptide aa 106-125; aa 1-20; aa 121-140; aa 136-155; aa 151-170; aa 16-35; aa 166-185; aa 181-199; aa 195-217; aa 31-50; aa 46-65; aa 61-80; aa 76-95; or aa 91-110 |
|  | Proteolipid Protein |
|  | Proteolipid Protein peptide aa 100-119; aa 10-29; aa 110-129; aa 1-19; aa 125-141; aa 137-150; aa 137-154; aa 150-163; aa 151-173; aa 158-166; aa 161-180; aa 178-191; aa 180-199; aa 190-209; aa 20-39; aa 205-220; aa 215-232; aa 220-239; aa 220-249; aa 248-259; aa 250-269; aa 265-277; aa 35-50; aa 40-59; aa 50-69; aa 65-84; aa 80-99; or aa 91-110 |
|  | Retinol Binding Protein |
|  | S100beta protein Assay Designs |
|  | Super Oxide Dismutase |
|  | Synuclein, beta |
|  | Synuclein, gamma |
| Tissue | Amydgala |
|  | Amydgala AD |
|  | Brain lysate |
|  | Brain Tissue Membrane |
|  | Cerebellar pedunculus |
|  | Cerebral meninges |
|  | Corpus Callosum |
|  | Corpus Callosum AD |
|  | Diencephalon |
|  | Fetal brain |
|  | Frontal lobe |
|  | Frontal lobe AD |
|  | Hippocampus |
|  | Hippocampus AD |
|  | Insula |
|  | Occipital lobe |
|  | Occipital lobe AD |
|  | Olfactory region |
|  | Optic Nerve |
|  | Parietal lobe |
|  | Parietal lobe AD |
|  | Pons |
|  | Pons AD |
|  | Postcentral gyrus |
|  | Postcentral gyrus AD |
|  | Precentral gyrus |
|  | Precentral gyrus AD |
|  | Spinal cord |
|  | Temporal lobe |
|  | Temporal lobe AD |
|  | Thalamus |
|  | Thalamus AD |
|  | Amyloid beta |
|  | AD related Amyloid beta 10-20 |
|  | Amyloid beta peptide 1-12; 12-28; 1-23; 1-38; beta 17-40; 25-35; or 34-42 |
|  | Amyloid bri protein precursor 227 |
|  | Amyloid DAN Protein Fragment 1-34 |
|  | Amyloid Precursor Protein |
|  | Amyloid protein no AB component |
|  | Secreted amyloid precursor protein (SAP) beta |
|  | Tau isoform variant 0N3R |
|  | Tau isoform variant 1N3R |
|  | Tau isoform variant 0N4R |
|  | Tau isoform variant 2N3R |
|  | Tau phospho Ser412 |
|  | Tau phospho Ser441 |
|  | Tau phospho Thr181 |
|  | Tau Protein human |
| Lipids | (±)9-HODE Cayman Chemical |
|  | 1 Palmitoyl-2-(5'oxo-Valeroyl)-sn-Glycero-3-Phosphocholine |
|  | 15a-hydroxycholestene |
|  | 15-ketocholestane |
|  | 15-ketocholestene |
|  | 1-Palmitoil-2-(9'oxo-Nonanoyl)-sn-Glycero-3-Phosphocholine |
|  | 1-Palmitoyl-2-Azelaoyl-sn-Glycero-3-Phosphocholine |
|  | 1-Palmitoyl-2-Glutaroyl-sn-Glycero-3-Phosphocholine |
|  | 5 α-cholestane-3 β,15 α-diol |
|  | 9(S)-HODE Cayman Chemical |
|  | Asialoganglioside-GM1 |
|  | Asialoganglioside-GM2 |
|  | Brain ceramides |
|  | Brain D-erythrosphingosine |
|  | Brain lysophosphatidylethanolamine |
|  | Brain L-α-lysophosphatidylserine |
|  | Brain L-α-phosphatidylcholine |
|  | Brain L-α-phosphatidyl-ethanolamine |
|  | Brain L-α-phosphatidylserine |
|  | Brain polar lipid extract |
|  | Brain sphingomyelin |
|  | Brain sulfatide |
|  | Brain total lipid extract |
|  | Cardiolipin |
|  | Ceramide |
|  | Ceramide 1-phosphate |
|  | Cholesterol |
|  | Disialogaglioside-GD1B |
|  | Disialogaglioside-GD2 |
|  | Disialoganglioside GD1a |
|  | Disialoganglioside GD3 |
|  | Fucosyl-GM1 |
|  | Galactocerebrosides |
|  | Ganglioside Mixture |
|  | Ganglioside-GM4 |
|  | Gangliotetraosylceramide asialo-GM1 |
|  | HDL |
|  | Hexacosanoic acid (26) |
|  | Hydroxy fatty acid ceramide |
|  | Isoprostane F2 I |
|  | Lactocerebrosides |
|  | Lactosylceramide |
|  | LDL |
|  | Lipid A, diphosphoryl from Salmonella enterica |
|  | Lipopolysaccharides from Escherichia coli |
|  | Lipopolysaccharides from Pseudomona aeruginosa |
|  | Lipopolysaccharides from Salmonella enterica |
|  | Lyso-GM1 |
|  | Monosialoganglioside GM1 |
|  | Monosialoganglioside GM2 |
|  | Monosialoganglioside GM3 |
|  | N-Hexanoyl-D-sphingosin |
|  | Non-hydroxy fatty acid ceramide |
|  | Phosphatidylinositol-4 phosphate |
|  | Squalene |
|  | Sulfatides |
|  | Tetracosanoic acid (24) |
|  | Tetrasialoganglioside-GQ1B |
|  | TNPAL Galactocerebroside |
|  | Total brain gangliosides |

TABLE 1-continued

362 CNS-Related Autoantigens

Total cerebroside
Trisialoganglioside GT1a
Trisialoganglioside-GT1B

The control of EAE by AHR activation correlated with a significant decrease in IgG serum antibodies to 97 myelin antigens, which are listed in Table 2.

TABLE 2

Specificity of IgG Antibodies Showing a Significant (FDR < 0.05) Downregulation in TCDD-Treated Mice

| Antigen | FDR |
| --- | --- |
| 70 kDa. Heat Shock Protein peptide aa 331-350 | 1.78E–05 |
| 60 kDa. Heat Shock Protein peptide aa 255-275 | 0.00547 |
| 60 kDa. Heat Shock Protein peptide aa 13-35 | 0.00547 |
| 32 kDa. Heat Shock protein | 0.00547 |
| Myelin Basic Protein peptide aa 138-147 | 0.00547 |
| Proteolipid Protein peptide aa 1-19 | 0.00547 |
| Proteolipid Protein peptide aa 161-180 | 0.00547 |
| Proteolipid Protein peptide aa 10-29 | 0.00547 |
| 60 kDa. Heat Shock Protein peptide aa 1-20 | 0.0055 |
| 70 kDa. Heat Shock Protein peptide aa 61-80 | 0.0055 |
| Ceramide | 0.0055 |
| Myelin-Associated Oligodendrocytic Basic Protein peptide aa 91-110 | 0.0055 |
| Proteolipid Protein peptide aa 137-150 | 0.0055 |
| NOGO | 0.00557 |
| Olygodendrocyte-Specific Protein peptide aa 76-95 | 0.00557 |
| b-Cristallin | 0.0058 |
| Myelin-Associated Oligodendrocytic Basic Protein peptide aa 121-140 | 0.00703 |
| 60 kDa. Heat Shock Protein peptide aa 225-244 | 0.00708 |
| Myelin Basic Protein peptide aa 113-132 | 0.00925 |
| Olygodendrocyte-Specific Protein peptide aa 46-65 | 0.00925 |
| Myelin Protein 2 peptide aa 91-110 | 0.00925 |
| Myelin-Associated Oligodendrocytic Basic Protein peptide aa 151-170 | 0.0093 |
| Myelin/oligodendrocyte glycoprotein peptide aa 31-50 | 0.0093 |
| NT-3 | 0.0093 |
| Proteolipid Protein peptide aa 40-59 | 0.0116 |
| 70 kDa. Heat Shock Protein peptide aa 421-440 | 0.0118 |
| Myelin Basic Protein peptide aa 173-186 | 0.0125 |
| 70 kDa. Heat Shock Protein peptide aa 121-140 | 0.0132 |
| 2',3'-cyclic nucleotide 3'-phosphodiesterase peptide aa 391-410 | 0.0132 |
| Olygodendrocyte-Specific Protein peptide aa 136-155 | 0.0132 |
| Olygodendrocyte-Specific Protein peptide aa 106-125 | 0.0134 |
| 70 kDa. Heat Shock Protein peptide aa 136-155 | 0.0141 |
| 2',3'-cyclic nucleotide 3'-phosphodiesterase peptide aa 406-421 | 0.0141 |
| Myelin-Associated Oligodendrocytic Basic Protein peptide aa 166-185 | 0.0143 |
| Myelin Protein 2 peptide aa 1-20 | 0.0143 |
| Myelin Protein 2 peptide aa 76-95 | 0.0144 |
| Proteolipid Protein peptide aa 125-141 | 0.0144 |
| Proteolipid Protein peptide aa 178-191 | 0.0144 |
| 40 kDa. Heat Shock Protein | 0.0145 |
| 2',3'-cyclic nucleotide 3'-phosphodiesterase peptide aa 106-125 | 0.0158 |
| Olygodendrocyte-Specific Protein peptide aa 195-217 | 0.0174 |
| 2',3'-cyclic nucleotide 3'-phosphodiesterase peptide aa 240-259 | 0.0187 |
| 70 kDa. Heat Shock Protein peptide aa 76-95 | 0.0194 |
| Proteolipid Protein peptide aa 265-277 | 0.0194 |
| Myelin Basic Protein peptide aa 89-101 | 0.0199 |
| Myelin Basic Protein peptide aa 71-92 | 0.0199 |
| Myelin-Associated Oligodendrocytic Basic Protein peptide aa 16-35 | 0.0199 |
| Proteolipid Protein peptide aa 265-277 | 0.0199 |
| 60 kDa. Heat Shock Protein peptide aa 46-65 | 0.0241 |
| 70 kDa. Heat Shock Protein peptide aa 166-185 | 0.0241 |
| 2',3'-cyclic nucleotide 3'-phosphodiesterase peptide aa 151-170 | 0.0241 |
| 2',3'-cyclic nucleotide 3'-phosphodiesterase peptide aa 376-395 | 0.0241 |
| Myelin Basic Protein peptide aa 11-30 | 0.0241 |
| Myelin/oligodendrocyte glycoprotein peptide aa 211-230 | 0.0241 |
| Proteolipid Protein peptide aa 265-277 | 0.0241 |
| 70 kDa. Heat Shock Protein peptide aa 181-199 | 0.0242 |
| Olygodendrocyte-Specific Protein peptide aa 31-50 | 0.0242 |
| Proteolipid Protein peptide aa 265-277 | 0.0242 |
| Myelin/oligodendrocyte glycoprotein peptide aa 91-110 | 0.0249 |
| Optic Nerve lysate | 0.0249 |
| 2',3'-cyclic nucleotide 3'-phosphodiesterase peptide aa 361-380 | 0.0258 |
| Lactosylceramide | 0.0258 |
| Myelin Protein 2 peptide aa 31-50 | 0.0258 |
| Myelin Basic Protein peptide aa 1-20 | 0.028 |
| NMDA receptor | 0.0285 |
| CNF | 0.0289 |
| 2',3'-cyclic nucleotide 3'-phosphodiesterase peptide aa 136-155 | 0.0292 |
| Myelin Basic Protein peptide aa 141-161 | 0.0298 |
| 70 kDa. Heat Shock Protein peptide aa 406-425 | 0.0307 |
| 2',3'-cyclic nucleotide 3'-phosphodiesterase peptide aa 210-229 | 0.0307 |
| Galactocerebrosides | 0.0307 |
| Myelin/oligodendrocyte glycoprotein peptide aa 46-65 | 0.0307 |
| Proteolipid Protein peptide aa 150-163 | 0.0307 |
| Proteolipid Protein peptide aa 265-277 | 0.0307 |
| Proteolipid Protein peptide aa 80-99 | 0.0307 |
| 60 kDa. Heat Shock Protein peptide aa 210-229 | 0.0323 |
| Proteolipid Protein peptide aa 137-154 | 0.0324 |
| 2',3'-cyclic nucleotide 3'-phosphodiesterase peptide aa 1-20 | 0.0337 |
| 2',3'-cyclic nucleotide 3'-phosphodiesterase peptide aa 225-244 | 0.0337 |
| Myelin-Associated Oligodendrocytic Basic Protein peptide aa 61-80 | 0.0337 |
| Proteolipid Protein peptide aa 158-166 | 0.0337 |
| Ceramide 1 phosphate | 0.0346 |
| Myelin-Associated Oligodendrocytic Basic Protein peptide aa 136-155 | 0.0369 |
| Myelin Basic Protein peptide aa 155-178 | 0.0379 |
| Myelin/oligodendrocyte glycoprotein peptide aa 106-125 | 0.0392 |
| Proteolipid Protein peptide aa 180-199 | 0.0408 |
| Myelin Protein 2 peptide aa 121-132 | 0.0413 |
| Myelin Basic Protein peptide aa 104-123 | 0.0419 |
| 70 kDa. Heat Shock Protein | 0.0421 |
| Non h fatty acid ceramide | 0.0421 |
| Myelin-Associated Glycoprotein | 0.0452 |
| Myelin Basic Protein peptide aa 143-168 | 0.0452 |
| 2',3'-cyclic nucleotide 3'-phosphodiesterase peptide aa 91-110 | 0.047 |
| 2',3'-cyclic nucleotide 3'-phosphodiesterase peptide aa 181-199 | 0.0476 |
| 70 kDa. Heat Shock Protein peptide aa 255-275 | 0.0486 |
| Brain ceramides | 0.0486 |
| Myelin Protein 2 peptide aa 46-65 | 0.0496 |

To further characterize the suppression of EAE by AHR activation we studied the activity of myelin specific T cells induced by vaccination with $MOG_{35-55}$/CFA in TCDD-treated mice. TCDD-treated mice showed a suppressed recall proliferative response to the $MOG_{35-55}$ peptide, however no differences were seen upon activation with antibodies to CD3 (see FIGS. 4c-d).

In addition, cells were stimulated in culture medium containing 100 μg/ml $MOG_{35-55}$ for 2 days or with PMA (50 ng/ml) (Sigma-Aldrich) and ionomycin (1 nM) (Calbiochem, San Diego, Calif., USA) for 4 hours, Golgistop (BD Biosciences) was added to the culture during the last 4 hours. After staining of surface markers, cells were fixed and permeabilized using Cytofix/Cytoperm and Perm/Wash buffer from BD Biosciences according to the manufacturer's instructions. All antibodies to cytokines (IFN-gamma, IL-17, IL-10) including the corresponding isotype controls were obtained from BD Biosciences. Cells were incubated (1:100) at 25° C. for 20 min and washed twice in Perm/Wash before analysis. Data were acquired on a FACSCalibur (BD Biosciences) and analyzed with FlowJo software (Tree Star, Ashland, Oreg., USA). When compared to the draining lymph node cells from control animals, cells from TCDD-treated mice secreted higher amounts of TGFb1 and lower amounts of IFNg and IL-17 upon activation with $MOG_{35-55}$ (see FIG.

4c); we did not detect significant amounts of IL-4 or IL-10. Moreover, AHR activation with TCDD led to a decrease in the frequency of CD4+IL-17+ and CD4+IFNg+ T cells in the draining lymph nodes (see FIG. 4F).

These data suggest that AHR activation interferes with the generation of the encephalitogenic T cell response.

Example 6

Treg Induced by AHR Activation Suppress EAE by a TGFb1-Dependent Mechanism

Figure 5A:
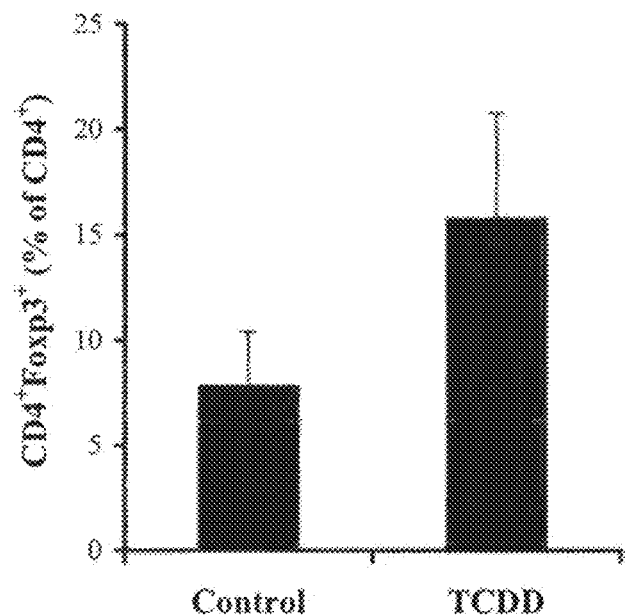
FIG. 5A is a bar graph illustrating the effects on EAE of TCDD, or oil as control, administered ip to C57BL/6 mice. EAE was induced 24 hours later by immunization with $MOG_{35-55}$/CFA. The frequency of $CD4^+FoxP3^+$ T cells in the spleen $CD4^+$ T-cell population was determined 21 days after EAE induction by FACS (mean+s.d. of five mice). *P<0.02, unpaired t-test).
Figure 5B:
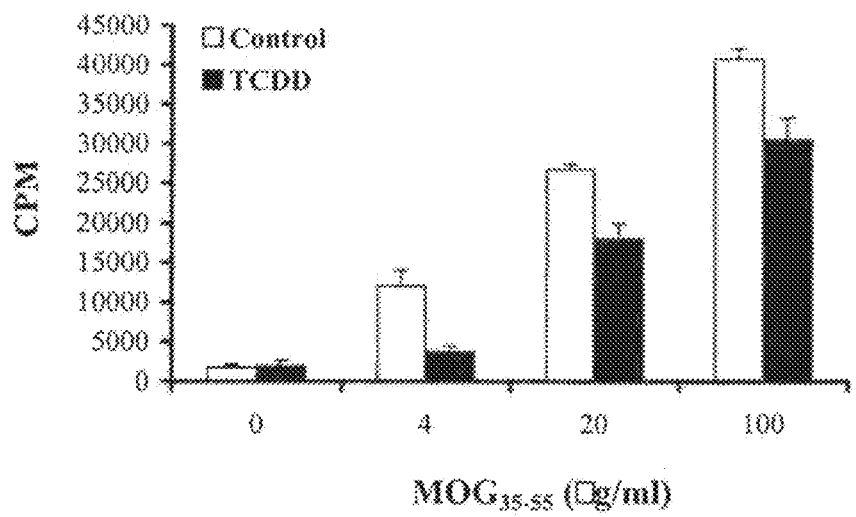
FIG. 5B is a bar graph illustrating the proliferative response to $MOG_{35-55}$ of $CD4^+CD25^-$ lymph node cells taken from TCDD or control treated animals 10 days after immunization with $MOG_{35-55}$/CFA. Cell proliferation is indicated as cpm+s.d. in triplicate wells.
Figure 5C:
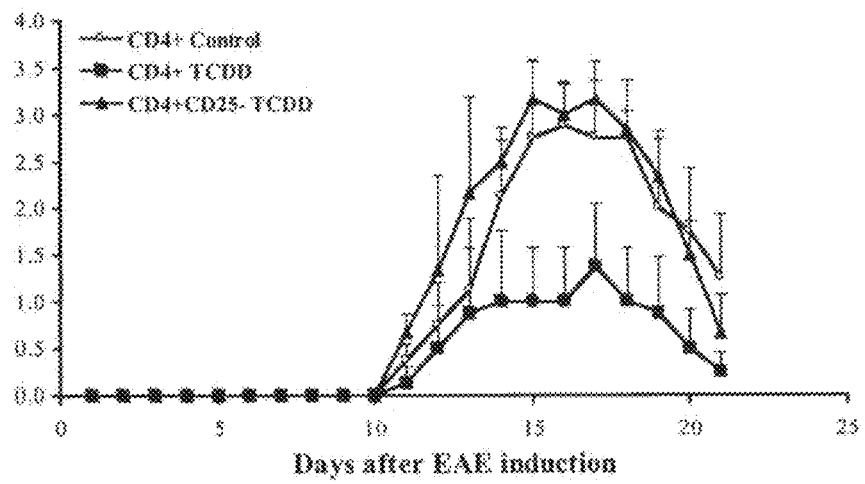
FIG. 5C is a line graph of EAE scores in mice treated with $CD4^+$ or $CD4^+ CD25^-$ T cells ($5\times10^6$) that were purified from TCDD or control treated mice 10 days after immunization with $MOG_{35-55}$/CFA. After 1 day, EAE was induced in the recipient mice with $MOG_{35-55}$/CFA. The course of EAE in these mice is shown as the mean EAE score+s.e.m. (P<0.001, two-way ANOVA, n=4).

The inhibition of the development of EAE by AHR activation with TCDD was associated with a significant increase in the frequency of CD4+Foxp3+ T cells (see FIG. 5A). To identify the mechanism responsible for the decreased proliferation to $MOG_{35-55}$ in TCDD-treated animals shown in FIG. 4D, the CD4+CD25+ Treg population was depleted with magnetic beads. Treg depletion recovered the recall response to $MOG_{35-55}$ in immunized mice treated with TCDD (see FIG. 5B), suggesting that the suppression observed in FIG. 4D resulted from the activity of the TCDD-treated mice, but not with cells isolated from vehicle-treated mice (P<0.001, two-way ANOVA, n=4; FIG. 5C). The control of the pathogenic T cell response was mediated by CD4+ CD25+ Treg, their depletion abrogated the protective effect of the transferred cells (P<0.001, two-way ANOVA, n=4; FIG. 5C).

Figure 5D:
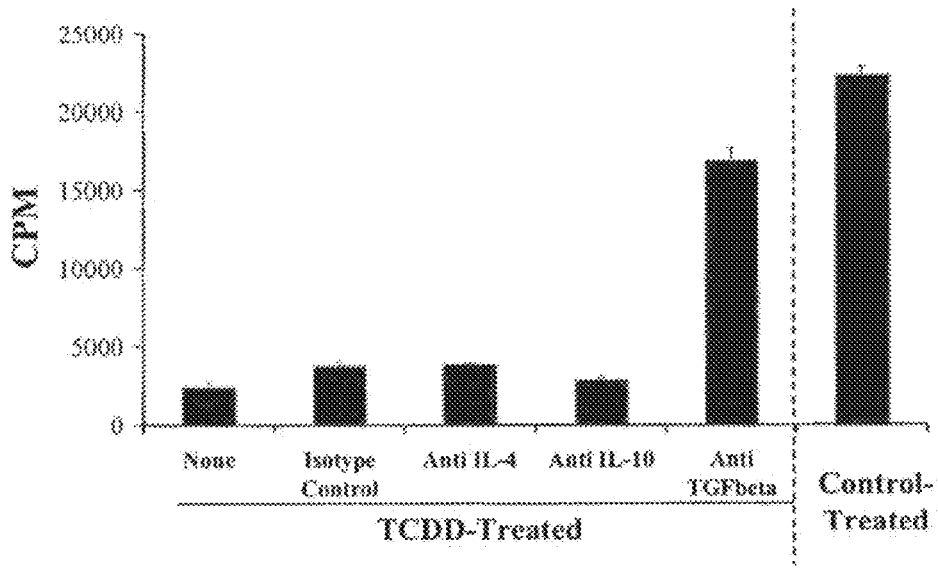
FIG. 5D is a bar graph showing the proliferative response of lymph node cells taken from TCDD-treated animals 10 days after immunization with $MOG_{35-55}$/CFA, activated in vitro with $MOG_{35-55}$ in the presence of blocking antibodies to IL-4, IL-10, TGFb or isotype control. Cell proliferation is indicated as cpm+s.d. in triplicate wells.
Figure 5E:
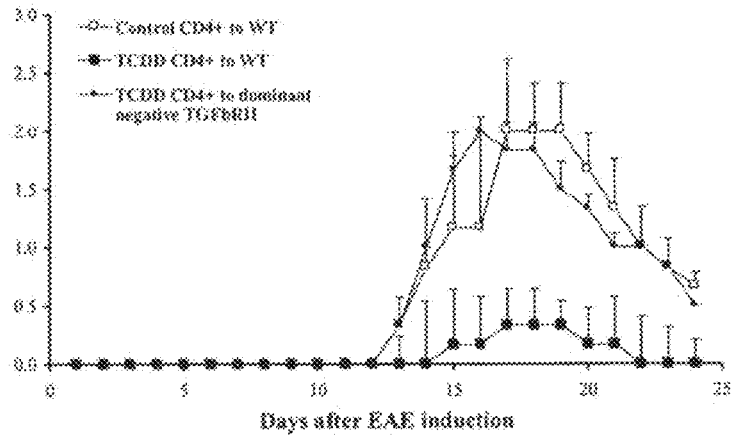
FIG. 5E is a line graph of EAE in naïve wild type (WT) or dominant negative TGFbRII mice injected with $CD4^+$ T cells ($5\times10^6$) purified from TCDD or control treated mice 10 days after immunization with $MOG_{35-55}$/CFA. After 1 day, EAE was induced in the recipient mice with $MOG_{35-55}$/CFA. The course of EAE in these mice is shown as the mean EAE score+s.e.m. (P<0.001, two-way ANOVA, n=4).
Figure 5F:
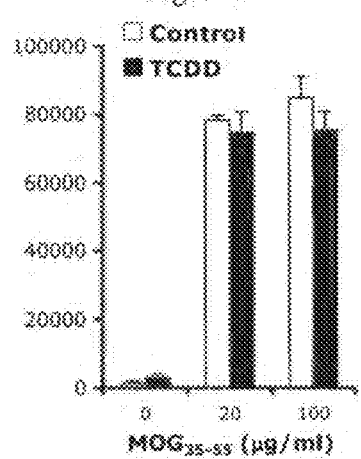
FIG. 5F is a bar graph of proliferation to $MOG_{35-55}$ of $CD4^+Foxp3:GFP^-$ lymph node cells from TCDD$^-$ or control-treated Foxp3gfp mice, (cpm+s.d. in triplicate wells).
Figure 5G:
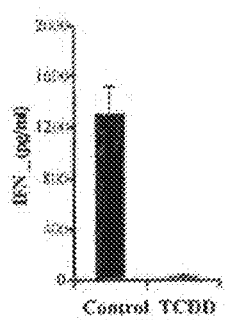
FIG. 5G is a bar graph of the recall cytokine response to $MOG_{35-55}$ of $CD4^+Foxp3:GFP^-$ lymph node cells taken from TCDD or control treated Foxp3gfp mice 10 days after immunization with $MOG_{35-55}$/CFA. Cytokine secretion is expressed as pg/m in triplicate wells.

Further characterization revealed that effector CD4+ Foxp3:GFP− T cells purified from TCDD-treated mice showed normal proliferation (FIG. 5F), but significantly decreased secretion of IL-17 and IFNγ upon activation with $MOG_{35-55}$ (see FIG. 5G).

Figure 5H:
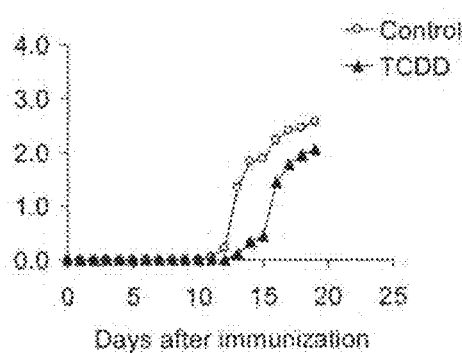
FIG. 5H is a line graph of clinical EAE scores. TCDD-treated mice showed a significant delay in the onset of EAE (P=0.03, Student's t-test, n=9).
Figure 5I:
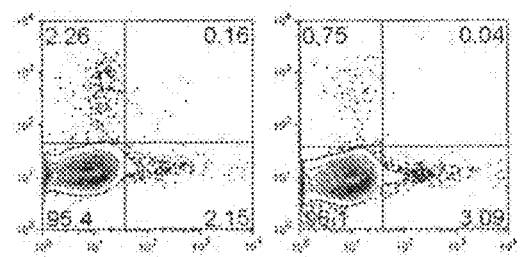
FIG. 5I is a pair of FACS plots from draining lymph node cells recovered on day 18, stimulated with PMA/ionomycin and stained for CD4 and intracellular IL-17 and IFNγ. The numbers in the quadrants show percentages of cytokine positive cells in the $CD4^+Foxp3:GFP^-$ T cell gate. Treatment with TCDD led to a significant decrease in the frequency of $CD4^+$ IL-17$^+$ T cells (P=0.03, Student's t-test, n=4).

To confirm that the protective effect of TCDD on EAE was Treg mediated we depicted the natural Treg with antibodies to CD25 prior to TCDD treatment. The difference between undepleted and depleted cell populations are shown in FIG. 5H. TCDD-treated mice showed a faster rebound in their Treg numbers (P<0.04) at day 7) (see FIG. 5H), concomitant with a significant delay in the onset of EAE (P<0.03) and a significant reduction in IL-17+ CD4+ T cells in the draining lymph nodes (P-<0.03; see FIGS. 5I and 5J). Moreover, the transfer of 5×10⁶ CD4+ T cells from TCDD-treated mice significantly inhibited the development of EAE, as shown in FIG. 5h and Table 5. This protective effect was lost when FC4+CD25+ cells were depleted, see FIG. 5h and Table 5. Together, these data suggest that AHR activation by TCDD results in the generation of CD4+ Foxp3+ Treg that control the encephalitogenic response.

TABLE 5

EAE Suppression in Treg Depleted Cell Populations

| Treatment | Incidence (positive/total) | Mean day of onset (Mean ± SD) | Mean maximum score (mean ± SD) |
|---|---|---|---|
| CD4+ control | 7/7 (100%) | 12.3 ± 1.9 | 2.7 ± 1.0 |
| CD4+ TCDD | 3/6 (57%) | 13.3 ± 0.6 | 0.7 ± 0.8* |
| CD4+CD25− TCDD | 3/4 (75%) | 11.0 ± 0.0 | 2.6 ± 1.8 |

Naïve C57BL/6 mice received CD4+ or CD4+CD25− T cells (5 × 10⁶) purified from TCDD or control treated mice 10 days after immunization with $MOG_{35-55}$/CFA. 24 hours later EAE was induced in the recipient mice with $MOG_{35-55}$/CFA, and the mice were monitored for EAE development. Statistical analysis was performed by comparing groups using one-way analysis of variance.
*P < 0.05 vs CD4+ control group.

TFGb1 has been linked to the suppressive activity of Treg in vitro and in vivo (Li et al., Annu Rev Immunol. 24, 99-146 (2006)). To asses the role played by TGFb1 in the inhibition of the recall response to $MOG_{35-55}$ by Treg (see FIGS. 4d and 5b), we activated lymph node cells from TCDD treated mice in the presence of blocking antibodies to IL-4, IL-10, TGFb1, or an isotype-matched control. FIG. 5d shows that incubation with antibodies to TGFb1, but not to IL-4 or IL-10 could recover the recall response to $MOG_{35-55}$.

To analyze the role played by TFGb1 in vivo in the control of EAE, we transferred CD4+ T cells from TCDD treated mice into naïve mice expressing a dominant negative variant of the TGFb receptor II on their T cells; T cells from these mice are unresponsive to the immunosuppressive effects of TGFb1 (Gorelik et al., Immunity, 12, 171-81 (2000)). As shown in FIG. 5E, transferred Treg cells could control EAE in wild type mice but not in mice harboring T cells unresponsive to TGFb1 (P<0.001, two-way ANOVA, n=4). Thus, Treg induced by the activation of AHR with TCDD inhibit the progression of EAE by a TGFb1-dependent mechanism.

Example 7

Endogenous AHR Ligand Control Treg Development In Vivo

Figure 6A:
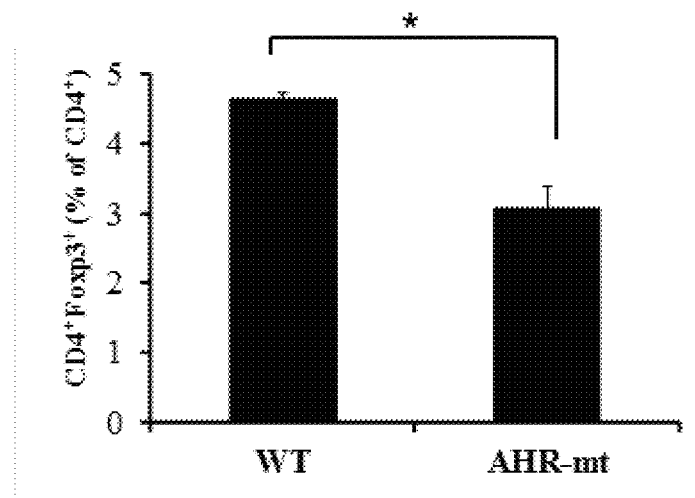
FIGS. 6A-C are bar graphs showing that endogenous AHR ligands control EAE development 6A, the frequency of $CD4^+$ Foxp3$^+$ T cells in the $CD4^+$ T-cell population was determined by FACS in the blood of wild type C57BL/6 and AHR-mt mice, and is presented as the mean+s.d. (n=5-11, P<0.03 t-test). 6B, EAE was induced in wild type C57BL/6J and AHR-mt mice by immunization with $MOG_{35-55}$/CFA. The course of EAE is shown as the mean EAE score+s.e.m. (P<0.0001; two-way ANOVA, n=6-8. 6C, ITE (100 mg/mouse), TA (100 mg/mouse) or PBS as a control were administered on daily basis to C57BL/6 mice. One day after the first administration, EAE wad induced by immunization with $MOG_{35-55}$/CFA. The course of EAE is shown as ht mean EAE score+s.e.m. (P<0.0001, two-way ANOVA, n=9).
Figure 6B:
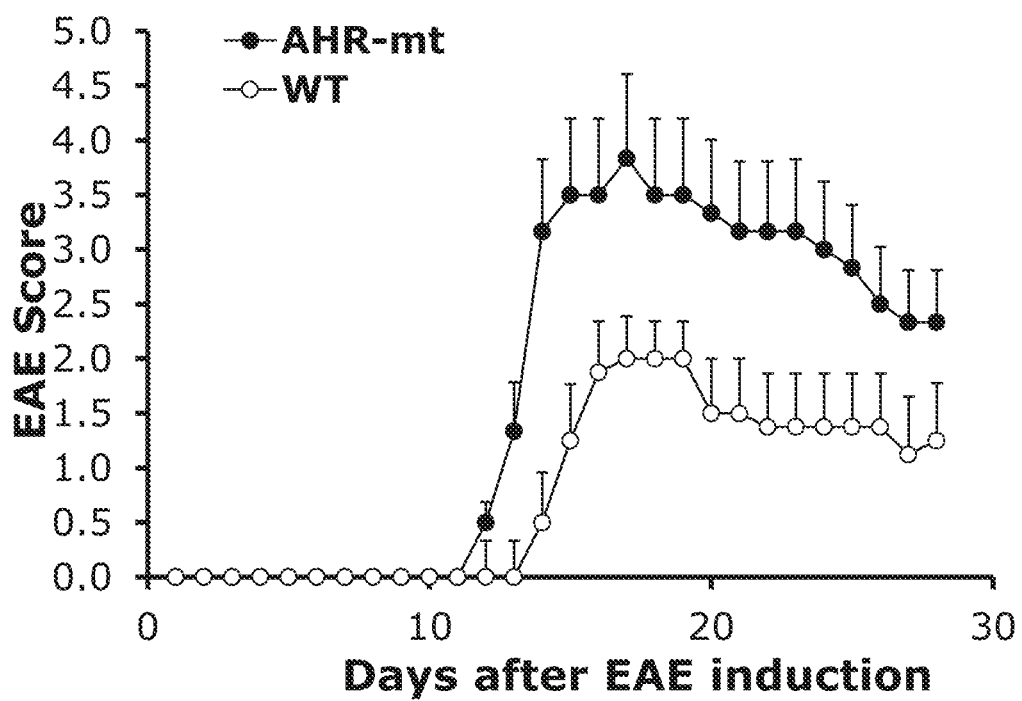

The observations described herein regarding the control of Treg development by AHR activation suggest that endogenous AHR ligands participate in immune regulation. In support of this, we have demonstrated that naïve AHR-d mice harbor lower levels of CD4+Foxp3+ T cells (P<0.03, t-test; see FIG. 6A), and higher levels of CD4+ CD25+Foxp3+ T cells. In addition, we have demonstrated that these cells develop a significantly stronger EAE, which is characterized by an earlier disease onset and a high clinical score (P<0.001, two-way ANOVA, n=6-8; see FIG. 6B).

Figure 6C:
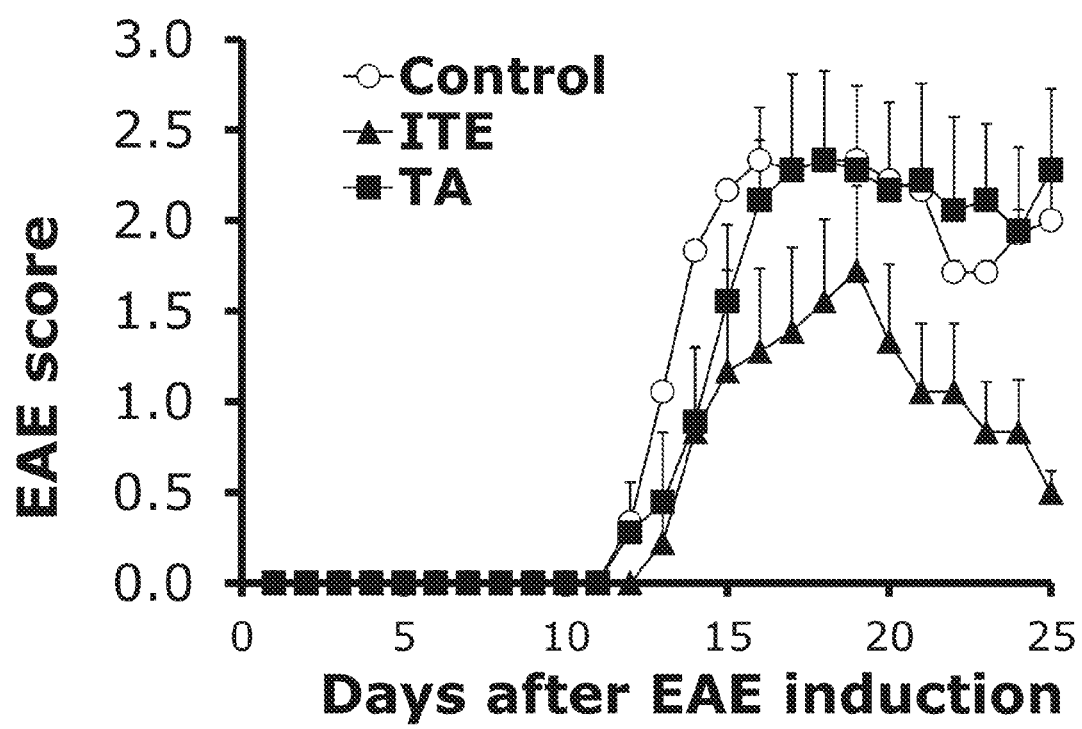

Several endogenous AHR ligands are described in the art[28]. Based on our results, AHR ligands such as TCDD could be useful in the control of Treg development. Our data additionally demonstrate that AHR ligands such as TCDD can be used to suppress the development and/or progression of EAE. Clearly, such technology would also be useful in the modulation of other immunological disorders such as autoimmune disorders. Two additional endogenous high affinity ligands for AHR are tryptaime (TA) (Heath-Pagliuso et al., Biochemistry. 37, 11508-15 (1998)), a derivative of tryptophan (Trp) catabolism and 2-(1'H-indole-3'-carbonyl)-thiazole-4-carboxylic acid methyl ester (ITE) (Song et al., Proc Natl Acad Sci USA, 99, 14694-9 Epub 2002 Oct. 30 (2002)), a molecule isolated from the lung. Interestingly, no toxicity has been reported for these AHR ligands in vivo, probably as a result of their short half-life (Henry et al., Arch Biochem Biophys. 450, 67-77 Epub 2006 Mar. 3 (2006)). To confirm the physiologic relevance of AHR activation for the control of Treg activity, we tested the effect of TA and ITE on EAE. Based on the short half-life of these molecules we administered them on a daily basis. The administration of ITE, and not TA, led to a significant reduction on EAE severity (P<0.001, two-way ANOVA, n=9; see FIG. 6c), likely due to rapid degradation of TA. This observation suggests that endogenous AHR ligands participate in the control of inflammation under physiological conditions.

Together, these result indicate that modulation of Foxp3 expression by modulating activity of a transcription factor that binds to Foxp3 can be used to affect Treg and control of the immune response in vivo.

Example 8

Expression Levels of Transcription Factors in Foxp3 Knock-In Mice

Mouse Treg and non-Treg were isolated from Foxp3gpf knock in mice, mRNA was prepared and Foxp3 (see FIG.

Figure 8A:
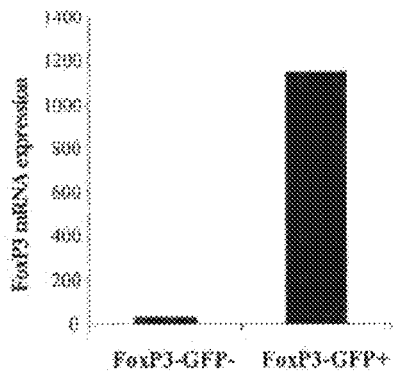
FIGS. 8A-E and 9A-E are bar graphs showing expression levels of transcription factors in cells transfected with Foxp3.
Figure 8B:
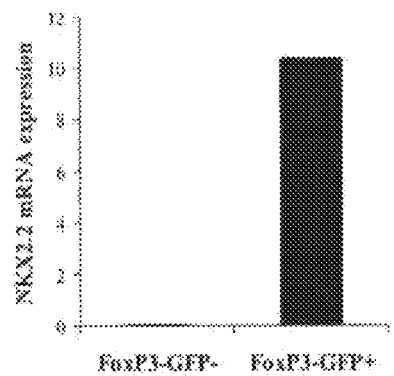
Figure 8C:
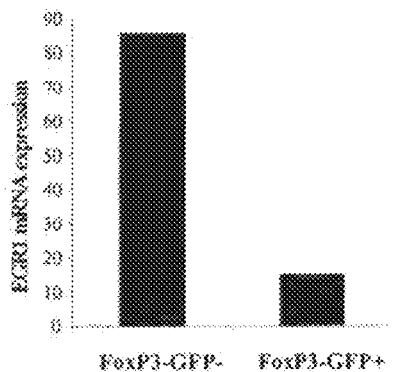
Figure 8D:
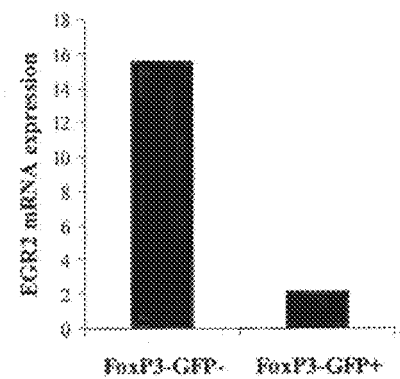
Figure 8E:
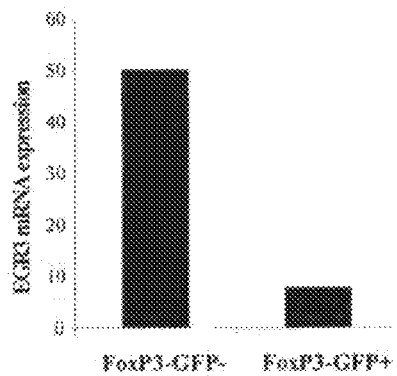

8A), NKX2.2 (see FIG. 8B), EGR1 (see FIG. 8C), EGR2 (see FIG. 8D) and EGR3 (see FIG. 8E expression was quantified by real time PCR. Foxp3gpf knock in mice have a GFP reporter inserted in the Foxp3 gene, producing GFP in Foxp3$^+$ Treg and therefore facilitating the identification and FACS sorting of GFP:Foxp3$^+$ Treg.

Figure 9A:
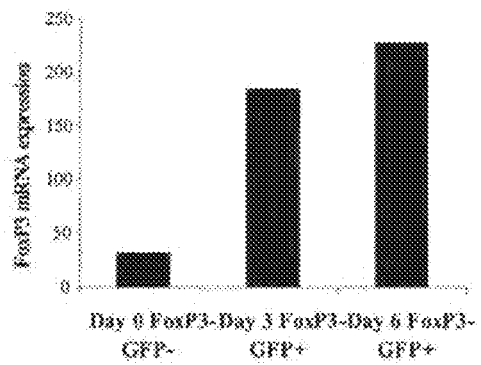
Figure 9B:
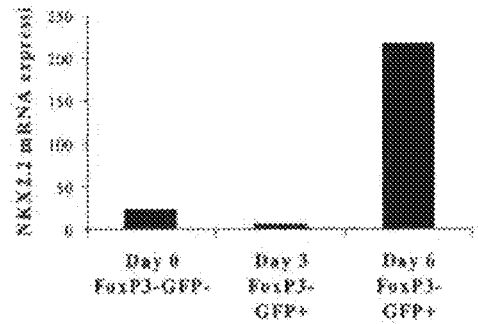
Figure 9C:
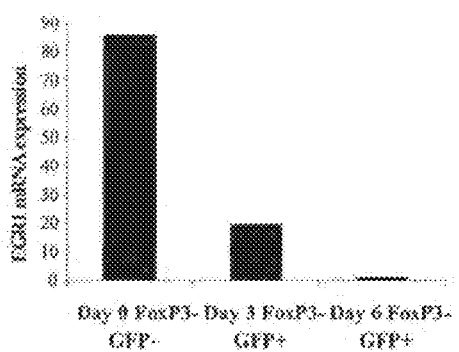
Figure 9D:
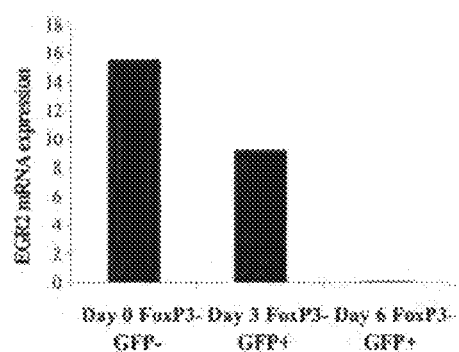
Figure 9E:
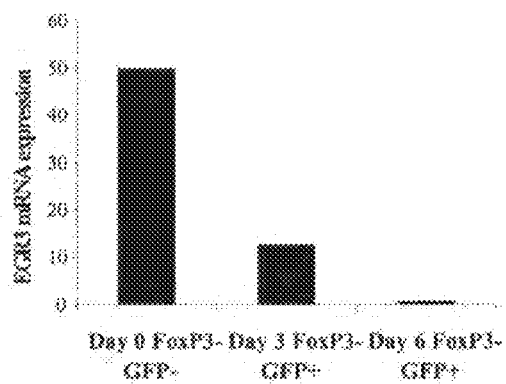
Figure 16A:
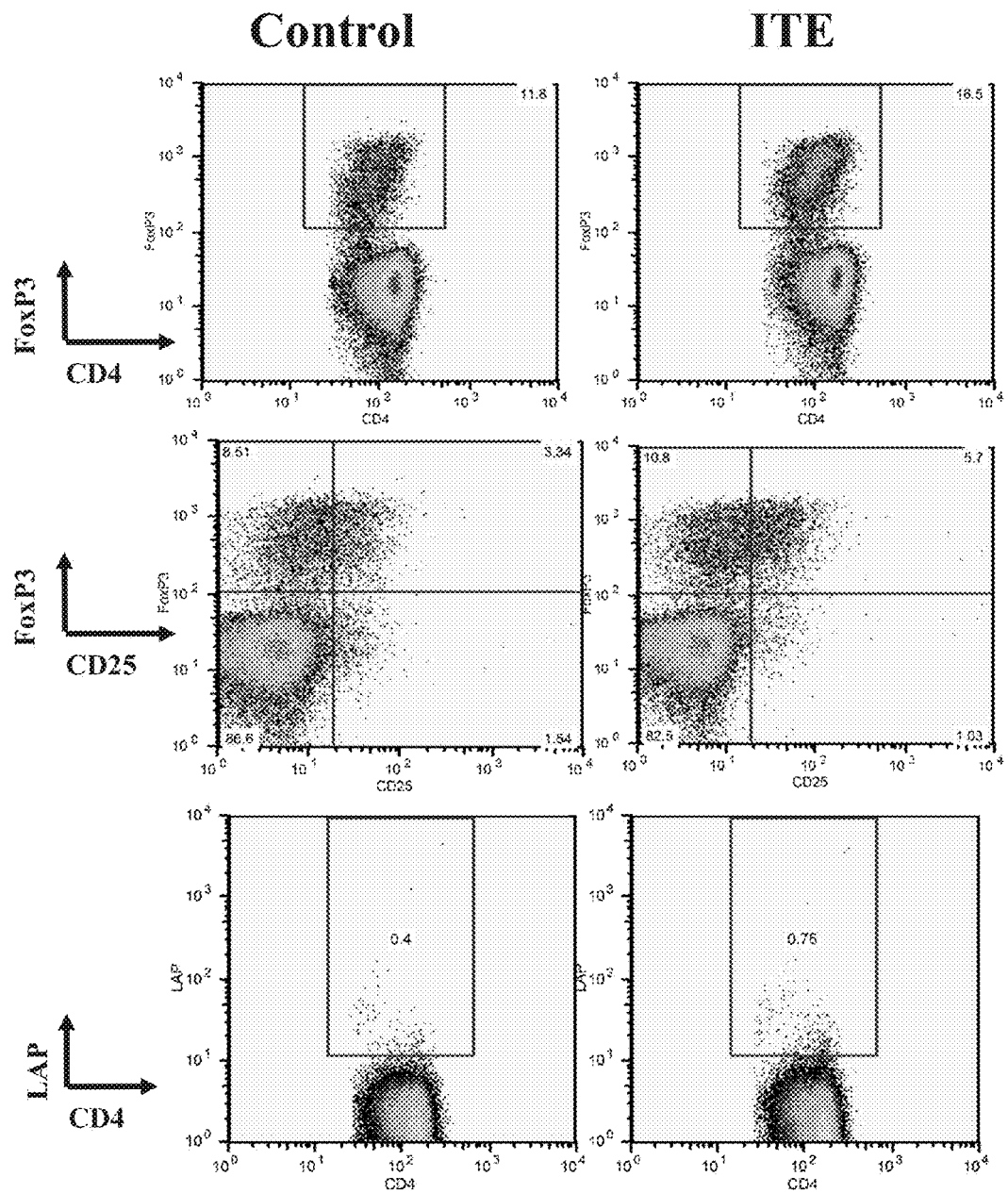
FIGS. 16A-B and 17A-B are FACS plots (16A-B) and bar graphs (17A-B) showing the induction of FoxP3$^+$ T$_{reg}$ by IP administration of ITE. EAE was induced in B6 mice (n=10), the mice were treated with ITE or vehicle, and T$_{reg}$ levels were analyzed by FACS on splenocytes at day 17 after EAE induction.
Figure 16B:
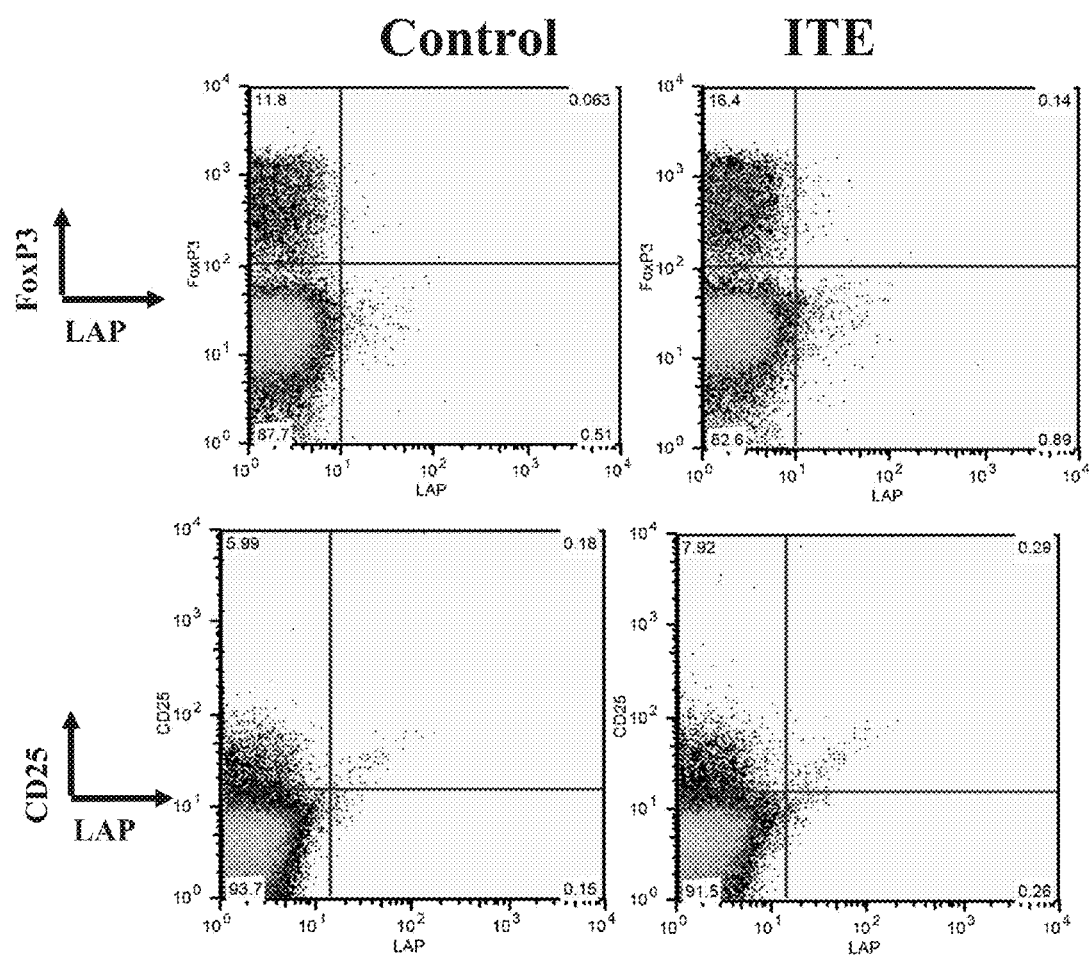
Figure 17A:
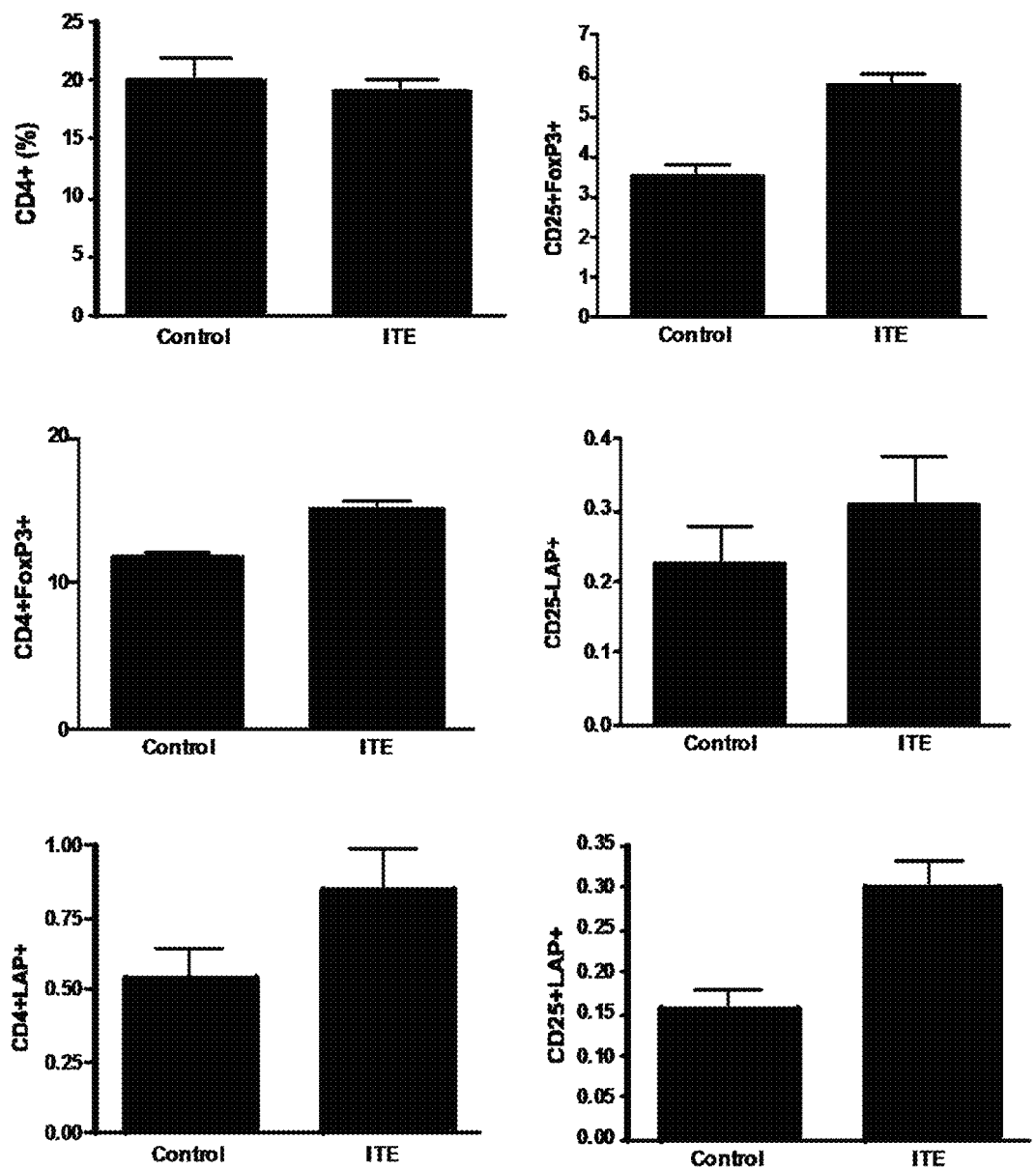
Figure 17B:
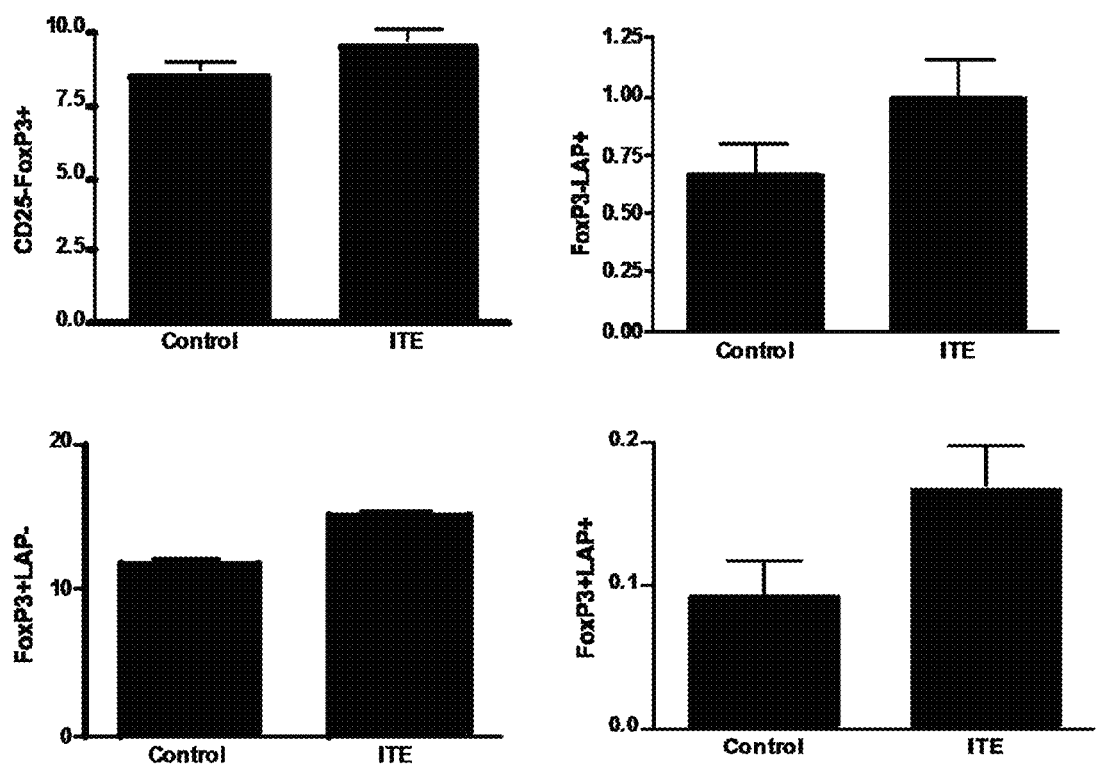
Figure 18A:
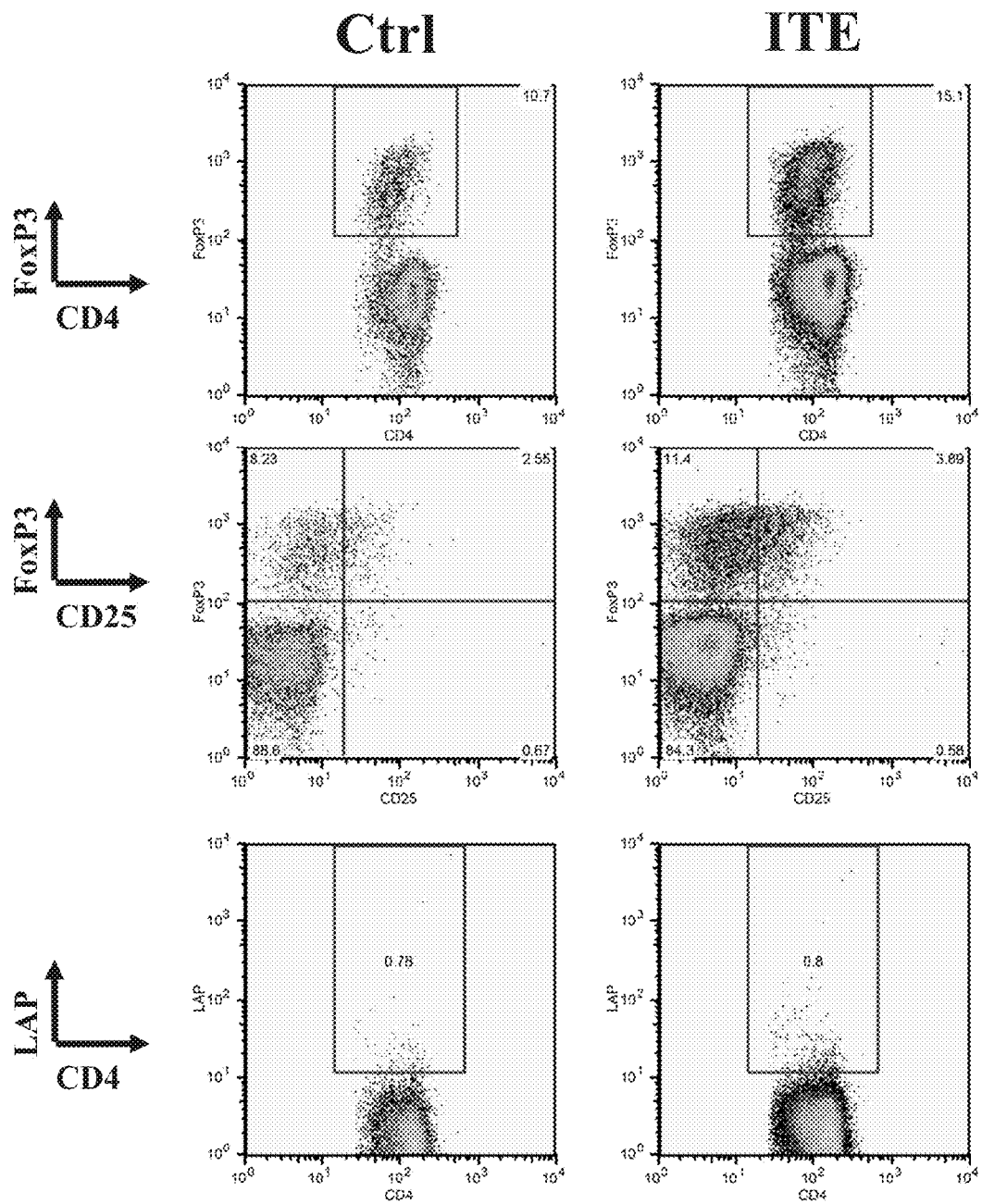
FIGS. 18A-B and 19A-B are FACS plots (18A-B) and bar graphs (19A-B) showing the induction of FoxP3+ Treg by oral administration of ITE. EAE was induced in B6 mice (n=10), the mice were treated with ITE or vehicle, and Treg levels were analyzed by FACS on splenocytes at day 17 after EAE induction.
Figure 18B:
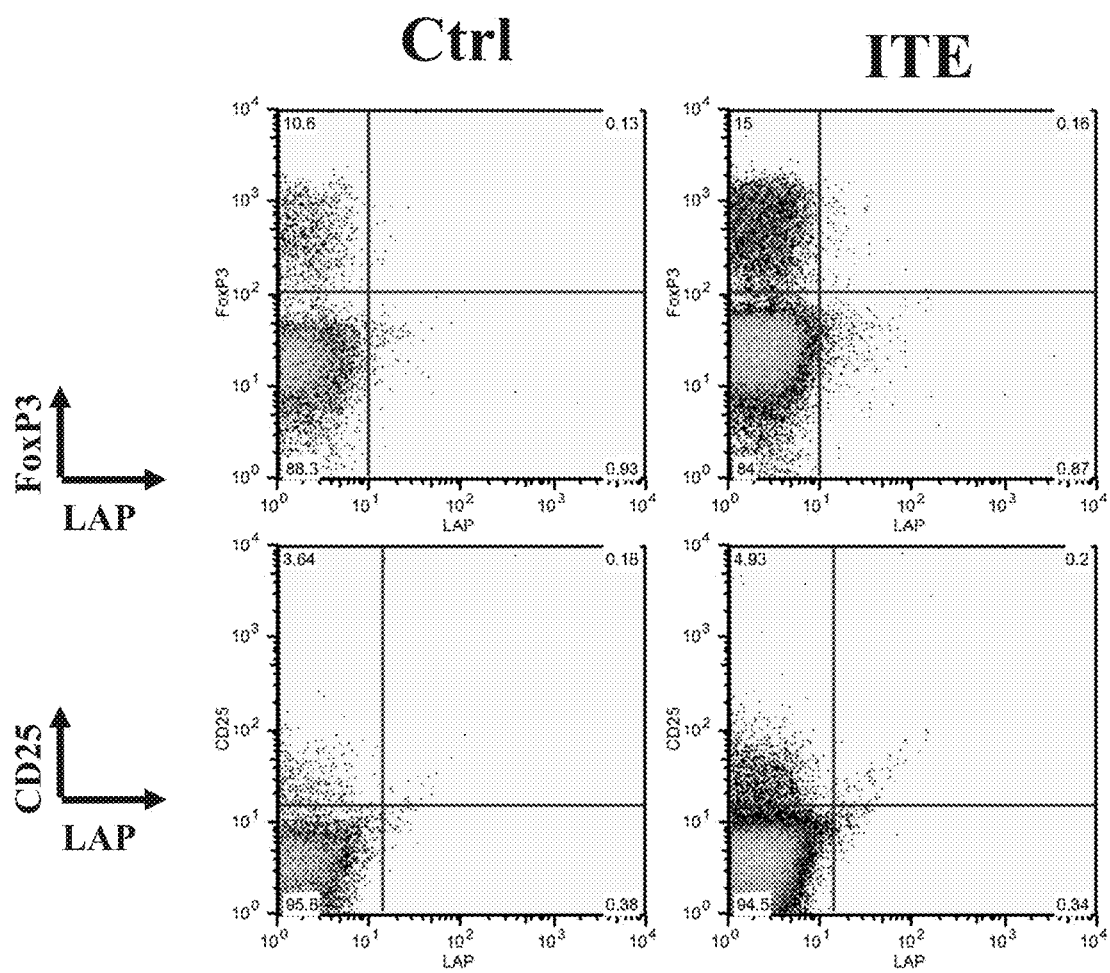
Figure 19A:
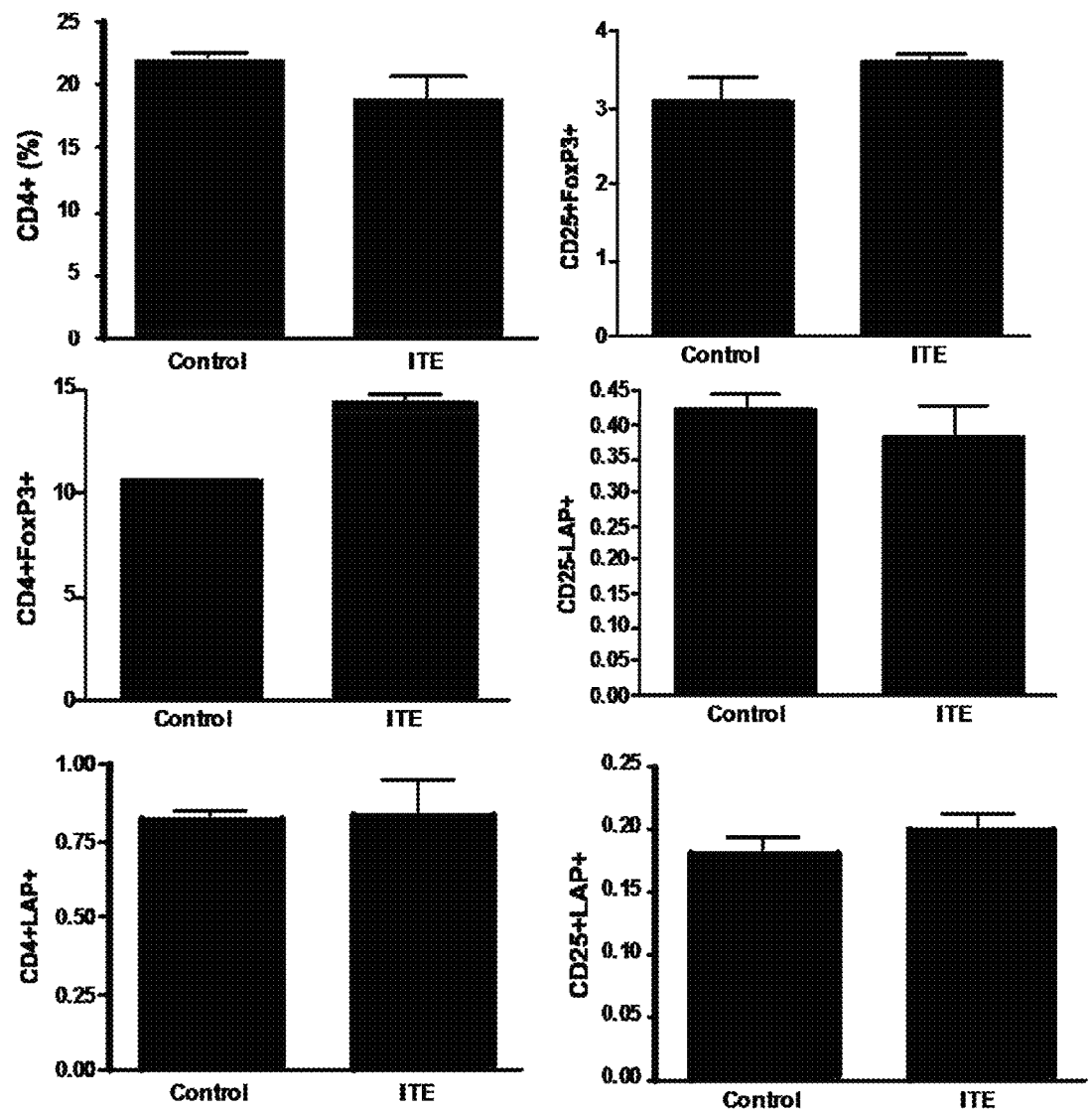
Figure 19B:
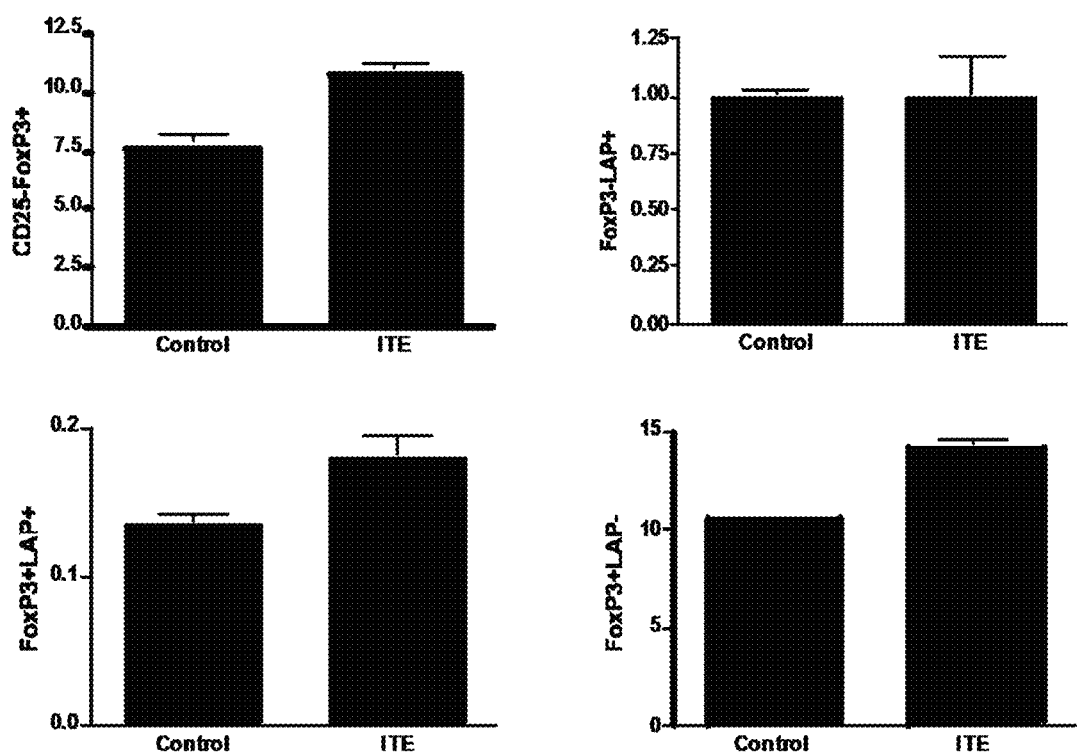
Figure 20A:
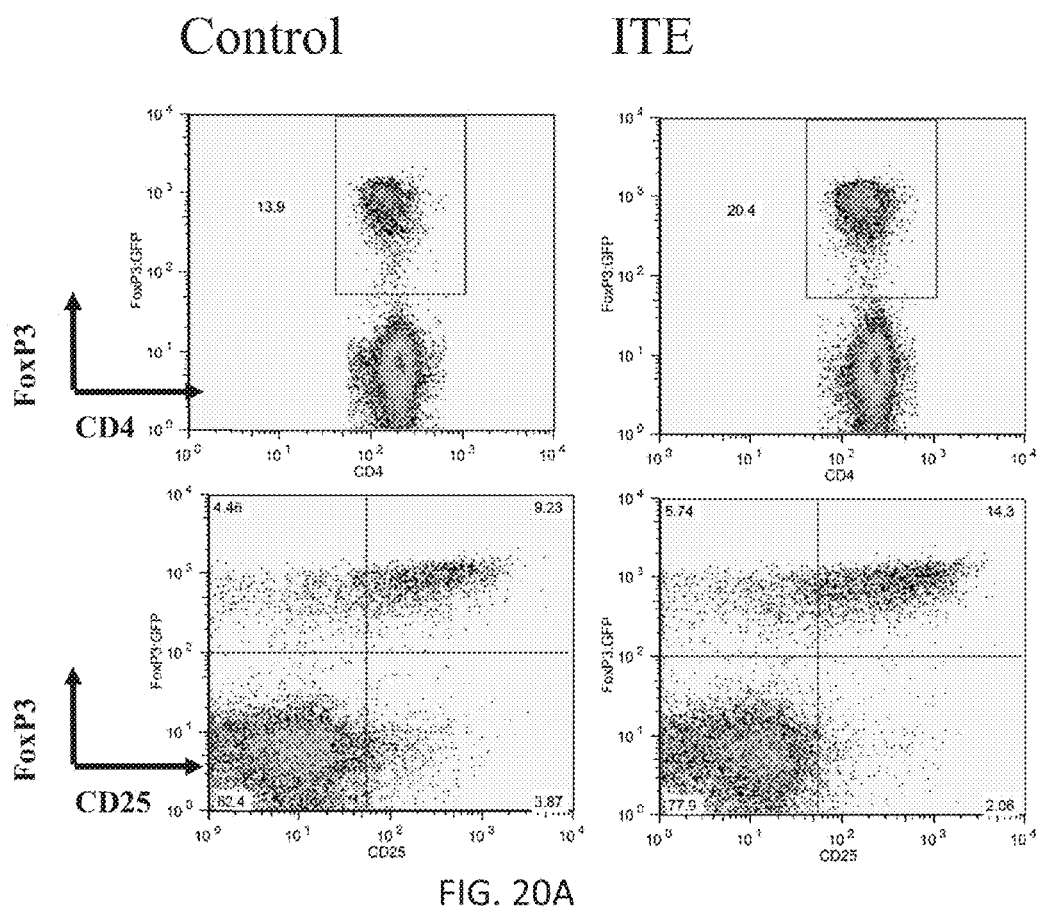
FIGS. 20A and B are FACS plots (20A) and bar graphs (20B) showing the: induction of FoxP:GFP3$^+$ T$_{reg}$ by IP administration of ITE to FoxP3$^{gfp}$ mice. B6 mice (n=3), the mice were treated with ITE or vehicle, immunized with CFA/MOG$_{35-55}$ and T$_{reg}$ levels were analyzed by FACS on splenocytes 10 days after immunization.
Figure 20B:
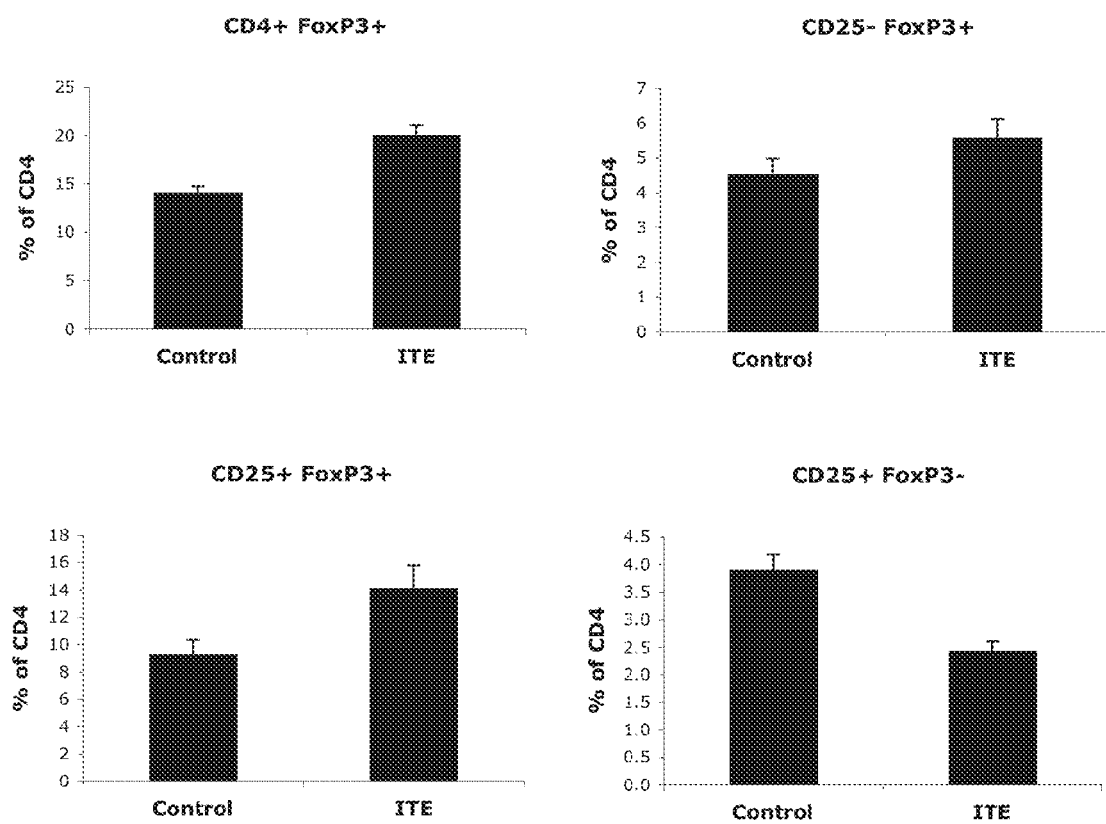
Figure 21A:
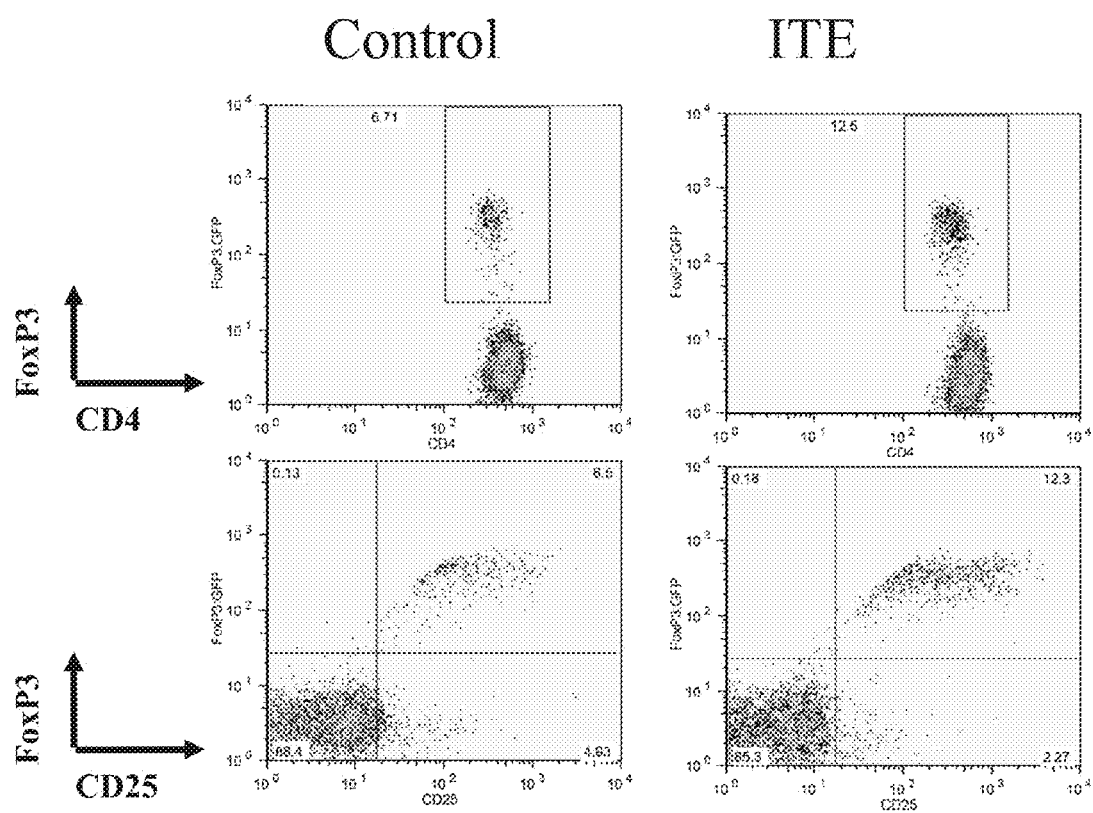
FIGS. 21A and B are FACS plots (21A) and bar graphs (21B) showing the induction of FoxP:GFP3$^+$ T$_{reg}$ by IP administration of ITE to FoxP3$^{gfp}$ mice. B6 mice (n=3), the mice were treated with ITE or vehicle, immunized with CFA/MOG$_{35-55}$ and T$_{reg}$ levels were analyzed by FACS on blood 10 days after immunization.
Figure 21B:
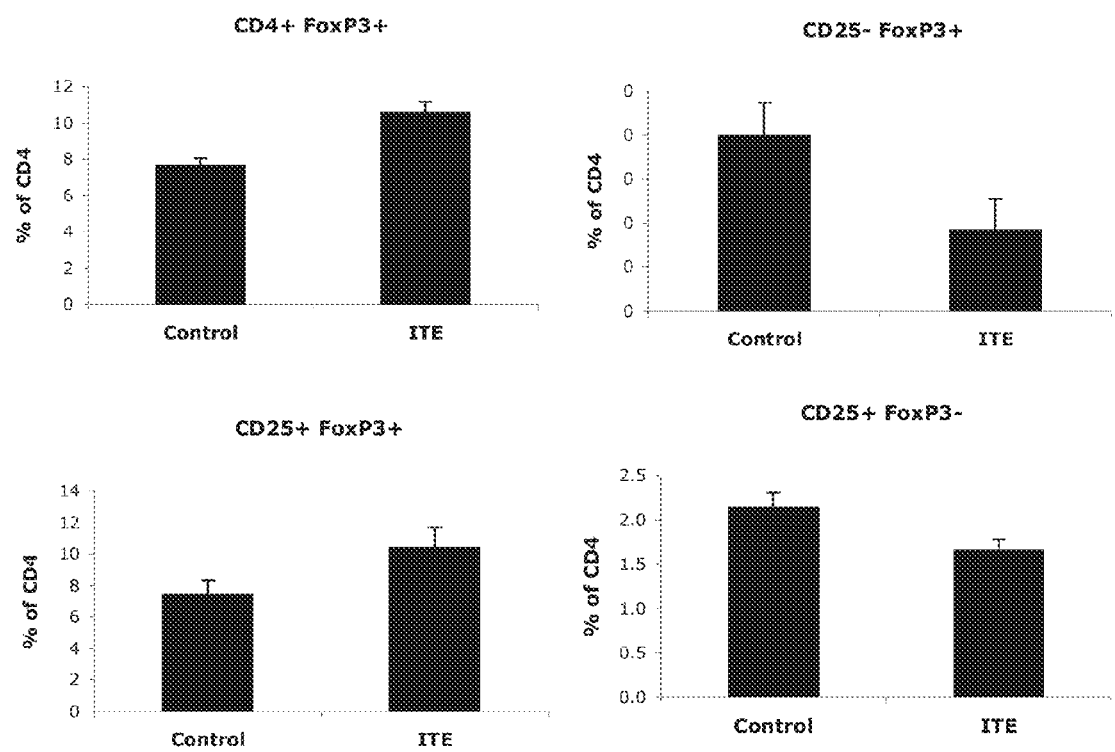

GFP$^-$ CD4$^+$ T cells were isolated from Foxp3gpf knock in mice, and then were activated in vitro with antibodies to CD3 and CD28 in the presence of TGFβ1 to induce Treg differentiation in vitro. mRNA was prepared at the beginning of the experiment and after 3 or 6 days in culture, and the expression of Foxp3 (see FIG. 9A), NKX2.2 (see FIG. 9B), EGR1 (see FIG. 9C), EGR2 (see FIG. 9D) and EGR3 (see FIG. 9E) expression was quantified in the Foxp3:GFP$^+$CD4$^+$ T cells by real time PCR.

These results indicate that expression of Foxp3 and the transcription factors EGR1, EGR2, EGR3 and NKX2.2 is correlated. Taken together, the reported effects that these TFs exert on the regulation of gene expression, the identification of TF binding sites on the Foxp3 gene, and the correlation between the expression of these TF and Fox 3, suggest that EGR1, EGR2, EGR3 and NKX2.2 play a role in the regulation of Foxp3 expression and the generation of Treg.

Example 9

Combination Treatment Using Tryptamine (TA)

As shown above, TA is rapidly degraded in vivo by monoamine oxidase inhibitors. As shown in FIG. 13, when combined with the monoamine oxidase inhibitor trans-2-Phenylcyclopropylamine hydrochloride (Tranylcypromine), TA effectively suppresses EAE suppression.

This observation suggests that TA is a TCDD-like ligand that, when used in combination with a monoamine oxidase inhibitor, can be used as a transcription factor ligand for promoting an increase in the number and/or activity of Treg.

Example 10

Modified Screening Assays

A modified zebrafish based screening assay was established by microinjecting fertilized zebrafish eggs with a BAC construct encoding the complete mouse Foxp3 locus, with a *renilla* reporter inserted after the Foxp3 methionine start codon (ATG). Six days after microinjection, *renilla* activity was determined in total zebrafish lysates. As shown in FIG. 14, murine Foxp3 was expressed in the microinjected fish as determined by *renilla luciferase* activity. The activity increased in the presence of TCDD in a dose-dependent manner.

These data suggest that zebrafish lines encoding murine Foxp3 can be used to screen for small molecules that increase or decrease Foxp3 expression levels.

Example 11

AHR Activation with its Non-Toxic Ligand ITE Induces Functional Treg

The ligand-activated transcription factor aryl hydrocarbon receptor (AHR) is a regulator of zebrafish, mouse and human Foxp3 expression and T$_{reg}$ differentiation (Quintana et al., Nature 23, 23 (2008)). AHR activation by its ligand 2,3,7,8-tetrachlorodibenzo-p-dioxin (TCDD) induced T$_{reg}$ that suppressed experimental autoimmune encephalomyelitis (EAE) by a TGFb1-dependent mechanism. These findings identify AHR as a therapeutic target of interest for the management of autoimmune disorders, but its therapeutic exploitation is limited by the well-characterized toxic features of TCDD (Baccarelli et al., Environ Health Perspect, 110, 1169 (2002)).

Several endogenous AHR ligands have been isolated, among them tryptophan derivatives like tryptaime (TA) (Heath-Pagliuso et al., Biochemistry. 37, 11508 (1998) and the mucosal associated 2-(1'H-indole-3'-carbonyl)-thiazole-4-carboxylic acid methyl ester (ITE) depicted in FIG. 1 (Song et al., Proc Natl Acad Sci USA 99, 14694 (Nov. 12, 2002)). Notably, although ITE and have been shown to be high affinity AHR ligands, they do not display the toxic effects reported by TCDD (Heath-Pagliuso et al., (119), supra; Henry et al., Arch Biochem Biophys. 450, 67 (2006)). As demonstrated herein, the non-toxic AHR ligand ITE administered intraperitoneally, orally or with pegylated gold nanoparticles can be used to induce functional T$_{reg}$.

To analyze the feasibility of using ITE to activate AHR in vivo in a therapeutic setup, we studied the effect of ITE on EAE development. EAE as induced on naïve C57BL/6 mice and ITE (200 mg/mice) was administered orally or intraperitoneally on daily basis. ITE administration, either orally or intraperitoneally, resulted in a significant delay on EAE development and a significant reduction of EAE clinical score (FIGS. 15A-B). Thus AHR activation by ITE induces functional T$_{reg}$ that can control EAE.

To study the mechanism by which the ITE-induced Treg control EAE we studied the ability of AHR activation by ITE to induce Treg. We treated naïve C57BL/6 mice with ITE (200 mg/mouse administered ip, daily) and immunized them with 100 mg/mouse of MOG35-55 in CFA. Spleens were prepared 10 days later and CD4+FoxP3+ Treg were quantified by FACS. Administration of ITE led to a significant increase in the number of CD4+FoxP3+Treg (FIGS. 16A-B and 17A-B). Notably, this increase resulted from the expansion of both CD25+ and CD25− CD4+FoxP3+Treg, but did lead to significant alterations in the levels of LAP+ regulatory T cells (FIGS. 16A-B and 17A-B). Thus AHR activation by ITE results in the expansion of the CD4+FoxP3+ Treg compartment.

To confirm the lack of toxicity of ITE, we administered it intraperitoneally for 14 days, 200 mg/mouse and studied the blood levels of biochemical indicators of liver function induction. Hepatocites are known to express high levels of AHR, this toxic effects of AHR activation are manifested in the liver. Table 6 shows that at day 14 we did not detect any significant difference in the biochemical indicators of liver function, confirming the lack of toxicity in ITE.

TABLE 6

ITE Administration Does Not Result in Liver Toxicity

| TEST | Units | Control | ITE | Reference Range |
| --- | --- | --- | --- | --- |
| ALT/GPT | U/L | 16 ± 2 | 19 ± 4 | 0-54 |
| AST/GOT | U/L | 79 ± 29 | 94 ± 17 | 9-74 |
| Alkaline Phosphatase | U/L | 75 ± 8 | 55 ± 11 | 36-300 |
| Total Bilirubin | mg/dL | 0 ± 0 | 0 ± 0 | 0.1-1.2 |
| Direct Bilirubin | mg/dL | 0 ± 0 | 0 ± 0 | 0.0-0.8 |
| Total Protein | g/dL | 6 ± 0 | 5 ± 0 | 4.4-8.0 |
| Albumin | g/dL | 2 ± 0 | 3 ± 0 | 2.9-5.4 |
| Globulin | g/dL | 3 ± 0 | 3 ± 0 | 2.0-4.0 |

To study the feasibility of administering ITE orally to activate AHR and induce functional Treg we treated naïve C57BL/6 mice with ITE (200 mg/mouse administered orally, daily) and immunized them with 100 mg/mouse of MOG35-

55 in CFA. Spleens were prepared 10 days later and CD4+ FoxP3+ Treg were quantified by FACS. Administration of ITE led to a significant increase in the number of CD4+ FoxP3+ Treg (FIGS. 18A-B and 19A-B). Notably, this increase resulted from the expansion of both CD25+ and CD25− CD4+FoxP3+ Treg, but did lead to significant alterations in the levels of LAP+ regulatory T cells (FIGS. 18A-B and 19A-B). Thus ITE can be administered orally to activate AHR and expand the CD4+FoxP3+ Treg compartment.

To confirm the ability of AHR Activation by ITE to expand the $T_{reg}$ compartment we used Foxp3$^{gpf}$ knock in mine. Foxp3$^{gpf}$ knock in mice have a GFP reporter inserted in the Foxp3 gene, producing a GFP:Foxp3 fusion protein that facilitates the identification and FACS sorting of GFP:FoxP3$^+$ $T_{reg}$ (Bettelli et al., Nature 441, 235 (2006)). Foxp3$^{gpf}$ knock in mice were treated with ITE (200 mg/mouse administered ip, daily) and immunized with 100 mg/mouse of MOG$_{35-55}$ in CFA. Ten days later and CD4$^+$FoxP3$^+$ $T_{reg}$ were quantified by FACS. Administration of ITE led to a significant increase in the number of CD4$^+$FoxP3GFP$^+$ $T_{reg}$ in blood and spleen (FIGS. 20A-B and 21A-B). Thus AHR activation by ITE results in the expansion of CD4$^+$ FoxP3$^+$ $T_{reg}$ compartment.

We then studied the effect of ITE administration on the encephalitogenic response against myelin. EAE was induced on naïve C57BL/6 mice and ITE (200 mg/mice) was administered orally or intraperitoneally on daily basis. Ten days after vaccination with MOG$_{35-55}$/CFA, ITE-treated mice showed a suppressed recall proliferative response to the MOG$_{35-55}$ peptide (FIG. 22); no differences were seen upon activation with antibodies to CD3 (FIG. 22). When compared to the splenocytes from control animals CD4$^+$ T cells from ITE-treated mice secreted higher amounts of TGFb1 and IL-10 and lower amounts of IL2, IL6, IFNg and IL17 upon activation with MOG$_{35-55}$ (FIG. 22). Similar results were observed on the recall response to MOG$_{35-55}$ of mice treated with orally administered ITE (FIG. 23).

Figure 24A:
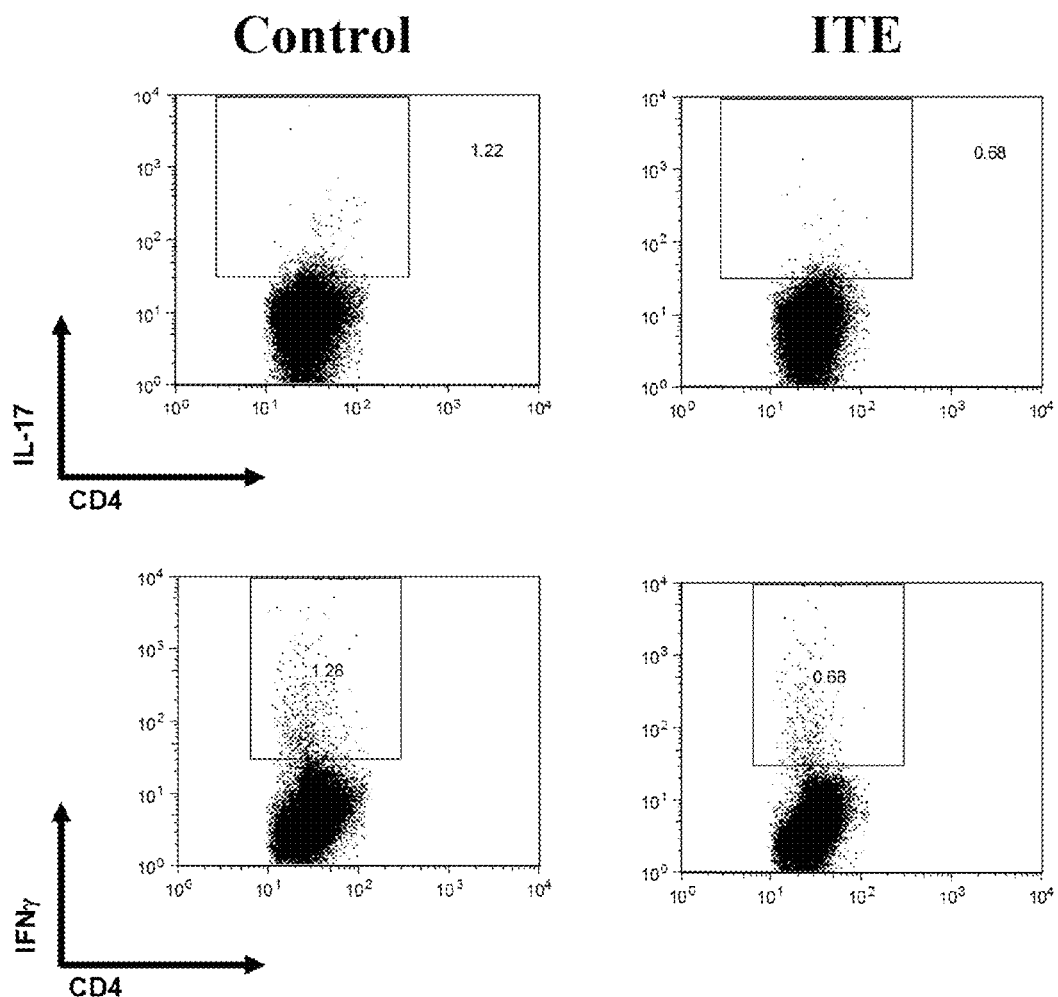
FIGS. 24A and B are FACS plots (24A) and bar graphs (24B) showing that oral-ITE decreases the recall response to MOG. EAE was induced in B6 mice (n=3), the mice were treated with ITE or vehicle, and the recall response to MOG$_{35-55}$ (left panels) or αC3 (right panels) on splenocytes was analyzed at day 17 after EAE induction.

To confirm the suppressive effects of AHR activation on the generation of T cells secreting IFNg and IL17, IFNg$^+$ and IL17$^+$ CD4$^+$ T cells were quantified by FACS in the draining lymph nodes ten days after footpad immunization and intraperitoneal administration of ITE (200 mg/mice). AHR activation with ITE led to a decrease in the frequency of CD4$^+$IL17$^+$ and CD4$^+$IFNg$^+$ T cells (FIG. 24). In accordance with these results, we found a significant reduction in the secretion of IL-17 and IFNg by lymph node cells from ITE-treated mice activated with MOG$_{35-55}$ or aCD3.

Figure 25B:
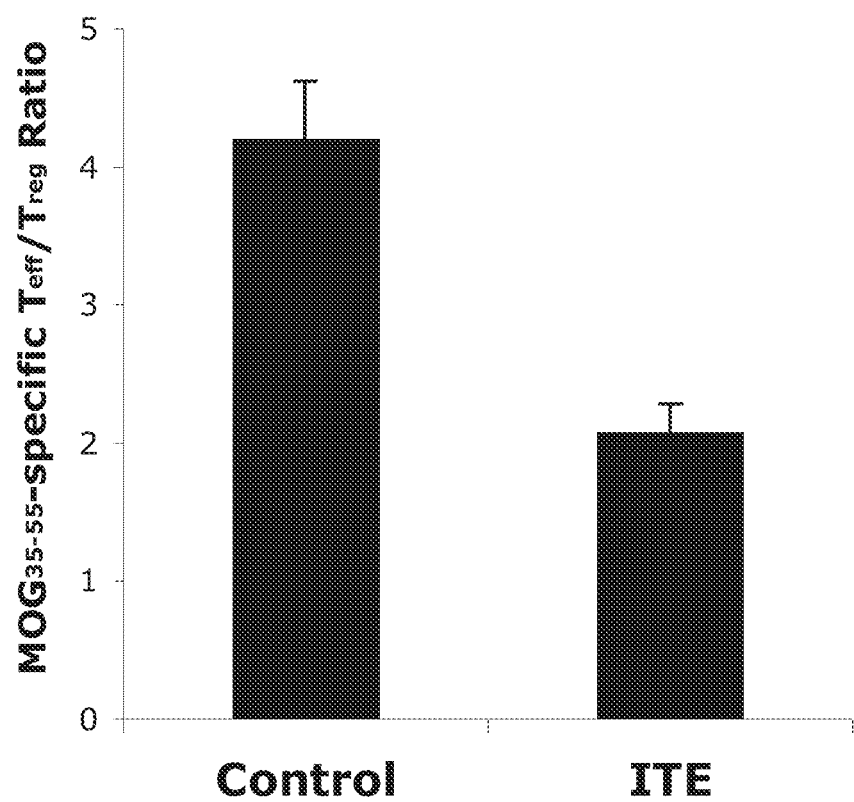
FIGS. 25A and B are FACS plots IP-ITE increases the Treg:Teff ratio of MOG$_{35-55}$ specific T cells. FoxP3$^{gfp}$ mice (n=3) were immunized with MOG$_{35-55}$ and treated with ITE (lower panels of 25A) or vehicle (upper panels of 25A), and the frequency of MOG$_{35-55}$-specific Treg and Teff cells was followed by FACS at day 10 after immunization.

To investigate the effect of AHR activation by ITE on the frequency of MOG$_{35-55}$ specific $T_{reg}$ and effector T cells ($T_{eff}$), Foxp3$^{gpf}$ knock in mice were immunized with MOG$_{35-55}$/CFA, treated daily with intraperitoneal ITE (200 mg/mice) and MOG$_{35-55}$-specific $T_{reg}$ (CD4$^+$ FoxP3:GFP$^+$) and $T_{eff}$ (CD4$^+$FoxP3:GFP$^-$) were analyzed by FACS using recombinant MHC class II tetramers containing MBP$_{35-55}$ or the control peptide TMEV$_{76-86}$. AHR activation with ITE led to a decrease in the frequency of MOG$_{35-55}$-specific $T_{eff}$ and to a concomitant increase in the frequency of MOG$_{35-55}$-specific $T_{reg}$, reducing the MOG$_{35-55}$-specific $T_{eff}/T_{reg}$ ratio by half (FIG. 25).

Figure 27B:
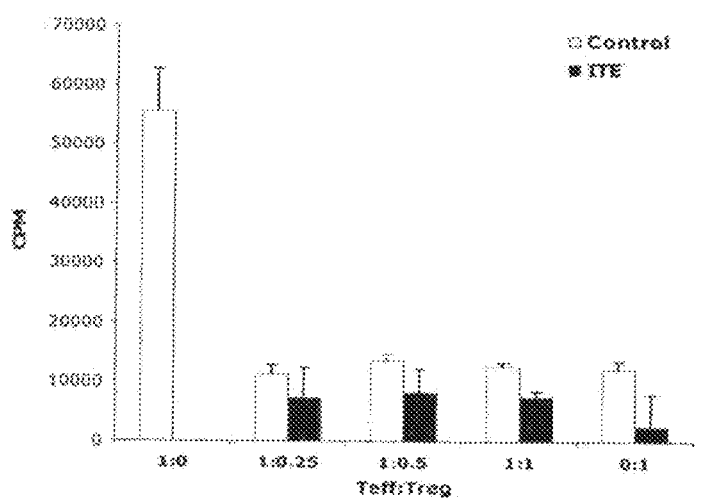
FIGS. 27A and B are bar graphs showing that IP-ITE potentiates MOG$_{35-55}$-specific T$_{reg}$ activity. FoxP3$^{gfp}$ mice (n=3) were immunized with MOG$_{35-55}$ and treated with ITE or vehicle, FoxP3:GFP$^+$ T$_{reg}$ were FACS-sorted 10 days after immunization and their suppressive activity was evaluated using 2D2 FoxP3:GFP$^-$ T cells as responders.
FIG. 27C is a bar graph showing that this effect could be inhibited with antibodies blocking to TGFb1.
Figure 27C:
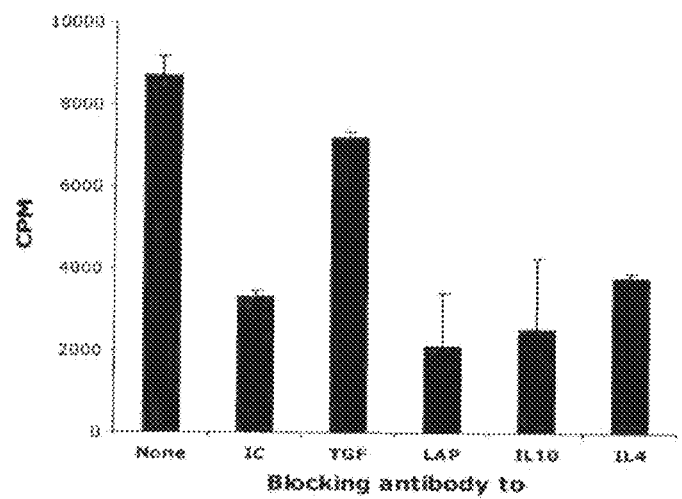

To investigate the active suppression of MOG$_{35-55}$-specific Teff by Tzeg, Foxp3$^{gpf}$ knock in mice were immunized with MOG$_{35-55}$/CFA, treated daily with intraperitoneal ITE (200 mg/mice) and the recall response to MOG$_{35-55}$ and a mitogenic antibody to CD3 antibody was studied on FACS-sorted CD4$^+$ T cells and CD4$^+$ FoxP3:GFP$^-$ $T_{eff}$. Purified CD4+ T cells from ITE-treated mice showed a suppressed response to MOG$_{35-55}$ but not to anti-CD3 (FIG. 26). This suppressed response to MOG$_{35-55}$ was lost upon removal of the CD4$^+$ FoxP3:GFP$^+$ $T_{reg}$ (FIG. 26). To further analyze the MOG$_{35-55}$-specific suppressive activity of the CD4$^+$ FoxP3:GFP$^+$ $T_{reg}$, they were cocultured at different ratios and assayed for the suppression of MOG$_{35-55}$ or anti-CD3-triggered proliferation of CD4$^+$FoxP3:GFP$^-$ $T_{eff}$ form 2D2 mice, which harbor a TCR specific for MOG$_{35-55}$. CD4$^+$FoxP3:GFP$^+$ $T_{reg}$, from ITE-treated mice displayed an increased MOG$_{35-55}$-specific suppressive activity, which could be inhibited with antibodies blocking antibodies to TGRb1 (FIGS. 27A-C). All in all, these data suggests that, similarly to what we have described for TCDD, AHR activation by ITE results in the expansion of antigen-specific CD4$^+$ FoxP3$^+$ $T_{reg}$ that suppress the encephalitogenic response in a TGFb1-dependent manner.

To demonstrate that the effect of ITE on EAE was mediated by $T_{reg}$, we purified CD4$^+$ T cells from mice protected from EAE by oral or intraperitoneal administration of ITE 14 days after EAE induction. Protection from EAE could be transferred to wild type naïve animals by the transfer of 5 10$^6$ CD4$^+$ T cells ITE-treated mice, but not with cells isolated from vehicle-treated mice (FIG. 28). The control of the pathogenic T cell response was mediated by CD4$^+$ CD25$^+$ $T_{reg}$, their depletion from the transferred population abrogated the protective effect of the transferred cells. Thus, the $T_{reg}$ induced by the activation of AHR with ITE inhibit the progression of EAE.

Figure 29:
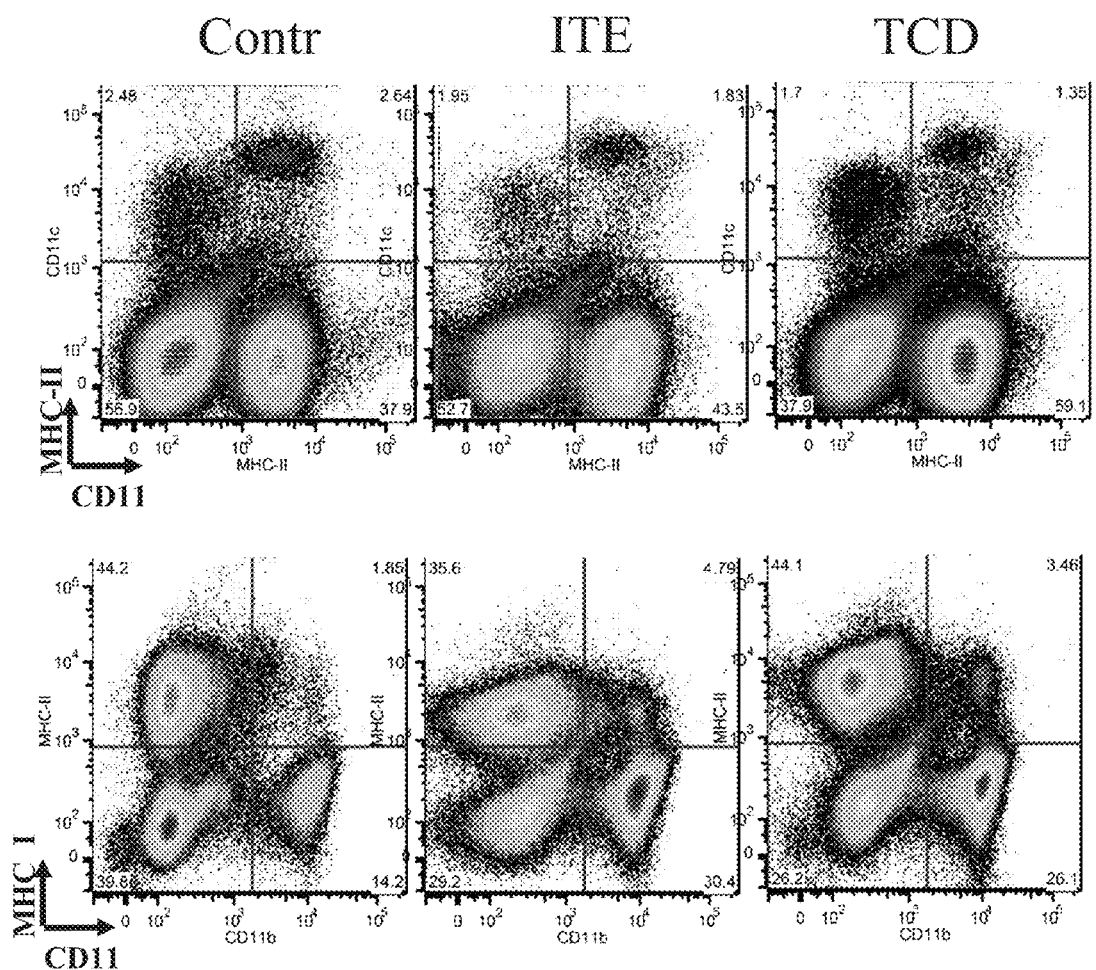
FIG. 29 is a set of six FACS plots showing modulation of APC populations by IP-ITE. EAE was induced in B6 mice (n=3), the mice were treated with ITE or vehicle, and APC were analyzed by FACS on splenocytes at day 17 after EAE induction.

AHR is known to be expressed by antigen presenting cells (APC) such as dendritic cells (CD11c$^+$) and macrophages (CD11b$^+$) (Vorderstrasse and Kerkvliet, Toxicol Appl Pharmacol. 171, 117 (2001); Laupeze et al., J Immunol. 168-2652 (2002); Hayashi et al., Carcinogenesis. 16, 1403 (1995); Komura et al., Mol Cell Biochem. 226, 107 (2001)). To analyze the effects that AHR activation by ITE might have on different APC populations, which can potentially influence the generation of $T_{eff}$ and $T_{reg}$ cells, we studied the effect of ITE and TCDD treatment on MHC class II expression by as dendritic cells (CD11c$^+$) and macrophages (CD11b$^+$). C57BL/6 mice were treated with ITE (200 mg/mouse administered ip, daily) or TCDD (1 mg/mouse administered ip on day 0) and immunized them with 100 mg/mouse of MOG$_{35-55}$ in CFA. Spleens were prepared 10 days later and MCH class I expression was investigated on CD11b$^+$ and CD11c$^+$ cells by FACS. Administration of ITE or TCDD resulted in a significant decrease in CD11c$^+$ MHC class II expression, which was concomitant with a significant increase in CD11b$^+$ MHC class II expression, which was concomitant with a significant increase in CD11b$^+$ MHC class II expression (FIG. 29). Since CD11c$^+$ MHC-II$^+$ and CD11b$^+$ MHC-II$^+$ have been recently linked to the induction of $T_{eff}$ and $T_{reg}$, respectively, these results suggest that changes in the different APC populations might contribute to the immunomodulatory effects of AHR activation by ITE.

Example 12

Administration of ITE-Loaded Nanoparticles Induces Functional Treg

Figure 30:
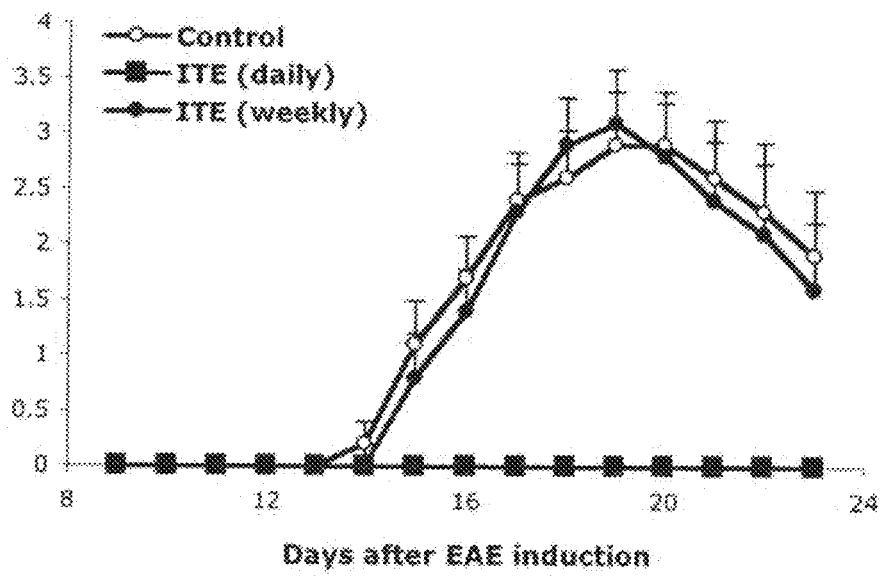
FIG. 30 is a line graph showing that weekly administration of ITE fails to suppress EAE development. EAE was induced in B6 mice (n=10) and the mice were treated daily or weekly with 200 µg/mouse of ITE or vehicle.

As noted above, administration of a single dose of 1 mg/mouse of the AHR ligand TCDD could prevent the development of EAE. To achieve similar effects on disease progression, 200 mg/mouse of ITE have to be administered daily throughout the experiment. ITE is a tryptophan derivative which is thought to have a short half-life in vivo as a result of the activity of specific enzymes. Indeed, administration of ITE at weekly intervals, instead of daily, results in a complete loss of its protective effects on EAE (FIG. 30).

Figure 31:
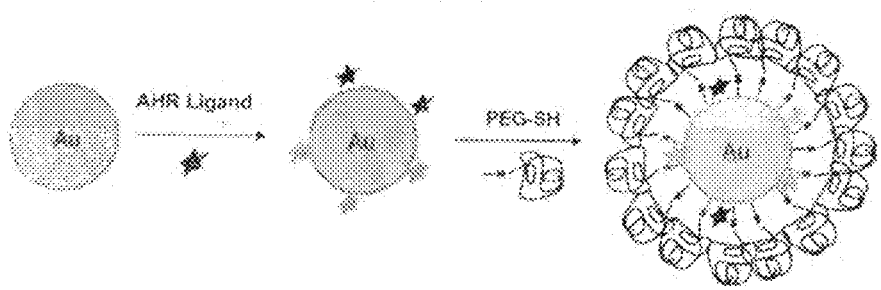
FIG. 31 is a schematic diagram of gold nanoparticles for AHR-ligand delivery.

Gold colloid has been in use for over 50 years in the treatment of rheumatoid arthritis, these gold colloid nanoparticles have been shown to have little to no long-term toxicity or adverse effects (Paciotti et al., Drug Deliv. 11, 169 (2004)). Due to their small size (10-100 nm diameter), gold colloid nanoparticles have large surface areas on which multiple small proteins or other molecules can be conjugated (Paciotti et al., Drug Deliv. 11, 169 (2004)). The PEGylation of gold colloid nanoparticles greatly enhances the overall stability of the molecule to which it is covalently bonded (Qian et al., Nat Biotechnol. 26, 83 (2008)). Moreover, recently it has been shown that PEGylated) gold colloid nanoparticles can be linked to specific antibodies to target them to specific cell types (Qian et al., Nat Biotechnol, 26, 83 (2008)). Thus, to increase the half-life of ITE and to facilitate its targeting to specific cell types, we constructed polyethylene glycol coated (PEGylated) gold colloid nanoparticles loaded with AHR ligands (FIG. 31).

PEGylated gold colloid nanoparticles carrying the AHR ligands FICZ, ITE or TCDD showed a typical spectrum of optical absorption (FIG. 32). Moreover, FICZ, ITE or TCDD-loaded nanoparticles activated luciferase expression on an AHR-reporter cell line to levels similar to those achieved by 10 nm TCDD.

Figure 33:
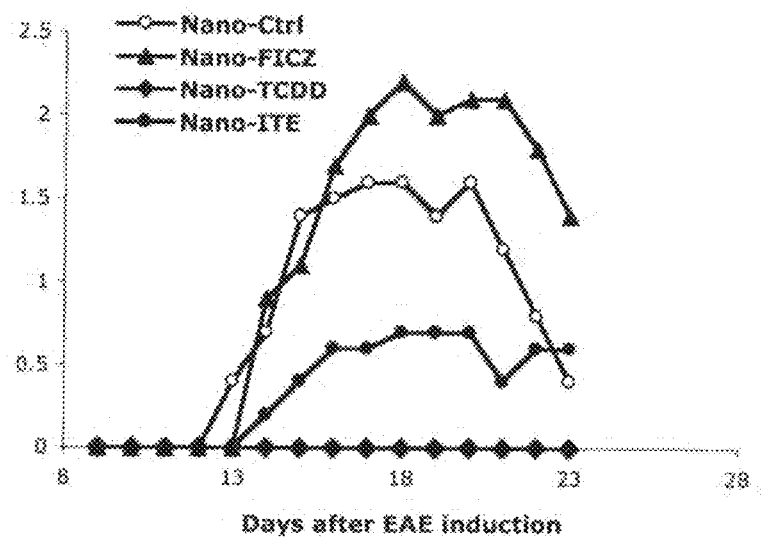
FIG. 33 is a bar graphs showing modulation of EAE by AHR-ligand nanoparticles. EAE wad induced in B6 mice (n=5), the mice were treated with nanoparticles weekly starting from day 0, and the animals were followed for signs of EAE.
Figure 34:
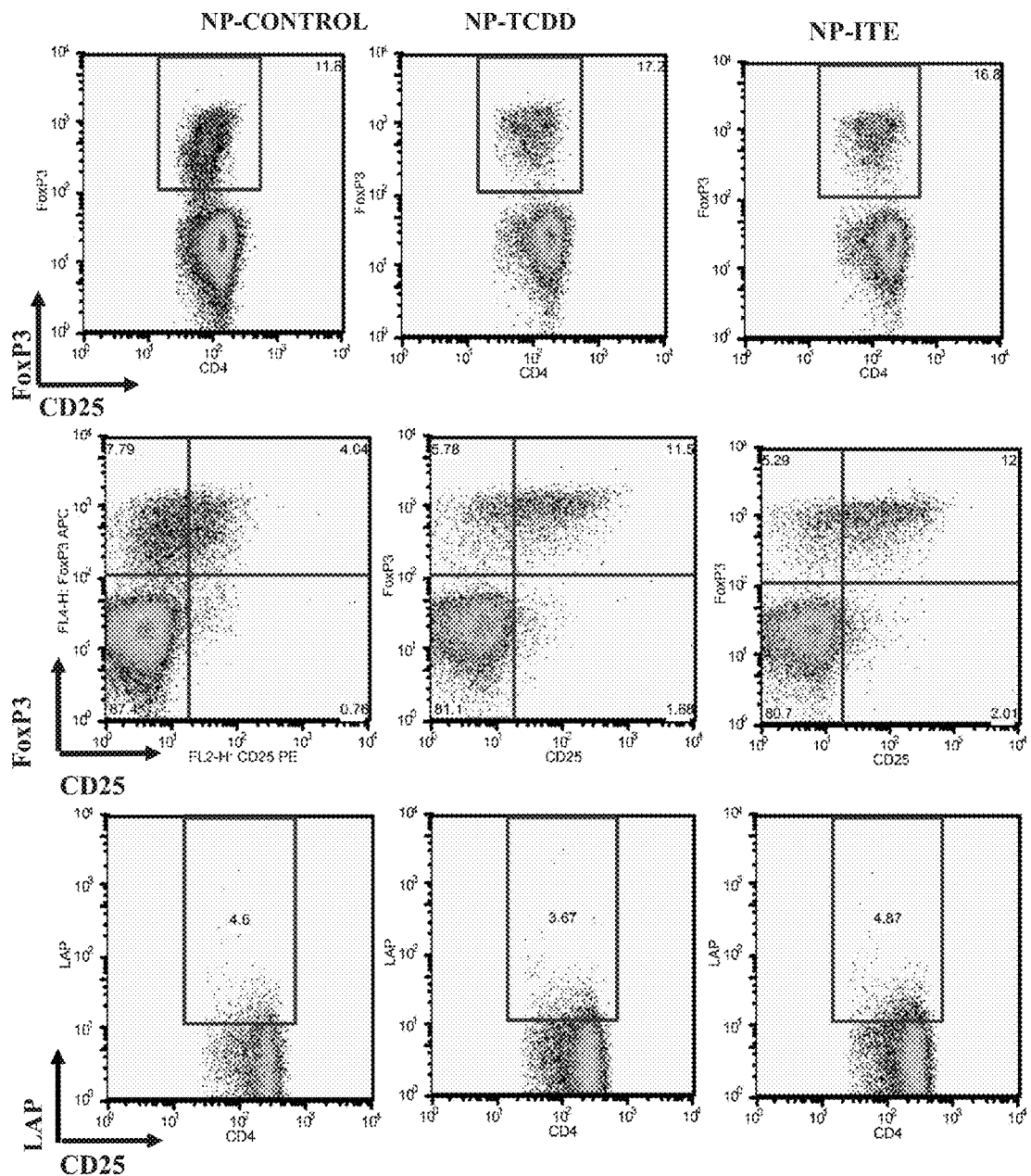
FIG. 34 is a set of nine FACS plots showing induction of FoxP3$^+$ Treg by nanoparticle-mediated delivery of ITE. EAE was induced in B6 mice (n=5), the mice were treated with nanoparticles weekly starting from day 0, and T$_{reg}$ levels were analyzed by FACS on splenocytes at day 22 after EAE induction.

To investigate the in vivo functionality of AHR-ligand loaded nanoparticles we induced EAE on naïve C57BL/6 mice and treated them, starting at day 0, weekly with 45 femtomoles of nanoparticles. Similarly to what we have described in our previous experiments, treatment with TCDD resulted in a complete suppression of EAE, while the AHR ligand FICZ worsened the disease (FIG. 33). Weekly administration of ITE-loaded nanoparticles resulted in a significant inhibition of EAE development (FIG. 34). Thus, the administration of ITE using nanoparticles augments its suppressive effect on EAE (compare FIGS. 31 and 33).

To study the effect of ITE-loaded nanoparticles on the $T_{reg}$ compartment we induced EAE on naïve C57BL/6 mice and treated them, staring at day 0, weekly with 45 femtomoles of nanoparticles. Spleens were prepared 21 days after EAE induction and $CD4^+FoxP3^+$ $T_{reg}$ were quantified by FACS. Administration of ITE-loaded nanoparticles led to a significant increase in the number of $CD4^+FoxP3^+$ $T_{reg}$ (FIG. 34); this increase resulted from the expansion of both $CD25^+$ and $CD25^-$ $CD4^+FoxP3^+$ $T_{reg}$ (FIG. 34). Thus ITE-loaded nanoparticles can be used to activate AHR and expand the $T_{reg}$ compartment.

Figure 35A:
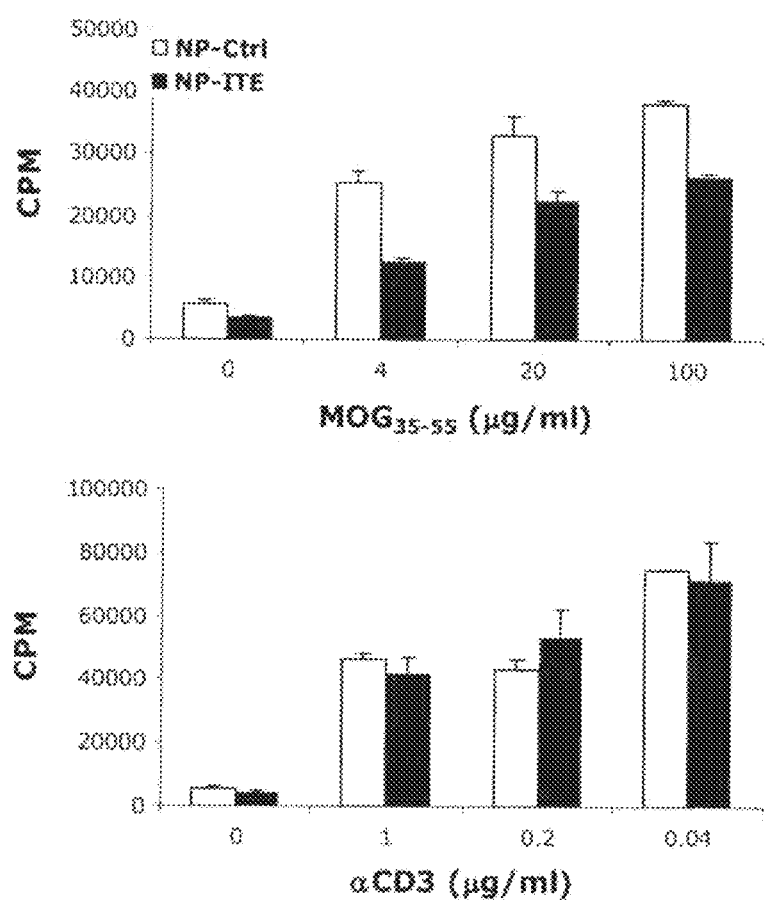
FIGS. 35A and B show nanoparticle-mediated delivery of ITE suppresses the recall response to MOG. EAE was induced in B6 mice (n=5), the mice were treated with ITE or vehicle, and the recall response to MOG$_{35-55}$ (35A, top) or αCD3 (35A, bottom) on splenocytes was analyzed at day 22 after EAE induction.

To study the mechanism by which the ITE-based nanoparticles control EAE we studied the activity of myelin specific T cells. We inducted EAE on naïve C57BL/6 mice and treated them, starting at day 0, weekly with 45 femtomoles of nanoparticles. Spleens were prepared 21 days after EAE wad induced and analyzed for their recall response to $MOG_{35-55}$ and anti-CD3. Mice treated with ITE-loaded nanoparticles showed a suppressed recall proliferative response to the $MOG_{35-55}$ peptide (FIG. 35); no differences were seen upon activation with antibodies to CD3 (FIG. 35). When compared to the splenocytes from control animals, $CD4^+$ T cells from mice treated with ITE-loaded nanoparticles secreted higher amounts of TGFb1 and IL-10 and lower amounts of IL2, IL6, IFNg and IL17 upon activation with $MOG_{35-55}$ (FIG. 35).

Example 13

Induction of Functional Human Regulatory T Cells by AHR Activation

Figure 36:
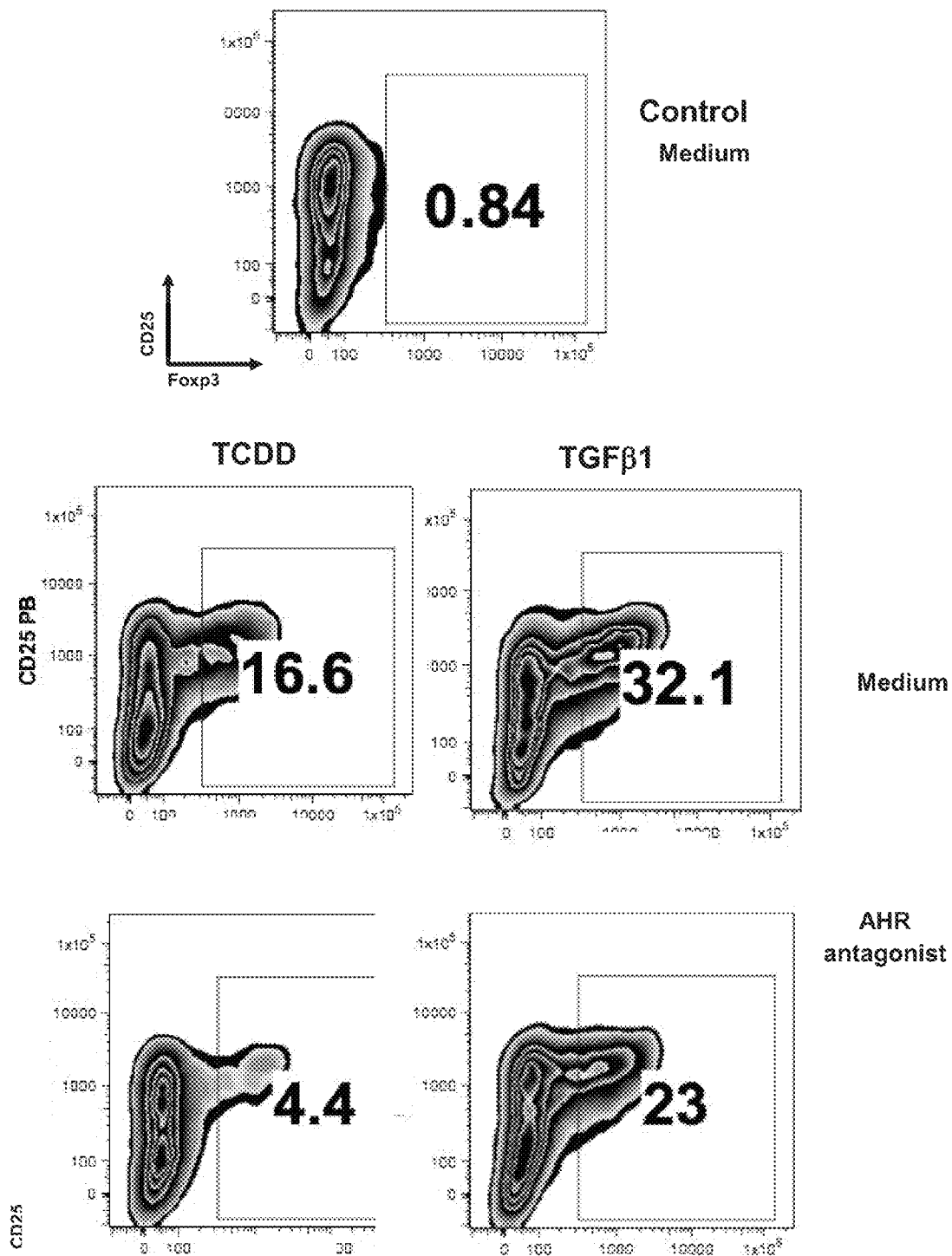
FIG. 36 is a set of FACS plots showing induction of human CD4+ FoxP3+ T cells by TCDD. CD4$^+$ CD62L$^+$ CD45RO$^-$ T cells were isolated by FACS and differentiated in vitro for 5 days with antibodies to CD3 and CD28 in the presence of TCDD 100 nm or TFGβ1 2.5 ng/ml or both.
Figure 37:
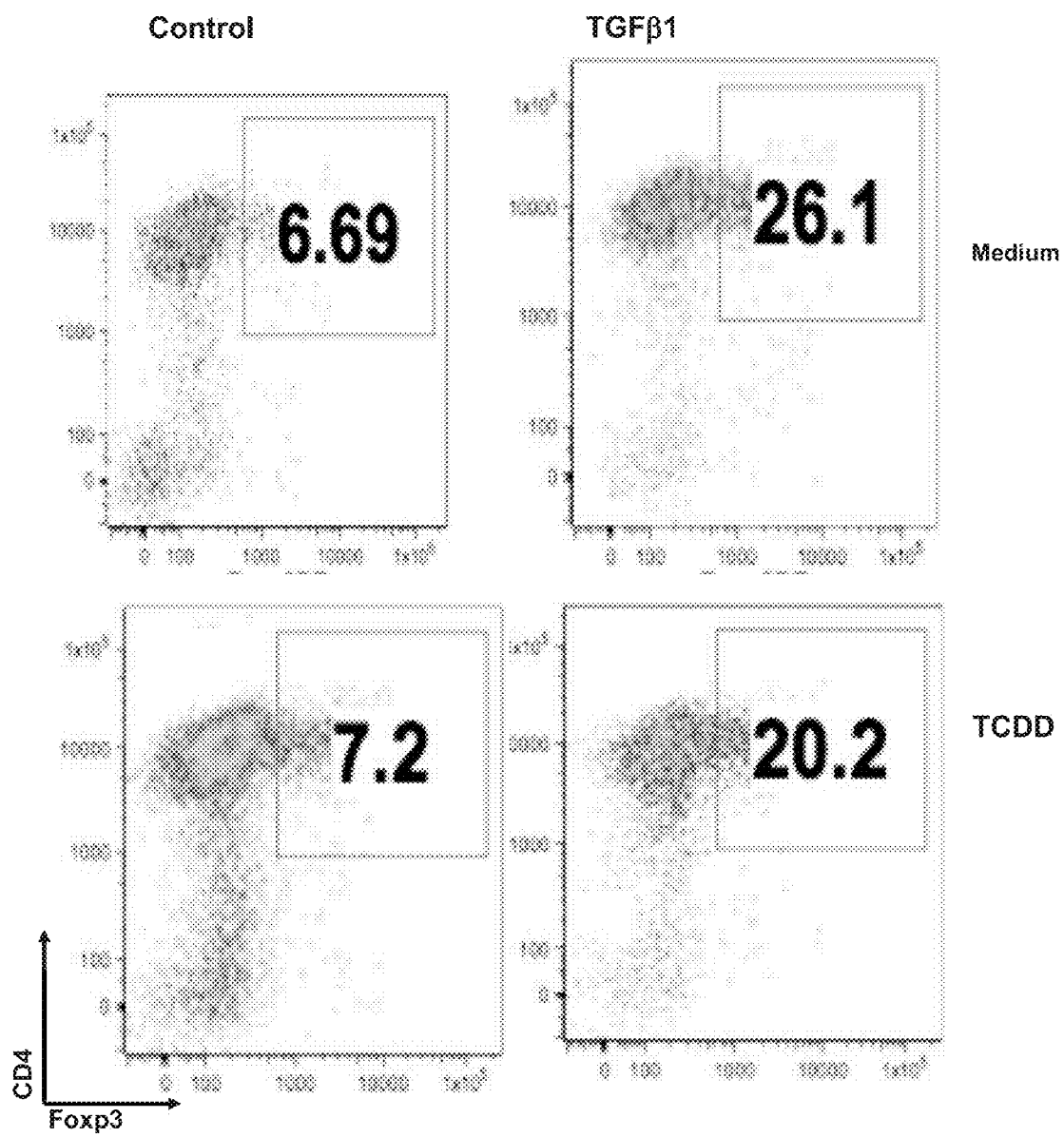
FIG. 37 is a set of four FACS plots demonstrating heterogeneity in the induction of human CD4$^+$ FoxP3$^+$ T cells by TCDD. CD4$^+$ CD62L$^+$ CD45RO$^-$ T cells were isolated by FACS and differentiated in vitro for 5 days with antibodies to CD3 and CD28 in the presence of TCDD 100 nm or TGFβ1 2.5 ng/ml or both.

To investigate the potential of AHR targeting for the induction of human $T_{reg}$ we activated purified naïve $CD4^+$ $CD62L^+$ $CD45RO^-$ T cells for healthy donors for 5 days with antibodies to CD3 and CD28 in the presence of TCDD 100 nM or TGFb1 2.5 ng/ml or both. T cell activation in the presence of TCDD resulted in the induction of $CD4^+$ $FoxP3^+$ T cells in some (FIG. 36) but not all human samples (FIG. 37).

Figure 38:
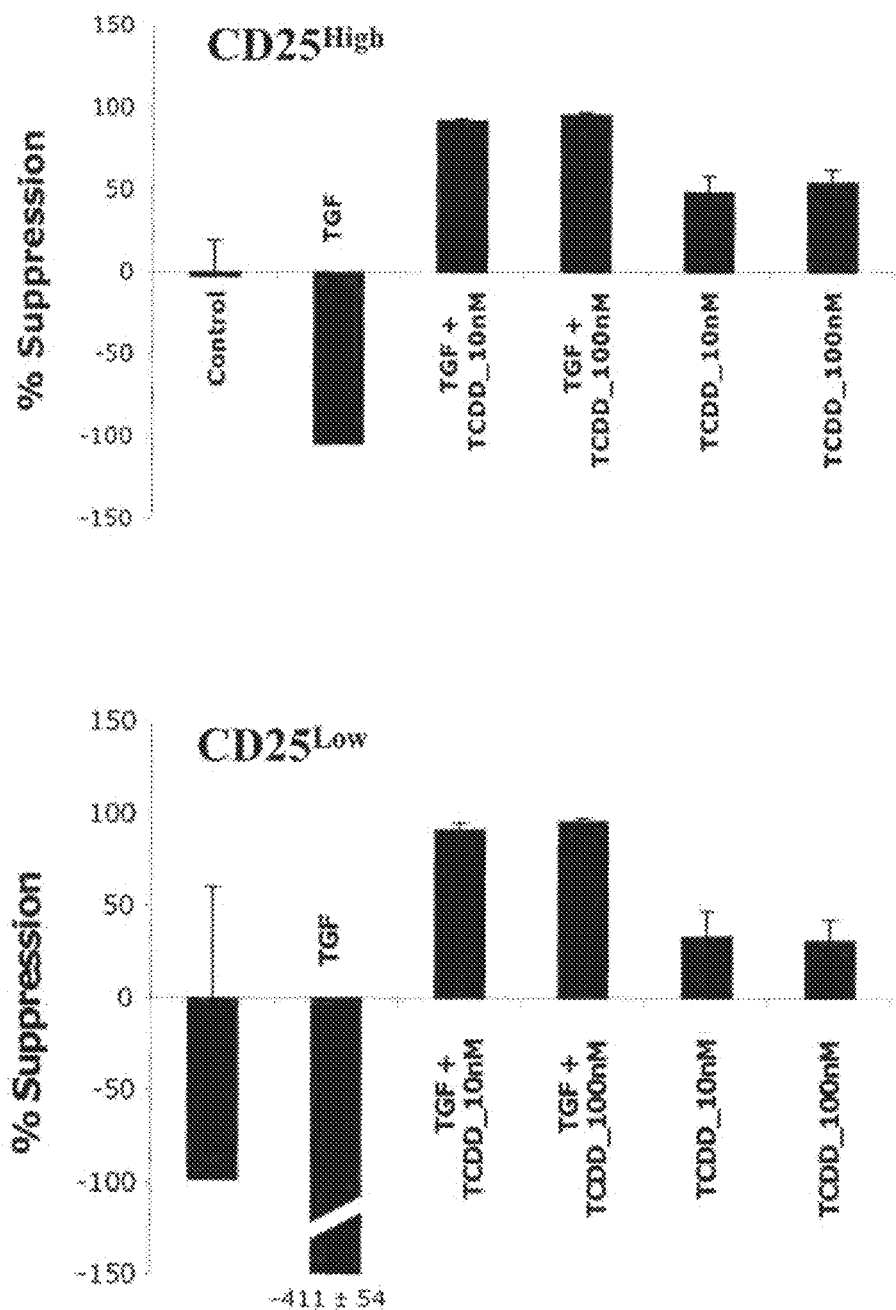
FIG. 38 is a pair of bar graphs showing activation of human T cells in the presence of TCDD induces suppressive T cells. CD4$^+$ CD62L+ CD45RO$^-$ T cells were isolated by FACS and differentiated in vitro for 5 days with antibodies to CD3 and CD28 in the presence of TCDD or TFGβ1 2.5 ng/ml or both, and after re-purification by FACS, CD4$^+$ CD25$^{High}$ and CD4$^+$ CD25$^{Low}$ T cells were assayed for their suppressive activity on on-treated effector T cells activated with antibodies to CD28 and CD3.

To study the functionality of the putative human $T_{reg}$ induced in the presence of TCDD we studied their suppressive activity of $CD4^+$ $CD25^{High}$ and $CD4^+$ $CD25^{Low}$ T cells following 5 days of activation in the of TCDD or TGFb1 2.5 ng/ml or both. Activation in the presence of TGFb1 did not result in the induction of suppressive T cells (FIG. 38). However, activation in the presence of TCDD led to the generation of both $CD4^+$ $CD25^{High}$ and $CD4^+$ $CD25^{Low}$ functional human regulatory T cells, as shown by their ability to inhibit the proliferation of responder T cells (FIG. 38). This effect of TCDD was amplified in the presence of TGFb1, as shown by the increased suppressive activity of the T cells generated under these conditions (FIG. 38).

Figure 39:
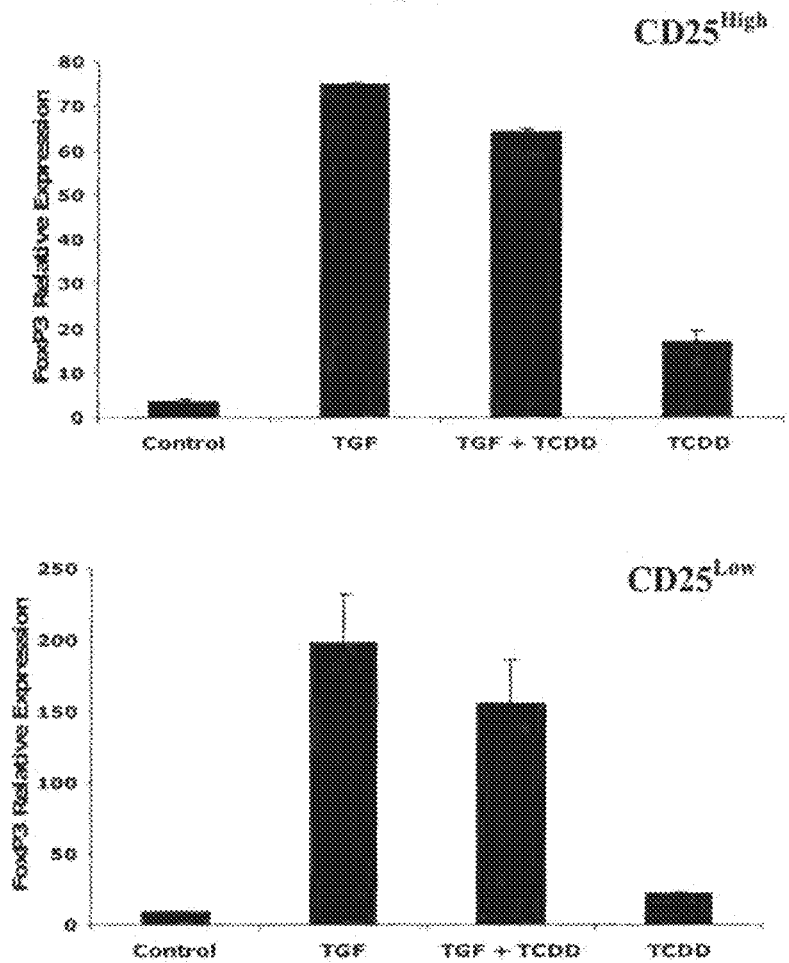
FIG. 39 is a: FoxP3 expression by in vitro differentiated human T cells. CD4$^+$ CD62L$^+$ CD45RO$^-$ T cells were isolated by FACS and differentiated in vitro for 5 days with antibodies to CD3 and CD28 in the presence of TCDD 100 nm or TFGβ1 2.5 ng/ml or both, and FoxP3 expression was analyzed by real-time PCR on CD25$^{High}$ or CD25$^{Low}$ sorted CD4 T cells.
Figure 40:
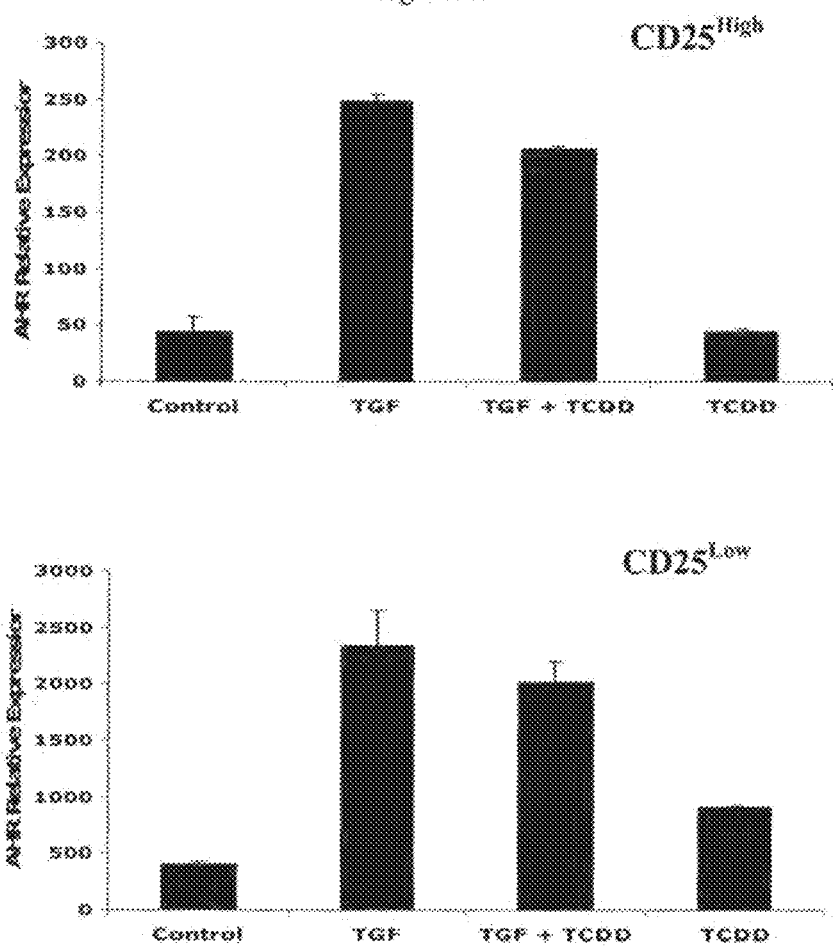
FIG. 40 is a pair of bar graphs showing AHR expression by in vitro differentiated human T cells. CD4$^+$ CD62L$^+$ CD45RO$^-$ T cells were isolated by FACS and differentiated in vitro for 5 days with antibodies to CD3 and CD28 in the presence of TCDD 100 nm or TGFβ1 2.5 ng/ml or both, and AHR expression was analyzed by real-time PCR on CD25$^{High}$ or CD25$^{Low}$ sorted CD4 T cells.
Figure 41:
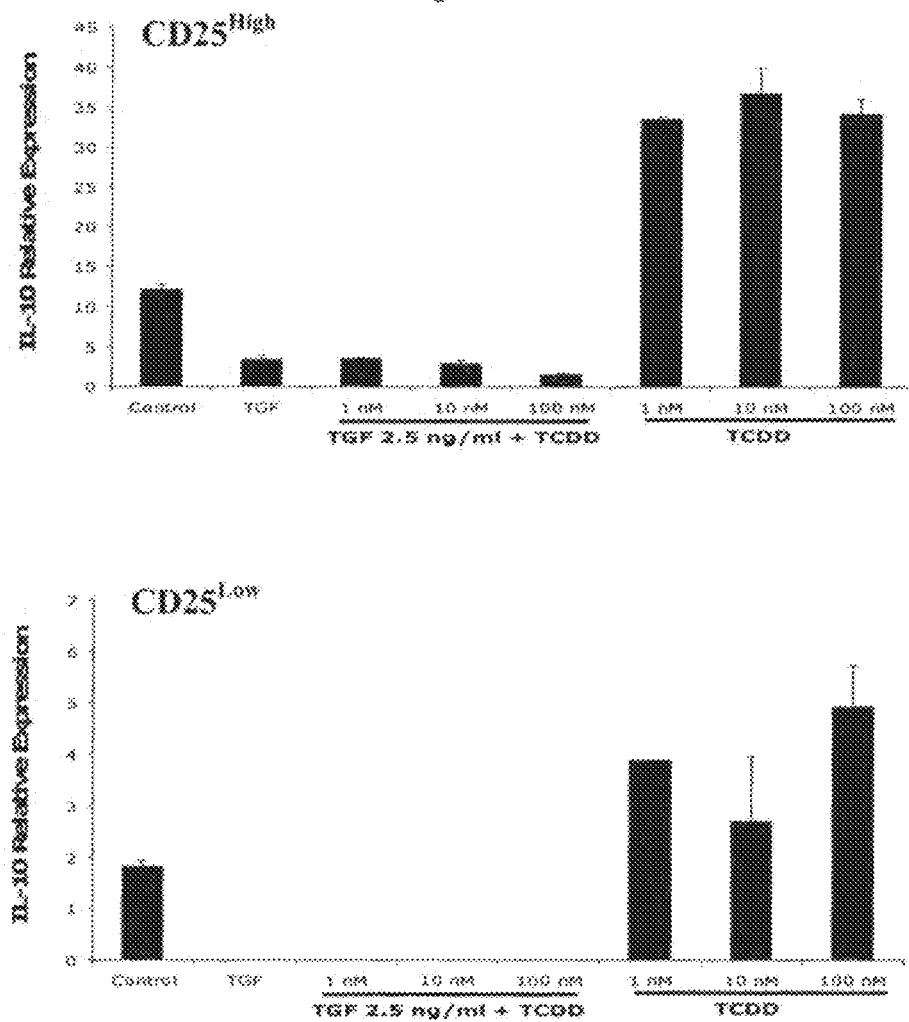
FIG. 41 is a pair of bar graphs showing IL-10 production by in vitro differentiated human T cells. CD4$^+$ CD62L$^+$ CD45RO$^-$ T cells were isolated by FACS and differentiated in vitro for 5 days with antibodies to CD3 and CD28 in the presence of TCDD 100 nm or TGFβ1 2.5 ng/ml or both, and IL-10 production was analyzed by real-time PCR on CD25$^{High}$ or CD25$^{Low}$ sorted CD4 T cells.

To investigate the mechanism mediating the suppressive activity of the TCDD-induced $T_{reg}$, we analyzed them by real time PCR for the expression of several genes that have been previously linked to the suppressive function of $T_{reg}$. FoxP3 expression was significantly up-regulated upon activation in the presence of TCDD and TGFb1 (FIG. 39), however it was also induced buy TGFb1 alone, suggesting that FoxP3 expression does not correlate with the induction of suppressive function via AHR activation. This is confirmed by the marginal induction of FoxP3 expression triggered by AHR activation with TCDD in the absence of TGFb1 (FIG. 39), although these cells expressed low levels of FoxP3 were suppressive in co-culture assays (FIG. 38). TGFb1 also up-regulated AHR expression levels several fold over the basal levels observed on T cells, however the AHR expression levels also did not correlate with the induction of suppressive activity as shown in co-culture assays (FIG. 40). Strikingly, TCDD treated expressed increased levels of IL-10, which where complete inhibited by TGFb1 (FIG. 41), Accordingly, IL-10-specific blocking antibodies could interfere with the suppressive activity of $T_{reg}$ induced, with TCDD, but not the of those induced with TGFb1 and TCDD (FIG. 42). Thus, TCDD-induced $CD4^+CD25^{High}$ T cells are FoxP3 regulatory cells whose suppressive activity is mediated, at least partially, via IL-10, resembling the phenotype of type 1 $T_{reg}$ (Roncarolo et al., Immunol Rev. 212, 28 (2006); Roncarolo and Gregori, Eur J Immunol. 38, 925 (2008)).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
a ligand that binds specifically to an aryl hydrocarbon receptor (AHR) transcription factor, and an antibody that selectively binds to an antigen present on a T cell, a B cell, a dendritic cell, or a macrophage, wherein the antibody and the ligand are linked to a biocompatible gold nanoparticle.

2. The composition of claim 1, wherein the ligand is a small molecule that competes for binding to the AHR competitively with 2,3,7,8 tetrachlorodibenzo-p-dioxin (TCDD) and activates AHR-dependent signaling.

3. The composition of claim 1, wherein the ligand is 2,3,7,8 tetrachlorodibenzo-p-dioxin (TCDD).

4. The composition of claim 1, wherein the ligand is tryptamine (TA).

5. The composition of claim 1, wherein the ligand is 2-(1-'H-indole-3'-carbonyl)-thiazole-4-carboxylic acid methyl ester (ITE).

6. The composition of claim 1, wherein the ligand is 6 formylindolo[3,2 b]carbazole (FICZ).

7. The composition of claim 1, further comprising a monoamine oxidase inhibitor.

8. The composition of claim 7, wherein the monoamine oxidase inhibitor is tranylcypromine.

9. The composition of claim 1, wherein the biocompatible gold nanoparticle is pegylated.

* * * * *

UNITED STATES PATENT AND TRADEMARK OFFICE
CERTIFICATE OF CORRECTION

PATENT NO. : 9,028,798 B2  
APPLICATION NO. : 13/745416  
DATED : May 12, 2015  
INVENTOR(S) : Howard Weiner et al.

Page 1 of 1

It is certified that error appears in the above-identified patent and that said Letters Patent is hereby corrected as shown below:

In the Claims

In column 128, lines 28-29 (approx.), in claim 5, delete "2-(1-1-′H-" and insert -- 2-(1′H- --;

In column 128, line 31 (approx.), in claim 6, delete "[3,2 b]" and insert -- [3,2-b] --.

Signed and Sealed this  
Twenty-fourth Day of November, 2015

Michelle K. Lee  
*Director of the United States Patent and Trademark Office*

SEQUENCE LISTING

<160> NUMBER OF SEQ ID NOS: 156

<210> SEQ ID NO 1
<211> LENGTH: 431
<212> TYPE: PRT
<213> ORGANISM: Homo sapiens

<400> SEQUENCE: 1

```
Met Pro Asn Pro Arg Pro Gly Lys Pro Ser Ala Pro Ser Leu Ala Leu
 1               5                  10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365
```

```
Arg Met Phe Ala Phe Phe Arg Asn His Pro Ala Thr Trp Lys Asn Ala
    370                 375                 380
Ile Arg His Asn Leu Ser Leu His Lys Cys Phe Val Arg Val Glu Ser
385                 390                 395                 400
Glu Lys Gly Ala Val Trp Thr Val Asp Glu Leu Glu Phe Arg Lys Lys
                405                 410                 415
Arg Ser Gln Arg Pro Ser Arg Cys Ser Asn Pro Thr Pro Gly Pro
            420                 425                 430

<210> SEQ ID NO 2
<211> LENGTH: 413
<212> TYPE: PRT
<213> ORGANISM: Danio rerio

<400> SEQUENCE: 2

Met Leu Leu Asn Ala Thr Gly Thr His Arg Gly Asp Asp Asn Arg Ser
1               5                   10                  15
Ser His Gln His Leu Tyr Gln Asp Glu Asp Cys Ala Thr Phe Ser Ile
                20                  25                  30
Ile Gln Met Lys Ser Arg Ile Ser Asn Ser Leu Leu Thr Ser Pro Lys
            35                  40                  45
Pro Met Ala Thr Lys Ile Ser Val Ala Leu Glu Ser Asp Leu Arg Gly
        50                  55                  60
Leu Gly Ser Ser Arg Asn Gln Asn Phe Thr Leu Gln Lys Gln Ser Ala
65                  70                  75                  80
Ser Gly Ser Thr Thr Lys Tyr Phe Lys Gln His Arg Pro Ser Val Leu
                85                  90                  95
Arg Lys Gly Asn Gln Pro Phe Pro Gln Ala Cys Ser Ala His Asp Trp
            100                 105                 110
Val Val Asp Thr Val Cys Lys Thr Glu Pro Asp Ser Glu Pro Ser Asp
        115                 120                 125
Ala Ile Pro Leu Tyr Thr Gly Gln Ser Glu Ser Arg Ile Gly Ala Tyr
130                 135                 140
Ala Ser Ser Pro Gln Pro Gly Ser Pro Glu Tyr Thr Gly Lys His Pro
145                 150                 155                 160
Tyr Ser Leu Ser Gly Asp Tyr Leu Cys Val Lys Gly Gln Cys Arg Trp
                165                 170                 175
Pro Gly Cys Ser Lys Ser Glu Asp Val Phe Thr Glu Tyr Gly His Phe
            180                 185                 190
Leu Arg His Leu Ser Thr Asp His Ala Pro Gly Asp Arg Ser Ile Gly
        195                 200                 205
Gln Leu Arg Met Gln Lys Asp Arg Val Gln His Met Glu Asn Gln Leu
210                 215                 220
Thr Ala Glu Arg Gln Lys Leu Gln Ala Met Gln Leu His Leu Leu Asp
225                 230                 235                 240
Gly Gly Asn Ile Val Glu Lys Pro Ala His Leu Ser Gly Leu Leu Gln
                245                 250                 255
Pro Ala Ser Ser Asn Asp His Tyr Asp Cys Glu Arg Ala Ala Thr Glu
            260                 265                 270
Ala Leu Thr Gln Gly Tyr Trp Gln Ile Ser Thr Ser Gln Val Ile Pro
        275                 280                 285
Gly Ile Ile Pro Ser Phe Glu Tyr Tyr Lys Thr Asn Met Arg Pro
290                 295                 300
Pro Phe Thr Tyr Ala Ser Met Ile Arg Trp Ala Ile Leu Lys Ser Pro
305                 310                 315                 320
```

```
Glu Lys Gln Leu Thr Leu Lys Glu Ile Tyr Gln Trp Phe Thr Ser Met
                325                 330                 335

Phe Phe Tyr Phe Arg His Asn Thr Ala Thr Trp Lys Asn Ala Val Arg
            340                 345                 350

His Asn Leu Ser Leu His Lys Cys Phe Val Arg Val Glu Gly Arg Lys
                355                 360                 365

Gly Ser Val Trp Thr Val Asp Glu Glu Glu Phe Leu Arg Arg Lys Gly
370                 375                 380

Gln Lys Leu His Arg Asp His Asp Met Asp Trp Met Ala Pro Phe Gln
385                 390                 395                 400

Leu Phe Pro Leu Thr Pro Gln Gly Glu Ser Tyr Gln Met
                405                 410

<210> SEQ ID NO 3
<211> LENGTH: 429
<212> TYPE: PRT
<213> ORGANISM: Mus musculus

<400> SEQUENCE: 3

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
                20                  25                  30

Ser Glu Leu Leu Gly Thr Arg Gly Ser Gly Gly Pro Phe Gln Gly Arg
            35                  40                  45

Asp Leu Arg Ser Gly Ala His Thr Ser Ser Ser Leu Asn Pro Leu Pro
50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
```

```
                275                 280                 285
Ser Val Leu Pro Ala Trp Ser Ala Pro Arg Glu Ala Pro Asp Gly Gly
    290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
            340                 345                 350

Ala Pro Glu Arg Gln Arg Thr Leu Asn Glu Ile Tyr His Trp Phe Thr
        355                 360                 365

Arg Met Phe Ala Tyr Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 4
<211> LENGTH: 28
<212> TYPE: DNA
<213> ORGANISM: Danio rerio

<400> SEQUENCE: 4
aagtgctttg tgcgtgttga aggaagga                                    28

<210> SEQ ID NO 5
<211> LENGTH: 28
<212> TYPE: DNA
<213> ORGANISM: Homo sapiens

<400> SEQUENCE: 5
aagtgctttg tgcgggtgga gagcgaga                                    28

<210> SEQ ID NO 6
<211> LENGTH: 28
<212> TYPE: DNA
<213> ORGANISM: Mus musculus

<400> SEQUENCE: 6
aagtgctttg tgcgagtgga gagcgaga                                    28

<210> SEQ ID NO 7
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 7
tccctctcaa ctcaggac                                               18

<210> SEQ ID NO 8
<211> LENGTH: 11
<212> TYPE: DNA
<213> ORGANISM: Artificial Sequence
<220> FEATURE:
<223> OTHER INFORMATION: Synthetically generated oligonucleotide
```

```
<400> SEQUENCE: 8
ggacacgcag c                                                          11

<210> SEQ ID NO 9
<211> LENGTH: 11
<212> TYPE: DNA
<213> ORGANISM: Artificial Sequence
<220> FEATURE:
<223> OTHER INFORMATION: Synthetically generated oligonucleotide

<400> SEQUENCE: 9
tgtgcgtgtt a                                                          11

<210> SEQ ID NO 10
<211> LENGTH: 12
<212> TYPE: DNA
<213> ORGANISM: Mus musculus

<400> SEQUENCE: 10
cagcgcgggc gg                                                         12

<210> SEQ ID NO 11
<211> LENGTH: 12
<212> TYPE: DNA
<213> ORGANISM: Mus musculus

<400> SEQUENCE: 11
cagcgcgggc gg                                                         12

<210> SEQ ID NO 12
<211> LENGTH: 12
<212> TYPE: DNA
<213> ORGANISM: Mus musculus

<400> SEQUENCE: 12
cagcgcgggc gg                                                         12

<210> SEQ ID NO 13
<211> LENGTH: 12
<212> TYPE: DNA
<213> ORGANISM: Mus musculus

<400> SEQUENCE: 13
cagcgcgggc gg                                                         12

<210> SEQ ID NO 14
<211> LENGTH: 12
<212> TYPE: DNA
<213> ORGANISM: Mus musculus

<400> SEQUENCE: 14
ccaccgccgc ca                                                         12

<210> SEQ ID NO 15
<211> LENGTH: 12
<212> TYPE: DNA
<213> ORGANISM: Mus musculus

<400> SEQUENCE: 15
ccaccgccgc ct                                                         12

<210> SEQ ID NO 16
<211> LENGTH: 11
```

```
<212> TYPE: DNA
<213> ORGANISM: Mus musculus

<400> SEQUENCE: 16
gggggcgcgg g                                                          11

<210> SEQ ID NO 17
<211> LENGTH: 11
<212> TYPE: DNA
<213> ORGANISM: Mus musculus

<400> SEQUENCE: 17
gcgggggcag g                                                          11

<210> SEQ ID NO 18
<211> LENGTH: 12
<212> TYPE: DNA
<213> ORGANISM: Mus musculus

<400> SEQUENCE: 18
gagcgtaggc gg                                                         12

<210> SEQ ID NO 19
<211> LENGTH: 12
<212> TYPE: DNA
<213> ORGANISM: Mus musculus

<400> SEQUENCE: 19
gagcgtaggc gg                                                         12

<210> SEQ ID NO 20
<211> LENGTH: 12
<212> TYPE: DNA
<213> ORGANISM: Mus musculus

<400> SEQUENCE: 20
gagcgtaggc gg                                                         12

<210> SEQ ID NO 21
<211> LENGTH: 12
<212> TYPE: DNA
<213> ORGANISM: Mus musculus

<400> SEQUENCE: 21
gagcgtaggc gg                                                         12

<210> SEQ ID NO 22
<211> LENGTH: 12
<212> TYPE: DNA
<213> ORGANISM: Mus musculus

<400> SEQUENCE: 22
acagccacgc gg                                                         12

<210> SEQ ID NO 23
<211> LENGTH: 11
<212> TYPE: DNA
<213> ORGANISM: Mus musculus

<400> SEQUENCE: 23
tacaggtgat t                                                          11

<210> SEQ ID NO 24
```

```
<211> LENGTH: 12
<212> TYPE: DNA
<213> ORGANISM: Mus musculus

<400> SEQUENCE: 24
acgcccgcgc gt                                                        12

<210> SEQ ID NO 25
<211> LENGTH: 12
<212> TYPE: DNA
<213> ORGANISM: Mus musculus

<400> SEQUENCE: 25
acgcccgcgc gt                                                        12

<210> SEQ ID NO 26
<211> LENGTH: 12
<212> TYPE: DNA
<213> ORGANISM: Mus musculus

<400> SEQUENCE: 26
acgcccgcgc gt                                                        12

<210> SEQ ID NO 27
<211> LENGTH: 12
<212> TYPE: DNA
<213> ORGANISM: Mus musculus

<400> SEQUENCE: 27
acgcccgcgc gt                                                        12

<210> SEQ ID NO 28
<211> LENGTH: 12
<212> TYPE: DNA
<213> ORGANISM: Mus musculus

<400> SEQUENCE: 28
gcgcgtgggc gg                                                        12

<210> SEQ ID NO 29
<211> LENGTH: 12
<212> TYPE: DNA
<213> ORGANISM: Mus musculus

<400> SEQUENCE: 29
gcgcgtgggc gg                                                        12

<210> SEQ ID NO 30
<211> LENGTH: 12
<212> TYPE: DNA
<213> ORGANISM: Mus musculus

<400> SEQUENCE: 30
gcgcgtgggc gg                                                        12

<210> SEQ ID NO 31
<211> LENGTH: 12
<212> TYPE: DNA
<213> ORGANISM: Mus musculus

<400> SEQUENCE: 31
gcgcgtgggc gg                                                        12
```

```
<210> SEQ ID NO 32
<211> LENGTH: 11
<212> TYPE: DNA
<213> ORGANISM: Mus musculus

<400> SEQUENCE: 32
gtgggcggga t                                                            11

<210> SEQ ID NO 33
<211> LENGTH: 11
<212> TYPE: DNA
<213> ORGANISM: Mus musculus

<400> SEQUENCE: 33
atgggggcaa c                                                            11

<210> SEQ ID NO 34
<211> LENGTH: 12
<212> TYPE: DNA
<213> ORGANISM: Mus musculus

<400> SEQUENCE: 34
ttgcgtaggc gg                                                           12

<210> SEQ ID NO 35
<211> LENGTH: 12
<212> TYPE: DNA
<213> ORGANISM: Mus musculus

<400> SEQUENCE: 35
ttgcgtaggc gg                                                           12

<210> SEQ ID NO 36
<211> LENGTH: 12
<212> TYPE: DNA
<213> ORGANISM: Mus musculus

<400> SEQUENCE: 36
ttgcgtaggc gg                                                           12

<210> SEQ ID NO 37
<211> LENGTH: 12
<212> TYPE: DNA
<213> ORGANISM: Mus musculus

<400> SEQUENCE: 37
ttgcgtaggc gg                                                           12

<210> SEQ ID NO 38
<211> LENGTH: 11
<212> TYPE: DNA
<213> ORGANISM: Mus musculus

<400> SEQUENCE: 38
gcgggcgggg g                                                            11

<210> SEQ ID NO 39
<211> LENGTH: 11
<212> TYPE: DNA
<213> ORGANISM: Mus musculus

<400> SEQUENCE: 39 gcggggggggg g                                                           11
```

```
<210> SEQ ID NO 40
<211> LENGTH: 11
<212> TYPE: DNA
<213> ORGANISM: Mus musculus

<400> SEQUENCE: 40
tgaaggtggg a                                                          11

<210> SEQ ID NO 41
<211> LENGTH: 11
<212> TYPE: DNA
<213> ORGANISM: Mus musculus

<400> SEQUENCE: 41
gtgggagcga g                                                          11

<210> SEQ ID NO 42
<211> LENGTH: 12
<212> TYPE: DNA
<213> ORGANISM: Mus musculus

<400> SEQUENCE: 42
gtgcataggc tg                                                         12

<210> SEQ ID NO 43
<211> LENGTH: 12
<212> TYPE: DNA
<213> ORGANISM: Mus musculus

<400> SEQUENCE: 43
gtgcataggc tg                                                         12

<210> SEQ ID NO 44
<211> LENGTH: 11
<212> TYPE: DNA
<213> ORGANISM: Mus musculus

<400> SEQUENCE: 44
gctggcccca c                                                          11

<210> SEQ ID NO 45
<211> LENGTH: 11
<212> TYPE: DNA
<213> ORGANISM: Mus musculus

<400> SEQUENCE: 45 cccccccca c                                                           11

<210> SEQ ID NO 46
<211> LENGTH: 12
<212> TYPE: DNA
<213> ORGANISM: Mus musculus

<400> SEQUENCE: 46
ccaaccacac aa                                                         12

<210> SEQ ID NO 47
<211> LENGTH: 11
<212> TYPE: DNA
<213> ORGANISM: Mus musculus

<400> SEQUENCE: 47
actcacctca g                                                          11
```

```
<210> SEQ ID NO 48
<211> LENGTH: 12
<212> TYPE: DNA
<213> ORGANISM: Mus musculus

<400> SEQUENCE: 48
acacccacac tg                                                          12

<210> SEQ ID NO 49
<211> LENGTH: 12
<212> TYPE: DNA
<213> ORGANISM: Mus musculus

<400> SEQUENCE: 49
acacccacac tg                                                          12

<210> SEQ ID NO 50
<211> LENGTH: 12
<212> TYPE: DNA
<213> ORGANISM: Mus musculus

<400> SEQUENCE: 50
acactcccgc ac                                                          12

<210> SEQ ID NO 51
<211> LENGTH: 12
<212> TYPE: DNA
<213> ORGANISM: Mus musculus

<400> SEQUENCE: 51
acactcccgc ac                                                          12

<210> SEQ ID NO 52
<211> LENGTH: 11
<212> TYPE: DNA
<213> ORGANISM: Mus musculus

<400> SEQUENCE: 52
cccgcaccca c                                                           11

<210> SEQ ID NO 53
<211> LENGTH: 11
<212> TYPE: DNA
<213> ORGANISM: Mus musculus

<400> SEQUENCE: 53
ttccctccca c                                                           11

<210> SEQ ID NO 54
<211> LENGTH: 12
<212> TYPE: DNA
<213> ORGANISM: Mus musculus

<400> SEQUENCE: 54
cctcccacac ac                                                          12

<210> SEQ ID NO 55
<211> LENGTH: 12
<212> TYPE: DNA
<213> ORGANISM: Mus musculus

<400> SEQUENCE: 55
```
cctcccacac ac                                                    12

<210> SEQ ID NO 56
<211> LENGTH: 12
<212> TYPE: DNA
<213> ORGANISM: Mus musculus

<400> SEQUENCE: 56
cctcccacac ac                                                    12

<210> SEQ ID NO 57
<211> LENGTH: 12
<212> TYPE: DNA
<213> ORGANISM: Mus musculus

<400> SEQUENCE: 57
cctcccacac ac                                                    12

<210> SEQ ID NO 58
<211> LENGTH: 12
<212> TYPE: DNA
<213> ORGANISM: Mus musculus

<400> SEQUENCE: 58
cctccctctc aa                                                    12

<210> SEQ ID NO 59
<211> LENGTH: 12
<212> TYPE: DNA
<213> ORGANISM: Mus musculus

<400> SEQUENCE: 59
ttgttggggc gg                                                    12

<210> SEQ ID NO 60
<211> LENGTH: 11
<212> TYPE: DNA
<213> ORGANISM: Mus musculus

<400> SEQUENCE: 60
gttggggcgg g                                                     11

<210> SEQ ID NO 61
<211> LENGTH: 11
<212> TYPE: DNA
<213> ORGANISM: Mus musculus

<400> SEQUENCE: 61 gcgggggag g                                                      11

<210> SEQ ID NO 62
<211> LENGTH: 11
<212> TYPE: DNA
<213> ORGANISM: Mus musculus

<400> SEQUENCE: 62
cccaggtggg t                                                     11

<210> SEQ ID NO 63
<211> LENGTH: 11
<212> TYPE: DNA
<213> ORGANISM: Mus musculus

<400> SEQUENCE: 63

```
gtgggggggag t                                                   11

<210> SEQ ID NO 64
<211> LENGTH: 11
<212> TYPE: DNA
<213> ORGANISM: Mus musculus

<400> SEQUENCE: 64
ccccccccca c                                                    11

<210> SEQ ID NO 65
<211> LENGTH: 12
<212> TYPE: DNA
<213> ORGANISM: Mus musculus

<400> SEQUENCE: 65
acacacactc at                                                   12

<210> SEQ ID NO 66
<211> LENGTH: 12
<212> TYPE: DNA
<213> ORGANISM: Mus musculus

<400> SEQUENCE: 66
acacacactc at                                                   12

<210> SEQ ID NO 67
<211> LENGTH: 11
<212> TYPE: DNA
<213> ORGANISM: Mus musculus

<400> SEQUENCE: 67
ccaaggtgag c                                                    11

<210> SEQ ID NO 68
<211> LENGTH: 11
<212> TYPE: DNA
<213> ORGANISM: Mus musculus

<400> SEQUENCE: 68 ctctcccccca c                                                   11

<210> SEQ ID NO 69
<211> LENGTH: 12
<212> TYPE: DNA
<213> ORGANISM: Mus musculus

<400> SEQUENCE: 69
gagggtgggt gt                                                   12

<210> SEQ ID NO 70
<211> LENGTH: 12
<212> TYPE: DNA
<213> ORGANISM: Mus musculus

<400> SEQUENCE: 70
gagggtgggt gt                                                   12

<210> SEQ ID NO 71
<211> LENGTH: 12
<212> TYPE: DNA
<213> ORGANISM: Mus musculus
```

-continued

<400> SEQUENCE: 71
gagggtgggt gt                                                               12

<210> SEQ ID NO 72
<211> LENGTH: 10
<212> TYPE: DNA
<213> ORGANISM: Mus musculus

<400> SEQUENCE: 72
ttaaggggtt                                                                  10

<210> SEQ ID NO 73
<211> LENGTH: 11
<212> TYPE: DNA
<213> ORGANISM: Mus musculus

<400> SEQUENCE: 73
tttaggtgtg t                                                                11

<210> SEQ ID NO 74
<211> LENGTH: 12
<212> TYPE: DNA
<213> ORGANISM: Mus musculus

<400> SEQUENCE: 74
ttacgtgggt gc                                                               12

<210> SEQ ID NO 75
<211> LENGTH: 12
<212> TYPE: DNA
<213> ORGANISM: Mus musculus

<400> SEQUENCE: 75
ttacgtgggt gc                                                               12

<210> SEQ ID NO 76
<211> LENGTH: 12
<212> TYPE: DNA
<213> ORGANISM: Mus musculus

<400> SEQUENCE: 76
ttacgtgggt gc                                                               12

<210> SEQ ID NO 77
<211> LENGTH: 10
<212> TYPE: DNA
<213> ORGANISM: Mus musculus

<400> SEQUENCE: 77
ttaagtcttt                                                                  10

<210> SEQ ID NO 78
<211> LENGTH: 11
<212> TYPE: DNA
<213> ORGANISM: Mus musculus

<400> SEQUENCE: 78 gcagcccccca c                                                               11

<210> SEQ ID NO 79
<211> LENGTH: 11
<212> TYPE: DNA
<213> ORGANISM: Mus musculus

```
<400> SEQUENCE: 79 cccacccccca g                                                         11

<210> SEQ ID NO 80
<211> LENGTH: 11
<212> TYPE: DNA
<213> ORGANISM: Mus musculus

<400> SEQUENCE: 80
tttaggtggt t                                                          11

<210> SEQ ID NO 81
<211> LENGTH: 10
<212> TYPE: DNA
<213> ORGANISM: Mus musculus

<400> SEQUENCE: 81
ttaggtggtt                                                            10

<210> SEQ ID NO 82
<211> LENGTH: 10
<212> TYPE: DNA
<213> ORGANISM: Mus musculus

<400> SEQUENCE: 82
acaagtattt                                                            10

<210> SEQ ID NO 83
<211> LENGTH: 12
<212> TYPE: DNA
<213> ORGANISM: Mus musculus

<400> SEQUENCE: 83
cctgccacgc ca                                                         12

<210> SEQ ID NO 84
<211> LENGTH: 12
<212> TYPE: DNA
<213> ORGANISM: Mus musculus

<400> SEQUENCE: 84
cctgccacgc ca                                                         12

<210> SEQ ID NO 85
<211> LENGTH: 11
<212> TYPE: DNA
<213> ORGANISM: Mus musculus

<400> SEQUENCE: 85
tgcaggtgag g                                                          11

<210> SEQ ID NO 86
<211> LENGTH: 12
<212> TYPE: DNA
<213> ORGANISM: Mus musculus

<400> SEQUENCE: 86 tggcggggggg gg                                                        12

<210> SEQ ID NO 87
<211> LENGTH: 12
<212> TYPE: DNA
```

```
<213> ORGANISM: Mus musculus

<400> SEQUENCE: 87
tggcgggggg gg                                                         12

<210> SEQ ID NO 88
<211> LENGTH: 11
<212> TYPE: DNA
<213> ORGANISM: Mus musculus

<400> SEQUENCE: 88 gcggggggg g                                                           11

<210> SEQ ID NO 89
<211> LENGTH: 11
<212> TYPE: DNA
<213> ORGANISM: Mus musculus

<400> SEQUENCE: 89
gggggggggg c                                                          11

<210> SEQ ID NO 90
<211> LENGTH: 12
<212> TYPE: DNA
<213> ORGANISM: Mus musculus

<400> SEQUENCE: 90
cttcccacgc tc                                                         12

<210> SEQ ID NO 91
<211> LENGTH: 11
<212> TYPE: DNA
<213> ORGANISM: Mus musculus

<400> SEQUENCE: 91
gacaggtgag t                                                          11

<210> SEQ ID NO 92
<211> LENGTH: 12
<212> TYPE: DNA
<213> ORGANISM: Mus musculus

<400> SEQUENCE: 92
ctgcccacac ct                                                         12

<210> SEQ ID NO 93
<211> LENGTH: 12
<212> TYPE: DNA
<213> ORGANISM: Mus musculus

<400> SEQUENCE: 93 ccaccccctgc ac                                                        12

<210> SEQ ID NO 94
<211> LENGTH: 12
<212> TYPE: DNA
<213> ORGANISM: Mus musculus

<400> SEQUENCE: 94 ccaccccctgc ac                                                        12

<210> SEQ ID NO 95
<211> LENGTH: 12
```

```
<212> TYPE: DNA
<213> ORGANISM: Mus musculus

<400> SEQUENCE: 95
ttgcgtggcc ag                                                          12

<210> SEQ ID NO 96
<211> LENGTH: 12
<212> TYPE: DNA
<213> ORGANISM: Mus musculus

<400> SEQUENCE: 96
ttgcgtggcc ag                                                          12

<210> SEQ ID NO 97
<211> LENGTH: 12
<212> TYPE: DNA
<213> ORGANISM: Mus musculus

<400> SEQUENCE: 97
ttgcgtggcc ag                                                          12

<210> SEQ ID NO 98
<211> LENGTH: 12
<212> TYPE: DNA
<213> ORGANISM: Mus musculus

<400> SEQUENCE: 98
ttgcgtggcc ag                                                          12

<210> SEQ ID NO 99
<211> LENGTH: 12
<212> TYPE: DNA
<213> ORGANISM: Mus musculus

<400> SEQUENCE: 99
ttgcatgggc tg                                                          12

<210> SEQ ID NO 100
<211> LENGTH: 12
<212> TYPE: DNA
<213> ORGANISM: Mus musculus

<400> SEQUENCE: 100
ttgcatgggc tg                                                          12

<210> SEQ ID NO 101
<211> LENGTH: 12
<212> TYPE: DNA
<213> ORGANISM: Mus musculus

<400> SEQUENCE: 101
ttgcatgggc tg                                                          12

<210> SEQ ID NO 102
<211> LENGTH: 12
<212> TYPE: DNA
<213> ORGANISM: Mus musculus

<400> SEQUENCE: 102
ttgcatgggc tg                                                          12

<210> SEQ ID NO 103
```

```
<211> LENGTH: 11
<212> TYPE: DNA
<213> ORGANISM: Mus musculus

<400> SEQUENCE: 103 gtggggggggg g                                                           11

<210> SEQ ID NO 104
<211> LENGTH: 11
<212> TYPE: DNA
<213> ORGANISM: Mus musculus

<400> SEQUENCE: 104
tcccacctaa t                                                            11

<210> SEQ ID NO 105
<211> LENGTH: 12
<212> TYPE: DNA
<213> ORGANISM: Mus musculus

<400> SEQUENCE: 105
acgcctactc tg                                                           12

<210> SEQ ID NO 106
<211> LENGTH: 12
<212> TYPE: DNA
<213> ORGANISM: Mus musculus

<400> SEQUENCE: 106
acgcctactc tg                                                           12

<210> SEQ ID NO 107
<211> LENGTH: 12
<212> TYPE: DNA
<213> ORGANISM: Mus musculus

<400> SEQUENCE: 107
acgcctactc tg                                                           12

<210> SEQ ID NO 108
<211> LENGTH: 11
<212> TYPE: DNA
<213> ORGANISM: Mus musculus

<400> SEQUENCE: 108
gtggtggcgg c                                                            11

<210> SEQ ID NO 109
<211> LENGTH: 11
<212> TYPE: DNA
<213> ORGANISM: Mus musculus

<400> SEQUENCE: 109
gtggcggcgg c                                                            11

<210> SEQ ID NO 110
<211> LENGTH: 12
<212> TYPE: DNA
<213> ORGANISM: Mus musculus

<400> SEQUENCE: 110
ccacctacat aa                                                           12
```

```
<210> SEQ ID NO 111
<211> LENGTH: 12
<212> TYPE: DNA
<213> ORGANISM: Mus musculus

<400> SEQUENCE: 111
ccacctacat aa                                                         12

<210> SEQ ID NO 112
<211> LENGTH: 12
<212> TYPE: DNA
<213> ORGANISM: Mus musculus

<400> SEQUENCE: 112
ccaaccaagc aa                                                         12

<210> SEQ ID NO 113
<211> LENGTH: 11
<212> TYPE: DNA
<213> ORGANISM: Mus musculus

<400> SEQUENCE: 113
ctcaccccca c                                                          11

<210> SEQ ID NO 114
<211> LENGTH: 11
<212> TYPE: DNA
<213> ORGANISM: Mus musculus

<400> SEQUENCE: 114
ctgcacctga g                                                          11

<210> SEQ ID NO 115
<211> LENGTH: 11
<212> TYPE: DNA
<213> ORGANISM: Mus musculus

<400> SEQUENCE: 115
tccgtcccca c                                                          11

<210> SEQ ID NO 116
<211> LENGTH: 11
<212> TYPE: DNA
<213> ORGANISM: Mus musculus

<400> SEQUENCE: 116
tttcacctat g                                                          11

<210> SEQ ID NO 117
<211> LENGTH: 11
<212> TYPE: DNA
<213> ORGANISM: Mus musculus

<400> SEQUENCE: 117
gctgctccct c                                                          11

<210> SEQ ID NO 118
<211> LENGTH: 11
<212> TYPE: DNA
<213> ORGANISM: Mus musculus

<400> SEQUENCE: 118
ttccacctga c                                                          11
```

```
<210> SEQ ID NO 119
<211> LENGTH: 11
<212> TYPE: DNA
<213> ORGANISM: Mus musculus

<400> SEQUENCE: 119
ggaaggtgag t                                                          11

<210> SEQ ID NO 120
<211> LENGTH: 10
<212> TYPE: DNA
<213> ORGANISM: Mus musculus

<400> SEQUENCE: 120
acaagtgctt                                                            10

<210> SEQ ID NO 121
<211> LENGTH: 12
<212> TYPE: DNA
<213> ORGANISM: Mus musculus

<400> SEQUENCE: 121
acgccccaac aa                                                         12

<210> SEQ ID NO 122
<211> LENGTH: 12
<212> TYPE: DNA
<213> ORGANISM: Mus musculus

<400> SEQUENCE: 122
aaaggtgggc gg                                                         12

<210> SEQ ID NO 123
<211> LENGTH: 12
<212> TYPE: DNA
<213> ORGANISM: Mus musculus

<400> SEQUENCE: 123
aaaggtgggc gg                                                         12

<210> SEQ ID NO 124
<211> LENGTH: 11
<212> TYPE: DNA
<213> ORGANISM: Mus musculus

<400> SEQUENCE: 124
gtgggcgggg g                                                          11

<210> SEQ ID NO 125
<211> LENGTH: 12
<212> TYPE: DNA
<213> ORGANISM: Mus musculus

<400> SEQUENCE: 125
gggcggggga gg                                                         12

<210> SEQ ID NO 126
<211> LENGTH: 12
<212> TYPE: DNA
<213> ORGANISM: Mus musculus

<400> SEQUENCE: 126
gggcggggga gg                                                         12
```

```
<210> SEQ ID NO 127
<211> LENGTH: 12
<212> TYPE: DNA
<213> ORGANISM: Mus musculus

<400> SEQUENCE: 127
gggcggggga gg                                                           12

<210> SEQ ID NO 128
<211> LENGTH: 11
<212> TYPE: DNA
<213> ORGANISM: Mus musculus

<400> SEQUENCE: 128 gtggggcaa g                                                             11

<210> SEQ ID NO 129
<211> LENGTH: 12
<212> TYPE: DNA
<213> ORGANISM: Mus musculus

<400> SEQUENCE: 129
ccacacaggc at                                                           12

<210> SEQ ID NO 130
<211> LENGTH: 12
<212> TYPE: DNA
<213> ORGANISM: Mus musculus

<400> SEQUENCE: 130
atgcctaagc gt                                                           12

<210> SEQ ID NO 131
<211> LENGTH: 12
<212> TYPE: DNA
<213> ORGANISM: Mus musculus

<400> SEQUENCE: 131
atgcctaagc gt                                                           12

<210> SEQ ID NO 132
<211> LENGTH: 12
<212> TYPE: DNA
<213> ORGANISM: Mus musculus

<400> SEQUENCE: 132
atgcctaagc gt                                                           12

<210> SEQ ID NO 133
<211> LENGTH: 11
<212> TYPE: DNA
<213> ORGANISM: Mus musculus

<400> SEQUENCE: 133
cttccctcca c                                                            11

<210> SEQ ID NO 134
<211> LENGTH: 11
<212> TYPE: DNA
<213> ORGANISM: Mus musculus

<400> SEQUENCE: 134
```

-continued ctccacctaa a                                                                11

<210> SEQ ID NO 135
<211> LENGTH: 11
<212> TYPE: DNA
<213> ORGANISM: Mus musculus

<400> SEQUENCE: 135
cccgcctcca c                                                                11

<210> SEQ ID NO 136
<211> LENGTH: 12
<212> TYPE: DNA
<213> ORGANISM: Mus musculus

<400> SEQUENCE: 136
atgtgttgga gt                                                               12

<210> SEQ ID NO 137
<211> LENGTH: 11
<212> TYPE: DNA
<213> ORGANISM: Mus musculus

<400> SEQUENCE: 137
cctaggtggg a                                                                11

<210> SEQ ID NO 138
<211> LENGTH: 21801
<212> TYPE: DNA
<213> ORGANISM: Mus musculus

<400> SEQUENCE: 138
gcacgcgcac caacccgcgc accactggcg ggcgtccccc aggcacccac accccggaac     60
ccccgggaac cgctccagga ggcggcagca gcgcctccaa ctccaccatc acgcgcccca    120
accgctccag acgcccagc gcgggcggca acgaaaatgt gggcaccagg taaaaccccc     180
cgccagcggg aacggggcac ggcggagagg gatcgggaaa agcctcctct tcctcctccc    240
cttcatcccc atcctcgcca tcgtcttcct catcagcccc gccaccgccg ccatcttgcc    300
cggtcgccgc cgccatcttg cccgccccgg gcccgcccca cggccggtag cggcgtagct    360
gcgccagagg cagccccagg gcctcgtcag cgaacagcac cctccgcggg gccaccgccg    420
cctcagccga ggcgcggggc tctcccgcag ccggcgacgg gggcgcggga tgccgcagcg    480
gtggctccac aggggccgtg cgcgccatat cggcggcggc ggcggcggca ccgacggcac    540
cggcggtggg accggcgggg gcagggcctg aaaaggcggg cagccaatga aaagccaga     600
acagggggt ggggctccag tggagcgtag gcggtgagct agagacaggt acggccaaca    660
gccaatggac agccacgcgg gagtgacgta caggtgattg acaagcagga gaagctagca    720
accaatgagg acgcccgcgc gtgggcggga tggaaggcgg gatgataacg gaatcaatgg    780
agaggcctga gtagggttaa tgcgggcccg aagatgtagc agcaggagta tgacaattag    840
tgggaaagtc tgagcacgaa gggcatggta ggcggcggga agatgaaatg gctacaagca    900
atggggggcaa cggggagcga acccagaggt ccaaaaactg ggagatccgc aggttgcgta    960
ggcggtgaga cgtaagacag ataaaatgaa cagccaatgg agaactgcac gcgaatgatg   1020
tagagacaga atgacgataa tagttgcaat gagccaatgg aggagtctag tgagcgcaca   1080
ctatggcttc aagaggtggt aacaaggtag atctagccaa tacagagact gaacagagac   1140
gggaaggctg tgtgtgagca gacatggagg cggggctgta gcgggcgggg gggggggga    1200

```
gcactaaggc atgtgaggag tgaaggtggg agcgagaaag aaatggggat ccagggtgaa    1260
ggctgttata tctcaaagga cagtgccagt atgggattaa ccaaagctga aactagagaa    1320
atgtagccag aaggaaactt tggaggcaag atgggaactc atacccacgg atggtagtgt    1380
aggtgctgtg aaggaaagca tgagtagcca ataaataggc tgagttggaa gaaggtgcat    1440
aggctgagcc tgagctattg agtgattgag cgcagaatca gaattcattc aaccagtaag    1500
atcggacctc tggggaatgg ctttacctt ccctaatctt ccatgactcc ccatggctcc      1560 acgaatacc agagcccta aaagcccaga ctgcaccgga ttgtgagacc aaagcaaaac      1620
agttctatca gttactgggt gtgtcctgct ggccccacac caccacacac acctcccagc    1680
cttattgtga ccaatgcaac tagccatgaa cgttcttaac tgttccttaa agtccccagt    1740
tgagcattga tgttcttcag acttggcac tattgcatga atcaatcgca aaataggaaa     1800
tagaaccttt ttggaagaat tagcttttc caactcacac ttagcacaca ttgactgata    1860
gtatgtcatc acaagcttat cagctaatgt acattcaaat cagagtcctg cccttcttgc    1920
tcattttgac actttgcacc ccacagtggc tttcttctcc ccccccca ctttcccaat      1980 ctcctctgct tagagtgctg tcccatctgt ttctttcatc tagtgaattc tttccattct    2040
ccctctgaga tggcacctcc tatgggaatg acctggactt tgccatcgtg ttcattcaca    2100 tatccccac tcccatttac taacttagta agacttagtg tttgccatat gccaggttca    2160
gggagtgctt ttatctaacc ctcataagac ccctaacagg aaggccccca cagtctctct    2220
gctcctcctg tctgtgtcca gggtcatgaa aggaatatgt ccagctacaa gtagcagaag    2280
aataatggca taatgaaggt agaactttt tttctcatct gaaagttcaa ggcagcaagt    2340
gctctcagga ctccatccta tctgcccatt ttgggtatca actgtgcccc ggtcttgcct    2400
cagagtctca ttcttcagca aatcctgcag gttatctacc caacgcattt tccaagcagg    2460
atatggtgat gtatgcctgt aatcccagca ctcaaggggc tgaggcagga gaatcacgga    2520
attccaagcc taggctacaa gtgtgacctt gtctaaaaaa taaaagggt taagtgtagc     2580 tcagcggtaa aaaccacttc ctagaaagtg catgggcccc atctctagca tcatttttt    2640 taaatcccaa atccacctt tcactaccac tccatcaaca ggaccagcac cagtcccagt    2700
cccctggact actgtagtca cctcccctg gttggtctcc atcccatgtt ctacccccta    2760
ttccatattc agccatctaa gacatcctct taagtcctaa cagcaatgtc tctcctctgc    2820
tcccaacacc ctctggcttc ctctacacta agaggaagag ccaaccttca ccatgtcgta    2880
agcgcacaag ccagctagcc ccgtctgacc ttcctcctgt tctctccctt ccagtcatgt    2940
cactccaacc acacaagact ccttgctgac cctgtacata tccagcacac tcacctcagg    3000
acacccacac tgacccttct ctcctggatc tgcagatctc cccatcactc tcttcttcat    3060
ctatgcctgc tctttgtcaa agatcccttt ccctgggaat gctcccctg acctgttaaa    3120 tcctgcccca ttcaccatca actcctagcc ctcccagttt gcttcccag gaacctacat     3180 gagccaatat agtaatggtg gagaggaaat accaccctct gacaagcaaa accctagcca    3240
ccatgctgca aagaccctag ctttacactt cagtaacctt aacactcccg cacccacagc    3300
cccattcaaa tagcctcctg gaaacctgtg tcacttaccc ctcatttact tatcctgcca    3360
cctctctgac caagttttcg cagaatggca ggaagatggt gacgaggata taaggaaga    3420 tgcagaccaa accatggacc ctgagaaaat gagtacctat tccaaaaaga gacaggtgac    3480
agggcagggg actagaactg tctcagagac atagaagata cagggactag ttgggcccaa    3540
```

```
gtgtacaggg agcagggacc attaactttg ggcatagct acagtcagct gcccattacc   3600
tgttaggtat gctcttcacc cctccctat tccctcccac acacaaccac aactgttaag   3660
ctcctaagat ccatgcagac ctccaaagta agaggacctc atcccacctc tgcccctccc   3720
tccctctcaa ctcaggacct cccccggctt ccaggcacca cacaggccat gtttggtctt   3780
agatgtgtcc caccaactta gaagccccaa ccagtgaaag ttttgctttg aactaatgat   3840
aggaagggtt gagggttttt ttttttaat tgttgttgtt gttggctggt attttgggt    3900
cttttttttt tctattcact ttgttttccc ctcttgtctt tataaagcca agccatcagt   3960
tccagtcttg ttatttccaa aaaggtgagt taagatgagg aaagtcagtc tcttttttgt   4020
tgttgttgtt ggggcggggg gaggtgctca gaagatagcc gaaagggaca aaaagtgcaa   4080
atgagggaaa gagcaaagga gtgtgggaat tgtttactag gttagcatca tgtgaataaa   4140
aacgtatttc tactttctct tcctcaggcc tgaagccagt cttgcaaaga ggtggtggtg   4200
gccatgcagt tggatacctg gaactcttag ctctctgcag gatgccaggg caccaaaggc   4260
tggaagcctt agccgtgcct tgtcaggaaa aactctgtgg aggctcgtct gtagtaaaca   4320
gtggttacag ggagccggtc tgtgccaaat cgaggacacg cagctgccag atcttgaata   4380
caaaccttaa aacctcacaa acatcaagtt ccagaggagt ctccaagtcc tagaacttct   4440
atgcacactgt tggcttcagg aaaactggtc acttcagagc ccaatgctaa ggaccccttat  4500
ttcccaaaat tgtgatctta agcaagctgc acctccattt tgcccatcgg tctaaaaaca   4560
atacagccat gatgagatgg acctcagagg gtgagaagtg tttggctctg tctggaatgt   4620
agaaaattct agttaaatgt tggctaccaa aattatgaca gctgtttaga atcctaaacc   4680
tttgcaaacg ggagtgtttc tttccttttg tttgtggttt tggtttttg tttttgtttt    4740
tttgtgttttt ttgtttttt cttttcttt ttacacggaa tctggctata tagccccaag    4800
caaccttaaa ctcttgattc ttctgcctca gtttctgggg tgctgggatt actggtatgt   4860
gatactggat gaaactggaa cttttcagag tagactgtta caaagtttag aatcatcagg   4920
ctatggctat attgttcctg acaggactag gaccctgggc cgctatgtgt atggttttt    4980
tgtttgtttg ttttaacaac ccagagcctt gtgcgtgtta acaagcact ctggcactga    5040
gctgcaatgg ccagccttc ttcccttgc ccttcttggt gatgctggct gcattaacag     5100
ccactggggc tgttcccagg tgggtggctg ctgggtcagg gcactcagca caaacatgat   5160
gtggggctca ctcagagact cgcagcagct tctgggagcc agccattctg agactctctg   5220
attctgtgaa tttgtggggg gagtacagcc cactttttc tccatgaatt gctttccatg    5280
cctcttgcct tctgtggaaa gaaaggctac aggagtggcc agctctgcca agccttggca   5340
acatgatggt ggtgatcata tgcatgcttg ctaaggaaat actgaggttt ggagcagaag   5400
gaagcctctg gagacagagc actaccccac ctctcccctg gctgcttccc attcacatgg   5460
caggcttcag atcccttctt ctgttcaacc cagcgatcct ccaacgtctc acaaacacaa   5520
tgctgtctct acctgcctcg ggatgccttt gtgatttgac ttattttccc tcagtttttt   5580
ttttctgact ctacacactt ttgtttaaga aattgtggtt tctcatgagc cctgttatct   5640
cattgatacc ttttacctct gtggtgaggg gaagaaatca tatttcaga tgacttgtaa    5700
agggcaaaga aaaacccaa aatttcaaaa tttccgttta agtctcataa gaaaagaata    5760
aacaaagtaa gagagcaaag aaaaaaaaac tacaagaacc ccccccccac cctgcaatta   5820
tcagcacaca cactcatcaa aaaaaaattg gattattaga agagcgaggt ctgcggcttc   5880
cacgccgtgg ttttcttct cggtataaaa gcaaagttgt ttttgataat gtggcagttt    5940
```

```
cccacaagcc aggctgatcc ccctctagca gtccacttca ccaaggtgag cgagtgtccc    6000
tgctctcccc caccagacac agctctgctg gcgaaagtgg cagagaggta ttgagggtgg    6060
gtgtcaggag cccaccagta cagctggaaa cacccagcca ctccaggtaa ggactttgga    6120
aactaatacc attcatccta aatgccagat aggtggagca gttggtcctt agacaggggc    6180
aaaaagaagt actttgattg tttgatgcac agataaacag gattttttt taacatatgt     6240 ctatcaactg ctggtctcca ggaatgccgg agctttaggc aactcaagat gctgtccagc    6300
tataactaga aactagaagt gcatctcttg tttcttttcc tcctgctgtc ttccatttct    6360
tctcctgtct cccctgctt ctttgcctgt ctctgccttc catcagtgcc cagtctctgt     6420
ctctttccca ggctctgact atatgcctgt ctgtctcttc cagcctggcc agccacagtc    6480
cctttctttc ctcccgctct ctgactctcg gctcatcttc cttcagctgc ttttgcaccc    6540
ggtattgagc gcagatattt gtacacaact ggcgcttaat aataatggct taagagctct    6600
gttttccaag aacgggcatt agttctgtgt gtcttaggtt tgtgagctgt caggtcagtc    6660
ttagcattta actgaccttc tgcttgtgtc acgcaagata acaccctcag tcagccacag    6720
tttagcaaag gactatatga ctgtgagcag aatccatgtg caaggagagc aggcagttca    6780
ggacgagggt gagctggtct ctgcaggttt agtgctgtgg cactgtgcct ggtatatggt    6840
gagttctcac tgtttgctat tagcattttt aaacaaatta gaatcgtgct atagattgga    6900
tttgtttctg ctctgttcaa gcgataccat ttttgtagca tactaaaata acgaacacgt    6960
gatcttttat gtctgccgtg actgtcctca catcaccatg aatttgatta cctgaattaa    7020
gtgctgatgg tgggatattt gggtttcttc tgattctaaa actccatacc tgactccatg    7080
gatcctgaaa atggagtagc tggggaagaa ggggtgtaca tcttaagggg ttttgccctc    7140
tctacaaatt gcttttccaa aacgttgtct tattttctgt tgtttctatt caagttaatt    7200
ttaggtgtgt gttaccattt ttaatccttc cccatcataa gaaaatgac aagtattaaa     7260 attttgcatt ttggttactt ttaatgacca ctgaccattt gtgctctgta ggctagagtt    7320
ttatgatcac attcttcatc ctactaaatt gctcatgatt tttcaaaatt gctaatagct    7380
cttaatttag aaaggataat aactattggc tatatgtata tgacacatat ttccctgaaa    7440
ttcatcattt gtgtgtatgt gtattttaat tgtattcatt tacttagttt atgagcatgc    7500
atgttcttcc tgcatgtgca ccatatgtgt gcctggtgcc cacagaggcc agaagatggt    7560
gtgggatctc atgggactgg agttacagat ggttacgtgg gtgctggcgc ttatgtggct    7620
tctttctatg gttttgtgtt taaaagcctt ttaccacttg aaaatgagaa gctacctcct    7680
ctacaagagc agcagtgctc ttacccatgg agccatctct ccagccctat ttgtatgggg    7740
ggggggggtc ttctgagaca aggtctcact ctatagccct gactggccta aaactcactg    7800
tatagaccag gctgacctca aactcacaaa gacccatcca tctgcctctg ccttctgaga    7860
agtgggatag aagacataca ccaccacggc gggcaatcac ttgctttttt tccctattta    7920
ttgtgctttg taatgcatgt gtcttttagg tctttagatt actctttct tgtggggctt      7980 ctgtgtatgg ttttgtgttt taagtctttt gcacttgaaa atgagataac tgttcacccc    8040
atgttggctt ccagtctcct ttatggcttc attttttcca tttactgcag aggtcaaaag    8100
tgtgggtatg ggagccagac tgtctggaac aacctagcct caactcaagt catctgtgtg    8160 aatttttaccc aggctcttaa cctctctgta cctccatttc ctcgtatgta ctgtgatgat   8220
tataacagta cctacctcag aggatctttc tgaggattat ttttattaat gatggtaggt    8280
```

```
gctcagcaca aggccaaaca acaatgatag acattaaaac gtatctctct agtgggtctg    8340
gaaattattc tagagcgtct gatgacagcg acatttcaag tgggcaggga ggtattggtg    8400
ggaaagtggg ctatctaccc agtcacttta ttttccccta attgtctcag aatcatttgt    8460
taatctgtcc tgcactgttc ctcatgttga aatgttgtgt tcatcacaaa ttccattccc    8520
tctgtgcatg ggtctctgcc acggttttct actctaatct gctccttagt gtttattctt    8580
gtacaaagcc cacactattt ttctgatgtt gctttgcaaa acaattcaat accagccatg    8640
ggtgtctctg gcacctagca gcatcagtcc tccagccaga ggccagtgat tattttcagt    8700
cctttctctc actccctctc tctctgtctc tgcatgtctg tctgtctgta tatgtctctg    8760
tcttgttcat tctttctctg tcacttttcc tctaaactgc tctcactgtc tctctctatg    8820
agcttgattc ctattccatc tcatgtttct ctctatatat ttctctatct gtatctcttc    8880
tatatctgta ttcacacaca tatgatatat atatatatat ctcaatatat atatatatat    8940
atatatatat atatatatat atatatatat atatatcaat atatatatct cataccatac    9000
catacataca tacggctata tagctccata agatttaccc cagccacgag acagaaagat    9060
gctggccttc ctcccacctcg tactcttccc tccccagtct agaagggcaa actgggctca    9120
gagatgagca gccccaccc ccaggcctca cagagatgtt gtgtcagagt taaatccaag    9180
agcagatctc agaattctca gtgggacctt gactttggca attccacatt gcaggcctta    9240
gtttacctct caggacccag gaggccatta acaggagacc tgaggtgccc ttccctcttc    9300
tacatcctca tgagttggat ccagtccata accatagcat ggggccaaat ctcacaagct    9360
ctggtctatg tgaggttctg ggccccatga gtcagaagtc ctagcggacc aaagaacact    9420
agtaacgatg gagaaatatc agttaagtat gaaccctcag agttcatact gcattccttg    9480
ggacaaccat tctggggccc ttccaaaaag cctggtggtg tgctctttcc atgagggcca    9540
ggccaaatgt cttcttcctc ttgtccctgt atctggaaga atgttataat ttggggaaag    9600
ttgtcccagg agagcgggtc tggagccata tgtaagtgac catttatcag tcatagacac    9660
ttgctcagca ttctgtatgt acgaactttg caagatggct cctgttactg tcccaaatta    9720
gacaggagga cagaaagacc ccagccttcc tccatcacat actcttccca gtctagaagg    9780
gcaaactggg ctcagagatg gacaggaagg ccccctttgtc ccaagagggc aaagcctgac    9840
cccagatcag gacagtagag ggtttttccaa tcctctgtca taatggagct caggagggag    9900
ggaggctgac attccagagc cagcaagagg ccttatggag ttttaagctt cctggcttta    9960
ggtggttccc atttctttgg gctctgggac atcaatacac acagtaagaa ggtggatcca    10020
tgcaccctac agagtctgtg ttcttgagat tctaaaatcc gttggctttg agaaatgata    10080
tcgtacagtt ctgagtttct gttactacag catttgaaga ctcaaggggg tctcaatatc    10140
catgaggcct gcctaatact caccaagcat ccaaccttgg gcccctctgg catccaagaa    10200
agacagaatc gatagaactt gggttttgca tggtagccag atggacgtca cctaccacat    10260
ccgctagcac ccacatcacc ctacctgggc ctatccggct acaggataga ctagccactt    10320
ctcggaacga aacctgtggg gtagattatc tgcccccttc tcttcctcct tgttgccgat    10380
gaagcccaat gcatccggcc gccatgacgt caatggcaga aaaatctggc caagttcagg    10440
ttgtgacaac agggcccaga tgtagacccc gataggaaaa catattctat gtcccagaaa    10500
caacctccat acagcttcta agaaacagtc aaacaggaac gccccaacag acagtgcagg    10560
aagctggctg gccagcccag ccctccaggt ccctagtacc actagacaga ccatatccaa    10620
ttcaggtcct cttctgaga atgtactgat gcatcacaca gtcacaccag ttccacaagt    10680
```

```
atttaaggag gagatttctt ataagttctg accaaacata aagagcactt caaaagtgac    10740
catggtccag ccatatgggt taagccaata tagtggaaaa ttctactcac caaacctgat    10800
ccgcatttgc ttgagctact gtaatgaagt atcacaaact gggggactta catagcatag    10860
aattatcatg ttagcgttct ggaggctata agaccaagat gaagacgtca gcagggttga    10920
ttcctcctgt aagtcctggc ctccttctca tctctgatgc tttcctttgc tgttctttct    10980
tggaggagca tcacctcatg gctgcctgcc tgcagtcttt cagctcatcg catcacggtt    11040
ctaggaagcc agtctcagct tccacagacc cagactcctc ttttcatgct aatgttttag    11100
cccgtgacac actagtctta ataccctaggt tctcatataa atctctcaac tctgataagc    11160
cccagacatg atagcaaaga agatgcaatt gccttccaaa acccttccgt gcttccccca    11220
ggctgttctc agaagctaca tgcccaacac atgtagtata tagtagaacg gagaatgaca    11280
tattcacatg cacacacaaa cacagcaggg aaaatgtaca tatatatact tcctagagaa    11340
aaatgaggca gtatcagcct gaaatggtgg tttataatcc cagtactcag aatgcagaaa    11400
caaggagttc aaggacagcc tgggtatata aggagttcca gactacaaga aaccctatct    11460
aaaaagaaaa ggaggtccca ggccatgaga agactataga attctgaacc tggctatcct    11520
cttaattaaa atcagggtag aattctatag tcagttcaag atctggttcc ctctctgact    11580
ggaagtatag gatcctgaaa aacgaaagcc acacttttaa gggactgtaa ggtagtgagg    11640
ctcagcacag ggacctgggt caccatgtag agctttgaag aggaaatcag aagactgcag    11700
tatggctaag ggaagaagtg gacttccaag cttggcagag attggagcta gtttgaggag    11760
cgcccaggga ccctcaatca agcaacccta tccctctttt tttcctggca cctgccacgc    11820
caattccaag acagaagaaa gcttagagaa gacagaccca tgctgtggcc ctgagctctg    11880
cagtactgaa ttcagctgca agtcttccct gcctctactg cttacctttg catttagcca    11940
catctgacta tcactgtata ctctgctcct ccatcctcta ccctccatct ccagtaatgc    12000
tcctgttgta gctgcttctg ccaaaaacct agacatcatc ttgacccttt ctctcatctc    12060
ctccatccaa gctcccggca acttctcctg actctgcctt cagacgagac ttggaagaca    12120
gtcacatctc agcagctcct ctgccgttat ccaggttggt agcagcaaca ccactcgcct    12180
cactattgca gtacacttcc cactagcaca gttccctgga gccttcctgc tcacagcatc    12240
caactgaatc ttgtgaggct atgcccaagt cattggaata aaaagatgag aagagagtcc    12300
aagacaagcc ccagtagaat cagcaaagac tatgtggcct gcacagagtg caggggggtac    12360 tggagggtcc cacaaaccaa ctccccatca ccccacattc acgacagagt ggtatggtgt    12420
atgtaagcaa gtgaggtgct ggacatgtgc atgtgtagaa tatatccatc aatctgtgtt    12480
cctgctgtca gggtagcata tatgtatgta agacagacca gaggtgtagt tatgaggcta    12540
tcttgcacca cccctggaat gcatgtgact ccattccact gttatccctg cagcctgcct    12600
ctgacaagaa cccaatgccc aaccctaggc cagccaagcc tatggctcct tccttggccc    12660
ttggcccatc cccaggagtc ttgccaagct ggaagactgc acccaagggc tcagaacttc    12720
tagggaccag gggctctggg ggaccccttcc aaggtcggga cctgcgaagt ggggcccaca    12780
cctcttcttc cttgaacccc ctgccaccat cccagctgca ggtgaggccc ggggcccaga    12840
atggggtaag cagggtgggg tacttgggcc tataggtgtc gacctttact gtggcatgtg    12900 gcggggggggg ggggggggggc tggggcacag gaagtggttt atgggtccca ggcaagtctg    12960
acttatgcag atattgcagg gccaagaaaa tccccactct ccaggcttca gagattcaag    13020
```

```
gctttcccca cccctcccaa tcctcatccc gataggagac cttatgattc catggacata    13080
gccatgtatc ctcatcccac tgtgacgaga tggctggggc ccaagaaggt aacagtgttg    13140
gggccagctc taccccttga aactgttgga ccttgataca ttcactctcc acgagcctca    13200
gattccactg atgtgaactg gatagttcca ttgttgctac cgtgtgagac tttagtaaag    13260
agctaatgaa tgagacacag aactattaag atgaggctca tggcatctca tggcatctcc    13320
cttctctctc cagctgccta cagtgcccct agtcatggtg gcaccgtctg ggcccgact     13380 aggtccctca ccccacctac aggcccttct ccaggacaga ccacacttca tgcatcaggt    13440
atggaatcgg agcaggctgg gaggagggaa caaagaggac agctgtggag cagagcccca    13500
agccccgctg agccatggtc catgtgttcc ccagctctcc actgtggatg cccatgccca    13560 gaccctgtg ctccaagtgc gtccactgga caacccagcc atgatcagcc tcccaccacc     13620
ttctgctgcc actggggtct ctccctcaa ggcccggcct ggcctgccac ctggtaacac     13680
cttcacagta tctccaagtt ctctaatctt tgagcatgtg caatgtaaac ttttctgaat    13740
tatagcccta tggaggtata aagggtctt aagagtcacg gaaactccaa cctccaaaaa     13800
aaaaaatatc agacttagaa ccttgaagac atagaatgca aaaaaaacca caaatcgcta    13860
ttatcagtca aaatgccatc acttaccaat gggcatcttt aggctgttat gtcagaagcc    13920
cttgactgtg ggaacagcag agtactatga gacagagtct tcaaggctca ggaaggggag    13980
gggccttctg gaacaagctg tagagtctaa cctgcagctc cagaagtacc ctgtctctac    14040
ccacagggat caatgtggcc agtctggaat gggtgtccag ggagccagct ctactctgca    14100
ccttcccacg ctcgggtaca cccaggaaag acaggtgagt tggcagggct ggcaagaaac    14160
ggcccctgcc cacacctcac cccaccccctg cacctattcc tctgctgaca tcccatattc   14220
tcccatcccc agcaacccttt tggctgcacc ccaaggatcc tacccactgc tggcaaatgg    14280
agtctgcaag tggcctggtt gtgagaaggt cttcgaggag ccagaagagt ttctcaagtg    14340
agtagcctga ccctacccac agagttctgc tgtctaggct tcacgtctca actcaccatc    14400
ctctcaatgg atgataataa gaatcataaa gattcagact ccatccctcc ctggctctgt    14460
gatcttgggc aagttatggg tctctaggcc cagtttacct cgcatgtatg aagagacata    14520
ataataaagg tatgtgctca tagttacctt cctgttacac gcagaaggat ctaaggccac    14580
agagaattaa gggtcaatca agctcacaca ggacctaagt gatgaatctt gaatatgaac    14640
acaggcagcc aggtccaga gcccacacgc ctaactgctt tgtcccgctt cccctcacac      14700
aaaacacatt cctgatcctc caatttctgt tcctctagat gactatagag ctcttgcctc    14760
tctgctctct atctgctgtc cctccccttc tgtatcttgc tagtcacccc taacttttgg    14820
caatggtgcg tgtttgcgtg ccaggccctt tgcatgggct gtgcctgaca cctgaaatgc    14880
catacccctg catacctcct gtctaacgtc atcccagcat tttggccaga ctcaaagggt    14940
aaataagctc aggcctggca gcccagagtt gctgaagcac atgtgtttaa ggcaagcaag    15000
ggggtggggg gggagcact gagcatagag aaatctccca aagggtctag gccgtcccta     15060
actgatacac taagccaaga ggcctgaccc accatggtca gctacatgga atcttctcct    15120
tactcaggca ctgccaagca gatcatctcc tggatgagaa aggcaaggcc cagtgcctcc    15180
tccagagaga agtggtgcag tctctggagc agcaggtaat gcctgcaggg tgtggctgcg    15240
gggtgtggct gcgggaaaga aggatgggag ggaggaccct gtgagggaag gcatgggcaa    15300
aagtgtgcct gagaacgacc aggtggaagc cccactttgg tgtacatccc cacagctgga    15360
gctggaaaag gagaagctgg gagctatgca ggcccacctg gctgggaaga tggcgctggc    15420
```

```
caaggctcca tctgtggtga gtacccaag  tccagaggca gcagacttca actgctgagg   15480
ggcaagacag gagcccataa ggaccaaatg tcttcttctc acatgcaagc cctgccctgt   15540
acagaccatt cccacctaat taatatgcca gatccaaaga cacgcctact ctgcttacaa   15600
accttctgac ctccaaaaca ttatgattct gccttttcag gcacataca  gaaggcagtg   15660
aactcacagg gccactgcaa aaaggaaaa  tggagggcct tatgttcaaa tttcaagata   15720
agctcagaac atcgaacagt gtgtgaccac acatttcaca tacccagtct caggctgata   15780
tgagtcttat actataacag aggtagctac caccatcatc ctaatgcaca aatgaggaca   15840
acttaggtca ggaagattta gttgatgctc ccaggttcac agttggtgct aggggattcc   15900
aattctgccc ctgctcaccc cagccctagc atctatggct tcatcgcatg ctcatgcctg   15960
tactctaaga tgctgcttta cagagctcca ccagagcctg caattgacta tagggtggtg   16020
cccttctcaa aagcattgac cttactggac acagtggcat gcacctgtag tcctggctac   16080
tggagaggct gaaggaggag cacttgaacc ctcaagttca aaaccagcct ggtcaacaca   16140
gagacaccct gactcttcta aaacacaaag aaacacggtt ggggagaaac ttgagaggga   16200
aaagtgattg ccatacaagg ataaggacct gagttttgct gggtggtggt ggcggcggcg   16260
catgcctttg atcccagcac ttgggaggca gaggcaggtg gatctctgtg agttggaagc   16320
cagcctggtc tataaagcta gttccagaac agccagagct acacgagaa  accctgtctt   16380
gaacacctct gacagaaaaa ggacctgagt ttagatgcca gcacccacac cagatgcagc   16440
actgtaaatc tgtaatccca gcatgtgtac acacaccaca catacaaatc agatagaaat   16500
atgaccaaat caggaaatgc aaattgtaaa ataaagtggg gttggggaac tggacagata   16560
gctcagggat taagagagct tgctgctctt tcagggacc  agagtttggt tcccagcacc   16620
ctcagagccg ctcacagcta tctctaactc cagttccagt ggatccaatg cacttttctg   16680
ccttccacag gtaccaggca cacatgcgat gcccagacat gcatgcaggc aaaactcccg   16740
tatacctaaa ataaaatgca agctgacttg gcagtaatct cagcccatcc tgtgctacat   16800
agtacatgtt agactagcct gtactacatg ctacatagta catgttagac tagcctgtac   16860
tacatgctac atagtacatg ttagactagc ctgtactaca gagcaagagc ccacctacat   16920
aaatatccaa ccaagcaagc aatcattttt taaagtaaaa tggaagactc agtgtggtgg   16980
cgcacgcacg cctttaatcc tagaactcgg gaggcagatg caggcagatc tctgtgagtt   17040
cgaagccagt ctggtctaca gagcctggtc tatacactga gctccaggac agccaagact   17100
acacagagaa accctgtctg gaagaaaaaa aaatatata  tatatatata tatatatata   17160
cataaaataa aaagtggaag ccagatgtgg tggcacacac ttataatcct agcactccag   17220
aggtagaact aggctagaag gtgcaaggcc aactagagat atatagtgag actgtctcag   17280
acaaaacgaa aatgaatagg caaacactca ggaggcagag gaagtgcatc tctgagagct   17340
gcaggccagt cagggctaca tagtaagacc ctgtcaataa taataataat ggcaataata   17400
atttaagac  caaaataaat agacatggat gaaggggaa  aggaatgaga agaaggaaga   17460
taagcgatga gggaggagat agggtgaaag tggtctgtat gtattacata catgtacaaa   17520
attgtctaaa aacaagttta actaataaga aaatacaaac taatgtttga aaggctacaa   17580
tgaaatgaca agcttaagtg tctcgattac cacacccctc ccaacccctc aggcctcaat   17640
ggacaagagc tcttgctgca tcgtagccac cagtactcag ggcagtgtgc tcccggcctg   17700
gtctgctcct cgggaggctc cagacggcgg cctgtttgca gtgcggaggc acctctgggg   17760
```

-continued

```
aagccatggc aatagttcct tcccaggtca gtggagtcca caccccagtg ccaggggta      17820 caaaggagct cccccacccc cctcaccccc actaagagct gggaggaaac tgcacctgag     17880
tttattaggc ttagaagccc tcaactgtta taaatgcata gccttgggcc ccgtgttttg     17940
ggggattgga gccaggcctg acctatttgg catctgctac ttcattcagt caccatgagg     18000
gaggagcctg gccaagtgag tccaaagagc cctctcttcc gtccccacct ccaggaagtc     18060
aggtgcactc aaccaagcta accaaccctc tcccacctgt caggcctggg ttgtgagttt     18120
accagggacc atagatattt ggtgtcaggc tggctatgcc acttgagctg cttacatgcc     18180
tttgatgtac aaattacttg actccttttt aaagtgagga gagctatttg gcaggagtac     18240
tgcaaagaag acacagctta cggcgggtac tcagtaaaca gtactatgtg tgagcataga     18300
ctgtccctcc cccttggtg ctagtggtag gaattgagac cttggattcc tgatgcagac      18360
aaaggtgggg taggggtga ggaggccaaa ggctctgatc tatgccaacc ttctgcagag      18420
ttcttccaca acatggacta cttcaagtac cacaatatgc gaccccottt cacctatgcc     18480 acccttatcc gatgggtaag cagggcaata gaggcccagc agctggtggg cggcaggggg     18540
ggagttgtgg tggggagtgc ttgcctccta cattgcacca agagcagaat tcacccatta    18600
acaaacctca gctctgagga gccccaagat gtgatccttc ttgatagctt cacctcagat     18660 ctagcccctca acccaaaact actgcaagcc aggtcagtgc aaagcaaact gtaacactac    18720
aaactaccct ttcctttgtc caccctatct ctaacatcac ccttgacctc atgcctcacc     18780
ctattctttc tccttccct tgacccacaa ttacaaagct atcatagctc agagggccga     18840
gagtaggctg ctccctcagc cacaaccctg aggaacatgc cccttattcc acctgactcc    18900
aacttccagg ccatcctgga agccccggag aggcagagga cactcaatga aatctaccat   18960
tggtttactc gcatgttcgc ctacttcaga aaccaccccg ccacctggaa ggtgagttcc    19020
tctgtacaca ctggcagctg ggatggctcc aaggatggtt agcctggggc tagacatgtg    19080
gggaaggagc aggtcagtct cagactcagg atgactgtca accctgtccc tgactggggt   19140
cccggtcccc cttccacaga atgccatccg ccacaacctg agcctgcaca agtgctttgt   19200
gcgagtggag agcgagaagg gagcagtgtg gaccgtagat gaatttgagt ttcgcaagaa    19260
gaggagccaa cgccccaaca agtgctccaa tccctgccct tgacctcaaa accaagaaaa     19320
ggtgggcggg ggaggggggcc aaaaccatga gactgaggct gtgggggcaa ggaggcaagt   19380
cctacgtgta cctatggaaa ccgggcgatg atgtgcctgc tatcagggcc tctgctccct   19440
atctagctgc cctcctagat catatcatct gccttacagc tgagaggggt gccaatccca    19500
gcctagcccc tagttccaac ctagccccaa gatgaacttt ccagtcaaag agccctcaca    19560
accagctata catatctgcc ttggccactg ccaagcagaa agatgacaga caccatccta    19620
atatttactc aacccaaacc ctaaaacatg aagagcctgc cttggtacat tcgtgaactt   19680
tcaaagttag tcatgcagtc acacatgact gcagtcctac tgactcacac cccaaagcac   19740
tcacccacaa catctggaac cacgggcact atcacacata ggtgtatata cagacccta    19800 cacagcaaca gcactggaac cttcacaatt acatcccccc aaaccacaca ggcataactg    19860
atcatacgca gcctcaagca atgcccaaaa tacaagtcag acacagcttg tcagaacacg    19920
ctcgtgtgca cgtacacaca tgcagcccct ccactctatc tcctgagttc catgaataca    19980
caccgactct ccaagatgta ccccacgtct cacttgccac tgaccccagt tccctaccca    20040
caagccccaa tccatgccta agcgtggccc acagaagaac ttctctttta tttgggatcc   20100
aaggcccctg gcccccagtg cccatccaat aaactgtggt cagctggaca atcaccctga    20160
```

| | |
|---|---|
| tcagatatgg gaacatataa gcagacagct gggtttaaga tcccagcagg agaaagcgga | 20220 |
| taccaaatga aagagagtgc tagaacaggt gcctcagcac tgtctccagc accccaaatt | 20280 |
| cctgcctgtg gttaggagac atccatcagg gctctaggcc tctcggaccc ggcccaagag | 20340 |
| gccagcattc tcctggcgaa gggctcggta gtcctcacag atcttctcca ggttgctcaa | 20400 |
| agtcttcttg cccatctctg tctcaatcta agaaacagg atgcacactt cttcagcccc | 20460 |
| tgcaggctgc ccctctactg aactcctccc tgctcctcct attcccgtaa cagcagcctg | 20520 |
| ttccttccca tcactgggct tctgggtatg tccttccctc cactccacct aaagcagcaa | 20580 |
| cttctgccat gggctctggg aggcattagg agccgcaagc taaaagccag ggctcagagt | 20640 |
| aggctactgg ctagcttcag gtcccaggca cagtgggcac gaaggcaaag cctctagctg | 20700 |
| ttagttgtct ggtttcaaag actctcagcg caaaacaagg aactatcccc tggcctgtct | 20760 |
| ccattcccct taccagtccc aggtctcacc tgctcctcaa gatctcgaac ttccctcatg | 20820 |
| atagtgcctg tgtcctcaat ggtctggatg agctgactgc aattctggag acagcaagaa | 20880 |
| tacaaggctt gcacctatgc tggccctctc cagccaaccc accaggcaca tggctcccct | 20940 |
| cacctcatgc agggcagcta ggtacttgta ggctttccga acagcatcat ccttcttagc | 21000 |
| atcctgataa gacaaagggg atctccgaga tatcagcaag ccattccccc ttttccacta | 21060 |
| ctctatgccc ctataagacc accctttact agtactttgc cttcatcctc cacagagcaa | 21120 |
| agctaggccc caagcaacag tgcacctaaa ggactcacag aggggcaggc aacaactcag | 21180 |
| tcccgcctcc accctcccgg aggccagcct gctccatacc ttgaacacaa gctcatcagt | 21240 |
| cactgcaaat gtccggtcga gcttcccaga gagagagttg atttccttct gcagttcctt | 21300 |
| tgtgtccgac aagatctggt agaaaccagg gtaactatca gtgcacatct tgggcaaggt | 21360 |
| agctgatcag tgataacact cacgtgccta tacttacatc cagtcagggc ccatgtcgct | 21420 |
| gtgttggggt gactattatg tgttggagtg tgcctgaaca gctctgccta gtagtgagca | 21480 |
| taaagtccct gtgtgatcac ccctatgctt gtctgcctac atgagccatc aatcagagcc | 21540 |
| acagtgacat catccttag tgatctcttc cttctgcttc cggatgttgc ccacaatctc | 21600 |
| caggatgcgc tgagtatagg ccagccggga cacatctttt ggcagagtct ccagctctga | 21660 |
| cacctaggtg ggaacatggc aggcgtgagc ccaagcccta taccacaacc acccttacaa | 21720 |
| cccagggccc taaagtaggc cttaccagct gcttatagac ctcctccttc cggcgagcct | 21780 |
| cctctgcagc tgctcgaaca c | 21801 |

<210> SEQ ID NO 139
<211> LENGTH: 18001
<212> TYPE: DNA
<213> ORGANISM: Danio rerio

<400> SEQUENCE: 139

| | |
|---|---|
| agacctcggt ataagccgga cgtcttcctc tgtttcttct tcatcttcat cgttactatt | 60 |
| gtcttcagaa cgttcaactc taaccgtctt gaaaagaccc tgttgtgagg ggatagatag | 120 |
| gaaattgttg ttatttccct gcgccattgc gtctgtttct gctgctgtca gattgcgctg | 180 |
| ctttacatag tgccaccgga gacccgagag ggtccgtcac cgtcctcgcc tcgaccgatc | 240 |
| taggcctgaa tcattgacat aaacgagaac cgcggtttgg agctcatact gcacacacgc | 300 |
| gaataaatgt ctaaatttag taggaagaac gtccatgctt ttccagaggt cagtaggaag | 360 |
| acgggttctg ctggattatc cctcccaccg agctcctgtt ggtcgctcca aaccgcacac | 420 |

```
gcccccctca gctatttaaa gtttaaagac aacttggggt ttattgtgag aataaacatt    480
cctcatcata ataattgcaa agaaaaaaa aaaaaaaacc tttatcaccc taatgatact    540
tcaatatcaa tagttattac tatctcctca gtaactaatt attgttaggc ctattttctt    600
tttttaaatc atgtgttata tattaatgtt atgatctttc tattaggtct aaaacaaata    660
agaaatatta aataatatt atgacaacag gaacaattaa tctttattgt tgtctgtgtt    720
gttaattaaa atgatgtcag tgcaggataa tttacgtgct taacatgtgt ttttaactaa    780
tattattgtc cattaaaatt cttatttcat tatttgttta tataaacaga acacatttac    840
aaacatataa gtcatataat aataataata ataataatta ttattattat tattaatttg    900
aattacttta tattacaata agtgtatatt tatattataa taaatatgtt ttacacatta    960
taaaacagca aattgttttt aaacagtgtt atgcaaaggt ttggcaaccc cttgcagaat   1020
ctgtaaaaac atgaaaatat tcaacaaaat aagagagatg aaacaatgtt attttttatt   1080
tagcactgtc ctgagtaaag cattttacag aaaatatgtt tacgtatatt ctacaaggca   1140
gaagaaaata gctgaaatca ttcaaataat cccctgctac agtgtgtcaa cctttggttt   1200
ttaatactat cagtttttt aatgtttatt catgagtgcc ttgtttgttc taaacagtta   1260
aactgctttc attcttcaga aaatcctcct tgtcctgcac attcttcagt cttccagcat   1320 atttgcata ttcaaaccct ttccagcagc gactgtgtaa ttttgagatc catttttaa   1380 tactgaggac aatcgaggga cactattaca ctattaaaaa ggttcaaatt ttcactgatg   1440
ctcaatggaa acatgatgta ttaagggatg cattatgatc gcttatattt tgtcataatt   1500
atttacattt ttacagaaga caacaaatat tagtttcttt cttctttgg tgtcacatta   1560 aaccacagag tgctgcaatt tcaattaaa gttataaatt attcaaaata tcaacacatg   1620
taaagattaa gttcagaatt tacaacaaat tgagtctctt tgagacattg aaaatactta   1680
ctagatgctc ataggaaaaa aaacaaatac aggcaaattt atacaattac agtgcatttt   1740
tgctaaatca gattgtgctc tcaggcatta ttagaattat tcaaataagt ttccagcctt   1800
tttgtcacta ttttaaatg tattttataa aaactttact ttttagataa ttatattagt   1860
tttttcaaag tcaaagtctt agccaaacag ctatagcatt tcaatgaaga tttccacacc   1920
atttactcgc actcaagtgg ttttaaaatt acaattattt gtttgtctgt tgaacacaaa   1980
ataattaatt ttgaagaatg ttgaaaagaa acaaccatt gacttccata ataggtacaa   2040
aaataccata aaatgttttt gtcctaacat tcttcaaaat atcttcgttt gtgttcaaca   2100
gaaactcaga aagaacagaa agaaactcaa aacaggtttg gaataagtgg aagatgaata   2160
aatgatgatg acaaaatggg tgaactatcc ctttaaggcc ttttagggaa gcaggcacct   2220
ataacgttcc aatagcttta aaaatcttta tgaaatttaa gaccaacaat ttttccaaac   2280
aagattttca cagacaaatg gtgcccctta aaatacattt cttattgcgt aattcaatcg   2340 gtgattttg agatgcaact gcttttatta ggtcagctaa caagatcaaa tggtgagaaa   2400
gaaagcgctc gattacagac cgatggtgtt taaagttatt gattgctaag cttttttaa   2460 cacttagact gagcaatcaa tcttgcttaa tatactgaaa tcaatatatg ctacaagtgc   2520
tgcatcaagg attcgacttg ctgcatatag tgagaaacca ggaatgcatt cataaccatt   2580
tatgtctaac ctttggtcct taaacacaaa aaagctgtct gcactttgaa ttatccctca   2640
cagtttataa aatagacctt aatgatgtgg aatagaccgt ttcaatgtgg taatgtcaat   2700
ggtcatgaac atttcctgct tgttgtcaaa caacttcaca accgtaaaaa gaggcaattt   2760
aatcacatct cagtgttagt taatacatca gttattgtat tgttattgtt gacatccctc   2820
```

```
aaaatggtct atatatacaa aagatataat tgctataacc tataacttat tatatggtgc    2880
tacattaaca atatgacaaa aaaaaacatt aattaaaaaa tgacaacaca gtttgcttta    2940
atgtttaatc ttacttgtgt ttttgtatct actacatctc tgtctaaatc attagcgcag    3000
gaacatactc aagatgacat gagctgctgt aaaacttaca cactcttcac attgaatgtt    3060
gacttgactg acagctgcag tcagattgta ttctaacacg tctttttcct ctctctgttt    3120
aggtttgctg aaaaatcaaa aagattgaaa aaggagact atgatggaga ttgcagttgg     3180
taaagctttt tttatttctg tcaggtattg tattagagat taatcttgat taaccataat    3240
aaagaatact catatttatc aggaaatacc agctattgtt gttttttatg cctatattta    3300
aaccaggagt aaaaaaagta tacgaaatac cctttatgaa atacaatgtg atgtaatata    3360
agtcacatat agacaattaa taaggaaaat gttcaaacta agtagttttg ttttaatatt    3420
tgtctattca tggcttatat aattttatag gatgttcaaa ctgactaaca taaatactgt    3480
tgtatatgaa gtaaatgca gttcaatcta tgtgaggaaa tatcaagatt acattttagc     3540
ttacaaagag taaatgtttc atttgaaata attaaaaact aatttggtgt taattttcct    3600 ttattttttac ttttcaaagt cctttaataa ttcatatggg tttgaattat gaatataaga   3660
atataatata tataaatatt tattttattt atttattttt tgtacttgat cttcccattg    3720
ctaagacata tgcttaaaca atctattagc ttttcatctt cataaatagt tctgaatgtt    3780 cgttttttata tgcatgtatt aagctggtta aaaaaaaaat gtttgcaagt ctgcattacg   3840
gtacatgcgc tttggagtgt cattattgtt gaacaatttg ttcaaaaaca ctcaaataac    3900
cttttcaacc acaggatgag gatgtttttt tcctgcgtta ttctaatcga cacacatgcg    3960
atcgacatgt acatatgttc agtctccccc ccagaacccg aatacaacgt cacacacaca    4020
ctgcaaacgg actttccgaa cacgtaatag gttatttttct ctgaaatctc attttccggt   4080
cttccggaat ggactttacc aggttttgat gtgaaatagc catcatgtgc cttaaactaa    4140
cataaataat gttcagtgtt attttaattat taataatttt gtaatttaat ctcagctatt   4200
aaatcagaat ggaagatgcg gtccataaaa attactttttt tagtaataag tagtatgttt   4260
taaaatatat gaaacacata taagaaaata tatattgcaa acaaaacatg cagagtcttt    4320
ttgtaatagt taagatggtt ttgggattga acacctcaac atccaagcga tagtttgtaa    4380
aaattgttta gattgtaaac cacttttaag caatacaaaa aacaatagta aaaccaaata    4440
ttgataaaaa atgtaagtgt aaaccccatc agaaatcact caggaaaata aaatcgtatt    4500
ctgctgcaat aagaagcttc taaaatagga aacagaaata acaaaatgcc acataatttt    4560
taaagaagat gtaaagagag ttaaaactac acacttgtgt atctgaaaac acacacacac    4620
acaccaacac ccagtaggga aactgtgtct attttccact gaatgtcacg ctaaacatta    4680 taaaagggggt gacctgaaca ttttccagat cactctaatt gctcactcat cgcatgcatc    4740
cgacacttgc acaacaggta agttctttttt gttttgtat ttgacttact tgcctttaac    4800
ctttattgcc tttattgcat aaaataaaaa agccatttaa tcactgaaat ttcataattt    4860
aaaagcttaa tatacaatat attataatat agagacttttt gctatttctt tcctaaaatt    4920 gttgccctttt gtagataatt gacagcagtg tttggaaatg aaagagttaa tttgttaaat   4980
ctgttgttag attatgatta cgattgactc acagcattgc atcatcaaat gtgcacaata    5040
tttggtcagt ttttgacaca acatcctgct ttgactttttt tcatattcaa agtaatttat   5100
taatcattta tttatcaatg gatgatttga agcaagatta aacaattcaa acagtgctaa    5160
```

```
aacagatttt aaaagtcaat attttgactt cttaaaatat tctcatatat ttttttcttt    5220
atattgccat tcattataca caaaatcgca ttggaaattt agattaatgt acaacactaa    5280
agctactgta aaaaatagtt ataaacttga tgtttctatt tatctcaaca tctcaagctg    5340
actaaaatat taagttaaac tttgtaaaac cttaacaaat taacaaatct attttaataa    5400
aacttttttt gtcatatcac ttttagcct attttttttt cttttcgtga cagaaaaaca    5460
cttaacaagc ttagcataaa aagactagca accaaactgt tttttcctaa agtgcagatg    5520
caaaatgagg tctgtgcaca gagtcagact cagggtttgg tctttctttc ctgctcagat    5580
gcaccacaaa ccccgttgct gaggaaagaa aagctaaaga acatatagag tgacagtctc    5640
aaggaaaagg gcgacagaca agaaaggtg tgggaggtaa aacatccttt cttctacaga     5700
gatcctgtag ttatcatagc aattccatca tgtgttagct aagctactac ctatgaaatc    5760
aatgttccat actataggag gatcaccaca cagaccgatg taaagggtaa gttacaaaac    5820
taaaaataca cttctagcgt atctgaggag aaaatgagta ggtgcgacat tttcgagaaa    5880
aaaaaaccta aacaaacaac aaggtcgacg cctcaagttc tttaccaaga aatcaagttg    5940
ctaatataag taatgtctct ctgaatgttg ttttaaaaaa ctctattgca atttattctt    6000
gtgaaaacaa acatctatat caagaacatt tttgttggct tgagtaagtt tttcagttgt    6060
tctaaagttt tctttattaa tttttataac agttcttgat cttgcactac aattcattta    6120
agagattctt aaaaatatcg gtgccacatg ggtcttcaaa ataactagag acaaacagt    6180 actaagagga aatcgtaacg attttgcttt gcatcaggct gtaatgactt gcttggtttt    6240
aacccttatt ttatgagttt gatagcatta gttaggtata attgtgaaat aaacagtatc    6300
tctaagggtt ggatcaccta attttatgtt caacatctta aatatgtgtt ttaacgtgta    6360
aaatttgttt tcattattgg cattgatgct tctatacaga acttttaaaa tcaaagacat    6420
tttccaattc tttagagcag acaaatgctc tgtaaaataa actgtgtttt ttaaaaccaa    6480
caaactgtta tacttgtaaa gctgttcaat tttttggggg aaacctaaaa tggttttct    6540 acaggatcat tgcacagaat tcaatttcag aacctttgtt tttaagtgta tgacaccttg    6600
atattactct tcatacgata ggctggtaac tataaatata ttcccgttat tgttgataac    6660
ttgattggca gatattgtac atattctata cagttttat aaaggacagt gatgggcact     6720
aaactgacag tcatcaacaa aaggaacaaa cttcattgag ttttgttgga taatgtatt    6780 aacgctgcaa ttttgtgttc attttagca gtcgatctgt gtttgctgga tcacagaatg     6840
tcgaactgat gcattgtaat ttgatgttta ttaattggtc agcatctcac agtgcagtgg    6900
gagtttgttc acccaaaaat taaaatttac tcaccgttaa cttacccaca attgttccaa    6960
atctttgtta gtttctttaa tctgttcaac ataaaagata tctttaagaa tgctggaaac    7020
cggttgccat tgacattcat agcaggaaac aaaaatgcaa ttcaaatatc tcccagtttc    7080
caacagaacc tctattgtgt ttaacagaag aaagaaactc aaagagggtt ggaacaagtg    7140
gaaggtgaca gaattttcat atttgggtga actatgcttt taagtaaata aaaaaatgat    7200
gaatagctat ttttgtattc taatgaaaca caattactgt atgaagagac aagttcttac    7260
cttggttgtt tcgcatactg tatgcctatg tgcctaaacg tcttactaaa cgtcccccat    7320
ttatttgttt tattttcttc aatttgcaca tgttcagcaa ctgccgcaga caatgcaatg    7380
ggtgttaatg caatagttaa tttagaactc cctaaattaa acaataaata aatcaaacct    7440
aaaatcagta attatcaaca gtaataaatc aagatggcga aactgggtct gcccaaatat    7500
tcaaaactgt cgttttactc tcaaatttac agtacagtac agtacatacc ctaaatatcc    7560
```

```
tggtctttga tttttatcat atcacttgtt cagagaaatg taagcgtaaa tgagtgggta    7620
tgaccagaga aatggaaaaa aagtgagtca aaatgtaatt tgtatgttcg tgggagagca    7680
ttgaggacag aatgcacttt gtgttctata tttgtaattg ttttttaatc attaattaca    7740
ggtttcaggt ttaattccac atctctgttg attgatagca ttagcattca taccgacact    7800
ctgaggtcag gtgactcaca gctcagctct aataattatc gttgtgacta taaattccac    7860
cgaagaacat gaaagttaaa actgacttca ctgaatagaa gagtttctaa agtatcgcaa    7920
tttcaaaatg aaacttgaaa ctgtcagtcc agactgttgt catatcttga tggatttaat    7980
tttggtgaat ggaactgaga gaagactgta ttcagactga gagatgaata atgagtttca    8040
ttgggttgaa taatcccggt cttatcaata tcaactctct gaggaaaaat gattggtgcg    8100
cattcactaa atacaatgac aacaacactg agaactactg aaatgtaaag aaccaaaaat    8160
gacatcccct tgcatgtaca atataaagaa tgatagattc tacacaattg atttgtgttg    8220
ggacaacatg aaggaattaa gtagattgac cataaaacaa ttaagttttc tactcaaaaa    8280
agtaaaaaaa attgtgttgt ttcagctcaa tttaaagttt aaattggttt gaacaatcag    8340
caaatataat tttttttttgt gtacgctgta caaaaatgct gggttccatg cagttacttc    8400
atgttgcacc aacacaaatc gattttttg atttaaagtt aaaatttcga gttaaatcg     8460 aagtaactt ttaacatttt tacaaattta agtgaattaa acaaagcaat taagttgtcc    8520
cccccaaaaa aacacaaaag aattcggctc agttttaata agcagtttga caaacagcaa    8580
atgtcagttt ttttgagtgt gtgtattagt ttaaattcag agggattcca ctgcttttag    8640
aaacgtgatg cataaaatag ttaatttgta gcatacaaaa tgcatttcta gcattatttg    8700
aaaacaataa aaataaaatg tttttactat tcagcatcta ttaagtctcc ttctgatcac    8760
atctagttgc ttgcttggaa accccccca ggtgaaaaaa tgacatttat cctacatttg    8820
atgtggttaa tgtgaaatgt caaagagaat aagcaacaca cgacttcttg agcagtttca    8880
gaaaaccgca atgaaatggt gctctaaaat ccaaaaactt ttttttttaaa attatttctc    8940 agaagttata tgcaacatcc ttgccgtaag tccatcctgg gttttataa tcaattgtgg    9000 gtaatttctc aattttgtgt aattaactat caaagtgaag caaatcacaa ctttttaaaa    9060
tttttatatt aataatgaga acagattgca aagggttcat ttaatagttc agtaaaaata    9120
caaatttaag atataataaa aggcgagtaa gcatgcatac atttctgtga aatgtgaagg    9180
tttgtgaaat ttagtggtac taaaattatt aattttgtac tacaatcgtc aaattactta    9240
aatgtgctgt tgcaatctgt ataattgcgt ttttattct atttataacc tatttattat    9300
aacgctcaca aatctaactg gatttcaaac atacaaaaat tatgtaattc aactatttgc    9360
ataaaaaatt gcacatattt taaatgtcca gtgcatttat aaagtattaa aatacatatc    9420
atgcatttaa cttagaaaaa tgtttgtttc acagtatgtg caaatgatgt ttttgcaaaa    9480
atatgtgggg cccacctccg ctttcctgac ctcttggtcc ttgctcaatg tgaaatgtgg    9540
tttgtgttca gaaagcacct gcaaatgtga acaagaaaa ggaaaaacaa ccctcatttc    9600
atttattaat gcataattat gctattttg gaaacaaagc aaaaggtgaa gctatctaag    9660
caggaaatac cttgtgttag tatttggagg ttgattcatt tcactcctaa tttagtagta    9720
tggttattaa aagtcatttg tgtcttcctg cttatttcta tataggtatg cttcttaatg    9780
ctactggaac acacagaggg gatgataaca ggagtagtca ccaacatctg taccaagatg    9840
aagactgtgc caccttttcc atcatacaga tgaagtccag aataagcaat tctcttctga    9900
```

```
cctcaccaaa accaatggct accaaggtaa tgaagcagaa gctgtcattt ctttgtatta    9960
ctacatgaac aatcttattc aacagaataa ataattgttc tctggttctc gcctgacttc   10020
aaatccatga tccaactaaa atatggatgc tggaaatcct tgaaaatgtt ttaattttaa   10080
tatagtgttt gacaaagtgc ttaggttttg gataaagtgc ttgaaaccaa agtacattta   10140
aggcaagtca tttcacttgg cggccatctt taaaatacac atactcgggc caacttcaaa   10200
ttatccaaaa ctgcttgaca agcttgcggt taaatttcat attattttca tattaagaat   10260
caacaataaa attaaacaac aactatctct ttagttttca ttcgtttatt cttttattca   10320
ttttcttctc ggcttagtcc ctttgttatt ccagggtcgc cacagtggaa tgaaccgcca   10380
acttatctag cacgttttta agcagcggat gcccttccag ccgcaacccc tttctgggaa   10440
acttccacac acacattcac actcatacac tatgaccaat tttagcctac ccagttcccc   10500
tgcactacat gtcttttggac tgtggggaaa accggagcac ccggaggaaa cccacgtgaa   10560
agcagggcaa actccacaca gaaacaccag ctgatccagc tgaggctcga accaacgacc   10620
ttcttgctgt gaggcaacag cactacctat tgcgccactg cgtcacctct ctttagtttt   10680
atttctaaat agttgaatca cacaaaatct gctgaaatta tgtctggttc aagcccctcc   10740
actagagact catcagtact gtatatagtg atcactgatt ggctcctgta ctagaaggcg   10800
gggcttcatt cgcattattg accgttataa ttttttcccat tcaaaactat acgagtgaga   10860
cattttgtgc attatattga ccttattctt tacgttgag cgggtacagc catttgaatt   10920
ttctttgttt gagacatcca ttctcattca cttgcattga tatatagaca ttttaaatgg   10980
cttgttatgc tgtttcatgt tgcaaactga gattttcaca ttataatatt ttactttta   11040
ggtataggca tgaacacact tgcttgtaga gcaagcagtt tgaccatttt ccgccgttta   11100
ttattcctag tcatttctcc cataagcaac tgaatcggaa gttctaaaac aatcgcaaaa   11160
attagtgcac ttccgcattg cagaataagg tcaatagtct tgttgagag tgcttgagaa   11220
tgtaattttg ttgctttcat aataattgat cttaataaat aggaaataat aatgaactat   11280
ttaaataaaa ttaaatacat attttttcctt ctgcataaac aatttaaaca gaatgcatgg   11340
atattatcac tttatgggtg aacaatgcct gactctaaaa tgaatgtaaa tttaagaaga   11400
aagatttcct ccatagtcca aagacatatg gtataggtaa attggataaa ctaaattggc   11460
cgtagtgcat gagtctgtgt gtgaatgaga aatgtgtggg tgttacccag cactgggggt   11520
tcacaagttt tttttgttg atctatctaa taaactttta cagatataac aaagtaattt   11580
tacagagaaa tttaaacaaa tattatttcc acccctagcc tctaaacaag ttgaaagaga   11640
gaaagaaga aaaaaataat gataattttta gaaagtaaac aaacaattat aaaaaaataa   11700
taaataataa ataaataaat aaattacgaa ataaaaaaca aattaattga aaataacatc   11760
tgtacagaat acacacatac cttgataacc caatattaca aaaattaatc ctcaggtatt   11820
tatataacgt acctaattat gtttgcattg caatcgaaag gccttaagac ttagatttac   11880
agtttgtaga gatacttaca tgctcagaaa agaaaattct aaatgtttca gaaaaagctc   11940
tagtattgcc atttattgta aacctgattt ttttttttcaa atggtgaagt tcattgcatc   12000
cagttgtcaa aactcagggg aaatctttga taataacaga atacaccgtc ttgctaacag   12060
tgtcaaaaat gcaagggcgt ttgcagtaca gctcgataac cctaccatat tcagagaaag   12120
tccaaaaagt gcaaaagag acacggttc gatgtgtatc tttgtcacag aagggaaaca   12180
cttgaaaatt gatagccaaa aagaaatgat tgatggacaa agccaaaaca tatgtatatg   12240
catgcaaaac ataggtgctt gattaaagtg atcaaatata gagtccatgt gttgagttat   12300
```

```
ttttgccaac ctcactttttg tccagtataa tcgaactcga actaattgta attggatgag   12360
gcaatgtcgt gcacagatag aggaggtatg agcacgggac aaaatctggt cccacgtctt   12420
gtcctcgaat gtaagattaa agtctgactc caactgttat ttaataaagg aaagagaggt   12480
agtagaaaaa gaggagatca gcctgtataa aatagacgtt gtaccttttgt tatgtaaggg   12540 tacttaaaaa atgtggtcaa gttgagattt tggtggaagg ttcgcaaaat ctggatatga   12600
gttttaacaa aatttctgcg ttgcaagtat ctaaagaaat gagtgctagg aagagacaat   12660
tttgtattaa atgtgaaaag ctgagaaaaa tattatcgac ataaaaatca ctgacagtgg   12720
atattcttgc cctctgccaa atattaaatg ctttatcatt aaatgatgtg ccagtgctg    12780 ttttcttact ggaagggcat ccactacgta aaacatatgc ccgagaaatt gacagttcat   12840
tttgctgtgg caacccacag cagcgatcat ggactaagcc gaaagaaaat taatgaatga   12900
atgaaagatg acacatttaa gagagttcat taaagtagtt taatgttggc cttgggcta    12960 acatgccatt taaaaatgtc cttactatac tatgctatgc tatgctaagt gctatagtgc   13020
tcaagattgt atttttttggg gatttcaaag atatctgttg ccttggagag tgacctcaga   13080
ggcctcggct catctcgcaa tcagaatttc actctacaaa agcaggtaca gtccagttgt   13140
aataggtttc acttttaaat caacactaaa ggatcacaaa gaattgaaaa taaattaaaa   13200
actctaagat gtcgcataat ttgatctaaa acatgatcct tgatttgttt ctgcttcctt   13260
tacctagagt gccagtggaa gtacaaccaa atactttaaa caacacagac catcagtgct   13320
acgtaaaggc aaccagcctt ttccacaagg tactgcttct gtagactata aaatatagaa   13380
aactatttac tttcaacagc cactttatta ggtacacttt gtagtactgg ataaactcc    13440 ctactgtact tgcaccattt tacgctttat aatatatggt ttcatatttt tacaccaatt   13500
tctgctttca tcatgtcaca taagaaatta aaactcatca aaccaggcaa ccgtttatta   13560
ttcttctgtt ggtgagctat tgtttattat agcctcagtt tcctgttttt ttttcttctt   13620
tgctgtcaag agtggcactg ttgtgctctt ctgctgctgt agcacatctg cttcacggtt   13680
tgatgcgttg ttttgcttct caaaccagtc tgatcattcc tctcacgtct gtcatcaaca   13740
aagctttcaa aaaaaagcca cttacttaat attttctttt tttctgacaa atttctgtaa   13800
tatgattgtg gataaaaatc tagaatctag aaatttcaga aaaacccatc acattcaaac   13860
aaacatgcca cattcaaagt cattaaaatc cccctttccc ctgttctaat gaacttcagc   13920
aaatcctctt gatcatgtct gcatgcctaa atgtattgag ttgctataaa agacaattga   13980
acaggtgtac ctaataaagt gaccagttag tgcatctctg aaagtgaatt tttcataatg   14040
ctctgcagca tgcagtgctc atgattgggt tgtggacacc gtgtgtaaga cagaacctga   14100
cagtgaacca tcagatgcca tccctcttta cactggccag tctgaaagca gaatcggtgc   14160
ttatgcgtca agccctcagc ctggcagccc ggagtatact gggaagtgag tatgtagttt   14220
gagaaaacaa acacaaatta ggatattcag tgctggaatg aaaatgtgga catccacttt   14280
gtaacattat tgtgtctata ttcatttcac ttttacaaat aagatataat gcaatatgtt   14340
ttgagctaaa ttaagcattt attattatta tccgcaggca tccatatagt ctttcaggtg   14400
actatctgtg tgttaaagga caatgcagat ggccagggtg ctcaaagagc gaagatgtat   14460
tcacagaata tggacattttc ttaaggtgag acacaaagtt aactaaaaca atctaaataa   14520
atacagcaat atcctatagc agtgtgtctg tttcataatc taggcacctt tctactgacc   14580
atgctcctgg agacagaagc ataggccagc tgaggatgca gaaagacaga gtacagcaca   14640
```

```
tggagaatca ggtatctttta cctcttatgt cacagggact aaataaatag gggtcaggag   14700
gttacaatat taataattgt attataaatg gatgcttgtt tatgatcctg cattatattt   14760
cctttatgaa cactactgat agttgactgc agaaagacaa aaactgcagg ctatgcagct   14820
acacttgctt gatgtgaaat ctacctctga ggtaagtttt tttaataaaa ttttataaga   14880
aaaatacact cactggcaac tgtattaggt acacataact agtatcgggt tggacccccc   14940
tttgccttca gaactgcctt aatcctttgt ggcatagatt caacacggca ctggaaatat   15000
ttctcagaga ttttcatatt gacataagag tatcatgcag ttgctgcaga tttgtcagtt   15060
acacatccac gatgcaaata tctcattcca gctactctac tggattgaga tctggtgaat   15120
gtggaggcca tttgagtaca gtgaactcat tgtcatgttc aagaaaccag tctgagatga   15180
ttcgcgcctt atgacatggc gcattatcct gctggaagta gccatcagaa gatgggtaca   15240
ctgtggtcat aaagagatag acatggtcag caacaatact caagtaggct gtagcttta   15300 cacaatgccc aattggtact tatggaccca aaatgtgcca agaaaatatc ccccacacca   15360
ttacaccacc acctgcctga actgttgata caaggcagga gggatccatg ctcttatgtt   15420
ggtgatgcca aatgacccta ccatctgaat gttacagcag aaatcgagac tcatccgacc   15480
aggcaacgtt tttccaattt tctattgtcc aattttggt gagaactggt ttgaactgca   15540
gcagattgtc ttgaccatgt ctacatgctt aaatgcattg agttgctgcc atgtgattgg   15600
ctgattagaa atttgcgtta acgagcagtt ggactggtgt acctaataaa gtggccagtg   15660
agtgtatact gtaaatataa aagttattgg acaacgttgg tttgttctgg agaaaaaaaa   15720
tcttaggcag ttattaatac tgaccfttaa aattgtttaa aaaatgtaa agactgattt   15780 tattacagcc aaaataaaag aaataagact ttcctcaaga aaagaatatt ataggtaata   15840
ctgtgaaaat ttcaaaatca cttggtaaga atatgtgtat ggaataaggt aaatatgtc   15900 tatggtaaaa aattataata tctgtgtatg gaagcaagga aaaatggtag catttttagga  15960 atgtatgtaa tgaacattgc agtctcctat cagctaactg tcatgtatgc ttataaaagg   16020
gatattcatc ttgcttttta actccttaat taattagttt tcacaccact gtattcttga   16080
gactaaagtt ttgacctgaa attacatcac accagacatc aatgatcctc agctaaccta   16140
caagactaaa acagggagag ttataaaaac caagtcaaaa ccttgtgtga gtgaccgata   16200
ctttaatgcc ggtaatcaaa ttatgccatc atgactgtgg gatctgttta ggttctggtt   16260
gtcatttgtg gttagtatta gctacatttt agggccagat gaaggccagg tgatatttga   16320
tgccaaaaat tatatattga tgtgattttc tccttctgat cttagggtgg caacattgtg   16380
gaaaagccgg cacatctgtc aggacttctg caacctgcat catcaaatga tcactatgac   16440
tgtgagagag cagcaactga agcgctaaca caaggatact ggcagatctc tacctcacaa   16500
gttataccag gtcattaaaa ttatactata aaacaccaat ttagaaatct agcttgtaaa   16560
tttaactcaa taacatcagt catgcaaatc tctacacaca caacacagta tgtgttattg   16620
ttttctattt ctgcccatag ggattatccc cagctttgag tattataagt tcacaaacat   16680
gaggccacct ttcacctacg cctccatgat acgatgggta agtattgctg aattaacatc   16740
ctgcatgtta cctttttgatt tcctgtcagt cacatcaaca atgttatgtt atgtcaggca   16800
atcctgaagt ccccagaaaa gcagcttaca ctgaaagaaa tttatcagtg gtttaccagc   16860
atgttcttct acttccgtca caacactgct acatggaagg tatgagatgt aatgtttgta   16920
ttgtacactt ttatttgtca ttccatgact cattggccac aaacaagcca atcccgaaac   16980
ccacagcctc tgttgtatat acacctgaaa actttcagaa gttgcacttg catgtcaatg   17040
```

```
aatgaatgac ttgatgaccc gactgtgaaa ttactgtgtt gtggatgact aatatgtaac   17100
ttcagtgtat aggtaattct tcttctctct gtctgtgtgt agaatgcggt tcgacataac   17160
ctcagccttc ataagtgctt tgtgcgtgtt gaaggaagga aaggttcagt ttggactgtg   17220
gatgaagagg aatttcttag aagaaaaggt caaaagttac acaggtaaac tcatttactc   17280
attatatgga tgactgcaac tgcattgttg ttgtatagtt agttgtatat gtacaagatg   17340
tttaaaaaaa gctgatttag gcctactgta aattaaaaac atctgcttaa atggatctga   17400
ttaagctgct tttatcgttg gaggcgtttg gtgaggttct gattatataa ttatataaat   17460
gagcaaatca aattcacccc cttttcactt cagggatcat gatatggact ggatggcacc   17520
atttcagctg tttcctttga ctccacaagg tgaatcttac cagatgtgag gccccaaaat   17580
ggcctctgac ttacattaat acaactaatg ttattagcta cattaaaaac acgatcgatg   17640
taaacgacac catttacata aatgtgcagt ctaaatatac ataaatgctg gcagtctatg   17700
tgagaaatca gttgttgttt agtttgaatg ttttgtgtca caaatattgt aagaatgtat   17760
attatttacc aaagtaaaag tttgtaattg ttataatctt tcatagattt aaataaaatt   17820
aatttaatca aaaatgataa tgcttaatga tatcgttaag tgtgtaaata cattcaataa   17880
gataaatgaa tgttgatgat atgtccttaa acattttatt ttacatcgta tttttactaa   17940
ttgtccaaat aaagcaatcc aatcaagcac tgtcgggctg tttttcagtg cattatacac   18000
a                                                                   18001

<210> SEQ ID NO 140
<211> LENGTH: 10
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 7
<223> OTHER INFORMATION: n = a or g
<220> FEATURE:
<221> NAME/KEY: misc_feature
<222> LOCATION: 8
<223> OTHER INFORMATION: n = c or g

<400> SEQUENCE: 140 tyaagtnntt                                                                 10

<210> SEQ ID NO 141
<211> LENGTH: 9
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 4
<223> OTHER INFORMATION: n = g or t

<400> SEQUENCE: 141 gcgngggcg                                                                   9

<210> SEQ ID NO 142
<211> LENGTH: 9
<212> TYPE: DNA
<213> ORGANISM: Artificial Sequence
<220> FEATURE:
<223> OTHER INFORMATION: Consensus sequence
```

```
<400> SEQUENCE: 142 gcggggggcg                                                          9

<210> SEQ ID NO 143
<211> LENGTH: 11
<212> TYPE: DNA
<213> ORGANISM: Artificial Sequence
<220> FEATURE:
<223> OTHER INFORMATION: Consensus sequence
<220> FEATURE:
<221> NAME/KEY: misc_feature
<222> LOCATION: 5
<223> OTHER INFORMATION: n = t or g
<220> FEATURE:
<221> NAME/KEY: misc_feature
<222> LOCATION: 9
<223> OTHER INFORMATION: n = c or a or t

<400> SEQUENCE: 143
tgcgnrggng k                                                       11

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
aggctcttct cacgcaactc                                              20

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
ctggggctac aaagggtgat                                              20

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
agctgcccat tacctgttag                                              20

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
ggaggtctgc atggatctta g                                            21

<210> SEQ ID NO 148
<211> LENGTH: 21
<212> TYPE: DNA
<213> ORGANISM: Artificial Sequence
<220> FEATURE:
<223> OTHER INFORMATION: Primer
```

<400> SEQUENCE: 148
gccttgtcag gaaaaactct g        21

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
gtcctcgatt tggcacagac        20

<210> SEQ ID NO 150
<211> LENGTH: 19
<212> TYPE: DNA
<213> ORGANISM: Artificial Sequence
<220> FEATURE:
<223> OTHER INFORMATION: Primer

<400> SEQUENCE: 150
cttgcccttc ttggtgatg        19

<210> SEQ ID NO 151
<211> LENGTH: 19
<212> TYPE: DNA
<213> ORGANISM: Artificial Sequence
<220> FEATURE:
<223> OTHER INFORMATION: Primer

<400> SEQUENCE: 151
ttgtgctgag tgccctgac        19

<210> SEQ ID NO 152
<211> LENGTH: 19
<212> TYPE: DNA
<213> ORGANISM: Artificial Sequence
<220> FEATURE:
<223> OTHER INFORMATION: Primer

<400> SEQUENCE: 152
gctttgtgcg agtggagag        19

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
agggattgga gcacttgttg        20

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
tcaggcatga accaccatac        20

<210> SEQ ID NO 155

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 155
aacatccaca cgtccagtga                                                20

<210> SEQ ID NO 156
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 156

Met Glu Val Gly Trp Tyr Arg Ser Pro Phe Ser Arg Val Val His Leu
 1               5                  10                  15

Tyr Arg Asn Gly Lys
            20
```